(12) United States Patent
Gross et al.

(10) Patent No.: US 10,478,249 B2
(45) Date of Patent: *Nov. 19, 2019

(54) CONTROLLED TISSUE ABLATION TECHNIQUES

(71) Applicant: PYTHAGORAS MEDICAL LTD., Herzliya (IL)

(72) Inventors: Yossi Gross, Moshav Mazor (IL); Gideon Meiry, Kibbutz Shomrat (IL); Yehuda Zadok, Holon (IL)

(73) Assignee: PYTHAGORAS MEDICAL LTD., Herzliya (IL)

( * ) Notice: Subject to any disclaimer, the term of this patent is extended or adjusted under 35 U.S.C. 154(b) by 370 days.

This patent is subject to a terminal disclaimer.

(21) Appl. No.: 15/330,790

(22) PCT Filed: May 7, 2015

(86) PCT No.: PCT/IB2015/053350
§ 371 (c)(1),
(2) Date: Nov. 7, 2016

(87) PCT Pub. No.: WO2015/170281
PCT Pub. Date: Nov. 12, 2015

(65) Prior Publication Data
US 2017/0215950 A1  Aug. 3, 2017

Related U.S. Application Data

(60) Provisional application No. 61/989,741, filed on May 7, 2014.

(51) Int. Cl.
*A61B 18/12* (2006.01)
*A61B 18/14* (2006.01)
(Continued)

(52) U.S. Cl.
CPC .......... *A61B 18/1492* (2013.01); *A61B 5/021* (2013.01); *A61B 5/4836* (2013.01);
(Continued)

(58) Field of Classification Search
CPC ................ A61B 5/4848; A61B 5/0538; A61B 2018/00511; A61B 18/1492; A61B 5/021;
(Continued)

(56) References Cited

U.S. PATENT DOCUMENTS 4,106,488 A   8/1978  Gordon
4,569,836 A   2/1986  Gordon
(Continued)

FOREIGN PATENT DOCUMENTS

CA   2900160   8/2014
CA   2956945   2/2016
(Continued)

OTHER PUBLICATIONS

An Office Action dated May 15, 2018, which issued during the prosecution of U.S. Appl. No. 14/972,756.
(Continued)

*Primary Examiner* — Jaymi E Della
*Assistant Examiner* — Sean W Collins
(74) *Attorney, Agent, or Firm* — Sughrue Mion, PLLC

(57) ABSTRACT

Apparatus and methods are described, including a method for use with tissue of a renal nerve (770) passing longitudinally within a wall of a renal artery (8) of a subject. Using one or more stimulating electrodes (850a, 850b) disposed within the renal artery, the tissue is stimulated by passing a stimulating current through the wall of the renal artery. Using a sensor (26), a rate of change of blood pressure of the subject is sensed, following the start of the stimulation of the tissue. In response to the rate of change, it is decided whether to ablate the tissue, and in response to deciding to
(Continued)

ablate the tissue, the tissue is ablated. Other applications are also described.

13 Claims, 53 Drawing Sheets

(51) Int. Cl.
| | |
|---|---|
| *A61N 1/36* | (2006.01) |
| *A61N 1/05* | (2006.01) |
| *G02B 6/30* | (2006.01) |
| *G02B 6/122* | (2006.01) |
| *A61B 5/021* | (2006.01) |
| *A61B 5/00* | (2006.01) |
| A61B 18/00 | (2006.01) |
| G02B 6/136 | (2006.01) |
| G02B 6/12 | (2006.01) |

(52) U.S. Cl.
CPC ....... *A61N 1/0551* (2013.01); *A61N 1/36007* (2013.01); *A61N 1/36017* (2013.01); *A61N 1/36117* (2013.01); *A61N 1/36135* (2013.01); *G02B 6/1228* (2013.01); *G02B 6/305* (2013.01); *A61B 2018/00404* (2013.01); *A61B 2018/00434* (2013.01); *A61B 2018/00511* (2013.01); *A61B 2018/00642* (2013.01); *A61B 2018/00666* (2013.01); *A61B 2018/00678* (2013.01); *A61B 2018/00702* (2013.01); *A61B 2018/00839* (2013.01); *A61B 2018/00863* (2013.01); *G02B 6/136* (2013.01); *G02B 2006/12061* (2013.01)

(58) Field of Classification Search
CPC ........ A61B 5/4836; A61B 2018/00678; A61B 2018/00863; A61B 2018/00839; A61B 2018/00702; A61B 2018/00666; A61B 2018/00642; A61B 2018/00434; A61B 2018/00404; A61N 1/36135; A61N 1/36117; A61N 1/36017; A61N 1/0551; A61N 1/36007; G02B 6/1228; G02B 6/305; G02B 2006/12061; G02B 6/136
See application file for complete search history.

(56) References Cited

U.S. PATENT DOCUMENTS

| | | | |
|---|---|---|---|
| 4,619,247 A | 10/1986 | Inoue | |
| 5,215,086 A | 6/1993 | Terry, Jr. et al. | |
| 5,251,634 A | 10/1993 | Weinberg | |
| 5,697,377 A | 12/1997 | Wittkampf | |
| 5,735,280 A | 4/1998 | Sherman et al. | |
| 5,776,063 A | 7/1998 | Dittrich et al. | |
| 5,807,285 A | 9/1998 | Vaitekunas | |
| 5,817,022 A | 10/1998 | Vesely | |
| 5,827,216 A | 10/1998 | Igo et al. | |
| 6,050,943 A | 4/2000 | Slayton | |
| 6,064,902 A | 5/2000 | Haissaguerre et al. | |
| 6,117,101 A | 9/2000 | Diederich | |
| 6,128,523 A | 10/2000 | Bechtold | |
| 6,161,048 A | 12/2000 | Sluijter | |
| 6,219,577 B1 | 4/2001 | Brown | |
| 6,233,477 B1 | 5/2001 | Chia | |
| 6,241,727 B1 | 6/2001 | Tu | |
| 6,246,899 B1 | 6/2001 | Chia | |
| 6,361,500 B1 | 3/2002 | Masters | |
| 6,405,732 B1 | 6/2002 | Edwards | |
| 6,425,877 B1 | 7/2002 | Edwards | |
| 6,440,077 B1 | 8/2002 | Jung | |
| 6,485,431 B1 | 11/2002 | Campbell | |
| 6,522,926 B1 | 2/2003 | Kieval | |
| 6,526,318 B1 | 2/2003 | Ansarinia | |
| 6,605,084 B2 | 8/2003 | Acker et al. | |
| 6,635,054 B2 | 10/2003 | Fjield et al. | |
| 6,641,579 B1 | 11/2003 | Bernardi | |
| 6,659,950 B2 | 12/2003 | Taheri | |
| 6,671,556 B2 | 12/2003 | Osorio et al. | |
| 6,684,105 B2 | 1/2004 | Cohen et al. | |
| 6,685,639 B1 | 2/2004 | Wang | |
| 6,692,490 B1 | 2/2004 | Edwards | |
| 6,701,931 B2 | 3/2004 | Sliwa et al. | |
| 6,736,835 B2 | 5/2004 | Pellegrino | |
| 6,740,040 B1 | 5/2004 | Mandrusov | |
| 6,805,129 B1 | 10/2004 | Pless et al. | |
| 6,845,267 B2 | 1/2005 | Harrison | |
| 7,001,336 B2 | 2/2006 | Mandrusov | |
| 7,022,105 B1 | 4/2006 | Edwards | |
| 7,037,306 B2 | 5/2006 | Podany et al. | |
| 7,149,574 B2 | 12/2006 | Yun | |
| 7,162,303 B2 | 1/2007 | Levin | |
| 7,226,440 B2 | 6/2007 | Gelfand et al. | |
| 7,311,701 B2 | 12/2007 | Gifford et al. | |
| 7,326,201 B2 | 2/2008 | Fjield et al. | |
| 7,430,449 B2 | 9/2008 | Aldrich | |
| 7,499,747 B2 | 3/2009 | Kieval | |
| 7,510,536 B2 | 3/2009 | Foley | |
| 7,553,284 B2 | 6/2009 | Vaitekunas | |
| 7,565,191 B2 | 7/2009 | Burbank et al. | |
| 7,617,005 B2 | 11/2009 | Demarais | |
| 7,647,115 B2 | 1/2010 | Levin et al. | |
| 7,653,438 B2 | 1/2010 | Deem | |
| 7,662,099 B2 | 2/2010 | Podany et al. | |
| 7,684,865 B2 | 3/2010 | Aldrich | |
| 7,706,882 B2 | 4/2010 | Francischelli | |
| 7,717,948 B2 | 5/2010 | Demarais | |
| 7,787,946 B2 | 8/2010 | Stahmann et al. | |
| 7,840,271 B2 | 11/2010 | Kieval | |
| 7,853,333 B2 | 12/2010 | Demarais | |
| 7,854,733 B2 | 12/2010 | Govari | |
| 7,901,359 B2 | 3/2011 | Mandrusov | |
| 7,974,696 B1 | 7/2011 | DiLorenzo | |
| 8,197,409 B2 | 6/2012 | Foley | |
| 8,391,970 B2 | 3/2013 | Tracey et al. | |
| 8,585,601 B2 | 11/2013 | Sverdlik et al. | |
| 8,696,581 B2 | 4/2014 | Sverdlik et al. | |
| 8,702,619 B2 | 4/2014 | Wang | |
| 9,014,821 B2 | 4/2015 | Wang | |
| 9,028,417 B2 | 5/2015 | Sverdlik et al. | |
| 9,381,063 B2 | 7/2016 | Gang et al. | |
| 9,408,549 B2 | 8/2016 | Brockway et al. | |
| 9,439,598 B2 | 9/2016 | Shimada et al. | |
| 9,566,456 B2 | 2/2017 | Sverdlik et al. | |
| 9,999,463 B2 | 6/2018 | Puryear et al. | |
| 2001/0003798 A1 | 6/2001 | McGovern | |
| 2001/0007940 A1 | 7/2001 | Tu | |
| 2002/0091427 A1 | 7/2002 | Rappaport | |
| 2002/0147446 A1 | 10/2002 | Ein-Gal | |
| 2002/0173688 A1 | 11/2002 | Chen | |
| 2002/0193787 A1 | 12/2002 | Qin et al. | |
| 2003/0018256 A1 | 1/2003 | Sasaki | |
| 2003/0045909 A1 | 3/2003 | Gross et al. | |
| 2003/0055421 A1 | 3/2003 | West | |
| 2003/0069590 A1 | 4/2003 | Rabiner | |
| 2003/0013968 A1 | 6/2003 | Fjield | |
| 2004/0034339 A1 | 2/2004 | Stoller | |
| 2004/0038857 A1 | 2/2004 | Tracey | |
| 2004/0097788 A1 | 5/2004 | Mourlas | |
| 2004/0122494 A1 | 6/2004 | Eggers et al. | |
| 2004/0162507 A1 | 8/2004 | Govari et al. | |
| 2004/0162550 A1 | 8/2004 | Govari et al. | |
| 2004/0193021 A1 | 9/2004 | Savage | |
| 2005/0020921 A1 | 1/2005 | Glassell | |
| 2005/0080469 A1 | 4/2005 | Larson et al. | |
| 2005/0165298 A1 | 7/2005 | Larson | |
| 2005/0192638 A1 | 9/2005 | Gelfand | |
| 2005/0203410 A1 | 9/2005 | Jenkins | |
| 2005/0222554 A1 | 10/2005 | Wallace et al. | |
| 2005/0251125 A1 | 11/2005 | Pless | |
| 2005/0288651 A1 | 12/2005 | Van Tassel et al. | |
| 2005/0288730 A1 | 12/2005 | Deem et al. | |
| 2006/0009753 A1 | 1/2006 | Fjield et al. | |

(56) References Cited

U.S. PATENT DOCUMENTS

| | | |
|---|---|---|
| 2006/0041277 A1 | 2/2006 | Deem |
| 2006/0058711 A1 | 3/2006 | Harhen et al. |
| 2006/0100514 A1 | 5/2006 | Lopath |
| 2006/0184048 A1 | 8/2006 | Saadat |
| 2006/0206150 A1 | 9/2006 | Demarais |
| 2006/0212076 A1 | 9/2006 | Demarais |
| 2006/0212078 A1 | 9/2006 | Demarais |
| 2006/0241523 A1 | 10/2006 | Sinelnikov et al. |
| 2006/0265014 A1 | 11/2006 | Demarais |
| 2006/0265015 A1 | 11/2006 | Demarais |
| 2006/0271111 A1 | 11/2006 | Demarais |
| 2006/0276852 A1 | 12/2006 | Demarais |
| 2006/0287648 A1 | 12/2006 | Schwartz |
| 2007/0004984 A1 | 1/2007 | Crum et al. |
| 2007/0021803 A1 | 1/2007 | Deem |
| 2007/0038259 A1 | 2/2007 | Kieval |
| 2007/0060972 A1 | 3/2007 | Kieval |
| 2007/0093420 A1 | 4/2007 | Yeomans |
| 2007/0112327 A1 | 5/2007 | Lee |
| 2007/0129760 A1 | 6/2007 | Demarais |
| 2007/0129761 A1 | 6/2007 | Demarais |
| 2007/0133849 A1 | 6/2007 | Young et al. |
| 2007/0135875 A1 | 6/2007 | Demarais |
| 2007/0142879 A1 | 6/2007 | Greenberg |
| 2007/0162085 A1 | 6/2007 | DiLorenzo |
| 2007/0167984 A1 | 6/2007 | Kieval |
| 2007/0167913 A1 | 7/2007 | Elkins et al. |
| 2007/0173899 A1 | 7/2007 | Levin et al. |
| 2007/0191906 A1 | 8/2007 | Caparso |
| 2007/0203549 A1 | 8/2007 | Demarais |
| 2007/0239077 A1 | 10/2007 | Azhari et al. |
| 2007/0265610 A1 | 11/2007 | Thapliyal et al. |
| 2007/0265687 A1 | 11/2007 | Deem |
| 2007/0282407 A1 | 12/2007 | Demarais |
| 2008/0004614 A1 | 1/2008 | Burdette |
| 2008/0015445 A1 | 1/2008 | Saadat |
| 2008/0033415 A1 | 2/2008 | Rieker et al. |
| 2008/0039746 A1 | 2/2008 | Franischelli |
| 2008/0058682 A1 | 3/2008 | Azhari et al. |
| 2008/0058702 A1 | 3/2008 | Arndt |
| 2008/0071173 A1 | 3/2008 | Aldrich |
| 2008/0091109 A1 | 4/2008 | Abraham |
| 2008/0108984 A1 | 5/2008 | Burdette |
| 2008/0125819 A1 | 5/2008 | Ben-David et al. |
| 2008/0140180 A1 | 6/2008 | Dolan et al. |
| 2008/0172104 A1 | 7/2008 | Kieval |
| 2008/0183248 A1 | 7/2008 | Rezai |
| 2008/0215111 A1 | 9/2008 | Kieval |
| 2008/0255449 A1 | 10/2008 | Sinelnikov |
| 2008/0255642 A1 | 10/2008 | Zarins |
| 2008/0281379 A1 | 11/2008 | Wesselink |
| 2008/0288017 A1 | 11/2008 | Kieval |
| 2008/0288031 A1 | 11/2008 | Kieval |
| 2008/0306570 A1 | 12/2008 | Rezai |
| 2008/0312521 A1 | 12/2008 | Solomon |
| 2008/0319513 A1 | 12/2008 | Pu |
| 2009/0024195 A1 | 1/2009 | Rezai et al. |
| 2009/0048514 A1 | 2/2009 | Azhari |
| 2009/0062790 A1 | 3/2009 | Malchano |
| 2009/0062873 A1 | 3/2009 | Wu et al. |
| 2009/0076409 A1 | 3/2009 | Wu |
| 2009/0112133 A1 | 4/2009 | Deisseroth |
| 2009/0118780 A1 | 5/2009 | DiLorenzo |
| 2009/0137900 A1 | 5/2009 | Bonner et al. |
| 2009/0155336 A1 | 6/2009 | Rezai |
| 2009/0187230 A1 | 6/2009 | DiLorenzo |
| 2009/0192506 A9 | 7/2009 | Vaska et al. |
| 2009/0234407 A1 | 9/2009 | Hastings et al. |
| 2009/0247912 A1 | 10/2009 | Warnking |
| 2009/0270741 A1* | 10/2009 | Vanney ............ A61B 5/02158 600/486 |
| 2009/0275827 A1 | 11/2009 | Aiken et al. |
| 2009/0287274 A1 | 11/2009 | Ridder |
| 2009/0326511 A1 | 12/2009 | Shivkumar |
| 2010/0004704 A1 | 1/2010 | Mazgalev |
| 2010/0010567 A1 | 1/2010 | Deem |
| 2010/0036292 A1 | 2/2010 | Darlington et al. |
| 2010/0042170 A1 | 2/2010 | Caparso |
| 2010/0105993 A1 | 4/2010 | Hassan |
| 2010/0113928 A1 | 5/2010 | Thapliyal |
| 2010/0130836 A1 | 5/2010 | Malchano |
| 2010/0137860 A1 | 6/2010 | Demarais |
| 2010/0137949 A1 | 6/2010 | Mazgalev |
| 2010/0137952 A1 | 6/2010 | Demarais et al. |
| 2010/0145428 A1 | 6/2010 | Cameron |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais |
| 2010/0191112 A1 | 7/2010 | Demarais |
| 2010/0204741 A1 | 8/2010 | Tweden |
| 2010/0217162 A1 | 8/2010 | Francischelli |
| 2010/0217369 A1 | 8/2010 | Gross |
| 2010/0222851 A1 | 9/2010 | Deem |
| 2010/0222854 A1 | 9/2010 | Demarais |
| 2010/0234728 A1 | 9/2010 | Foley |
| 2010/0256436 A1 | 10/2010 | Partsch |
| 2010/0268297 A1 | 10/2010 | Neisz |
| 2010/0305392 A1 | 12/2010 | Gross et al. |
| 2010/0312094 A1 | 12/2010 | Guttman et al. |
| 2011/0009734 A1 | 1/2011 | Foley |
| 2011/0015548 A1 | 1/2011 | Aldrich |
| 2011/0022133 A1 | 1/2011 | Bradford |
| 2011/0040171 A1 | 2/2011 | Foley |
| 2011/0040214 A1 | 2/2011 | Foley |
| 2011/0060324 A1 | 3/2011 | Wu |
| 2011/0092781 A1 | 4/2011 | Gertner |
| 2011/0092880 A1 | 4/2011 | Gertner |
| 2011/0112394 A1 | 5/2011 | Mishelevich |
| 2011/0112400 A1 | 5/2011 | Emery |
| 2011/0118598 A1 | 5/2011 | Gertner |
| 2011/0118600 A1 | 5/2011 | Gertner |
| 2011/0118725 A1 | 5/2011 | Mayse |
| 2011/0137149 A1 | 6/2011 | Gertner |
| 2011/0137298 A1 | 6/2011 | Chen |
| 2011/0172527 A1 | 6/2011 | Gertner |
| 2011/0172528 A1 | 6/2011 | Gertner |
| 2011/0172529 A1 | 6/2011 | Gertner |
| 2011/0178570 A1 | 6/2011 | Demarais |
| 2011/0184337 A1 | 6/2011 | Evans |
| 2011/0178541 A1 | 7/2011 | Azhari |
| 2011/0184322 A1 | 7/2011 | Brawer |
| 2011/0196248 A1 | 8/2011 | Grunwald |
| 2011/0207758 A1 | 8/2011 | Sobotka et al. |
| 2011/0208173 A1 | 8/2011 | Sobotka et al. |
| 2011/0208175 A1 | 8/2011 | Sobotka et al. |
| 2011/0251524 A1 | 10/2011 | Azhari |
| 2011/0257523 A1 | 10/2011 | Hastings et al. |
| 2011/0257564 A1 | 10/2011 | Demarais et al. |
| 2011/0257641 A1 | 10/2011 | Hastings et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0282203 A1 | 11/2011 | Tsoref |
| 2011/0282249 A1 | 11/2011 | Tsoref |
| 2011/0306851 A1 | 12/2011 | Wang |
| 2012/0029500 A1 | 2/2012 | Jenson |
| 2012/0029505 A1 | 2/2012 | Jenson |
| 2012/0029509 A1 | 2/2012 | Smith et al. |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0089047 A1 | 4/2012 | Ryba et al. |
| 2012/0095371 A1 | 4/2012 | Sverdlik et al. |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0130363 A1 | 5/2012 | Kim |
| 2012/0150049 A1 | 6/2012 | Zielinski et al. |
| 2012/0157992 A1 | 6/2012 | Smith et al. |
| 2012/0172680 A1 | 7/2012 | Gelfand et al. |
| 2012/0191079 A1 | 7/2012 | Moll et al. |
| 2012/0197198 A1 | 8/2012 | Demarais |

(56) References Cited

U.S. PATENT DOCUMENTS

| | | |
|---|---|---|
| 2012/0197243 A1 | 8/2012 | Sherman et al. |
| 2012/0265198 A1 | 10/2012 | Crow et al. |
| 2012/0265227 A1 | 10/2012 | Sverdlik et al. |
| 2012/0290024 A1 | 11/2012 | Zhang et al. |
| 2012/0296240 A1 | 11/2012 | Azhari |
| 2012/0296329 A1 | 11/2012 | Ng |
| 2013/0012866 A1 | 1/2013 | Deem |
| 2013/0013024 A1 | 1/2013 | Levine |
| 2013/0085489 A1 | 4/2013 | Fain et al. |
| 2013/0103028 A1 | 4/2013 | Tsoref |
| 2013/0131743 A1 | 5/2013 | Yamasaki et al. |
| 2013/0165926 A1 | 6/2013 | Mathur |
| 2013/0204242 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218029 A1 | 8/2013 | Cholette et al. |
| 2013/0218054 A1 | 8/2013 | Sverdlik et al. |
| 2013/0218068 A1 | 8/2013 | Sverdlik et al. |
| 2013/0231655 A1 | 9/2013 | Budzelaar et al. |
| 2013/0274614 A1 | 10/2013 | Shimada et al. |
| 2013/0274735 A1 | 10/2013 | Hastings et al. |
| 2013/0289369 A1 | 10/2013 | Margolis |
| 2013/0303876 A1 | 11/2013 | Gelfand et al. |
| 2013/0310674 A1 | 11/2013 | Deno et al. |
| 2013/0310823 A1 | 11/2013 | Gelfand et al. |
| 2013/0322724 A1 | 12/2013 | Florent et al. |
| 2013/0324987 A1 | 12/2013 | Leung et al. |
| 2013/0324989 A1 | 12/2013 | Leung et al. |
| 2013/0331813 A1 | 12/2013 | Barbut et al. |
| 2014/0005706 A1 | 1/2014 | Gelfand et al. |
| 2014/0012133 A1 | 1/2014 | Sverdlik et al. |
| 2014/0018788 A1 | 1/2014 | Engelman et al. |
| 2014/0088561 A1 | 3/2014 | Levin et al. |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0243809 A1 | 8/2014 | Gelfand et al. |
| 2014/0257263 A1 | 9/2014 | Azamian et al. |
| 2014/0276036 A1 | 9/2014 | Collins et al. |
| 2014/0276063 A1 | 9/2014 | Park et al. |
| 2014/0276742 A1 | 9/2014 | Nabutovsky et al. |
| 2014/0288551 A1 | 9/2014 | Bharmi et al. |
| 2015/0011843 A1 | 1/2015 | Toth et al. |
| 2015/0045649 A1 | 2/2015 | O'Dea et al. |
| 2015/0073400 A1 | 3/2015 | Sverdlik et al. |
| 2015/0148601 A1 | 5/2015 | Weiner et al. |
| 2015/0164401 A1 | 6/2015 | Toth et al. |
| 2015/0173673 A1 | 6/2015 | Toth et al. |
| 2015/0216590 A1 | 8/2015 | Wang et al. |
| 2015/0224326 A1 | 8/2015 | Toth et al. |
| 2015/0245867 A1 | 9/2015 | Gross |
| 2015/0257779 A1 | 9/2015 | Sinelnikov et al. |
| 2015/0289929 A1 | 10/2015 | Toth et al. |
| 2015/0297113 A1 | 10/2015 | Kassab et al. |
| 2015/0297139 A1 | 10/2015 | Toth |
| 2016/0000499 A1 | 1/2016 | Lennox et al. |
| 2016/0106498 A1 | 4/2016 | Highsmith et al. |
| 2016/0113699 A1 | 4/2016 | Sverdlik et al. |
| 2016/0128767 A1 | 5/2016 | Azamian et al. |
| 2016/0324572 A1 | 11/2016 | Gross et al. |
| 2016/0338773 A1 | 11/2016 | Shimada et al. |
| 2017/0007157 A1 | 1/2017 | Gross et al. |
| 2017/0007158 A1 | 1/2017 | Gross et al. |
| 2017/0027460 A1 | 2/2017 | Shimada et al. |
| 2017/0035310 A1 | 2/2017 | Shimada et al. |
| 2017/0056104 A1 | 3/2017 | Asirvatham et al. |
| 2017/0172651 A1 | 6/2017 | Gross et al. |
| 2018/0221087 A1 | 8/2018 | Puryear et al. |
| 2018/0280082 A1 | 10/2018 | Puryear et al. |

FOREIGN PATENT DOCUMENTS

| | | |
|---|---|---|
| CN | 102551878 | 7/2012 |
| CN | 203089369 U | 7/2013 |
| EP | 2460486 | 6/2012 |
| WO | 1999/40957 | 8/1999 |
| WO | 03/097162 | 11/2003 |
| WO | 2006/072928 | 7/2006 |
| WO | 07/134258 | 11/2007 |
| WO | 2008/003058 | 1/2008 |
| WO | 2009/073528 | 6/2009 |
| WO | 2010/067360 | 6/2010 |
| WO | 2011/024159 | 3/2011 |
| WO | 2011/141918 | 11/2011 |
| WO | 2012/100211 | 7/2012 |
| WO | 2012/120495 | 9/2012 |
| WO | 2012/122157 | 9/2012 |
| WO | 2013/030738 | 3/2013 |
| WO | 2013/030743 | 3/2013 |
| WO | 2013/049601 | 4/2013 |
| WO | 2013/111136 | 8/2013 |
| WO | 2013/121424 | 8/2013 |
| WO | 2013/157009 | 10/2013 |
| WO | 2014/029355 | 2/2014 |
| WO | 2014/068577 | 5/2014 |
| WO | 2014/071223 | 5/2014 |
| WO | 2014/123512 | 8/2014 |
| WO | 2014/160832 | 10/2014 |
| WO | 2014/175853 | 10/2014 |
| WO | 2015/057696 | 4/2015 |
| WO | 2015/138225 | 9/2015 |
| WO | 2015/170281 | 11/2015 |
| WO | 2015/175948 | 11/2015 |

OTHER PUBLICATIONS

An Office Action dated Jul. 19, 2018, which issued during the prosecution of U.S. Appl. No. 15/147,081.

An International Search Report and a Written Opinion both dated Jun. 11, 2018, which issued during the prosecution of Applicant's PCT/IL2018/050231.

An Office Action dated Sep. 6, 2018, which issued during the prosecution of U.S. Appl. No. 15/001,615.

An Office Action dated Nov. 30, 2017, which issued during the prosecution of U.S. Appl. No. 14/794,737.

An Office Action dated Dec. 15, 2017, which issued during the prosecution of U.S. Appl. No. 14/795,529.

An International Search Report and a Written Opinion both dated Dec. 14, 2017, which issued during the prosecution of Applicant's PCT/IL2017/050967.

An International Search Report and a Written Opinion both dated Nov. 10, 2017, which issued during the prosecution of Applicant's PCT/IL2017/050533.

Buch E et al., "Intra-pericardial balloon retraction of the left atrium: A novel method to prevent esophageal injury during catheter ablation," Heart Rhythm 2008;5:1473-1475.

Cassak D, "Endosense: Facing technology and financing challenges in AF," In-Vivo: The Business & Medicine Report, 36-44, Mar. 2010.

Di Biase L et al., "Prevention of phrenic nerve injury during epicardial ablation: Comparison of methods for separating the phrenic nerve from the epicardial surface," Heart Rhythm 2009;6:957-961.

Matsuo S et al., "Novel technique to prevent left phrenic nerve injury during epicardial catheter ablation," Circulation 2008;117:e471.

Nakahara S et al., "Intrapericardial balloon placement for prevention of collateral injury during catheter ablation of the left atrium in a porcine model," Heart Rhythm 2010;7:81-87.

Shen J et al., "The surgical treatment of atrial fibrillation Heart Rhythm," vol. 6, No. 8S, August Supplement 2009.

Sacher F et al., "Phrenic Nerve Injury After Catheter Ablation of Atrial Fibrillation," Indian Pacing Electrophysiol J. Jan.-Mar. 2007; 7(1): 1-6.

A Restriction Requirement dated Feb. 25, 2013, which issued during the prosecution of U.S. Appl. No. 12/780,240.

Tanaka S et al., "Development of a new vascular endoscopic system for observing inner wall of aorta using intermittent saline jet" World Congress on Medical Physics and Biomedical Engineering, Sep. 7-12, 2009, Munich, Germany.

(56) References Cited

OTHER PUBLICATIONS

Tearney GJ et al., "Three-Dimensional coronary artery microscopy by intracoronary optical frequency domain imaging" JACC Cardiovasc Imaging. Nov. 2008; 1(6): 752-761.
An Office Action dated Aug. 21, 2015, which issued during the prosecution of U.S. Appl. No. 13/771,853.
William E. Cohn, et al., "Contrast pericardiography facilitates intrapericardial navigation under fluoroscopy", Ann Thorac Surg 2010; 90: 1537-40. Accepted for publication Jun. 7, 2010.
Srijoy Mahapatra, et al., "Pressure frequency characteristics of the pericardial space and thorax during subxiphoid access for epicardial ventricular tachycardia ablation", Heart Rhythm 2010; 7:604-609.
Schuessler RB et al., "Animal studies of epicardial atrial ablation," Heart Rhythm, vol. 6, No. 12S, S41-S45, December Supplement 2009.
An English translation of an Office Action dated Nov. 18, 2016, which issued during the prosecution of Chinese Patent Application No. 2013800692612.
An International Search Report and a Written Opinion both dated Oct. 26, 2011, which issued during the prosecution of Applicant's PCT/IL11/00382.
An International Search Report and a Written Opinion both dated Sep. 17, 2012, which issued during the prosecution of Applicant's PCT/IL2012/000100.
An International Preliminary Report on Patentability dated Nov. 20, 2012, which issued during the prosecution of Applicant's PCT/IL11/00382.
An International Search Report dated Jul. 31, 2008, which issued during the prosecution of Applicant's PCT/US07/68818.
An Office Action dated Dec. 20, 2012, which issued during the prosecution of U.S. Appl. No. 11/653,115.
An Office Action dated Feb. 19, 2013, which issued during the prosecution of U.S. Appl. No. 13/010,555.
Fajardo et al., Effects of Hyperthermia in a Maligant Tumor, Cancer 45:613-623 (1980).
Short et al., Physical Hyperthermia and Cancer Therapy, Proceedings of the IEEE 68:133-142 (1980) p. 136, col. 2, para 6.
U.S. Appl. No. 60/370,190, filed Apr. 8, 2002.
U.S. Appl. No. 60/307,124, filed Jul. 23, 2001.
An Office Action dated May 17, 2013, which issued during the prosecution of U.S. Appl. No. 12/780,240.
An Invitation to pay additional fees dated Jun. 7, 2013, which issued during the prosecution of Applicant's PCT/IL2013/050134.
An International Search Report and a Written Opinion both dated Aug. 12, 2013 which issued during the prosecution of Applicant's PCT/IL2013/050134.
An International Search Report and a Written Opinion both dated Feb. 18, 2011 which issued during the prosecution of Applicant's PCT/IL2010/000683.
An International Preliminary Report of patentability dated Feb. 28, 2012 which issued during the prosecution of Applicant's PCT/IL2010/000683.
F. Mahfoud et al., Catherter-Based renal denervation increases insulin sensitivity and improves glucose metabolism. European Heart Journal 2010.
F. Mahfoud et al., Effects of Renal Sympathetic Denervation on Glucose Metabolism in Patients with Resistant Hypertension: A Pilot Study. Circulation 2011: 123 1940-1946.
Tai et al., Analysis of Nerve Conduction Including by Direct Current, J Comput Neuro. Published Online on 2009.
Ariav et al., Electrical Stimulation Induced Relaxation of Isolated Pig Aortas, Scientific Sessions 2011. American Heart Association. Abstract.
Stella et al., Cardiovascular Effects of Efferent renal nerve stimulation, Clin and Exper. Theory and Practice, 97-111, 1987.
Mortimer and Bhadra., Peripheral Nerve and Muscle Stimulation, Chapter 4.2, 1-48, 2004.
Stella et al., Effects of afferent renal nerve stimulation on renal hemodynamic and excretory functions, American Journal of physiology, 576-583, 1984.

Renal Sympathetic denervation in patients with treatment resistant hypertension, (1-7) Published online Nov. 2010.
Zhang et al., Mechanism of Nerve conduction Block induced by High-Frequency Biphasic Electrical Currents, IEEE Biomedical Engineering vol. 53 No. 12, 2006.
Bhadra et al., Reduction of the Onset Response in High-Frequency Nerve Block with Amplitude Ramps from Non-Zero Amplitudes, 650-653, 2009 IEEE.
Tai et al., Stimulation of Nerve Block by High-Frequency Sinusoidal Electrical Current Based on the Hodgkin-Huxley Model, IEEE Neural Systems and Rehabilitation engineering, vol. 13 No. 3, 2005.
Tsui, Electrical Nerve Stimulation, Springer Atlas of Ultrasound, pp. 9-18, 2008.
Bartus et al., Denervation (ablation) of Nerve Terminalis in renal arteries: early results of interventional treatment of arterial hypertension in Poland, Kardiologia Polska 2013, 71, 2: 152-158.
Krum et al., Catherter-Based Renal sympathetic denervation for resistant hypertension: A multicentre safety and proof-of-principle cohort study, Lancet 2009.
Chinushi M. et al., Blood pressure and autonomic responses to electrical stimulation of the renal arterial nerve before and after ablation of the renal artery, Pubmed, Hyper tension, Feb. 2013 61;(2) 450-6.
Wojakowski and Tendera, Renal sympathetic nerve in pathopysiology of resistant hypertension, European Society of Cardiology, downloaded on Jun. 2013.
Chinushi et al., Hemodynamic Responses and Histological Effects of Radiofrequency catheter Ablation to renal artery Sympathetic nerve. Abstract, downloaded on Jun. 2013.
Berjano, Biomedical Engineering Online Theoretical modeling for Radiofrequency Ablation: state-of-the-art and challenges for the future, published Apr. 2006.
Young and Henneman, Reversible block of nerve Conduction by Ultrasound, Archive of Neurology vol. 4, 1961.
Ballantine et al., Focal Destruction of nervous tissue by focused ultrasound :Biophysical factors influencing its Application, Medical Acoustics Research Group, 1956.
Colucci et al., Focused Ultrasound effects on nerve action potential in vitro, Department of Radiology, Harvard Medical Scholl, Ultrasound Med Biolog. 2009, 35(10); 1773-174.
Damianou, MRI Monitoring of the effects of tissue interfaces in the penetration of high intensity focused ultrasound in kidney in vivo, Ultrasound in Med & Bilo., vol. 30 No. 9, 2004.
Daum et al., In vivo Demonstration of noninvasive thermal surgery of the liver and kidney using an ultrasonic phase array, Ultrasound in Med & Bilo., vol. 25 No. 7, 1087-1098, 1999.
Foley et al., Image guided HIFU Neurolysis of peripheral nerve to treat Spasticity and Pain, Ultrasound in Med & Bilo., vol. 30 No. 9, 1199-1207, 2004.
Foley et al., Image guided High-Intensity focused Ultrasound for Condition block of peripheral nerves, Biomed Engineering, vol. 35 No. 1, 2007.
Zhang and Solomon, Nerve Ablation by high Intensity focused Ultrasound (HIFU) in swine model: Investigating HIFU as a non invasive Nerve block tool, WCIO 2011. Abstract.
Hynynen et al., Noninvasive arterial occlusion using MRI-Guided focused Ultrasound, Ultrasound in Med & Bilo., vol. 22 No. 8, 1071-1077, 1996.
Iwamoto et al., focused Ultrasound for Tactile Felling display, ICAT 2001.
Lele, Effects of Ultrasonic radiation on peripheral Nerve, with Observation on local Hearting, Experimental Neurology 8, 47-83, 1963.
Miharn et al., Temporally-Specific modification of Myelinated Axon excitability in vitro following a single ultrasound pulse,Ultrasound in Med & Bilo., 1990.
Rubin et al., Acute effects of Ultrasound on skeletal muscle oxygen tension , blood flow and capillary density, Ultrasound in Med & Bilo., vol. 16 No. 3, 271*277, 1990.
Renal sympathetic nerve ablation for Uncontrolled Hypertension, The New England journal of medicine, 932-934, 2009.

(56) References Cited

OTHER PUBLICATIONS

Wu et al., Preliminary Experience using high Intensity focused Ultrasound for the treatment of patient with advanced stage renal malignancy. The Journal of Urology, vol. 170, 2237-2240, 2003.
Young and Henneman, Functional Effects of focused Ultrasound on Mammalian nerves, Science New Series, vol. 134, No. 3489, 1961, 1521-1522.
Mizelle et al., Role of Renal nerve in Compensatory adaptation to chronic reduction in sodium intake, American Physiological Society, 1987.
Gibson, the Present Status of Renal Sympathectomy, California and Western Medicine, vol. 45, No. 1, 1936.
Kassab et al., Renal Denervation Attenuates the Sodium Retention and Hypertension Associated With Obesity, Hypertension, 1997. Abstract.
Winternitz et al., Role of the Renal Sympathetic Nerves in the Development and Maintenance of Hypertension in the Spontaneously Hypertensive Rat, J. Clin Invest 66(5), 1980. Abstract.
Augustyniak et al., Sympathetic overactivity as a cause of hypertension in chronic renal failure, Hypertension vol. 20, Issue 1, 2002. Abstract.
Brief introduction to bioimpedance (from www.ucl.ac.uk-medphys-research-eit).
Fletcher, Effect of episodic hypoxia on sympathetic activity and blood pressure, Respyration Pysiology, vol. 119, issue 2-3, 2000. Abstract.
Fletcher et al., Blood pressure response to chronic episodic hypoxia: the renin-angiotensin system, Journal of Applied physiology, 2001.
Illis, Spinal Cord Synapses in the Cat: The Reaction of the Boutons Termineaux at the Motoneurone Surface to Experimental Denervation, Brain a Journal of Neurology, vol. 87 issue 3, 1963, First page only.
Kopelman et al., Upper dorsal thoracoscopic sympathectomy for palmar hyperhidrosis. The use of harmonic scalpel versus diathermy. Ann Chir Gynaecol. 2001;90(3):203-5. Abstract.
Hashmonai et al., Thoracoscopic sympathectomy for palmar hyperhidrosis, Surgical Endoscopy May 2001, vol. 15, Issue 5, pp. 435-441.
Yoshimoto et al., Relationship between renal sympathetic nerve activity and renal blood flow during natural behavior in rats, American Journal of Physiology vol. 286, 2004.
DiBona. Dynamic Analysis of patterns of renal sympathetic nerve activity: Implications of renal functions, Exp Physiol. 90.2 pp. 159-161, 2004.
Valente et al., Laparoscopic renal denervation for intractable ADPKD-related pain, Nephrology Dialysis Transplantation vol. 6 issue 1, 2000.
An International Search Report and a Written Opinion both dated Aug. 11, 2015 which issued during the prosecution of Applicant's PCT/IB2015/053350.
An International Preliminary Report on Patentability dated Nov. 8, 2016, which issued during the prosecution of Applicant's PCT/IB2015/053350.
An Advisory Action dated Aug. 8, 2016, which issued during the prosecution of U.S. Appl. No. 13/771,853.
European Search Report dated Jun. 7, 2016, which issued during the prosecution of Applicant's European App No. 13850508.6.
U.S. Appl. No. 61/811,880, filed Apr. 15, 2013.
Schwarz et al;(2015) Autonomix presentation at TCT—Guidewire-Based Autonomic Neural Sensing From the Artery Lumen.
An International Search Report and a Written Opinion both dated Apr. 17, 2014 which issued during the prosecution of Applicant's PCT/IL2013/050903.
Luscher TF, Mahfoud F. Renal nerve ablation after symplicity htn-3: Confused at the higher level? Eur Heart J. 2014;35:1706-1711.
Lu (2015) Selective Proximal Renal Denervation Guided by Autonomic Responses Evoked via High-Frequency Stimulation in a Preclinical Canine Model.

Straub et al., 'A bacteria-induced switch of sympathetic effector mechanisms augments local inhibition of TNF-a and IL-6 secretion in the spleen' Jul. 2000 The FASEB Journal vol. 14 No. 10 1380-1388.
Gestel et al., 'Autonomic dysfunction in patients with chronic obstructive pulmonary disease (COPD)' J Thorac Dis 2010; 2:215-222.
Hering et al., 'Renal Denervation in Moderate to Severe CKD' J Am Soc Nephrol. [Jul. 2012]; 23(7): 1250-1257.
Jonson et al, 'Afferent electrical stimulation of mesenteric nerves inhibits duodenal HC03 secretion via a spinal reflex activation of the splanchnic nerves in the rat' [1988] Acta Physiologica Scandinavica, 133: 545-550. doi: 10.1111/j.1748-1716.1988.tb08439.x.
Jonson et al., 'Splanchnic nerve stimulation inhibits duodenal HC03-secretion in the rat' Am J Physiol. [Dec. 1988];255 (6 Pt 1):G709-12.
Schwan, H.P. and Kay, C.F., 1956. Specific resistance of body tissues.*Circulation Research*, 4(6), pp. 664-670.
Kees et al., 'Via beta-adrenoceptors, stimulation of extrasplenic sympathetic nerve fibers inhibits lipopolysaccharideinduced TNF secretion in perfused rat spleen' J Neuroimmunol. Dec. 2003;145(1-2):77-85.
pcta.org, 'New (Dec. 6, 2013) Medtronic Multi-Electrode Renal Denervation Device Gets CE Mark and Australian Approval' http://www.ptca.org/news/2013/1206_MEDTRONIC_SYMPLICITY.html.
BusinessWire, 'St. Jude Medical Receives European Approval for New Renal Denervation System That Reduces Total Ablation Time by More Than 80 Percent' (Aug. 29, 2013) 2013 European Society of Cardiology.
mananatomy.com, 'Duodenum' http://www.mananatomy.com/digestive-system/duodenum.
Rosas-Ballina et al., 'Splenic nerve is required for cholinergic anti-inflammatory pathway control of TNF in endotoxemia' Aug. 5, 2008, vol. 105, No. 31 www.pnas.org/cgi/doi10.1073/pnas.0803237105.
Krum, H., et al. "Device-based antihypertensive therapy: therapeutic modulation of the autonomic nervous system." Circulation 123.2 (2011): 209.
Kilgore, Kevin L., et al. "Combined direct current and high frequency nerve block for elimination of the onset response." Engineering in Medicine and Biology Society, 2009. EMBC 2009. Annual International Conference of the IEEE. IEEE, 2009.
Bohm (2014) Symplicity HTN-3 trial_ what is it and what does it mean?
Ruilope (2014) Was there real denervation in the Symplicity HTN-3 trial.
Esler (2010) Renal sympathetic denervation in patients with treatment-resistant hypertension (The Symplicity HTN-2 Trial).
Renal Catheterization—SymplicityTM Renal Denervation System—downloaded from medtronicrdn.com Jun. 26, 2013.
An Office Action dated Mar. 11, 2016, which issued during the prosecution of U.S. Appl. No. 13/771,853.
Persu A, Jin Y, Fadl Elmula FE, Jacobs L, Renkin J, Kjeldsen S. Renal denervation after symplicity htn-3: An update.Curr Hypertens Rep. 2014;16:460.
Renal denervation and symplicity htn-3: "Dubium sapientiae initium" (doubt is the beginning of wisdom). Circ Res. 2014;115:211-214.
Patel HC, Hayward C, Di Mario C. Symplicity htn 3: The death knell for renal denervation in hypertension? Glob Cardiol Sci Pract. 2014;2014:94-98.
An Office Action dated Jan. 8, 2015, which issued during the prosecution of U.S. Appl. No. 13/771,853.
An International Preliminary Report on Patentability dated May 5, 2015, which issued during the prosecution of Applicant's PCT/IL2013/050903.
U.S. Appl. No. 61/841,485, filed Jul. 1, 2013.
Changfeng (2009) Analysis of nerve conduction block induced by direct current.
Tsui (2008) Chapter 2 of Atlas of ultrasound and nerve stimulation guided regional anesthesia.
Changfeng (2005) Simulation of nerve block by high frequency sunusoidal electrical current.

(56) References Cited

OTHER PUBLICATIONS

Warchol-Celinska E, Januszewicz A, Prejbisz A, Kadziela J. Renal denervation after the symplicity htn-3 trial. Postepy Kardiol Interwencyjnej. 2014;10:75-77.
Calhoun DA, Jones D, Textor S, Goff DC, Murphy TP, Toto RD, White A, Cushman WC, White W, Sica D, Ferdinand K, Giles TD, Falkner B, Carey RM. Resistant hypertension: Diagnosis, evaluation, and treatment: A scientific statement from the American Heart Association professional education committee of the council for high blood pressure research Circulation. 2008.
Schlaich MP, Sobotka PA, Krum H, Whitbourn R, Walton A, Esler MD. Renal denervation as a therapeutic approach for hypertension: Novel implications for an old concept. Hypertension. 2009;54:1195-1201.
Esler MD, Bohm M, Sieved H, Rump CL, Schmieder RE, Krum H, Mahfoud F, Schlaich MP. Catheter-based renal denervation for treatment of patients with treatment-resistant hypertension: 36 month results from the Symplicity htn-2 randomized clinical trial. Eur Heart J. 2014;35:1752-1759.
U.S. Appl. No. 61/862,561, filed Aug. 6, 2013.
U.S. Appl. No. 61/722,293, filed Nov. 5, 2012.
"Blood pressure response to renal nerve stimulation in patients undergoing renal denervation: a feasibility study", Gal et al., Journal of Human Hypertension (2014), 1-4, Macmillan Publishers Limited.
Sarafidis PA, Bakris GL. Resistant hypertension: An overview of evaluation and treatment. J Am Coll Cardiol. 2008;52:1749-1757.
Mahfoud F, Cremers B, Janker J, Link B, Vonend O, Ukena C, Linz D, Schmieder R, Rump LC, Kindermann I, Sobotka PA, Krum H, Scheller B, Schlaich M, Laufs U, Bohm M. Renal hemodynamics and renal function after catheter-based renal sympathetic denervation in patients with resistant hypertension. Hypertension. 2012;60:419-424.
Kjeldsen SE, Fadl Elmula FE, Persu A, Jin Y, Staessen JA. Renal sympathetic denervation in the aftermath of symplicity htn-Blood Press. 2014;23:256-261.
Kandzari DE, Bhatt DL, Sobotka PA, O'Neill WW, Esler M, Flack JM, Katzen BT, Leon MB, Massaro JM, Negoita M, Oparil S, Rocha-Singh K, Straley C, Townsend RR, Bakris G. Catheter-based renal denervation for resistant hypertension: Rationale and design of the symplicity htn-3 trial. Clin Cardiol. 2012;35:528-535.
European Search Report dated May 9, 2017, which issued during the prosecution of Applicant's European App No. 16203956.4.
Krum H, Schlaich MP, Sobotka PA, Bohm M, Mahfoud F, Rocha-Singh K, Katholi R, Esler MD. Percutaneous renal denervation in patients with treatment-resistant hypertension: Final 3-year report of the symplicity htn-1 study. Lancet. 2014;383:622-629.
Esler M. Illusions of truths in the symplicity htn-3 trial: Generic design strengths but neuroscience failings. J Am Soc Hypertens. 2014;8:593-598.
Schmieder RE. Hypertension: How should data from symplicity htn-3 be interpreted? Nat Rev Cardiol. 2014;11:375-376.
Pathak A, Ewen S, Fajadet J, Honton B, Mahfoud F, Marco J, Schlaich M, Schmieder R, Tsioufis K, Ukena C, Zeller T. From symplicity htn-3 to the renal denervation global registry: Where do we stand and where should we go? Eurointervention. 2014;10:21-23.
Pokushalov, Evgeny, et al. "A randomized comparison of pulmonary vein isolation with versus without concomitant renal artery denervation in patients with refractory symptomatic atrial fibrillation and resistant hypertension." *Journal of the American College of Cardiology* 60.13 (2012): 1163-1170.
Ruilope, L.M. and Arribas, F., 2014. Resistant Hypertension and Renal Denervation. Considerations on the Results of the Symplicity HTN-3 Trial.*Revista Española de Cardiología*, 67(11), pp. 881-882.
An Office Action dated Apr. 6, 2017, which issued during the prosecution of U.S. Appl. No. 13/771,853.
U.S. Appl. No. 61/989,741, filed May 7, 2014.
U.S. Appl. No. 62/158,139, filed May 7, 2015.
An International Search Report and a Written Opinion both dated May 24, 2017, which issued during the prosecution of Applicant's PCT/IL2017/050029.
An Invitation to pay additional fees dated Mar. 28, 2017, which issued during the prosecution of Applicant's PCT/IL2017/050029.
Notice of Allowance together with the English translation dated May 4, 2017 which issued during the prosecution of Chinese Patent Application No. 2013800692612.
An Office Action dated Jun. 15, 2017, which issued during the prosecution of U.S. Appl. No. 14/440,431.
An Invitation to pay additional fees dated Sep. 11, 2017, which issued during the prosecution of Applicant's PCT/IL2017/050533.

\* cited by examiner

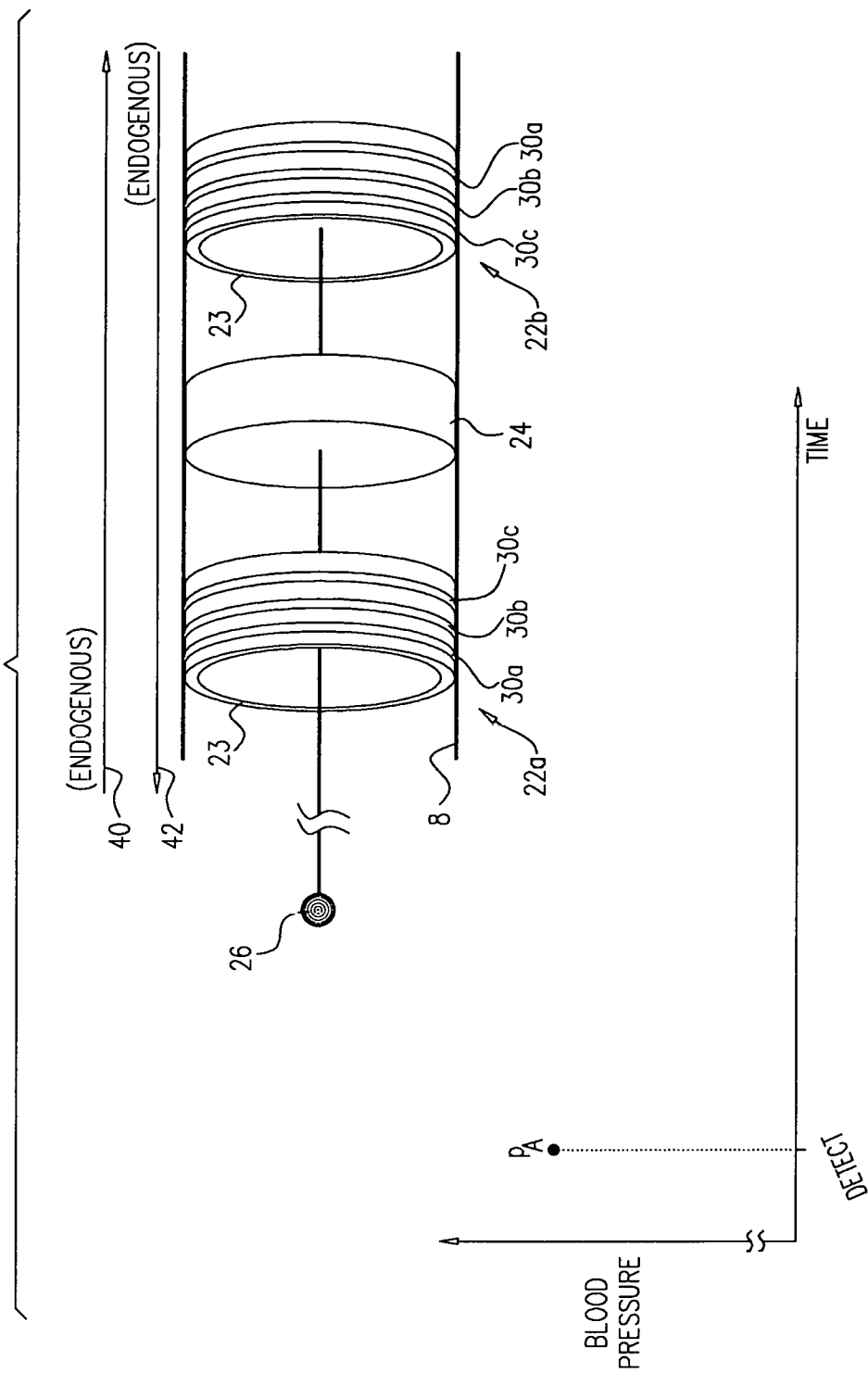

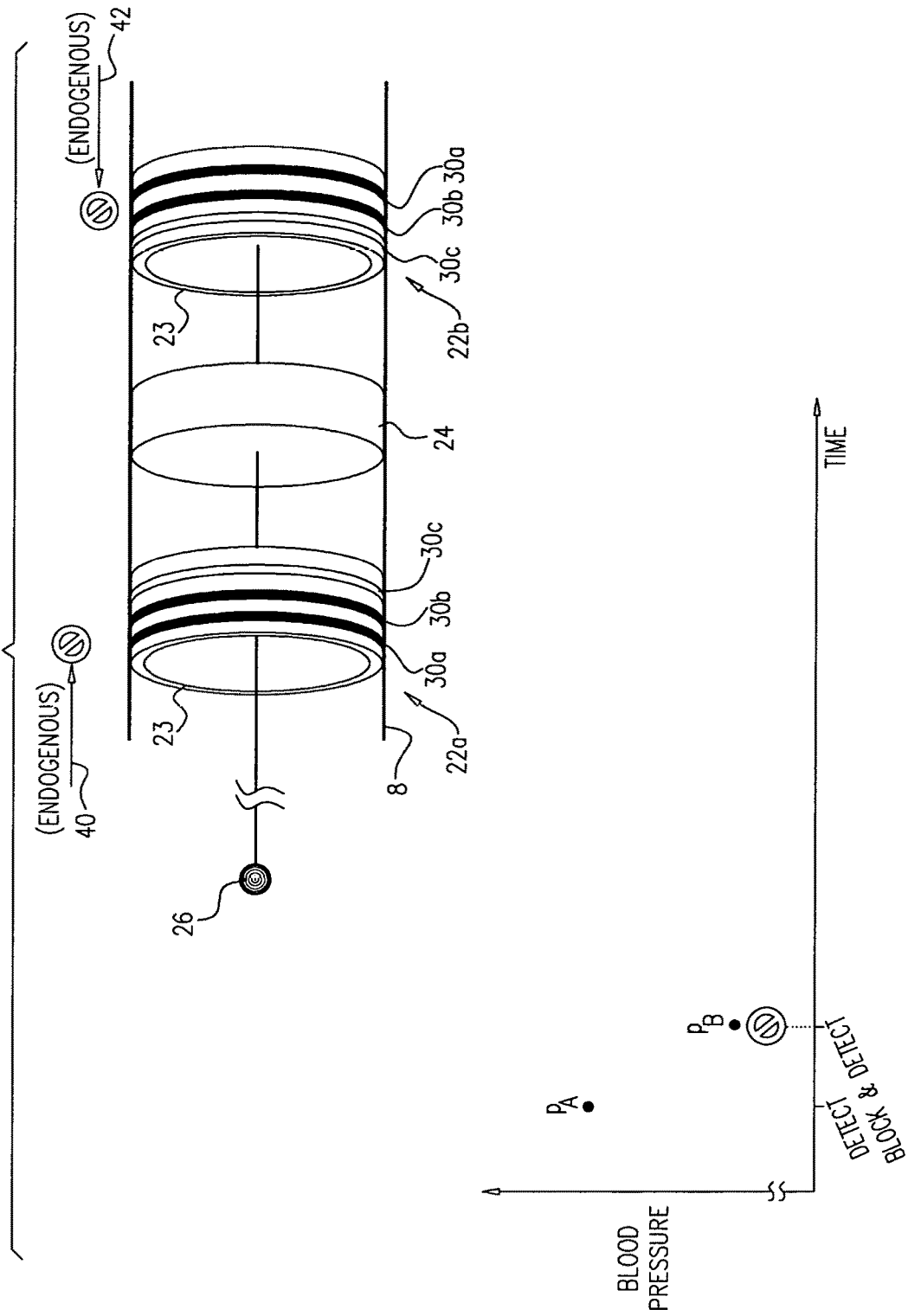

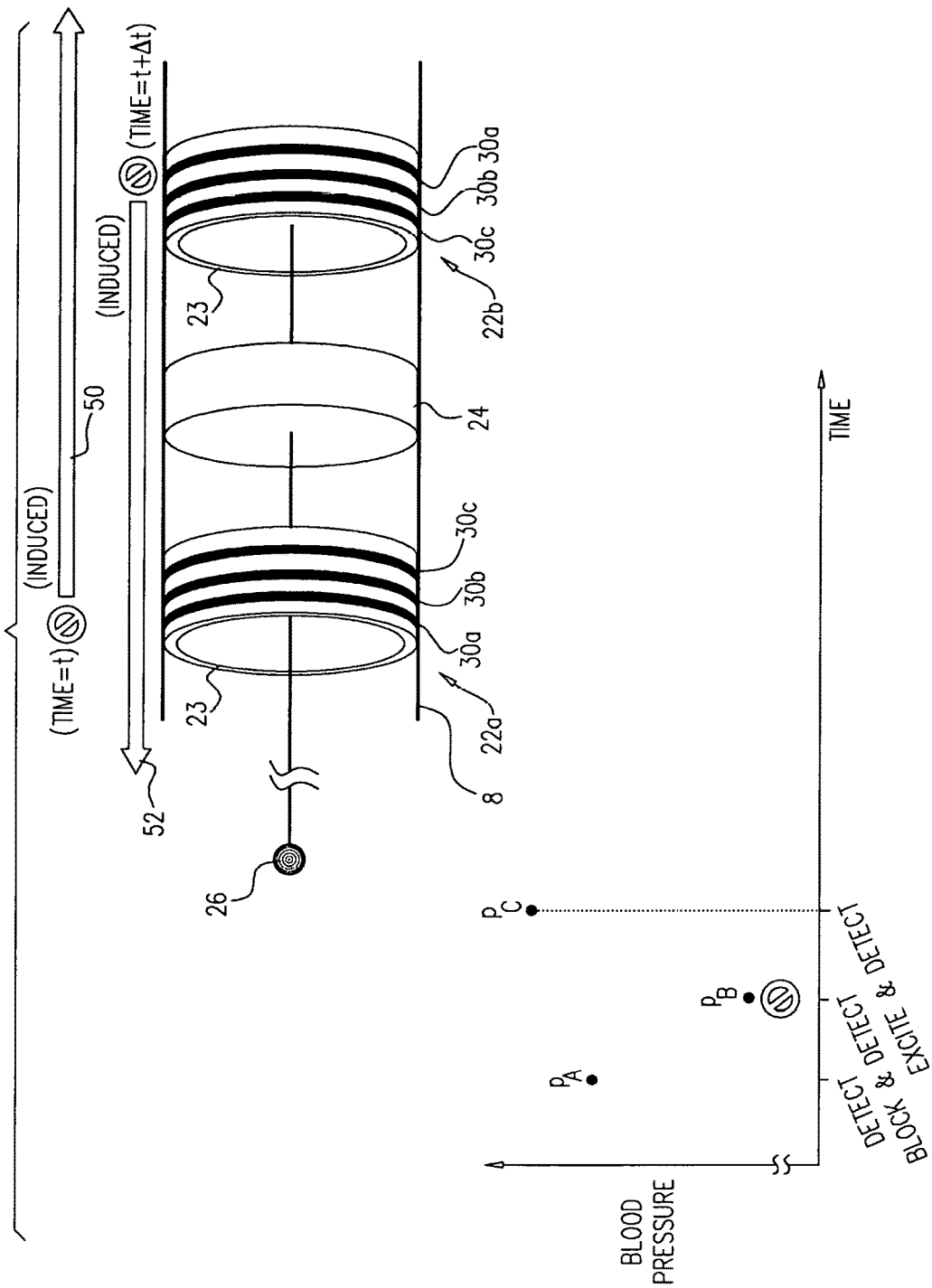

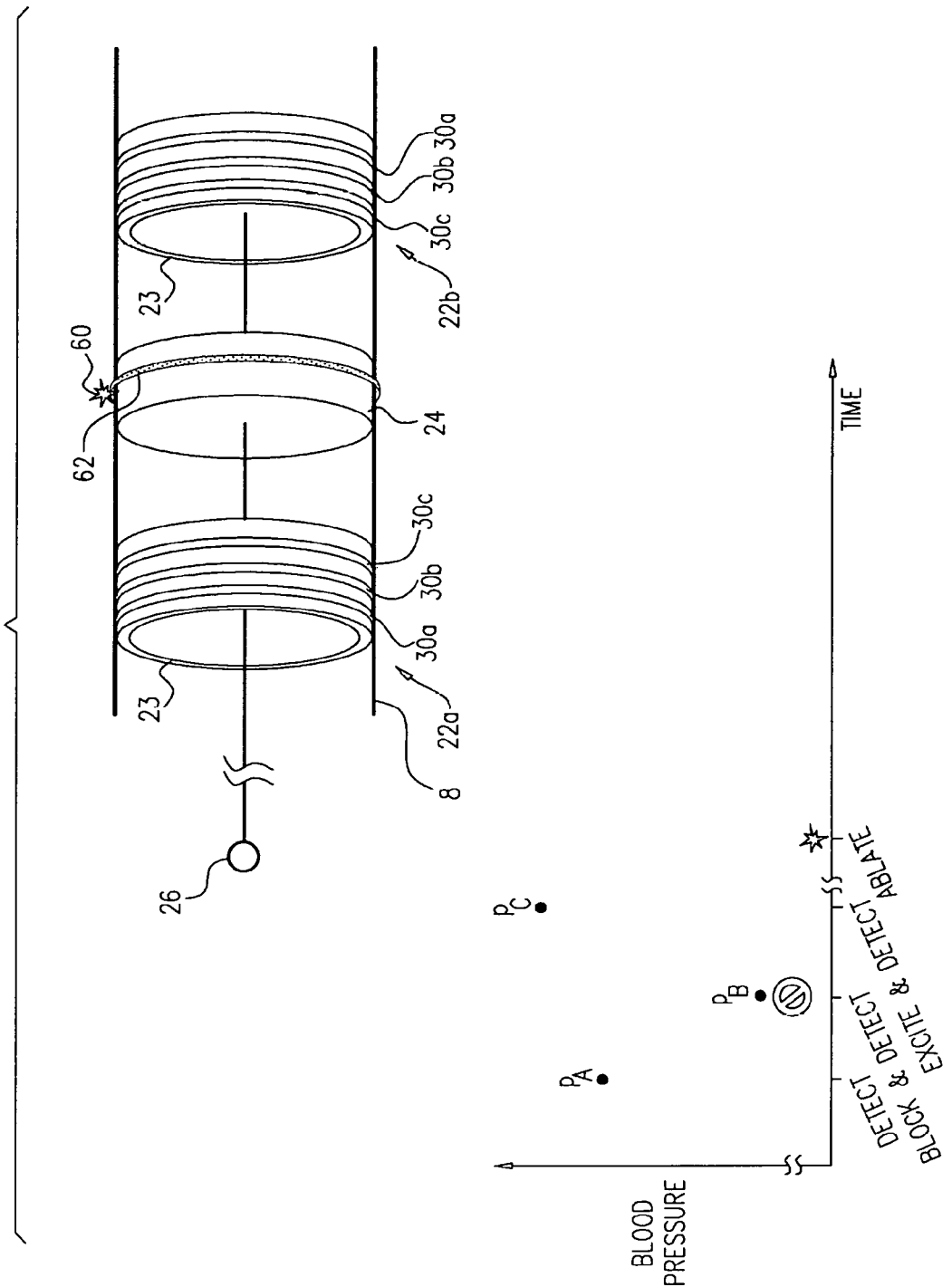

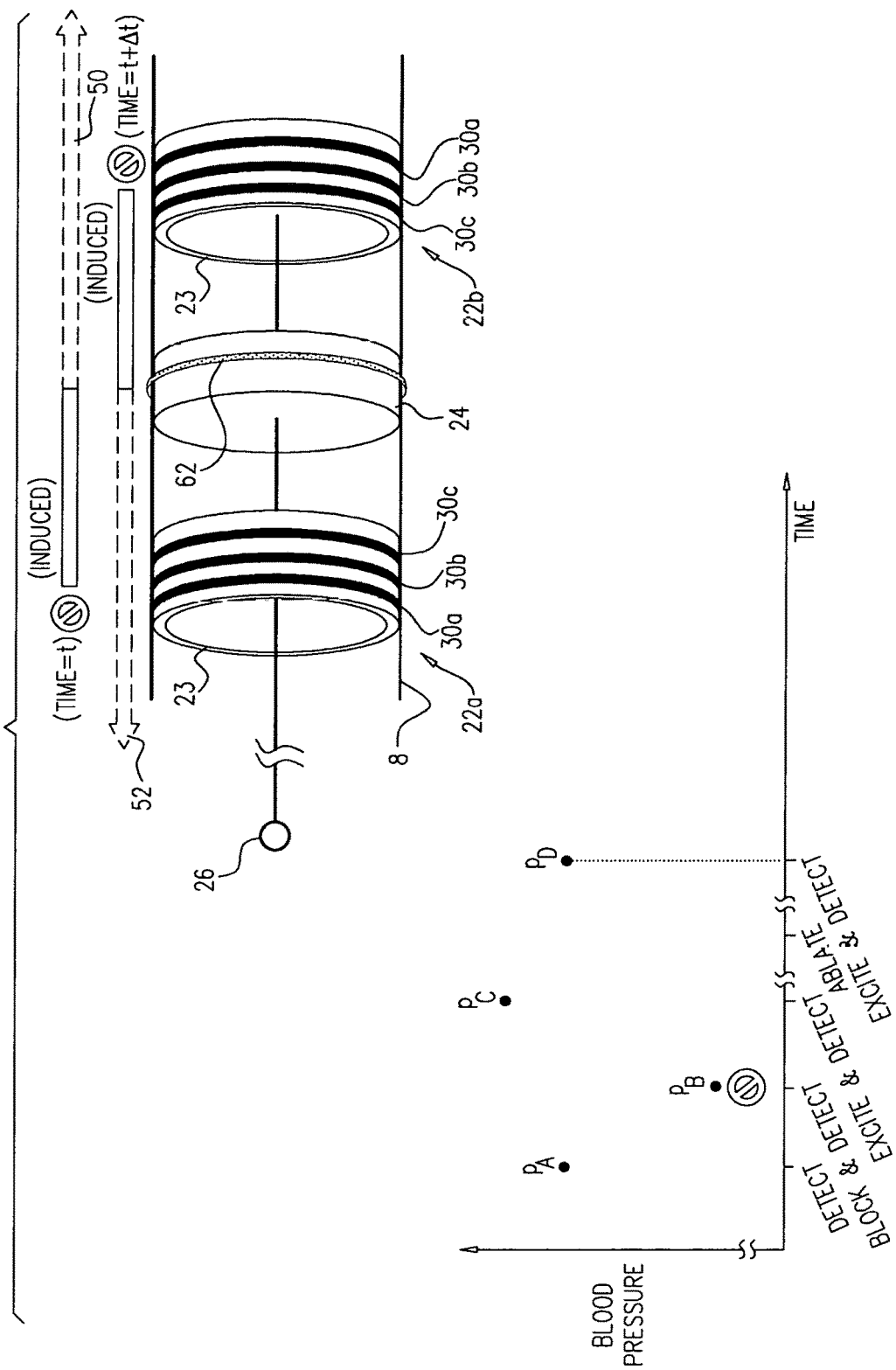

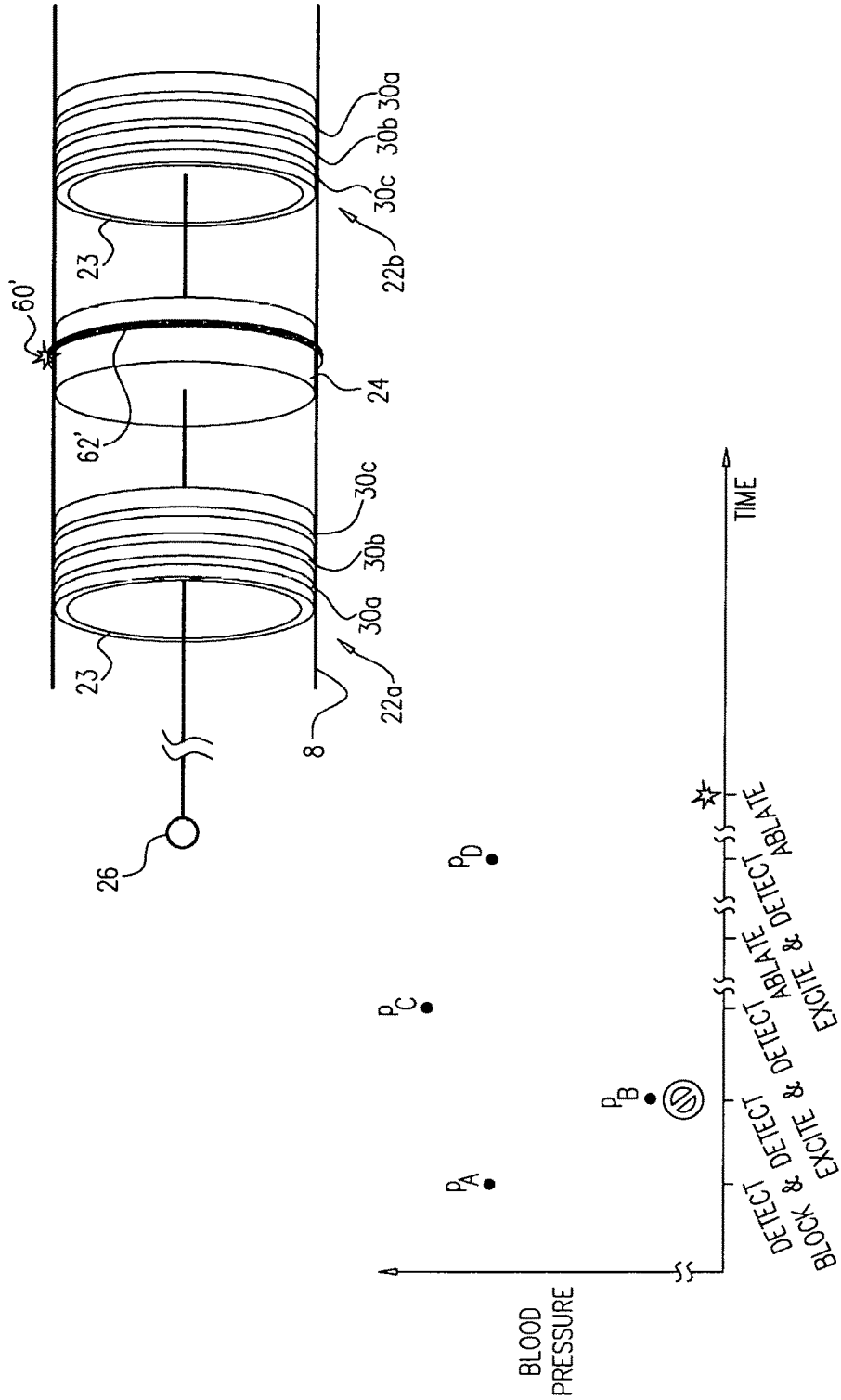

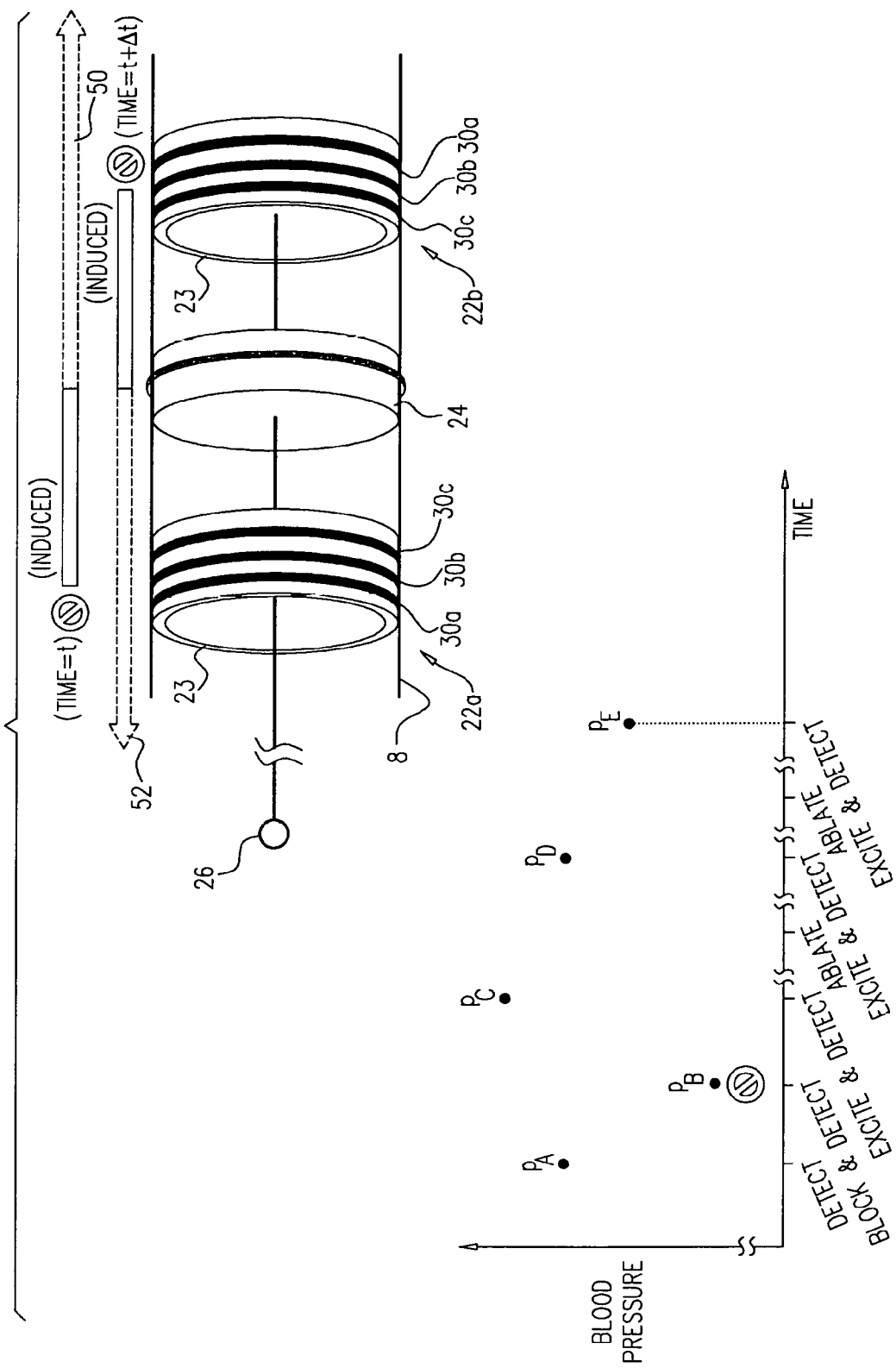

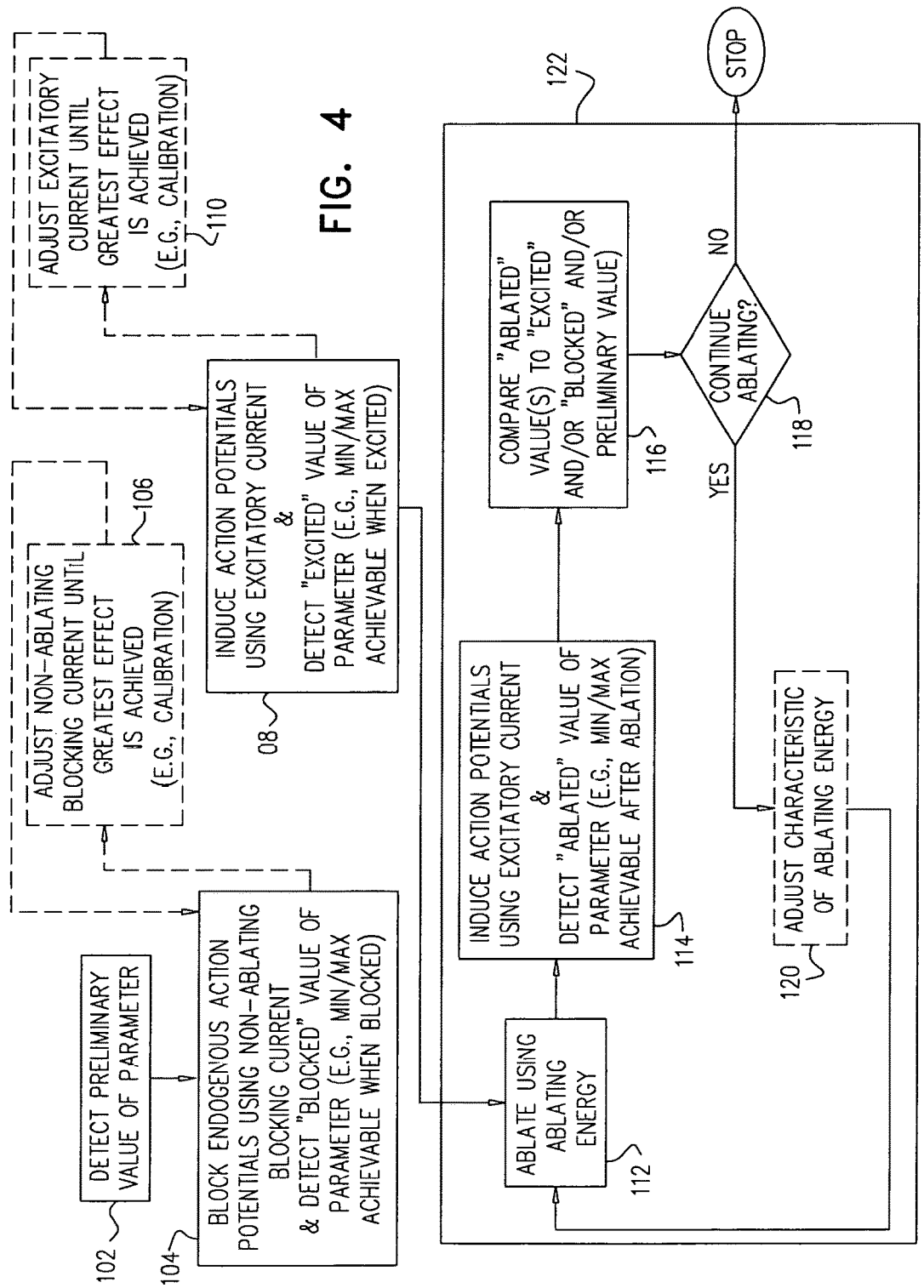

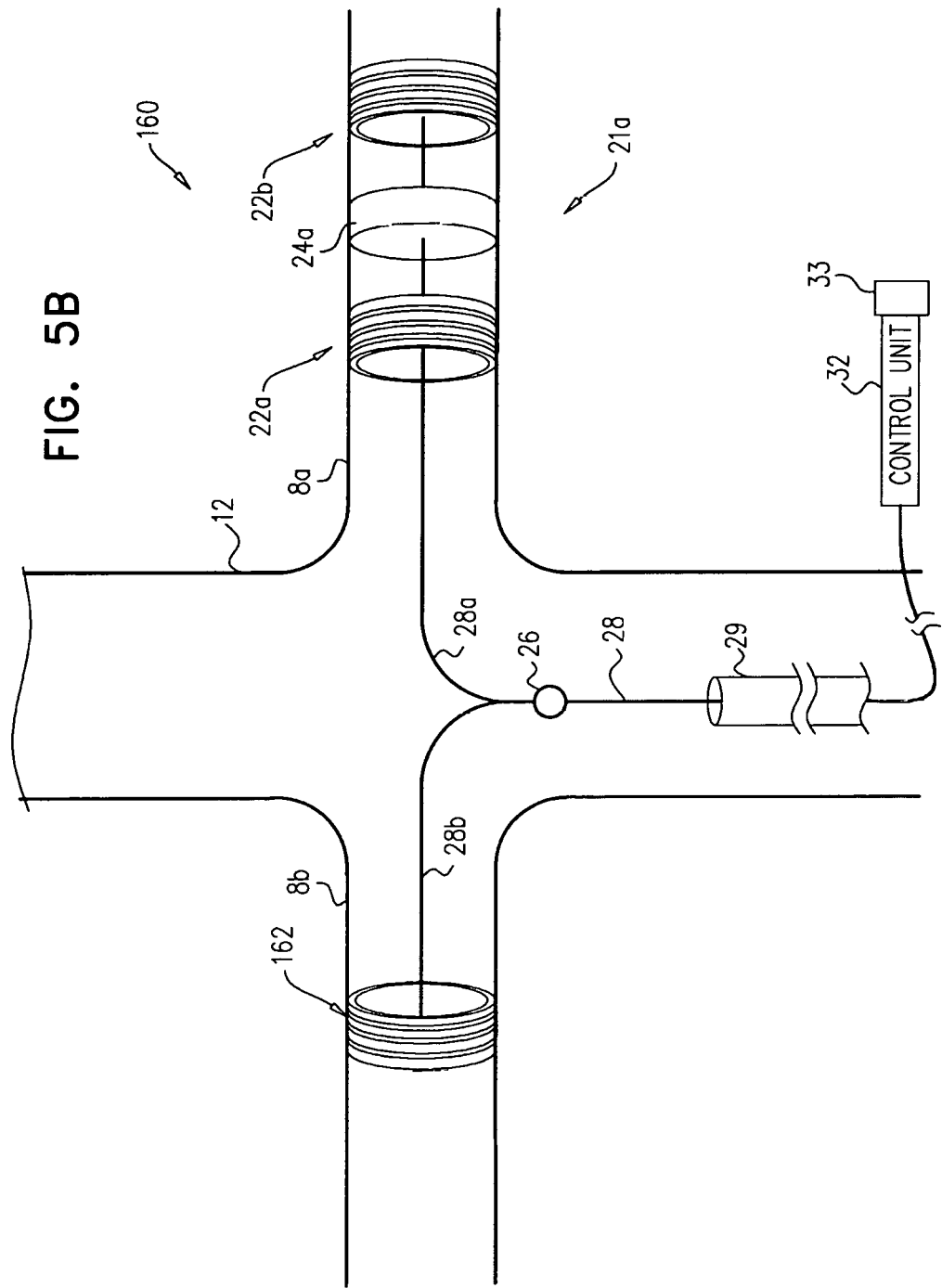

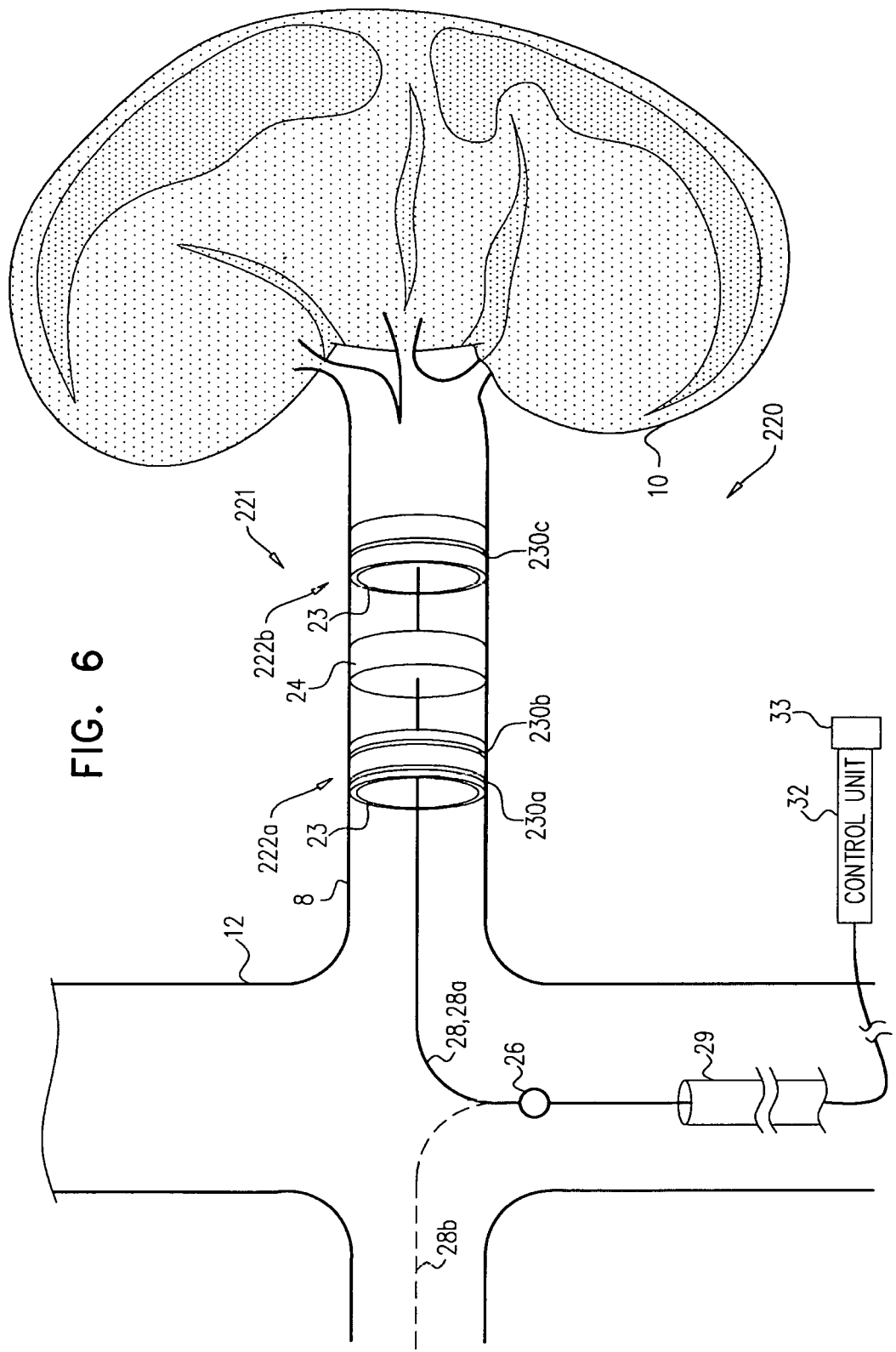

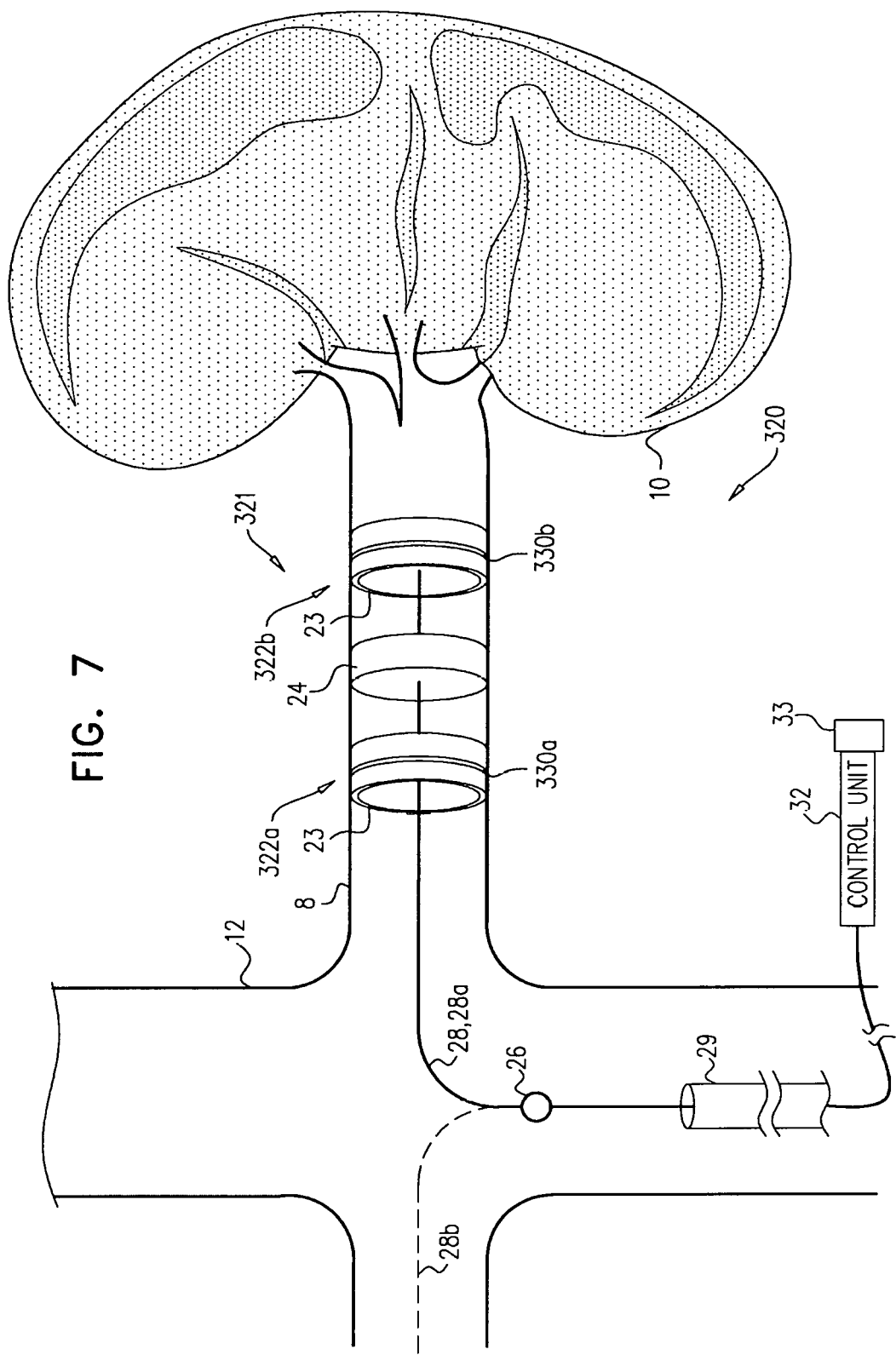

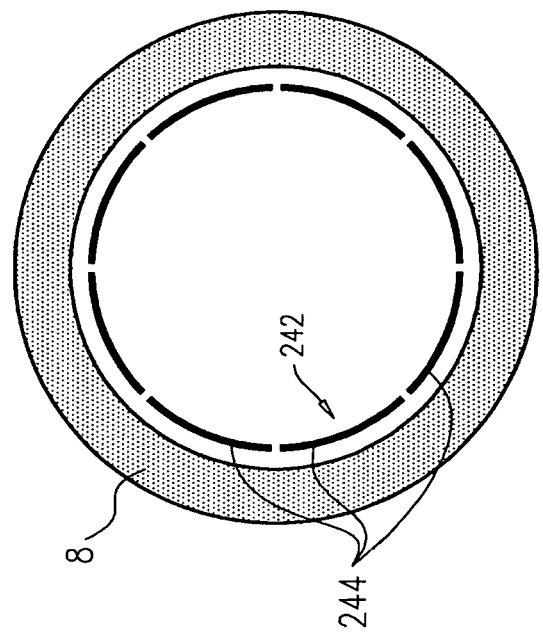
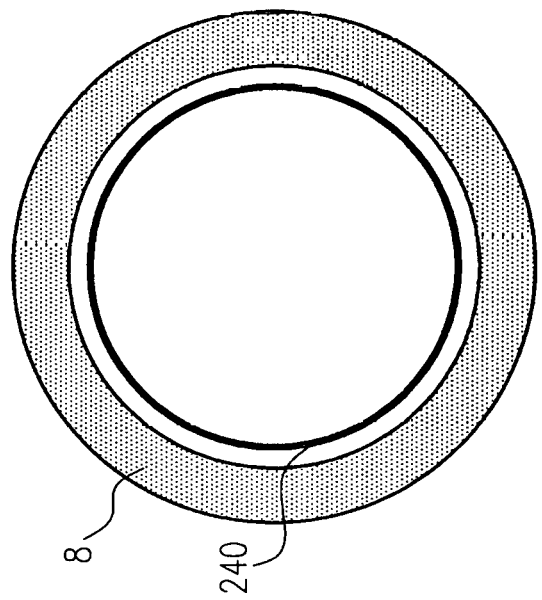

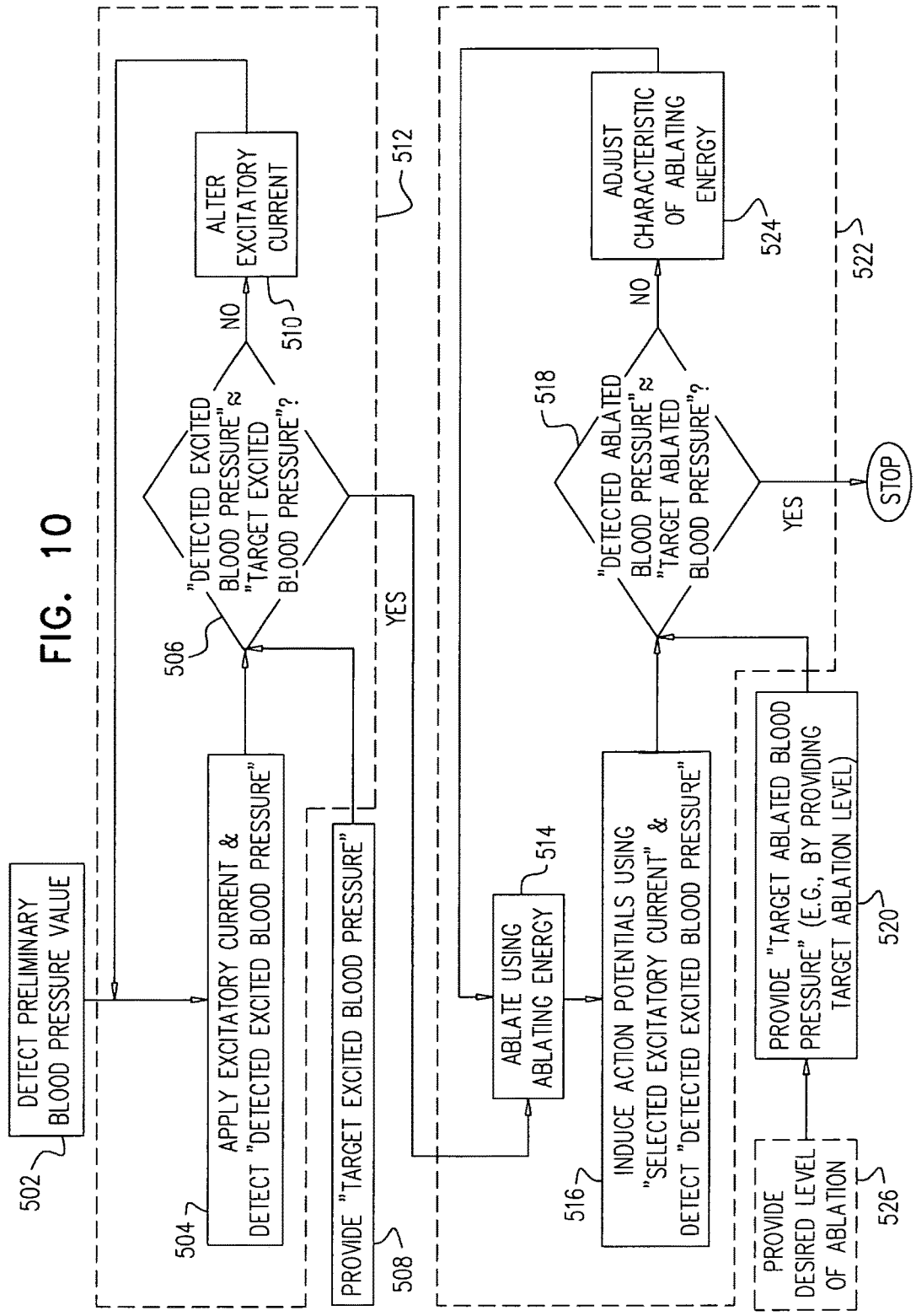

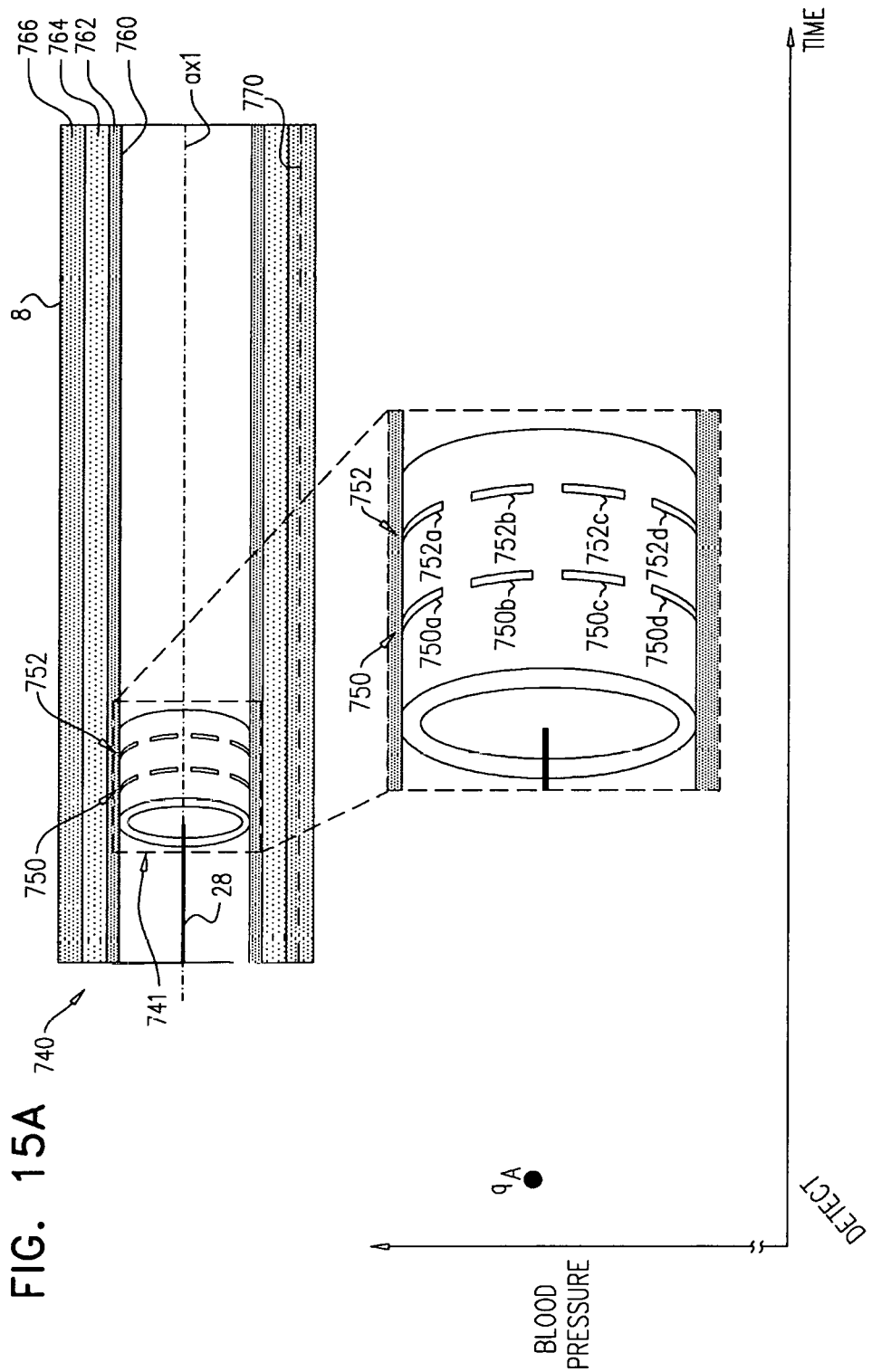

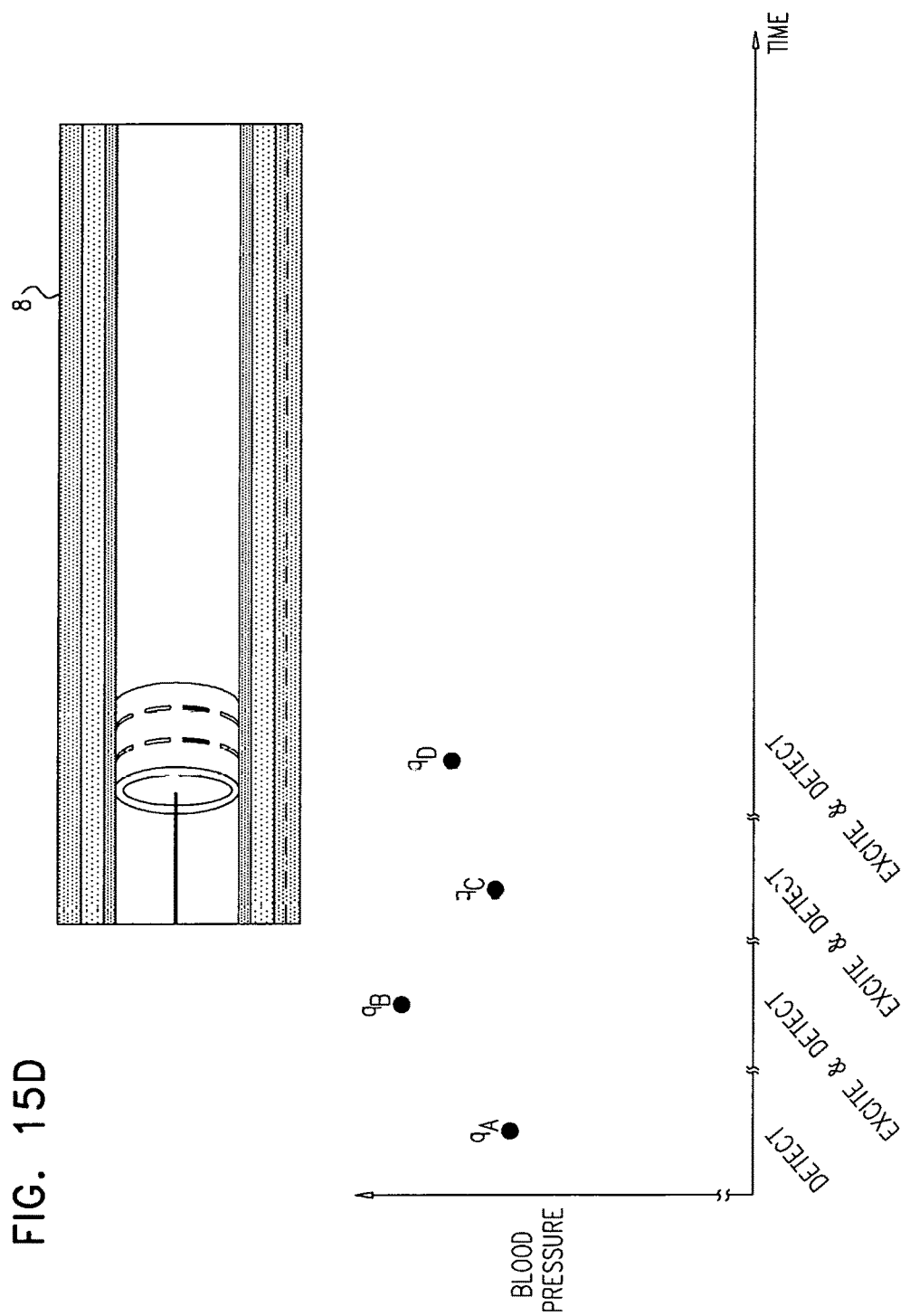

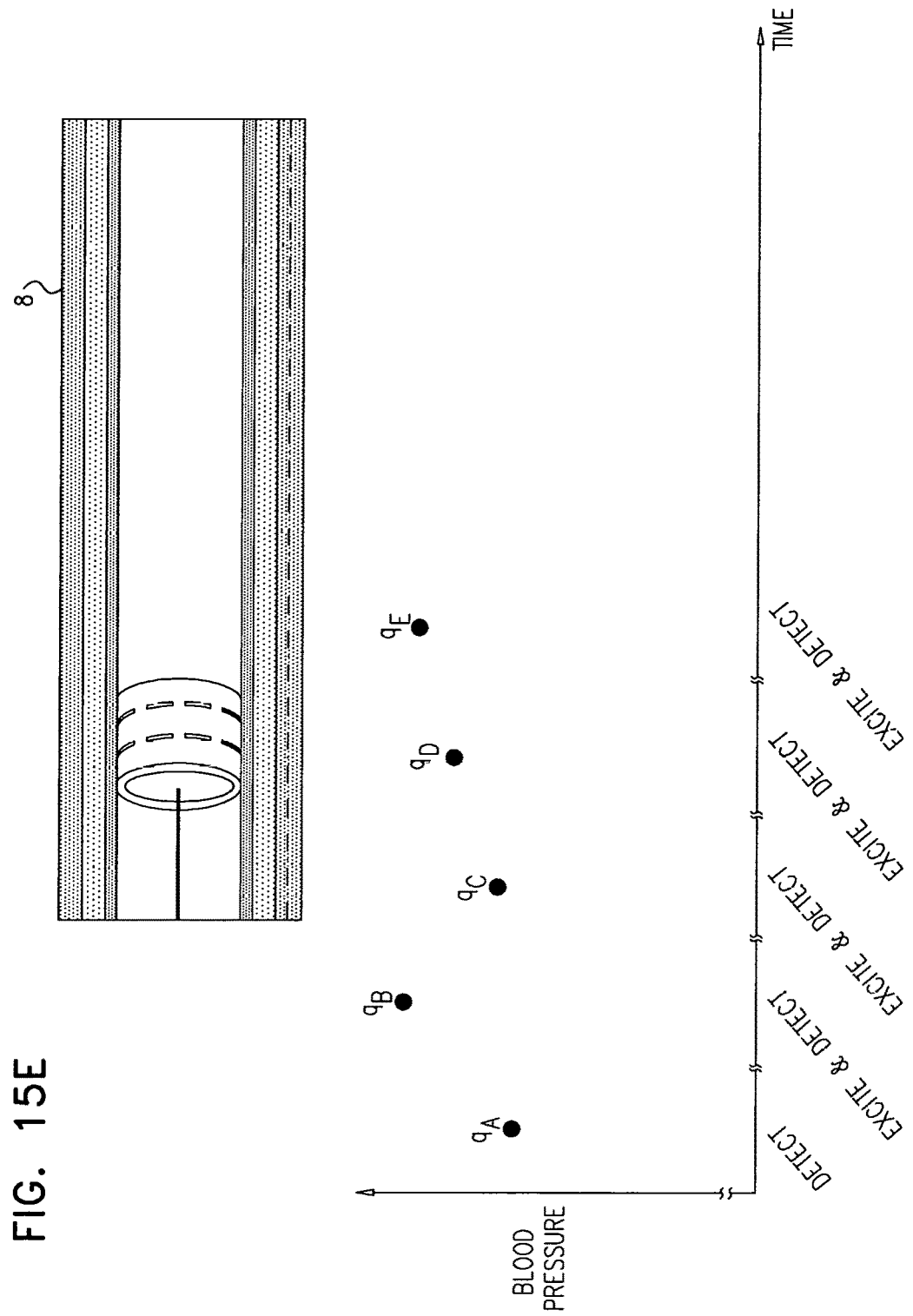

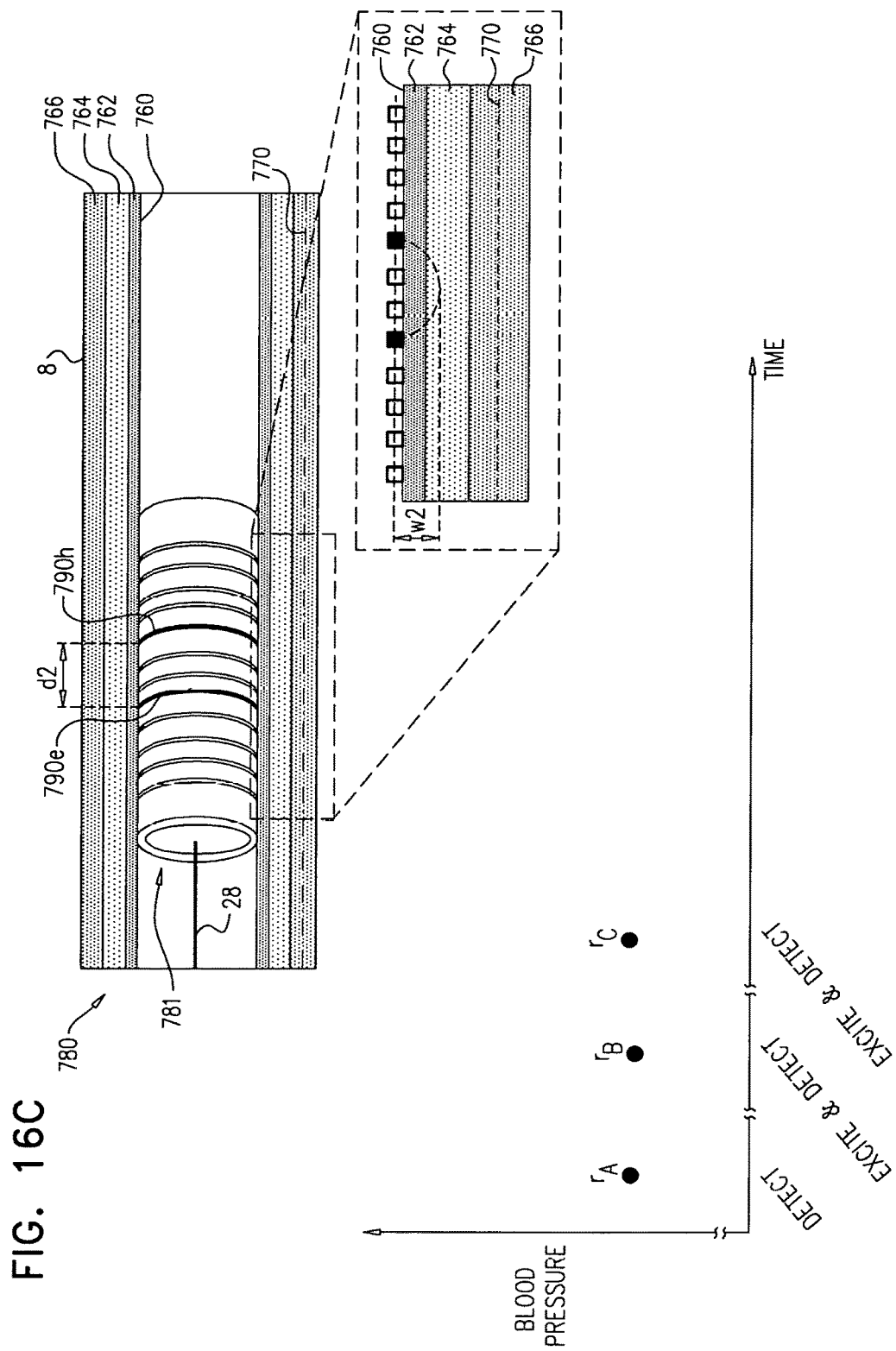

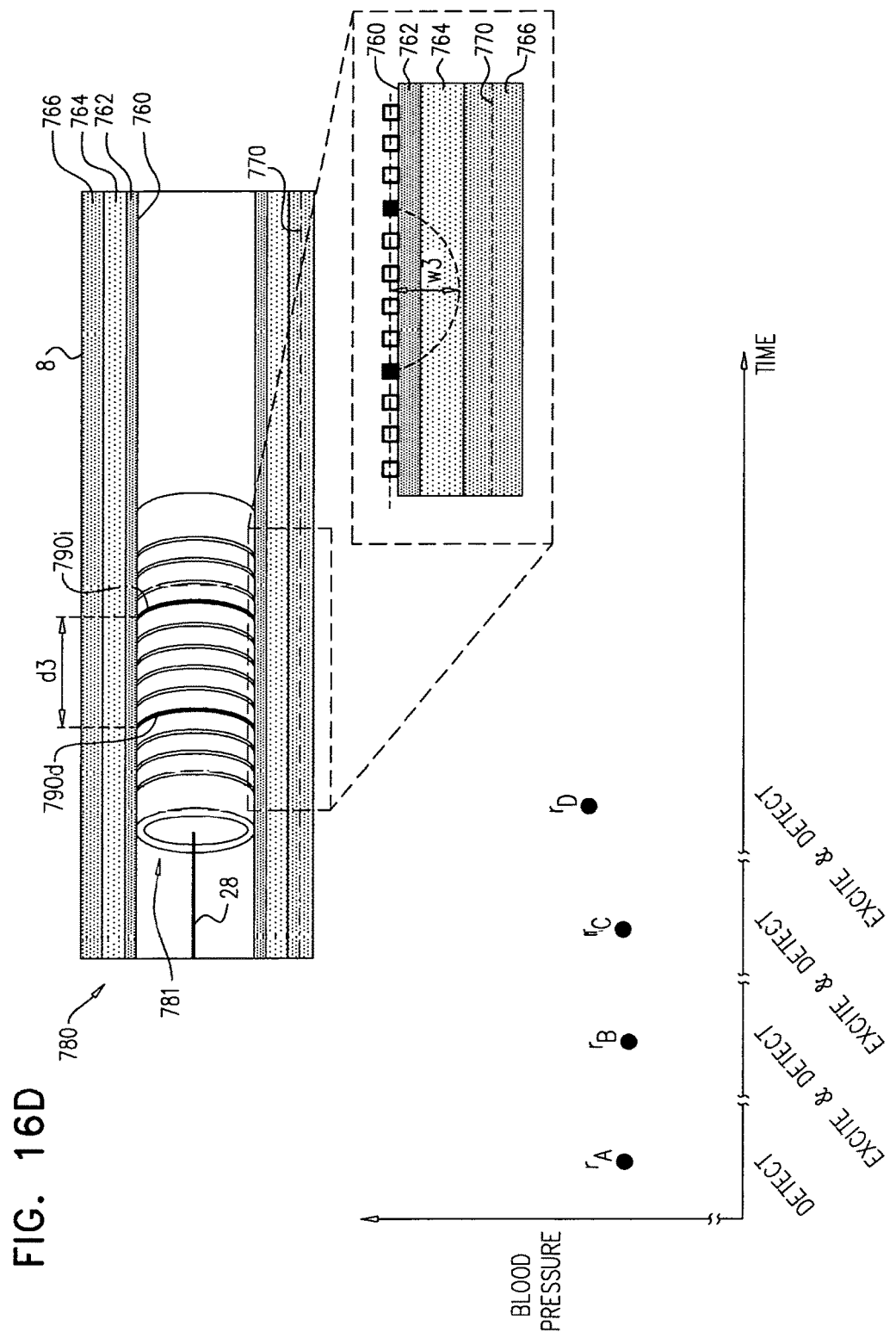

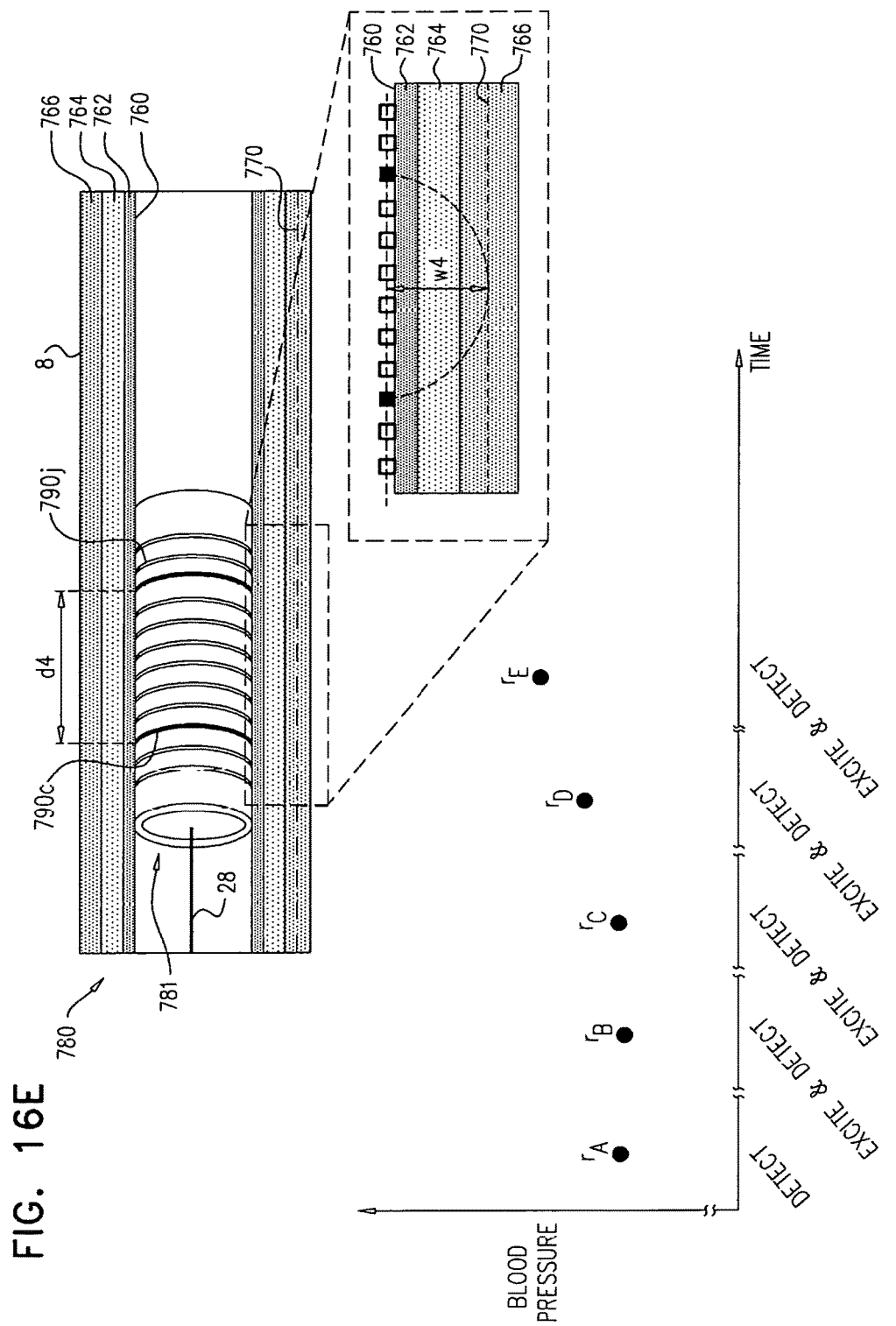

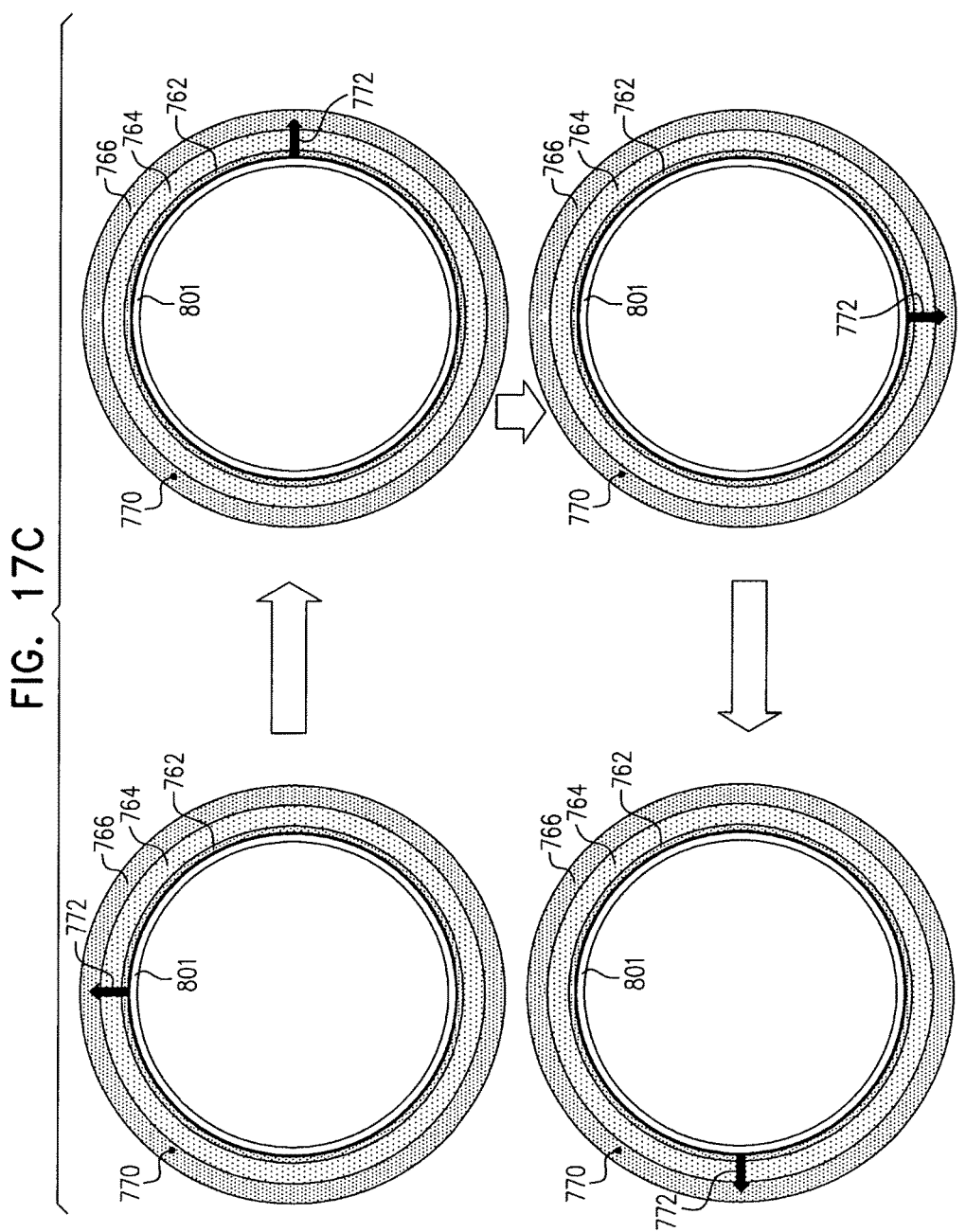

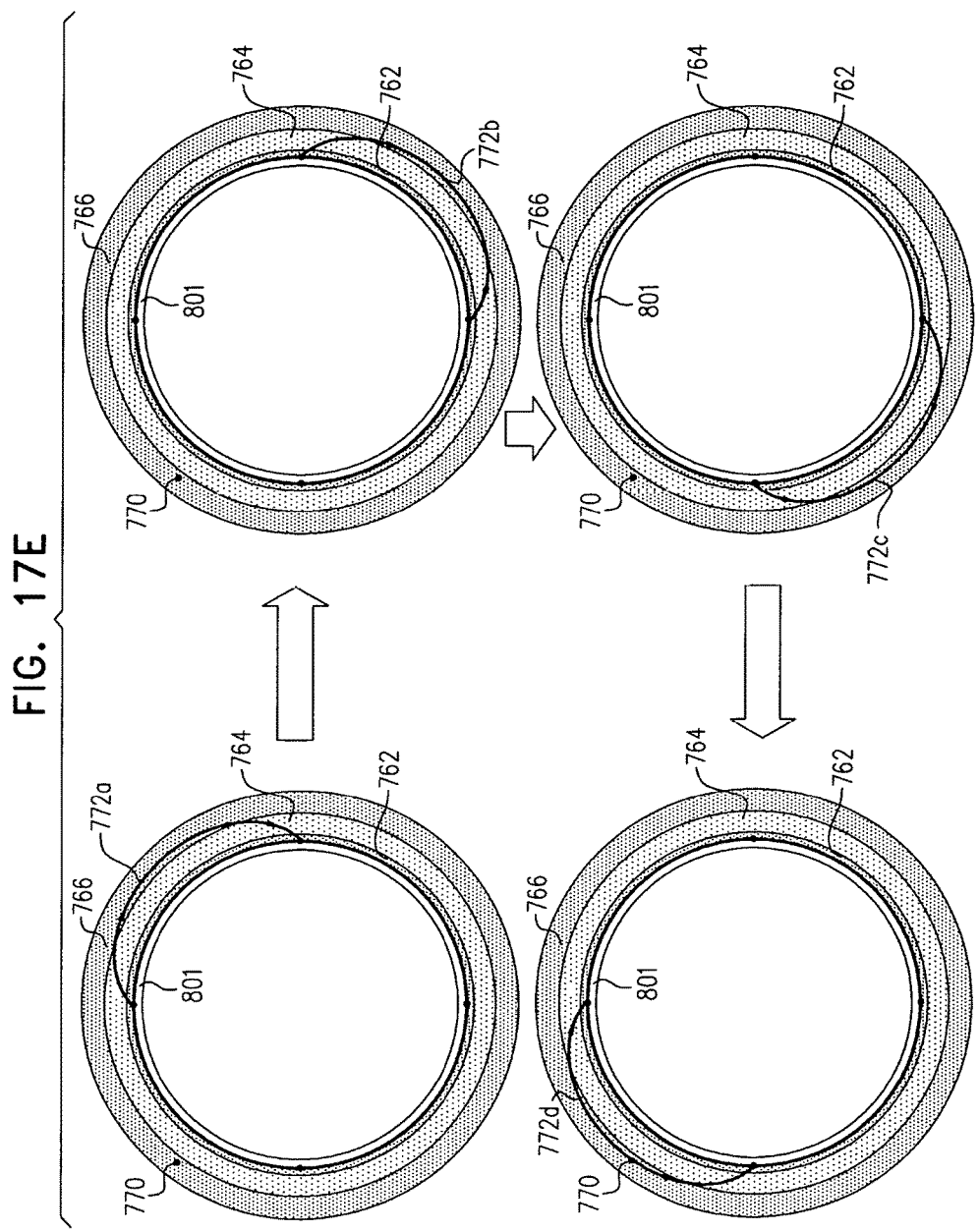

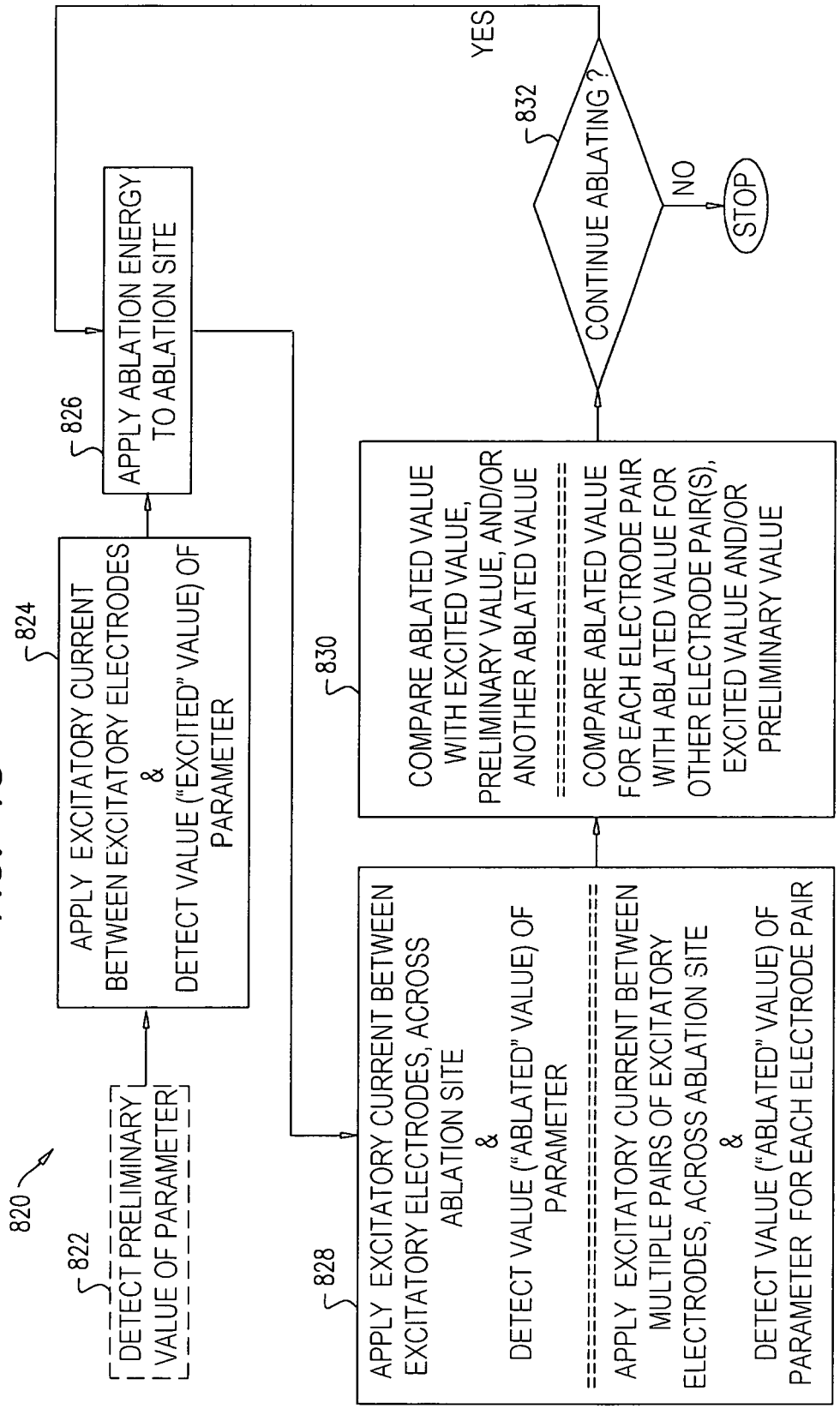

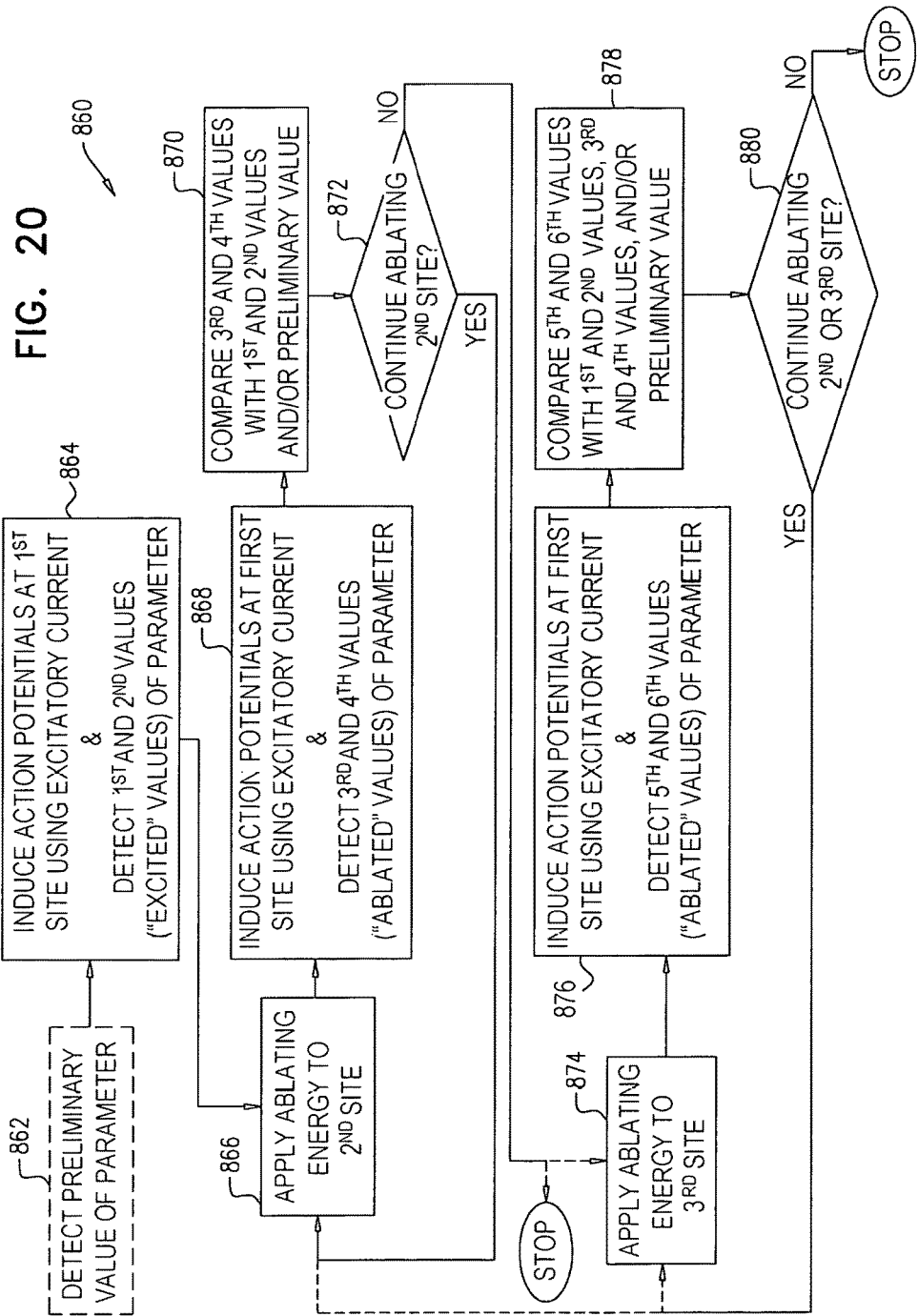

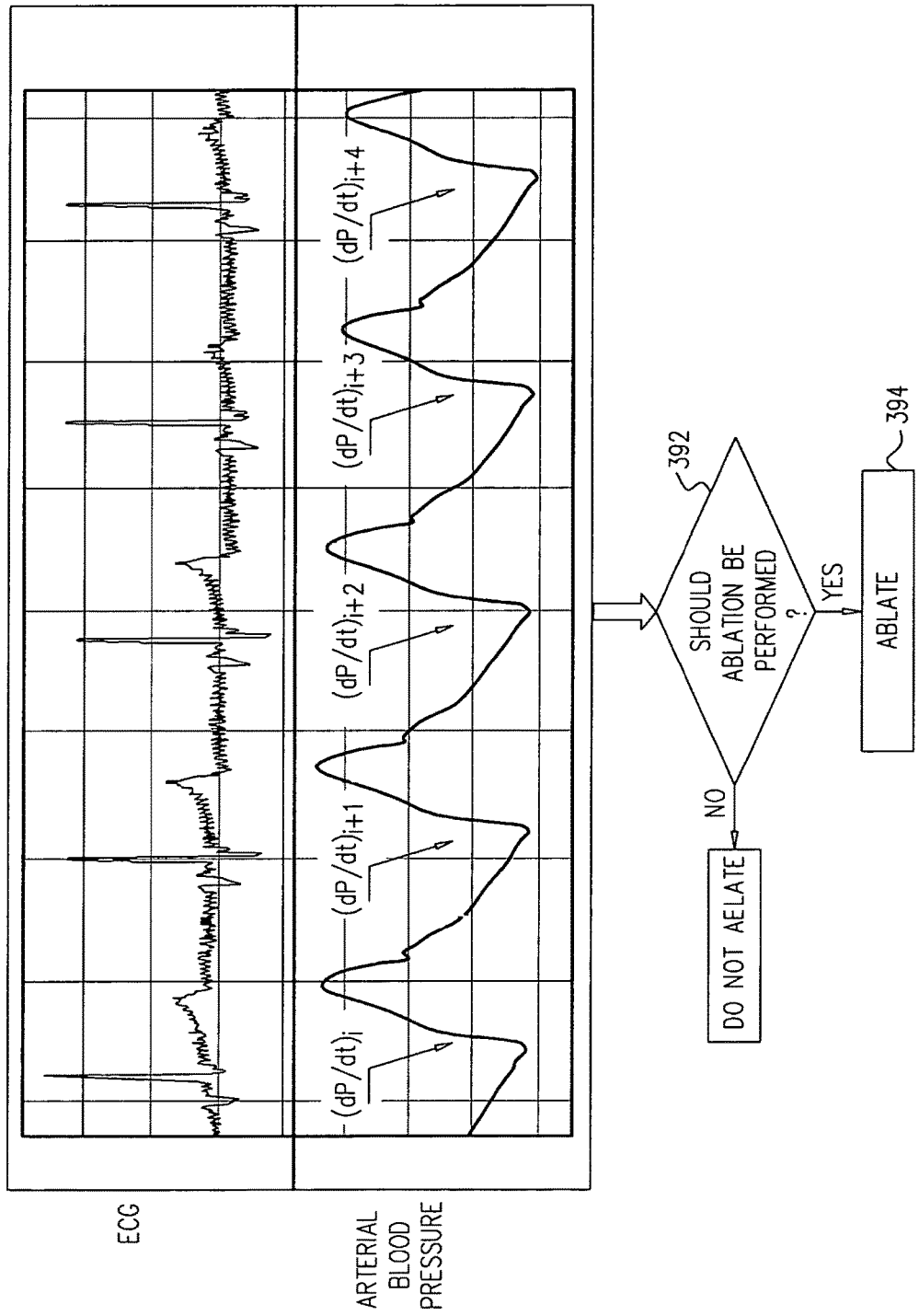

CONTROLLED TISSUE ABLATION TECHNIQUES

CROSS-REFERENCE TO RELATED APPLICATIONS

The present application is the U.S. National Phase of PCT application IB2015/053350 to Gross et. al., filed May 7, 2015, which published as WO 2015/170281, and which claims the benefit of U.S. Provisional Application 61/989,741, filed May 7, 2014, entitled "Controlled Tissue Ablation Techniques," which is assigned to the assignee of the present application and is incorporated herein by reference.

FIELD OF THE INVENTION

Applications of the present invention relate generally to ablation of tissue. Some applications of the present invention relate more specifically to ablation of tissue of the renal artery.

BACKGROUND

Hypertension is a prevalent condition in the general population, particularly in older individuals. Sympathetic nervous pathways, such as those involving the renal nerve, are known to play a role in regulating blood pressure. Ablation of renal nerve tissue from the renal artery is a known technique for treating hypertension.

SUMMARY OF THE INVENTION

Some applications of the invention comprise detecting one or more values indicative of a parameter of a subject while blocking endogenous action potentials and/or initiating induced action potentials in a nerve of the subject. Based on these one or more values, according to various applications of the invention, decisions are made by a human operator and/or automatically by a control unit. These decisions may include, inter alia: (1) Whether a subject is a suitable candidate for nerve ablation treatment, (2) which site(s) are preferable for application of ablation energy for nerve ablation treatment, (3) which inter-electrode distance is preferable for application of the ablation energy, (4) whether a previous application of ablation energy was sufficient, and/or (5) whether ablation energy should alternatively or additionally be applied to another site of the nerve.

There is further provided, in accordance with some applications of the present invention, apparatus for use with tissue of a renal nerve passing longitudinally within a wall of a renal artery of a subject, the apparatus including:
a transvascular catheter, configured to be placed within the renal artery;
one or more stimulating electrodes coupled to the catheter and configured to stimulate the tissue by passing a stimulating current through the wall of the renal artery;
a sensor configured to sense a blood pressure of the subject, following a start of the stimulation of the tissue; and
a control unit, configured to:
compute a rate of change of the sensed blood pressure of the subject,
compare the rate of change to a threshold, and
generate an output in response to the comparison.

In some applications, the control unit is configured to compute the rate of change of the sensed blood pressure by computing a rate of change of blood pressure for each of one or more heartbeats.

In some applications, the control unit is configured to compute the rate of change of blood pressure for each of the one or more heartbeats by computing a maximum rate of change of blood pressure for each of the one or more heartbeats.

In some applications, the control unit is configured to compute the rate of change of the sensed blood pressure by computing a rate of change of mean arterial pressure (MAP).

In some applications, the control unit is configured to compute the rate of change of mean arterial pressure by computing the rate of change of mean arterial pressure over a period of time that begins within ten seconds of the start of the stimulation.

In some applications, the control unit is configured to compute the rate of change of mean arterial pressure by computing the rate of change of mean arterial pressure over a period of time that ends within two minutes of the start of the stimulation.

In some applications, the control unit is configured to compute the rate of change of mean arterial pressure by computing the rate of change of mean arterial pressure up to an end of the stimulation.

In some applications,
the control unit is further configured to compute the threshold, by computing a rate of change of the sensed blood pressure of the subject following a start of a first stimulation of the tissue by the stimulating electrodes, and
the control unit is configured to:
compute the rate of change of the sensed blood pressure of the subject, following a start of a second stimulation of the tissue by the stimulating electrodes,
compare the rate of change to the threshold, and
generate the output in response to the comparison.

There is further provided, in accordance with some applications of the present invention, a method for use with tissue of a renal nerve passing longitudinally within a wall of a renal artery of a subject, the method including:
using one or more stimulating electrodes disposed within the renal artery, stimulating the tissue by passing a stimulating current through the wall of the renal artery;
using a sensor, sensing a rate of change of blood pressure of the subject, following a start of the stimulation of the tissue;
in response to the rate of change, deciding whether to ablate the tissue; and
in response to deciding to ablate the tissue, ablating the tissue.

In some applications, sensing the rate of change of blood pressure includes sensing respective rates of change of blood pressure during one or more heartbeats, and deciding whether to ablate the tissue includes deciding whether to ablate the tissue in response to the respective rates of change of blood pressure.

In some applications, sensing the respective rates of change of blood pressure during the one or more heartbeats includes sensing respective maximum rates of change of blood pressure during the one or more heartbeats, and deciding whether to ablate the tissue in response to the respective rates of change of blood pressure includes deciding whether to ablate the tissue in response to the respective maximum rates of change of blood pressure.

In some applications, sensing the rate of change of blood pressure includes sensing a rate of change of mean arterial pressure (MAP), and deciding whether to ablate the tissue includes deciding whether to ablate the tissue in response to the rate of change of MAP.

In some applications, sensing the rate of change of mean arterial pressure includes sensing the rate of change of mean arterial pressure over a period of time that begins within ten seconds of the start of the stimulation.

In some applications, sensing the rate of change of mean arterial pressure includes sensing the rate of change of mean arterial pressure over a period of time that ends within two minutes of the start of the stimulation.

In some applications, sensing the rate of change of mean arterial pressure includes sensing the rate of change of mean arterial pressure up to an end of the stimulation.

In some applications,
  stimulating the tissue includes stimulating the tissue during a second stimulation,
  the method further includes, prior to the second stimulation:
    using the one or more stimulating electrodes to stimulate the tissue by passing a stimulating current through the wall of the renal artery, during a first stimulation;
    using the sensor, sensing a rate of change of blood pressure of the subject, following a start of the first stimulation; and
    performing a first ablation of the tissue, and
  deciding whether to ablate the tissue includes deciding whether to perform a second ablation of the tissue, in response to a difference between (i) the rate of change of blood pressure of the subject following the start of the first stimulation, and (ii) the rate of change of blood pressure of the subject following the start of the second stimulation.

In some applications,
  stimulating the tissue includes stimulating the tissue by passing a stimulating current through the wall of the renal artery at each of a plurality of sites,
  sensing the rate of change of blood pressure includes sensing a rate of change of blood pressure for each of the stimulations, and
  deciding whether to ablate the tissue includes (a) deciding to ablate the tissue at at least one of the sites, and (b) deciding not to ablate the tissue at at least another one of the sites, in response to the sensed rates of change of blood pressure.

In some applications, the plurality of sites includes a plurality of longitudinal sites along the wall of the renal artery, and passing the respective stimulating currents through the wall of the renal artery at the plurality of sites includes passing the respective stimulating currents through the wall of the renal artery at the plurality of longitudinal sites.

In some applications, the plurality of sites includes a plurality of circumferential sites along the wall of the renal artery, and passing the respective stimulating currents through the wall of the renal artery at the plurality of sites includes passing the respective stimulating currents through the wall of the renal artery at the plurality of circumferential sites.

There is further provided, in accordance with some applications of the present invention, a method for determining an approximate distance of a nerve from a wall of a blood vessel of a subject, the method including:
  providing a transvascular catheter including a plurality of stimulating electrodes coupled to the catheter;
  advancing the catheter to a location within the blood vessel;
  for each pair of a plurality of pairs of the electrodes:
    driving a non-ablating current between the pair, and
    using a physiological sensor, sensing a physiological response of the subject to the non-ablating current; and
  in response to the sensing, determining the approximate distance.

In some applications, the method further includes determining an angular position of the nerve with respect to a circumference of the blood vessel, in response to the sensing.

In some applications, the method includes determining the approximate distance of a renal nerve from a wall of a renal artery of the subject.

In some applications, sensing the physiological response includes sensing a change in blood pressure of the subject.

In some applications, the method further includes:
  in response to the approximate distance, selecting an ablation modality from a plurality of distinct ablation modalities; and
  ablating the nerve, using the selected ablation modality.

In some applications, selecting the ablation modality includes selecting the ablation modality from at least two of: radiofrequency (RF) ablation, ultrasound ablation, chemical ablation, and cryoablation.

In some applications, selecting the ablation modality includes selecting the ablation modality from (a) RF ablation, and (b) an ablation modality that is not RF ablation.

In some applications, the method further includes determining whether the approximate distance is less than a threshold, and selecting the ablation modality includes:
  selecting RF ablation, if the approximate distance is less than the threshold; and
  selecting the ablation modality that is not RF ablation, if the approximate distance is not less than the threshold.

In some applications, the method further includes determining whether the approximate distance is greater than a threshold,
  the selected ablation modality is RF ablation, and
  ablating the nerve includes:
    if the approximate distance is greater than the threshold, ablating the nerve using unipolar RF ablation, and
    if the approximate distance is not greater than the threshold, ablating the nerve using bipolar RF ablation.

In some applications, the method further includes:
  in response to the approximate distance, setting a power of an ablation signal; and
  ablating the nerve, by passing the ablation signal through the nerve.

In some applications, the method further includes:
  in response to the approximate distance, identifying a pair of ablating electrodes; and
  ablating the nerve, by driving an ablating current between the pair of ablating electrodes.

In some applications, each electrode of the pair of the ablating electrodes is also one of the stimulating electrodes.

There is further provided, in accordance with some applications of the present invention, a method for determining an approximate distance of a nerve from a wall of a blood vessel of a subject, the method including:
  providing a transvascular catheter including one or more stimulating electrodes coupled to the catheter;
  advancing the catheter to a location within the blood vessel;
  using at least one of the electrodes, driving a plurality of non-ablating currents into the wall of the blood vessel, the non-ablating currents having respective amplitudes that are different from each other;
  using a physiological sensor, sensing a physiological response of the subject to each of the non-ablating currents; and in response to the sensing, determining the approximate distance.

There is further provided, in accordance with some applications of the present invention, a method for use with a nerve passing longitudinally within a wall of a blood vessel of a subject, the method including:

providing a transvascular catheter including a plurality of stimulating electrodes coupled to the catheter;

advancing the catheter to a location within the blood vessel;

for each pair of a plurality of pairs of the electrodes:
driving a non-ablating current between the pair, and
using a physiological sensor, sensing a physiological response of the subject to the non-ablating current;

in response to the sensing, selecting an ablation modality from a plurality of distinct ablation modalities; and ablating the nerve, using the selected ablation modality.

There is further provided, in accordance with some applications of the present invention, a method for use with a nerve passing longitudinally within a wall of a blood vessel of a subject, the method including:

providing a transvascular catheter including a plurality of stimulating electrodes coupled to the catheter;

advancing the catheter to a location within the blood vessel;

for each pair of a plurality of pairs of the electrodes:
driving a non-ablating current between the pair, and
using a physiological sensor, sensing a physiological response of the subject to the non-ablating current;

in response to the sensing, setting a power of an ablation signal; and ablating the nerve, by passing the ablation signal through the nerve.

There is further provided, in accordance with some applications of the present invention, a method for use with a nerve passing longitudinally within a wall of a blood vessel of a subject, the method including:

providing a transvascular catheter including a plurality of stimulating electrodes coupled to the catheter;

advancing the catheter to a location within the blood vessel;

for each pair of a plurality of pairs of the electrodes:
driving a non-ablating current between the pair, and
using a physiological sensor, sensing a physiological response of the subject to the non-ablating current;

in response to the sensing, identifying a pair of ablating electrodes; and ablating the nerve, by driving an ablating current between the pair of ablating electrodes.

There is further provided, in accordance with some applications of the present invention, a method for locating and ablating a nerve passing longitudinally within a wall of a blood vessel of a subject, the method including:

providing a transvascular catheter including a plurality of stimulating electrodes coupled to the catheter;

moving the catheter to one or more locations within the blood vessel;

at each of the one or more locations:
using the stimulating electrodes to drive one or more first-precision-locating stimulating electric currents into the wall of the blood vessel, and
using a physiological sensor, sensing a physiological response of the subject to the first-precision-locating stimulating electric currents;

in response to the respective physiological responses, locating the nerve to a first degree of precision;

in response to locating the nerve to the first degree of precision, using the stimulating electrodes to drive one or more sets of one or more second-precision-locating stimulating electric currents into the wall of the blood vessel;

using the physiological sensor, sensing a physiological response of the subject to each of the sets of second-precision-locating stimulating electric currents;

in response to the physiological response of the subject to each of the sets of second-precision-locating stimulating electric currents, locating the nerve to second degree of precision that is greater than the first degree of precision; and in response to locating the nerve to the second degree of precision, ablating the nerve.

In some applications, the method includes:
moving the catheter to a first location within the blood vessel;

using the stimulating electrodes to drive one or more first-precision-locating stimulating electric currents into the wall of the blood vessel at the first location;

in response to sensing the physiological response of the subject to the first-precision-locating stimulating electric currents at the first location, moving the catheter to a second location within the blood vessel;

using the stimulating electrodes to drive one or more first-precision-locating stimulating electric currents into the wall of the blood vessel at the second location; and in response to sensing the physiological response of the subject to the first-precision-locating stimulating electric currents at the second location, locating the nerve to the first degree of precision, by identifying that the nerve is more likely to be located at the second location than at the first location.

In some applications, driving the first-precision-locating stimulating electric currents into the wall of the blood vessel includes driving each of the first-precision-locating stimulating electric currents between (a) a first one of the stimulating electrodes, and (b) a second one of the stimulating electrodes that is longitudinally separated from the first one of the stimulating electrodes.

In some applications,
driving the first-precision-locating stimulating electric currents into the wall of the blood vessel includes driving a plurality of first-precision-locating stimulating electric currents into the wall at a plurality of positions along a circumference of the wall, such that the first-precision-locating stimulating electric currents span a first range of the circumference of the wall, and driving the one or more sets of second-precision-locating stimulating electric currents into the wall of the blood vessel includes driving each of the sets of second-precision-locating stimulating electric currents into the wall of the blood vessel such that each of the sets spans a second range of the circumference that is smaller than the first range.

In some applications, driving the one or more sets of second-precision-locating stimulating electric currents into the wall of the blood vessel includes driving at least one second-precision-locating stimulating electric current between (a) one of the plurality of stimulating electrodes, and (b) an electrode that is disposed outside a body of the subject.

In some applications, driving the one or more sets of second-precision-locating stimulating electric currents into the wall of the blood vessel includes:

driving a first one of the sets into the wall of the blood vessel at a first location; and driving a second one of the sets into the wall of the blood vessel at a second location that is longitudinally separated from the first location.

In some applications, driving the first one of the sets into the wall of the blood vessel at the first location includes driving at least one second-precision-locating stimulating electric current between two of the plurality of stimulating electrodes that are separated circumferentially from one another along the catheter, and driving the second one of the sets into the wall of the blood vessel at the second location includes driving at least one second-precision-locating stimulating electric current between another two of the plurality of stimulating electrodes that are separated circumferentially from one another along the catheter.

There is further provided, in accordance with some applications of the present invention, a method for use with a renal nerve of a subject, the nerve innervating an ipsilateral kidney of the subject, the method including:

initiating action potentials at a first site of the nerve by applying a first application of excitatory current to the nerve;

within 60 seconds after a start of the first application, measuring a first blood pressure value of the subject;

after at least 60 seconds from the start of the first application, measuring a second blood pressure value of the subject;

subsequently to applying the first application of excitatory current, applying a first application of ablation energy to a second site of the nerve, a distance between the second site and the ipsilateral kidney being greater than a distance between the first site and the ipsilateral kidney;

subsequently to applying the first application of ablation energy, initiating action potentials at the first site by applying a second application of excitatory current to the nerve;

within 60 seconds after a start of the second application of excitatory current, measuring a third blood pressure value of the subject;

after at least 60 seconds from the start of the second application of excitatory current, measuring a fourth blood pressure value of the subject; and at least in part dependently on a relationship between (1) a difference between the first and second blood pressure values, and (2) a difference between the third and fourth blood pressure values, applying a second application of ablation energy to the nerve.

There is further provided, in accordance with an application of the present invention, an inventive concept including:

1. Apparatus for use with a renal nerve of a renal artery of a subject, the renal nerve innervating an ipsilateral kidney of the subject, the apparatus comprising:

a transvascular catheter, having a distal portion that is configured to be transluminally advanced to the renal artery and comprises:

an electrode unit, configured to apply an excitatory current to a rust portion of the renal nerve;

an ablation unit, disposed proximally from the electrode unit, and configured to apply ablation energy to a second portion of the renal nerve that is further from the kidney than is the first portion of the renal nerve; and a control unit, configured:

to receive a preliminary blood pressure value of the subject, to receive a target excited blood pressure value, to iteratively:

(a) drive the electrode unit to apply an excitatory current to the first portion of the renal nerve, (b) receive a detected excited blood pressure value, indicative of a blood pressure of the subject after a start of the application of the excitatory current, and (c) alter a value of at least one property of the excitatory current, until the detected excited blood pressure value crosses a first threshold defined at least in part based on the target excited blood pressure value, and subsequently, to iteratively:

(d) drive the ablation unit to apply ablating energy to the second portion of the renal nerve, (e) subsequently, drive the electrode unit to apply, to the first portion of the renal nerve, a selected excitatory current a characteristic of which is at least part based on the value of the at least one property at which the detected excited blood pressure value crossed the first threshold, and (f) receive a detected ablated blood pressure value, indicative of a blood pressure of the subject after a start of the application of the selected excitatory current, until the detected ablated blood pressure value crosses a second threshold defined at least in part based on a target ablated blood pressure value that is generated at least in part based on the preliminary blood pressure value and at least in part based on at least one excited blood pressure value selected from the group consisting of (i) the target excited blood pressure value and (ii) the detected excited blood pressure value.

2. The apparatus according to inventive concept 1, wherein the ablation unit comprises a radio-frequency ablation unit, and is configured to apply the ablating energy by applying a radio-frequency current having a frequency of between 5 kHz and 1 GHz.

3. The apparatus according to inventive concept 1, wherein the control unit is configured such that, after the first iteration of steps d, e and f, the control unit drives the ablation unit to apply the ablating energy by driving the ablation unit to apply ablating energy that is different in at least one characteristic thereof compared to the ablating energy applied in the previous iteration of steps d, e and f.

4. The apparatus according to inventive concept 1, wherein the control unit is configured to generate the target excited blood pressure value at least in part responsively to the preliminary blood pressure value.

5. The apparatus according to inventive concept 1, wherein the control unit comprises a user interface, and is configured to receive the target excited blood pressure value via the user interface.

6. The apparatus according to any one of inventive concepts 1-5, wherein the electrode unit comprises a plurality of sub-electrodes configured to be arranged in a broken arc that traces an inner wall of the renal artery.

7. The apparatus according to inventive concept 6, wherein the control unit is configured to drive the plurality of sub-electrodes to simultaneously apply the excitatory current.

8. The apparatus according to inventive concept 7, wherein each of the plurality of sub-electrodes is independently addressable by the control unit.

9. The apparatus according to inventive concept 7, wherein the control unit is configured to balance the excitatory current across the plurality of sub-electrodes.

10. The apparatus according to any one of inventive concepts 1-5, wherein:

the renal nerve of the renal artery includes a renal nerve of a first renal artery of the subject, the distal portion of the transvascular catheter comprises a first distal portion of the transvascular catheter, configured to be transluminally advanced to the first renal artery, and the transvascular catheter is bifurcated so as to have the first distal portion and a second distal portion, the second distal portion being configured to be transluminally advanced to the second renal artery.

11. The apparatus according to inventive concept 10, wherein the second distal portion is separate from but identical to the first distal portion.

12. The apparatus according to any one of inventive concepts 1-5, further comprising a pressure sensor, wherein the control unit is configured to receive the preliminary blood pressure value, the detected excited blood pressure value, and the detected ablated blood pressure value, from the pressure sensor.

13. The apparatus according to inventive concept 12, wherein the transvascular catheter comprises the pressure sensor, and the pressure sensor is disposed proximally from the distal portion.

14. The apparatus according to inventive concept 13, wherein the pressure sensor is disposed with respect to the distal portion such that when the distal portion is disposed in the renal artery of the subject, the pressure sensor is disposed in the aorta of the subject.

15. The apparatus according to inventive concept 13, wherein the pressure sensor is disposed more than 2 cm proximally from the distal portion.

16. The apparatus according to any one of inventive concepts 1-5, wherein the control unit is configured to generate the target ablated blood pressure value at least in part responsively to (1) the preliminary blood pressure value and (2) at least one excited blood pressure value selected from the group consisting of: (i) the target excited blood pressure value and (ii) the detected excited blood pressure value.

17. The apparatus according to inventive concept 16, wherein the control unit is configured to generate the target excited blood pressure value at least in part responsively to a value indicative of a target degree of ablation of the renal nerve.

18. The apparatus according to inventive concept 17, wherein the control unit comprises an interface, and is configured to receive the value indicative of the target degree of ablation via the interface.

There is further provided, in accordance with an application of the present invention, an inventive concept including:

19. Apparatus for facilitating ablation of nerve tissue of a blood vessel of a subject, the apparatus comprising:
a transvascular catheter comprising:
an electrode unit, disposed at a distal portion of the transvascular catheter;
an ablation unit, disposed proximally from the electrode unit; and
a blood pressure sensor, disposed proximally from the ablation unit; and a control unit, configured:
to drive the electrode unit to apply a non-ablative electrical current to a first portion of the nerve tissue,
to drive the ablation unit to apply ablative energy to a second portion of the nerve tissue, and
to receive, from the blood pressure sensor, at least one value indicative of a blood pressure of the subject.

20. The apparatus according to inventive concept 19, wherein the ablation unit comprises a radio-frequency ablation unit, and the control unit is configured to drive the ablation unit to apply the ablative energy by driving the ablation unit to apply a radio-frequency current having a frequency of between 5 kHz and 1 GHz.

21. The apparatus according to inventive concept 19, wherein:
the distal portion of the transvascular catheter comprises a first distal portion of the transvascular catheter.
the electrode unit comprises a first electrode unit,
the ablation unit comprises a second electrode unit,
the transvascular catheter is bifurcated so as to have the first distal portion and a second distal portion, and
the transvascular catheter further comprises:
a second electrode unit, disposed at the second distal portion of the catheter, and
a second ablation unit, disposed proximally from the second electrode unit.

22. The apparatus according to inventive concept 19, wherein the control unit is configured to apply the ablative energy in response to at least the at least one value.

23. The apparatus according to inventive concept 19, wherein the distal portion of the transvascular catheter is configured to be advanced into the blood vessel of the subject, and the transvascular catheter is configured such that, when the electrode unit is disposed within the blood vessel of the subject, the blood pressure sensor is disposed in another blood vessel of the subject.

24. The apparatus according to inventive concept 19, wherein the blood pressure sensor is disposed more than 2 cm proximally from the ablation unit.

25. The apparatus according to any one of inventive concepts 19-24, wherein the electrode unit comprises a plurality of sub-electrodes configured to be arranged in a broken arc that traces an inner wall of the blood vessel.

26. The apparatus according to inventive concept 25, wherein the control unit is configured to drive the plurality of sub-electrodes to simultaneously apply the non-ablative electrical current.

27. The apparatus according to inventive concept 26, wherein each of the plurality of sub-electrodes is independently addressable by the control unit.

28. The apparatus according to inventive concept 26, wherein the control unit is configured to balance the non-ablative electrical current across the plurality of sub-electrodes.

There is further provided, in accordance with an application of the present invention, an inventive concept including:

29. Apparatus for facilitating ablation of nerve tissue of a subject, the nerve tissue conducting endogenous action potentials to an anatomical structure of the subject, the structure being capable of altering a parameter of the subject at least in part responsively to the endogenous action potentials, the apparatus comprising:
a sensor, configured to detect a factor indicative of the parameter of the subject;
an ablation unit, configured to be percutaneously advanced to a site adjacent to a first portion of the nerve tissue of the subject;
at least one electrode unit, configured to be percutaneously advanced to a site adjacent to a second portion of the nerve tissue of the subject; and
a control unit, configured to:
drive the electrode unit to initiate induced action potentials in the second portion of the nerve tissue of the subject by applying an excitatory current to the second portion of the nerve tissue, the action potentials inducing the structure to alter the parameter of the subject,
receive, from the sensor, information indicative of the factor, and at least in part responsively to the information, drive the ablation unit to apply ablative energy to the first portion of the tissue.

30. The apparatus according to inventive concept 29, wherein the ablation unit comprises a radio-frequency ablation unit, and the control unit is configured to drive the ablation unit to apply the ablative energy by driving the ablation unit to apply a radio-frequency current having a frequency of between 5 kHz and 1 GHz.

31. The apparatus according to inventive concept 29, wherein the electrode unit is configured to be positioned with respect to the ablation unit such that the induced action potentials propagate toward the first portion of the nerve of the subject.

32. The apparatus according to inventive concept 29, wherein:
the ablation unit comprises a first ablation unit, and the at least one electrode unit comprises a respective first at least one electrode unit, and
the apparatus further comprises a second ablation unit and a second respective at least one electrode unit.

33. The apparatus according to any one of inventive concepts 29-32, wherein the electrode unit comprises a plurality of sub-electrodes configured to be arranged in a broken arc.

34. The apparatus according to inventive concept 33, wherein the control unit is configured to drive the plurality of sub-electrodes to simultaneously apply the excitatory current.

35. The apparatus according to inventive concept 33, wherein each of the plurality of sub-electrodes is independently addressable by the control unit.

36. The apparatus according to inventive concept 33, wherein the control unit is configured to balance the excitatory current applied by each of the plurality of sub-electrodes.

37. The apparatus according to any one of inventive concepts 29-32, wherein the control unit is further configured to drive the electrode unit to apply a non-ablative blocking current to the second portion of the nerve.

There is further provided, in accordance with an application of the present invention, an inventive concept including:

38. Apparatus for facilitating ablation of nerve tissue of a blood vessel of a subject, the apparatus comprising an intravascular device, the intravascular device comprising:
a first electrode unit, disposed at a first longitudinal site of the intravascular device, and configured to initiate action potentials in a first portion of the nerve tissue that is adjacent to the first electrode unit;
a second electrode unit, disposed at a second longitudinal site of the intravascular device, and configured to block action potentials in a second portion of the nerve tissue that is adjacent to the second electrode unit; and
an ablation unit, disposed at a third longitudinal site of the intravascular device that is between the first longitudinal site and the second longitudinal site, the ablation unit being configured to ablate a third portion of the nerve tissue that is adjacent to the ablation unit and between the first portion of the nerve tissue and the second portion of the nerve tissue.

39. The apparatus according to inventive concept 38, wherein the first electrode unit comprises a plurality of sub-electrodes configured to be arranged in a broken arc that traces an inner wall of the blood vessel.

40. The apparatus according to any one of inventive concepts 38-39, wherein the blood vessel includes a first blood vessel, the intravascular device comprises a first intravascular device configured to be placed within the first blood vessel, and the apparatus further comprises a second intravascular device, configured to be placed within a second blood vessel of the subject.

41. The apparatus according to inventive concept 40, wherein the second intravascular device is separate from but identical to the first intravascular device.

42. The apparatus according to any one of inventive concepts 38-39, wherein the first electrode unit is configured to initiate unidirectional action potentials in the first portion of the nerve tissue, such that the unidirectional action potentials propagate toward the second portion of the nerve tissue.

43. The apparatus according to inventive concept 42, wherein the unidirectional action potentials comprise first unidirectional action potentials, and the second electrode unit is further configured to initiate second unidirectional action potentials in the second portion of the nerve tissue, such that the second unidirectional action potentials propagate toward the first portion of the nerve tissue.

There is further provided, in accordance with an application of the present invention, an inventive concept including:

44. Apparatus for facilitating ablation of nerve tissue of a blood vessel of a subject, the apparatus comprising:
an intravascular device, configured to be placed within the blood vessel, and comprising a plurality of electrodes disposed at respective longitudinal sites of the intravascular device; and
a control unit, configured to:
during at least a first period, inhibit action potentials in the nerve tissue from propagating past the intravascular device by driving at least one of the electrodes to apply a non-ablative blocking current to the nerve tissue,
during a second period, initiate action potentials in the nerve tissue by driving at least one of the electrodes to apply an excitatory current to the nerve tissue,
during a third period that is subsequent to at least one of the periods selected from the group consisting of: the first period and the second period, drive the intravascular device to apply ablative energy to a portion of the nerve tissue.

45. The apparatus according to inventive concept 44, wherein the control unit is configured to inhibit action potentials in the nerve tissue during at least part of the third period.

46. The apparatus according to any one of inventive concepts 44-45, wherein the blood vessel includes a first blood vessel, the intravascular device comprises a first intravascular device configured to be placed within the first blood vessel, and the apparatus further comprises a second intravascular device, configured to be placed within a second blood vessel of the subject.

47. The apparatus according to inventive concept 46, wherein the second intravascular device is separate from but identical to the first intravascular device.

48. The apparatus according to any one of inventive concepts 44-45, wherein the intravascular device comprises an ablation unit, and wherein the control unit is configured to drive the intravascular device to apply the ablative energy by driving the ablation unit to apply the ablative energy.

49. The apparatus according to inventive concept 48, wherein the plurality of electrodes comprises at least (1) a first electrode disposed at a first longitudinal site of the intravascular device that is on a first side of the ablation unit, and (2) a second electrode disposed at a second longitudinal site of the intravascular device that is on an opposite side of the ablation unit to the first longitudinal site.

50. The apparatus according to inventive concept 49, wherein the control unit is configured:

to drive the at least one of the electrodes to apply the blocking current during the first period by driving the first electrode to apply the blocking current to the nerve tissue, and to drive the at least one of the electrodes to apply the excitatory current during the second period by driving the second electrode to apply the excitatory current to the nerve tissue.

51. The apparatus according to inventive concept 50, wherein the plurality of electrodes comprises a third electrode, disposed at a third longitudinal site of the intravascular device that is on the first side of the ablation unit, and wherein the control unit is configured to drive the blocking current between the first electrode and the third electrode.

52. The apparatus according to inventive concept 48, wherein the intravascular device further comprises at least a first electrode unit:

comprising at least one of the electrodes of the plurality of electrodes, configured to initiate unidirectional action potentials in the nerve tissue, and oriented with respect to the ablation unit such that the unidirectional action potentials propagate toward the portion of the nerve tissue, the control unit being configured to initiate action potentials in the nerve tissue by driving the first electrode unit to initiate the unidirectional action potentials in the nerve tissue.

53. The apparatus according to inventive concept 48, wherein:

the at least first electrode unit comprises at least a second electrode unit, the first electrode unit is disposed at a first longitudinal site of the intravascular device that is on a first side of the ablation unit, the second electrode unit is disposed at a second longitudinal site of the intravascular device that is on an opposite side of the ablation unit to the first longitudinal site, and is oriented inversely to the first electrode unit.

54. The apparatus according to inventive concept 48, wherein the ablation unit comprises an electrode of the plurality of electrodes, and the control unit is configured to drive the ablation unit to apply the ablative energy by driving the electrode of the ablation unit to apply ablative radio-frequency current.

55. The apparatus according to inventive concept 48, wherein the ablation unit comprises an ultrasound transducer, and the control unit is configured to drive the ablation unit to apply the ablative energy by driving the ultrasound transducer to apply ablative ultrasound energy.

56. The apparatus according to any one of inventive concepts 44-45, wherein the control unit is configured:

to receive (1) a first value of the subject, the first value being indicative of a blood pressure of the subject after a start of the application of the blocking current, and (2) a second value of the subject, the second value being indicative of a blood pressure of the subject after a start of the application of the excitatory current, and to drive the intravascular device to apply the ablative energy at least in part responsively to a difference between the first value and the second value.

57. The apparatus according to inventive concept 56, wherein:

the application of the excitatory current comprises a first application of the excitatory current, the application of ablative energy comprises a first application of ablative energy, and the control unit is configured:

during a fourth period that is subsequent to the third period, to initiate action potentials in the nerve tissue by driving at least one of the electrodes to apply a second application of the excitatory current to the nerve tissue, to receive a third value of the subject, the third value being indicative of a blood pressure of the subject after a start of the second application of the excitatory current, and at least in part responsively to a difference between the second value and the third value, to drive the intravascular device to apply a second application of the ablative energy to the portion of the nerve tissue.

58. The apparatus according to inventive concept 56, further comprising a sensor, configured to be intravascularly placed within the subject, wherein the control unit is configured to receive the first value and the second value from the sensor.

There is further provided, in accordance with an application of the present invention, an inventive concept including:

59. Apparatus for facilitating ablation of nerve tissue of a subject, the apparatus comprising:

an ablation unit, configured to be percutaneously advanced to a site adjacent to a first portion of the nerve tissue of the subject;

at least one electrode unit, coupled to the ablation unit, and configured to be percutaneously advanced to a site adjacent to a second portion of the nerve tissue of the subject, and to initiate unidirectional action potentials in the nerve tissue, such that the unidirectional action potentials propagate toward the first portion of the nerve tissue; and a control unit, configured:

to drive the ablation unit to ablate, at least in part, the first portion of the nerve tissue of the subject, and to drive the at least one electrode unit to initiate the unidirectional action potentials by applying an excitatory current to the second portion of the nerve tissue.

60. The apparatus according to inventive concept 59, wherein the at least one electrode unit comprises a first electrode unit and a second electrode unit, the first electrode unit being coupled to the ablation unit on a first side of the ablation unit, and the second electrode unit being coupled to the ablation unit on a second side of the ablation unit, each electrode unit being configured to initiate unidirectional action potentials in the nerve tissue, such that the action potentials propagate toward the first portion of the nerve tissue.

61. The apparatus according to inventive concept 59, wherein the ablation unit comprises a radio-frequency ablation unit, and wherein the control unit is configured to drive the radio-frequency ablation unit to ablate the first portion of the nerve tissue by applying an ablative radio-frequency current to the first portion of the nerve tissue.

62. The apparatus according to inventive concept 59, wherein the ablation unit comprises an ultrasound ablation unit, and wherein the control unit is configured to drive the ultrasound ablation unit to ablate the first portion of the nerve tissue by applying ablative ultrasound energy to the first portion of the nerve tissue.

63. The apparatus according to inventive concept 59, wherein the electrode unit is configured to apply a non-ablative blocking current to the second portion of the nerve tissue of the subject, the non-ablative blocking current being configured to reversibly block endogenous action potentials from propagating through the second portion of the nerve tissue, and wherein the control unit is configured to drive the at least one electrode unit to apply the non-ablative blocking current.

64. The apparatus according to any one of inventive concepts 59-63, wherein the site includes a blood vessel, the nerve tissue includes nerve tissue of the blood vessel, and the at least one electrode unit comprises a plurality of sub-electrodes configured to be arranged in a broken arc that traces an inner wall of the blood vessel.

65. The apparatus according to inventive concept 64, wherein the control unit is configured to drive the plurality of sub-electrodes to simultaneously apply the excitatory current.

66. The apparatus according to inventive concept 65, wherein each of the plurality of sub-electrodes is independently addressable by the control unit.

67. The apparatus according to inventive concept 65, wherein the control unit is configured to balance the excitatory current across the plurality of sub-electrodes.

68. The apparatus according to any one of inventive concepts 59-63, wherein the nerve tissue includes nerve tissue of a blood vessel of the subject, and wherein at least the ablation unit is configured to be transluminally delivered to the blood vessel of the subject.

69. The apparatus according to inventive concept 68, wherein the electrode unit is configured to be transluminally delivered to the blood vessel of the subject.

70. The apparatus according to inventive concept 68, wherein the blood vessel includes a renal artery of the subject, and wherein at least the ablation unit is configured to be transluminally delivered to the renal artery of the subject.

71. The apparatus according to any one of inventive concepts 59-63, further comprising a longitudinal member, having a distal portion that is configured to be percutaneously advanced toward the nerve tissue of the subject, and wherein the ablation unit and the at least one electrode unit are coupled to the longitudinal member.

72. The apparatus according to inventive concept 71, wherein:
the ablation unit comprises a first ablation unit, and the at least one electrode unit comprises a respective first at least one electrode unit,
the apparatus further comprises a second ablation unit and a second respective at least one electrode unit, and
the distal portion of the longitudinal member is bifurcated so as to have (i) a first distal portion that is coupled to the first ablation unit and the first at least one electrode unit, and (ii) a second distal portion that is coupled to the second ablation unit and the second at least one electrode unit, each of the distal portions being configured to be transluminally advanced into a respective renal artery of the subject.

73. The apparatus according to any one of inventive concepts 59-63, further comprising a sensor, configured to detect a physiological response of the subject to the unidirectional action potentials initiated by the electrode unit.

74. The apparatus according to inventive concept 73, further comprising a longitudinal member, configured to be percutaneously advanced toward the nerve tissue of the subject, and wherein the ablation unit, the electrode unit, and the sensor are coupled to the longitudinal member.

75. The apparatus according to inventive concept 73, wherein the sensor is configured to be disposed in an aorta of the subject.

76. The apparatus according to inventive concept 73, wherein the sensor comprises a blood pressure sensor.

77. The apparatus according to inventive concept 73, wherein the control unit is configured to receive information indicative of the detected physiological response, and to drive the ablation unit at least in part responsively to the information indicative of the detected physiological response.

78. The apparatus according to inventive concept 77, wherein the control unit is configured:
to drive, during a first period, the at least one electrode unit to apply a non-ablative blocking current to the second portion of the nerve tissue of the subject, the blocking current being configured to temporarily block endogenous action potentials from propagating through the second portion of the nerve tissue.
to receive a first value of a factor indicative of the response, the first value being detected after a start of the application of the non-ablative blocking current, and
to drive the ablation unit at least in part responsively to the received first value.

79. The apparatus according to inventive concept 78, wherein the control unit is configured:
to drive, during a second period, the at least one electrode unit to apply the excitatory current,
to receive a second value of the factor, the second value being detected after a start of the application of the excitatory current, and
to drive the ablation unit at least in part responsively to the received second value.

80. The apparatus according to inventive concept 78, wherein the sensor is configured to detect the first value of the factor after the start of the application of the non-ablative blocking current, and to provide the first value of the factor to the control unit.

There is further provided, in accordance with an application of the present invention, an inventive concept including:

81. Apparatus for facilitating ablation of nerve tissue of a blood vessel of a subject, the apparatus comprising:
an intravascular device, configured to be placed within the blood vessel, and comprising a plurality of electrodes disposed at respective longitudinal sites of the intravascular device;
a sensor, configured to be intravascularly placed within the subject; and
a control unit, configured to:
drive at least one of the electrodes to apply a non-ablative electrical current to the nerve tissue,
receive from the sensor a first value of the subject, the first value being indicative of a blood pressure of the subject after a start of the application of the non-ablative electrical current,
subsequently drive at least one of the electrodes to apply a first application of ablative energy to the nerve tissue,
receive from the sensor a second value of the subject, the second value being indicative of the blood pressure of the subject after the first application of the ablative energy, and
at least in part responsively to a difference between the first value and the second value, drive at least one of the electrodes to apply a second application of the ablative energy to the nerve tissue.

82. The apparatus according to inventive concept 81, wherein the control unit is configured to drive the at least one of the electrodes to apply the first application of ablative energy by driving the at least one of the electrodes to apply a radio-frequency current having a frequency of between 5 kHz and 1 GHz.
83. The apparatus according to any one of inventive concepts 81-82, wherein at least one of the plurality of electrodes comprises a plurality of sub-electrodes configured to be arranged in a broken arc that traces an inner wall of the blood vessel.
84. The apparatus according to inventive concept 83, wherein the control unit is configured to drive the plurality of sub-electrodes to simultaneously apply the non-ablative electrical current.
85. The apparatus according to inventive concept 84, wherein each of the plurality of sub-electrodes is independently addressable by the control unit.
86. The apparatus according to inventive concept 84, wherein the control unit is configured to balance the non-ablative electrical current across the plurality of sub-electrodes.
87. The apparatus according to any one of inventive concepts 81-82, wherein the blood vessel includes a first blood vessel, the intravascular device comprises a first intravascular device configured to be placed within the first blood vessel, and the apparatus further comprises a second intravascular device, configured to be placed within a second blood vessel of the subject.
88. The apparatus according to inventive concept 87, wherein the second intravascular device is separate from but identical to the first intravascular device.

There is further provided, in accordance with an application of the present invention, an inventive concept including:

89. A method for use with nerve tissue of a subject, the nerve tissue conducting endogenous action potentials to an anatomical structure of the subject, the structure being capable of altering a parameter of the subject at least in part responsively to the endogenous action potentials, the method comprising:
initiating action potentials in a first portion of the nerve tissue by applying an excitatory current to the first portion of the nerve tissue, wherein applying the excitatory current comprises, after a start of the application of the excitatory current, performing a detection of a factor indicative of the parameter of the subject; and
subsequently, applying ablating energy to a second portion of the nerve tissue, at least in part in response to the detection.
90. The method according to inventive concept 89, wherein initiating action potentials in a first portion of the nerve tissue comprises initiating action potentials in a first portion of a postganglionic neuron of the subject, and wherein applying ablating energy to a second portion of the nerve tissue comprises applying ablating energy to a second portion of the postganglionic neuron.
91. The method according to inventive concept 89, wherein the subject suffers from a condition in which the parameter is affected by overactivity of a sympathetic nervous system of the subject, initiating action potentials in the first portion of the nerve tissue comprises initiating action potentials in a first portion of nerve tissue of the sympathetic nervous system, and applying ablating energy to the second portion of the nerve tissue comprises applying ablating energy to a second portion of the nerve tissue of the sympathetic nervous system.
92. The method according to inventive concept 89, wherein the subject suffers from a condition in which the parameter is affected by overactivity of a parasympathetic nervous system of the subject, initiating action potentials in the first portion of the nerve tissue comprises initiating action potentials in a first portion of nerve tissue of the parasympathetic nervous system, and applying ablating energy to the second portion of the nerve tissue comprises applying ablating energy to a second portion of the nerve tissue of the parasympathetic nervous system.
93. The method according to inventive concept 89, wherein performing the detection after the start of the application of the excitatory current comprises performing the detection during the application of the excitatory current.
94. The method according to inventive concept 89, wherein performing the detection after the start of the application of the excitatory current comprises performing the detection after the application of the excitatory current.
95. The method according to inventive concept 89, wherein initiating action potentials comprises initiating unidirectional action potentials in the nerve tissue.
96. The method according to any one of inventive concepts 89-95, further comprising identifying that the subject suffers from premature ejaculation, wherein initiating action potentials comprises initiating action potentials in response to the identifying.
97. The method according to inventive concept 96, wherein:
initiating action potentials in the first portion of the nerve tissue comprises initiating action potentials in a first portion of a dorsal nerve of the subject, and
applying ablating energy to the second portion of the nerve tissue comprises applying ablating energy to a second portion of the dorsal nerve of the subject.
98. The method according to inventive concept 96, wherein:
initiating action potentials in the first portion of the nerve tissue comprises initiating action potentials in a first portion of a pudendal nerve of the subject, and
applying ablating energy to the second portion of the nerve tissue comprises applying ablating energy to a second portion of the pudendal nerve of the subject.
99. The method according to inventive concept 96, wherein:
initiating action potentials in the first portion of the nerve tissue comprises initiating action potentials in a first portion of a sacral nerve of the subject, and
applying ablating energy to the second portion of the nerve tissue comprises applying ablating energy to a second portion of the sacral nerve of the subject.
100. The method according to inventive concept 96, wherein performing the detection of the factor comprises detecting an ejaculation of the subject.
101. The method according to inventive concept 96, wherein performing the detection of the factor comprises detecting an electromyogram value.
102. The method according to inventive concept 96, wherein initiating action potentials comprises initiating action potentials during a second period, performing the detection of the factor comprises performing a second detection of the factor, and the method further comprises performing, during a first period, a first detection of the factor indicative of the parameter of the subject.
103. The method according to inventive concept 102, wherein performing the first detection comprises detecting a first ejaculation of the subject, and performing the second detection comprises detecting a second ejaculation of the subject.
104. The method according to inventive concept 102, wherein performing the first detection comprises detecting a first electromyogram value, and performing the second detection comprises detecting a second electromyogram value.

105. The method according to any one of inventive concepts 89-95, further comprising identifying that the subject suffers from erectile dysfunction, wherein initiating action potentials comprises initiating action potentials in response to the identifying.

106. The method according to inventive concept 105, wherein:
initiating action potentials in the first portion of the nerve tissue comprises initiating action potentials in a first portion of a dorsal nerve of the subject, and
applying ablating energy to the second portion of the nerve tissue comprises applying ablating energy to a second portion of the dorsal nerve of the subject.

107. The method according to inventive concept 105, wherein performing the detection comprises detecting an electromyogram value.

108. The method according to inventive concept 105, wherein performing the detection comprises detecting a blood pressure.

109. The method according to inventive concept 105, wherein initiating action potentials comprises initiating action potentials during a second period, performing the detection of the factor comprises performing a second detection of the factor, and the method further comprises performing, during a first period, a first detection of the factor indicative of the parameter of the subject.

110. The method according to inventive concept 109, wherein performing the first detection comprises detecting a first electromyogram value, and performing the second detection comprises detecting a second electromyogram value.

111. The method according to inventive concept 109, wherein performing the first detection comprises detecting a first blood pressure, and performing the second detection comprises detecting a second blood pressure.

112. The method according to any one of inventive concepts 89-95, further comprising identifying that the subject suffers from overactive bladder, wherein initiating action potentials comprises initiating action potentials in response to the identifying.

113. The method according to inventive concept 112, wherein:
initiating action potentials in the first portion of the nerve tissue comprises initiating action potentials in a first portion of a hypogastric nerve of the subject, and
applying ablating energy to the second portion of the nerve tissue comprises applying ablating energy to a second portion of the hypogastric nerve of the subject.

114. The method according to inventive concept 112, wherein:
initiating action potentials in the first portion of the nerve tissue comprises initiating action potentials in a first portion of a sacral nerve of the subject, and
applying ablating energy to the second portion of the nerve tissue comprises applying ablating energy to a second portion of the sacral nerve of the subject.

115. The method according to inventive concept 112, wherein performing the detection comprises detecting urinary urgency of the subject.

116. The method according to inventive concept 112, wherein performing the detection comprises detecting an electromyogram value.

117. The method according to inventive concept 112, wherein performing the detection comprises detecting pressure in a bladder of the subject.

118. The method according to inventive concept 112, wherein initiating action potentials comprises initiating action potentials while a bladder of the subject is at a pre-defined level of fullness.

119. The method according to inventive concept 112, wherein initiating action potentials comprises initiating action potentials during a second period, performing the detection of the factor comprises performing a second detection of the factor, and the method further comprises performing, during a first period, a first detection of the factor indicative of the parameter of the subject.

120. The method according to inventive concept 119, wherein performing the first detection comprises detecting a first urinary urgency, and performing the second detection comprises detecting a second urinary urgency.

121. The method according to inventive concept 119, wherein performing the first detection comprises detecting a first electromyogram value, and performing the second detection comprises detecting a second electromyogram value.

122. The method according to inventive concept 119, wherein performing the first detection comprises detecting a first pressure in a bladder of the subject, and performing the second detection comprises detecting a second pressure in the bladder of the subject.

123. The method according to any one of inventive concepts 89-95, further comprising identifying that the subject suffers from hypertension, wherein initiating action potentials comprises initiating action potentials in response to the identifying.

124. The method according to inventive concept 123, wherein:
initiating action potentials in the first portion of the nerve tissue comprises initiating action potentials in a first portion of a renal nerve of the subject, and
applying ablating energy to the second portion of the nerve tissue comprises applying ablating energy to a second portion of the renal nerve of the subject.

125. The method according to inventive concept 123, wherein:
initiating action potentials in the first portion of the nerve tissue comprises initiating action potentials in a first portion of a glossopharyngeal nerve of the subject, and
applying ablating energy to the second portion of the nerve tissue comprises applying ablating energy to a second portion of the glossopharyngeal nerve of the subject.

126. The method according to inventive concept 123, wherein:
initiating action potentials in the first portion of the nerve tissue comprises initiating action potentials in a first portion of a Nerve of Hering of the subject, and
applying ablating energy to the second portion of the nerve tissue comprises applying ablating energy to a second portion of the Nerve of Hering of the subject.

127. The method according to inventive concept 123, wherein performing the detection of the factor comprises detecting a blood pressure of the subject.

128. The method according to inventive concept 123, wherein initiating action potentials comprises initiating action potentials during a second period, performing the detection of the factor comprises performing a second detection of the factor, and the method further comprises performing, during a first period, a first detection of the factor indicative of the parameter of the subject.

129. The method according to inventive concept 128, wherein performing the first detection comprises detecting a first blood pressure of the subject, and performing the second detection comprises detecting a second blood pressure of the subject.

130. The method according to any one of inventive concepts 89-95, further comprising identifying that the subject suffers from chronic obstructive pulmonary disease, wherein initiating action potentials comprises initiating action potentials in response to the identifying.
131. The method according to inventive concept 130, wherein:
initiating action potentials in the first portion of the nerve tissue comprises initiating action potentials in a first portion of a vagus nerve of the subject, and
applying ablating energy to the second portion of the nerve tissue comprises applying ablating energy to a second portion of the vagus nerve of the subject.
132. The method according to inventive concept 130, wherein performing the detection of the factor comprises detecting a breathing-related factor of the subject.
133. The method according to inventive concept 132, wherein detecting the breathing-related factor comprises detecting an airflow.
134. The method according to inventive concept 132, wherein detecting the breathing-related factor comprises measuring a dimension of an airway of the subject.
135. The method according to inventive concept 132, wherein detecting the breathing-related factor comprises detecting blood chemistry of the subject.
136. The method according to inventive concept 130, wherein initiating action potentials comprises initiating action potentials during a second period, performing the detection of the factor comprises performing a second detection of the factor, and the method further comprises performing, during a first period, a first detection of the factor indicative of the parameter of the subject.
137. The method according to inventive concept 136, wherein performing the first detection comprises performing a first detection of a breathing-related factor of the subject, and performing the second detection comprises performing a second detection of the breathing-related factor of the subject.
138. The method according to inventive concept 137, wherein performing the first detection of the breathing-related factor of the subject comprises detecting a first airflow, and wherein performing the second detection of the breathing-related factor of the subject comprises detecting a second airflow.
139. The method according to any one of inventive concepts 89-95, further comprising identifying that the subject suffers from congestive heart failure, wherein initiating action potentials comprises initiating action potentials in response to the identifying.
140. The method according to inventive concept 139, wherein:
initiating action potentials in the first portion of the nerve tissue comprises initiating action potentials in a first portion of a sympathetic nerve that innervates a heart of the subject, and
applying ablating energy to the second portion of the nerve tissue comprises applying ablating energy to a second portion of the sympathetic nerve that innervates the heart of the subject.
141. The method according to inventive concept 139, wherein performing the detection comprises detecting a heart rate of the subject.
142. The method according to inventive concept 139, wherein performing the detection comprises detecting a blood pressure of the subject.
143. The method according to inventive concept 139, wherein initiating action potentials comprises initiating action potentials during a second period, performing the detection of the factor comprises performing a second detection of the factor, and the method further comprises performing, during a first period, a first detection of the factor indicative of the parameter of the subject.
144. The method according to inventive concept 143, wherein performing the first detection comprises detecting a first heart rate of the subject, and performing the second detection comprises detecting a second heart rate of the subject.
145. The method according to inventive concept 143, wherein performing the first detection comprises detecting a first blood pressure of the subject, and performing the second detection comprises detecting a second blood pressure of the subject.
146. The method according to any one of inventive concepts 89-95, further comprising identifying that the subject suffers from uterine bleeding, wherein initiating action potentials comprises initiating action potentials in response to the identifying.
147. The method according to inventive concept 146, wherein:
initiating action potentials in the first portion of the nerve tissue comprises initiating action potentials in a first portion of a lumbar splancnic nerve of the subject, and
applying ablating energy to the second portion of the nerve tissue comprises applying ablating energy to a second portion of the lumbar splancnic nerve of the subject.
148. The method according to inventive concept 146, wherein:
initiating action potentials in the first portion of the nerve tissue comprises initiating action potentials in a first portion of a nerve that extends from a hypogastric plexus of the subject, and
applying ablating energy to the second portion of the nerve tissue comprises applying ablating energy to a second portion of the nerve that extends from the hypogastric plexus of the subject.
149. The method according to inventive concept 146, wherein performing the detection of the factor comprises detecting uterine bleeding of the subject.
150. The method according to inventive concept 146, wherein performing the detection of the factor comprises detecting a blood pressure.
151. The method according to inventive concept 146, wherein performing the detection of the factor comprises detecting a dimension of a blood vessel of the subject.
152. The method according to inventive concept 146, wherein initiating action potentials comprises initiating action potentials during a second period, performing the detection of the factor comprises performing a second detection of the factor, and the method further comprises performing, during a first period, a first detection of the factor indicative of the parameter of the subject.
153. The method according to inventive concept 152, wherein performing the first detection comprises detecting a first uterine bleeding of the subject, and performing the second detection comprises detecting a second uterine bleeding of the subject.
154. The method according to inventive concept 152, wherein performing the first detection comprises detecting a first blood pressure, and performing the second detection comprises detecting a second blood pressure.
155. The method according to inventive concept 152, wherein performing the first detection comprises performing a first measurement of a blood vessel dimension, and performing the second detection comprises performing a second measurement of the blood vessel dimension.

156. The method according to any one of inventive concepts 89-95, further comprising identifying that the subject suffers from nervous stomach, wherein initiating action potentials comprises initiating action potentials in response to the identifying.

157. The method according to inventive concept 156, wherein:
initiating action potentials in the first portion of the nerve tissue comprises initiating action potentials in a first portion of a vagus nerve of the subject, and
applying ablating energy to the second portion of the nerve tissue comprises applying ablating energy to a second portion of the vagus nerve of the subject.

158. The method according to inventive concept 156, wherein performing the detection of the factor comprises detecting gastric pH.

159. The method according to inventive concept 156, wherein performing the detection of the factor comprises detecting gastric movement.

160. The method according to inventive concept 156, wherein initiating action potentials comprises initiating action potentials during a second period, performing the detection of the factor comprises performing a second detection of the factor, and the method further comprises performing, during a first period, a first detection of the factor indicative of the parameter of the subject.

161. The method according to inventive concept 160, wherein performing the first detection comprises detecting a first detection of gastric pH, and performing the second detection comprises detecting a second detection of gastric pH.

162. The method according to inventive concept 160, wherein performing the first detection comprises performing a first detection of gastric movement, and performing the second detection comprises performing a second detection of gastric movement.

163. The method according to any one of inventive concepts 89-95, further comprising identifying that the subject suffers from primary hyperhidrosis, wherein initiating action potentials comprises initiating action potentials in response to the identifying.

164. The method according to inventive concept 163, wherein:
initiating action potentials in the first portion of the nerve tissue comprises initiating action potentials in a first portion of a sympathetic nerve that innervates sweat glands of the subject, and
applying ablating energy to the second portion of the nerve tissue comprises applying ablating energy to a second portion of the sympathetic nerve that innervates sweat glands of the subject.

165. The method according to inventive concept 163, wherein performing the detection of the factor comprises detecting transepidermal water loss.

166. The method according to inventive concept 163, wherein performing the detection of the factor comprises detecting perspiration.

167. The method according to inventive concept 166, wherein detecting perspiration comprises detecting conduction between electrodes.

168. The method according to inventive concept 163, wherein initiating action potentials comprises initiating action potentials during a second period, performing the detection of the factor comprises performing a second detection of the factor, and the method further comprises performing, during a first period, a first detection of the factor indicative of the parameter of the subject.

169. The method according to inventive concept 168, wherein performing the first detection comprises performing a first detection of perspiration, and performing the second detection comprises performing a second detection of perspiration.

170. The method according to inventive concept 168, wherein performing the first detection comprises performing a first detection of transepidermal water loss, and performing the second detection comprises performing a second detection of transepidermal water loss.

171. The method according to any one of inventive concepts 89-95, further comprising identifying that the subject suffers from an inflammatory condition, wherein initiating action potentials comprises initiating action potentials in response to the identifying.

172. The method according to inventive concept 171, wherein:
initiating action potentials in the first portion of the nerve tissue comprises initiating action potentials in a first portion of a splenic nerve of the subject, and
applying ablating energy to the second portion of the nerve tissue comprises applying ablating energy to a second portion of the splenic nerve of the subject.

173. The method according to inventive concept 171, wherein performing the detection of the factor comprises detecting tumor-necrosis factor alpha in blood of the subject.

174. The method according to inventive concept 171, wherein initiating action potentials comprises initiating action potentials during a second period, performing the detection of the factor comprises performing a second detection of the factor, and the method further comprises performing, during a first period, a first detection of the factor indicative of the parameter of the subject.

175. The method according to inventive concept 174, wherein performing the first detection comprises performing a first detection of tumor-necrosis factor alpha in blood of the subject, and detecting the second detection comprises performing a second detection of tumor-necrosis factor alpha in the blood of the subject.

176. The method according to any one of inventive concepts 89-95, further comprising identifying that the subject suffers from obesity, wherein initiating action potentials comprises initiating action potentials in response to the identifying.

177. The method according to inventive concept 176, wherein:
initiating action potentials in the first portion of the nerve tissue comprises initiating action potentials in a first portion of a nerve that conducts action potentials between a celiac plexus of the subject and an organ of the gastrointestinal system of the subject, and
applying ablating energy to the second portion of the nerve tissue comprises applying ablating energy to a second portion of the nerve that conducts action potentials between the celiac plexus of the subject and the organ of the gastrointestinal system of the subject.

178. The method according to inventive concept 176, wherein performing the detection of the factor comprises detecting an electromyogram value.

179. The method according to inventive concept 176, wherein performing the detection of the factor comprises performing the detection using ultrasound.

180. The method according to inventive concept 176, wherein initiating action potentials comprises initiating action potentials during a second period, performing the detection of the factor comprises performing a second detection of the factor, and the method further comprises performing, during a first period, a first detection of the factor indicative of the parameter of the subject.

181. The method according to inventive concept 180, wherein performing the first detection comprises detecting a first electromyogram value, and performing the second detection comprises detecting a second electromyogram value.

182. The method according to inventive concept 180, wherein performing the first detection comprises performing the first detection using ultrasound, and performing the second detection comprises performing the second detection using ultrasound.

183. The method according to any one of inventive concepts 89-95, wherein applying the excitatory current comprises applying a first application of excitatory current, and the method further comprises:
subsequently to applying the ablating energy, applying a second application of excitatory current; and
after the start of the second application of excitatory current, performing another detection of the factor indicative of the parameter of the subject.

184. The method according to inventive concept 183, wherein applying ablating energy comprises applying a first application of ablating energy, and the method further comprises at least in part responsively to the detection and at least in part responsively to the other detection, applying a second application of ablating energy.

185. The method according to any one of inventive concepts 89-95, wherein initiating action potentials comprises initiating action potentials during a second period, performing the detection of the factor comprises performing a second detection of the factor, and the method further comprises performing, during a first period, a first detection of the factor indicative of the parameter of the subject.

186. The method according to inventive concept 185, wherein applying the excitatory current comprises applying a first application of excitatory current, and the method further comprises:
subsequently to applying the ablating energy, applying a second application of excitatory current; and
after the start of the second application of excitatory current, performing a third detection of the factor indicative of the parameter of the subject.

187. The method according to inventive concept 186, wherein applying ablating energy comprises applying a first application of ablating energy, and the method further comprises at least in part responsively to the second detection and at least in part responsively to the third detection, applying a second application of ablating energy.

188. The method according to inventive concept 187, wherein applying the second application of ablating energy comprises applying the second application of ablating energy at least in part responsively to the first detection.

189. The method according to inventive concept 185, further comprising, responsively to the first detection and the second detection, determining a sensitivity of the parameter to action potentials in the nerve tissue.

190. The method according to inventive concept 185, wherein applying ablating energy comprises iteratively repeating the steps of:
(a) applying ablating energy,
(b) subsequently, applying, to the first portion of the nerve, a selected excitatory current a characteristic of which is at least in part based on a value of at least one property of the excitatory current, and
(c) after a start of the application of the selected excitatory current, detecting a detected ablated value of the factor, until the detected ablated value crosses a threshold defined at least in part based on a target ablated value that has been generated at least in part based on the first detection and the second detection.

191. The method according to inventive concept 185, wherein applying the excitatory current comprises iteratively repealing the steps of:
(a) applying the excitatory current,
(b) after the start of the application of the excitatory current, detecting a detected excited value of the factor, and
(c) altering a value of at least one property of the excitatory current,
until the detected excited value crosses a threshold defined at least in part on a target excited value of the factor, wherein detecting the detected excited value of the factor that crossed the threshold comprises performing the second detection of the factor.

192. The method according to any one of inventive concepts 89-95, wherein the nerve tissue includes nerve tissue associated with a blood vessel of the subject, applying the excitatory current comprises applying the excitatory current from within the blood vessel, and applying ablating energy comprises applying energy from within the blood vessel.

193. The method according to inventive concept 192, wherein the blood vessel includes a renal artery of the subject, applying the excitatory current comprises applying the excitatory current from within the renal artery, and applying ablating energy comprises applying energy from within the renal artery.

There is further provided, in accordance with an application of the present invention, an inventive concept including:
194. A method for use with nerve tissue of a subject, the nerve tissue conducting endogenous action potentials to an anatomical structure of the subject, the structure being capable of altering a parameter of the subject at least in part responsively to the endogenous action potentials, the method comprising:
during a first period, performing a first detection of a factor indicative of the parameter of the subject at rest;
during a second period, initiating action potentials in the nerve tissue by applying an excitatory current to the nerve tissue and, after the start of the application of the excitatory current, performing a second detection of the factor indicative of the parameter of the subject; and
at least in part responsively to the first detection and to the second detection, selecting the subject for a treatment comprising ablation of the nerve tissue.

There is further provided, in accordance with an application of the present invention, an inventive concept including:
195. A method for use with a carotid body of a subject, the carotid body being capable of inducing endogenous action potentials that affect blood pressure of the subject, the method comprising:
applying an excitatory current to the carotid body;
after a start of the application of the excitatory current, performing a detection of a factor indicative of blood pressure of the subject; and
subsequently, applying ablating energy to the carotid body, at least in part in response to the detection.

196. The method according to inventive concept 195, wherein performing the detection after the start of the application of the excitatory current comprises performing the detection during the application of the excitatory current.
197. The method according to inventive concept 195, wherein performing the detection after the start of the application of the excitatory current comprises performing the detection after the application of the excitatory current.
198. The method according to inventive concept 195, wherein stimulating comprises stimulating during a second period, performing the detection of the factor comprises performing a second detection of the factor, and the method further comprises performing, during a first period, a first detection of the factor.
199. The method according to any one of inventive concepts 195-198, wherein applying the excitatory current comprises applying a first application of excitatory current, and the method further comprises:
    subsequently to applying the ablating energy, applying a second application of excitatory current; and
    after the start of the second application of excitatory current, performing another detection of the factor.
200. The method according to inventive concept 199, wherein applying ablating energy comprises applying a first application of ablating energy, and the method further comprises at least in part responsively to the detection and at least in part responsively to the other detection, applying a second application of ablating energy.
201. The method according to any one of inventive concepts 195-198, wherein applying the excitatory current comprises applying the excitatory current during a second period, performing the detection of the factor comprises performing a second detection of the factor, and the method further comprises performing, during a first period, a first detection of the factor.
202. The method according to inventive concept 201, wherein applying the excitatory current comprises applying a first application of excitatory current, and the method further comprises:
    subsequently to applying the ablating energy, applying a second application of excitatory current; and
    after the start of the second application of excitatory current, performing a third detection of the factor indicative of the parameter of the subject.
203. The method according to inventive concept 202, wherein applying ablating energy comprises applying a first application of ablating energy, and the method further comprises at least in part responsively to the second detection and at least in part responsively to the third detection, applying a second application of ablating energy.
204. The method according to inventive concept 203, wherein applying the second application of ablating energy comprises applying the second application of ablating energy at least in part responsively to the first detection.
205. The method according to inventive concept 201, further comprising, responsively to the first detection and the second detection, determining a sensitivity of the parameter to action potentials induced by the carotid body.
206. The method according to inventive concept 201, further comprising, responsively to the first detection and the second detection, selecting the subject for a treatment comprising ablation of the nerve tissue.
207. The method according to inventive concept 201, wherein applying ablating energy comprises iteratively repeating the steps of:
    (a) applying ablating energy,
    (b) subsequently, applying, a selected excitatory current a characteristic of which is at least in part based on a value of at least one property of the excitatory current, and
    (c) after a start of the application of the selected excitatory current, detecting a detected ablated value of the factor,
    until the detected ablated value crosses a threshold defined at least in part based on a target ablated value that has been generated at least in part based on the first detection and the second detection.
208. The method according to inventive concept 201, wherein applying the excitatory current comprises iteratively repeating the steps of:
    (a) applying the excitatory current,
    (b) after the start of the application of the excitatory current, detecting a detected excited value of the factor, and
    (c) altering a value of at least one property of the excitatory current,
    until the detected excited value crosses a threshold defined at least in part on a target excited value of the factor, wherein detecting the detected excited value of the factor that crossed the threshold comprises performing the second detection of the factor.

There is further provided, in accordance with an application of the present invention, an inventive concept including:
209. A method for use with a renal nerve of a subject, the renal nerve innervating an ipsilateral kidney of the subject, the method comprising:
    receiving a preliminary blood pressure value of the subject;
    iteratively repeating the steps of:
        (a) inducing action potentials in the renal nerve by applying an excitatory current to a first portion of the renal nerve,
        (b) receiving a detected excited blood pressure value, indicative of a blood pressure of the subject after a start of the application of the excitatory current, and
        (c) altering a value of at least one property of the excitatory current,
    until the detected excited blood pressure value crosses a first threshold defined at least in part based on a pre-determined target excited blood pressure value; and
    subsequently, iteratively repeating the steps of:
        (d) applying ablating energy to a second portion of the renal nerve that is further from the kidney than is the first portion of the renal nerve,
        (e) subsequently, applying, to the first portion of the renal nerve, a selected excitatory current a characteristic of which is at least in part based on the value of the at least one property at which the detected excited blood pressure value crossed the first threshold, and
        (f) receiving a detected ablated blood pressure value, indicative of a blood pressure of the subject after a start of the application of the selected excitatory current,
    until the detected ablated blood pressure value crosses a second threshold defined at least in part based on a target ablated blood pressure value that is generated at least in part based on the preliminary blood pressure value and at least in part based on at least one excited blood pressure value selected from the group consisting of: (i) the target excited blood pressure value and (ii) the detected excited blood pressure value.

210. The method according to inventive concept 209, wherein applying ablating energy comprises applying a radio-frequency current having a frequency of between 5 kHz and 1 GHz.
211. The method according to inventive concept 209, wherein receiving the target ablated blood pressure value comprises receiving a target ablated blood pressure value that is manually inputted by a healthcare provider.
212. The method according to inventive concept 209, wherein:
the renal nerve includes a first renal nerve of the subject that innervates a first kidney that is ipsilateral to the first renal nerve; and
inducing action potentials in the renal nerve comprises (i) inducing action potentials in the first renal nerve, and (ii) inducing action potentials in a second renal nerve that innervates a second kidney that is ipsilateral to the second renal nerve.
213. The method according to inventive concept 209, wherein, subsequently to the first iteration of steps d, e and f, during at least one iteration of steps d, e and f, applying ablating energy comprises applying ablating energy that is different in at least one characteristic thereof compared to the ablative energy applied in a previous iteration of steps d, e and f.
214. The method according to inventive concept 209, further comprising detecting, using a sensor, the detected excited blood pressure value.
215. The method according to inventive concept 209, further comprising detecting, using a sensor, the detected ablated blood pressure value.
216. The method according to inventive concept 209, further comprising generating the target excited blood pressure value at least in part responsively to the preliminary blood pressure value.
217. The method according to inventive concept 209, wherein receiving the target excited blood pressure value comprises receiving a target excited blood pressure value that is manually inputted by a healthcare provider.
218. The method according to any one of inventive concepts 209-217, wherein applying the excitatory current to the first portion of the renal nerve comprises applying the excitatory current via a plurality of sub-electrodes arranged in a broken arc that traces an inner wall of a renal artery of the subject.
219. The method according to inventive concept 218, wherein applying the excitatory current comprises applying the excitatory current simultaneously via the plurality of sub-electrodes.
220. The method according to inventive concept 219, wherein the plurality of sub-electrodes includes a plurality of independently addressable sub-electrodes, and applying the excitatory current comprises applying the excitatory current via the plurality of independently addressable sub-electrodes.
221. The method according to inventive concept 219, further comprising balancing the excitatory current across the plurality of sub-electrodes.
222. The method according to any one of inventive concepts 209-217, further comprising generating the target ablated blood pressure value at least in part responsively to (1) the preliminary blood pressure value and (2) at least one excited blood pressure value selected from the group consisting of (i) the target excited blood pressure value and (ii) the detected excited blood pressure value.
223. The method according to inventive concept 222, wherein generating the target ablated blood pressure value comprises generating the target excited blood pressure value at least in part responsively to a value indicative of a target degree of ablation of the renal nerve.
224. The method according to inventive concept 223, further comprising receiving, via a manual input, the value indicative of the target degree of ablation.

There is further provided, in accordance with an application of the present invention, an inventive concept including:
225. A method for ablating nerve tissue of a renal artery of a subject, the method comprising:
applying a non-ablative electrical current to the nerve tissue;
subsequently applying a first application of ablative energy to the nerve tissue;
receiving (1) a first value of the subject, the first value being indicative of a blood pressure of the subject after a start of the application of the non-ablative electrical current and before the first application of ablative energy, and (2) a second value of the subject, the second value being indicative of the blood pressure of the subject after the first application of ablative energy; and
at least in part responsively to a difference between the first value and the second value, applying a second application of ablative energy to the nerve tissue.
226. The method according to inventive concept 225, wherein applying the first application of ablative energy comprises applying a first application of a radio-frequency current having a frequency of between 5 kHz and 1 GHz.
227. The method according to inventive concept 225, wherein the renal nerve innervates an ipsilateral kidney of the subject, applying the non-ablative electrical current comprises applying the non-ablative electrical current to a first portion of the nerve tissue, and applying the first application of ablative energy comprises applying the first application of ablative energy to a second portion of the nerve tissue that is further from the kidney than is the first portion of the nerve tissue.
228. The method according to inventive concept 225, wherein applying the second application of the ablative energy comprises applying a second application of ablative energy that has an intensity that is greater than an intensity of the first application of the ablative energy.
229. The method according to inventive concept 225, wherein receiving the first value comprises receiving a first value that is indicative of a blood pressure of the subject after an end of the application of the non-ablative electrical current.
230. The method according to inventive concept 225, further comprising receiving a preliminary value indicative of the parameter of the subject before the application of the non-ablative electrical current, wherein applying the ablative energy comprises applying the ablative energy at least in part responsively to (1) the difference between the first value and the second value, and (2) the preliminary value.
231. The method according to inventive concept 225, wherein receiving the first value indicative of the parameter of the subject after the start of the application of the non-ablative electrical current comprises receiving the first value indicative of the parameter of the subject during the application of the non-ablative electrical current.
232. The method according to inventive concept 225, wherein receiving the first value indicative of the parameter of the subject after the start of the application of the non-ablative electrical current comprises receiving the first value indicative of the parameter of the subject after the application of the non-ablative electrical current.

233. The method according to inventive concept 225, wherein the non-ablative electrical current includes an excitatory current, and wherein applying the non-ablative electrical current comprises initiating action potentials in the nerve tissue using the excitatory current.

234. The method according to inventive concept 225, wherein the non-ablative electrical current includes a blocking current, and wherein applying the non-ablative electrical current comprises blocking action potentials in the nerve tissue using the blocking current.

235. The method according to any one of inventive concepts 225-234, wherein:
the renal artery includes a first renal artery of the subject, and
applying the non-ablative electrical current comprises applying the non-ablative electrical current to the nerve tissue of the first renal artery and to nerve tissue of a second renal artery of the subject.

236. The method according to inventive concept 235, wherein applying the non-ablative electrical current comprises applying the non-ablative electrical current to the nerve tissue of the first renal artery and to nerve tissue of the second renal artery generally at the same time.

237. The method according to any one of inventive concepts 225-234, wherein applying the non-ablative electrical current comprises applying the non-ablative electrical current via a plurality of sub-electrodes arranged in a broken arc that traces an inner wall of the renal artery.

238. The method according to inventive concept 237, wherein applying the non-ablative electrical current comprises applying the non-ablative electrical current simultaneously via the plurality of sub-electrodes.

239. The method according to inventive concept 237, wherein the plurality of sub-electrodes includes a plurality of independently addressable sub-electrodes, and applying the non-ablative electrical current comprises applying the non-ablative electrical current via the plurality of independently addressable sub-electrodes.

240. The method according to inventive concept 238, further comprising balancing the non-ablative electrical current across the plurality of sub-electrodes.

There is further provided, in accordance with an application of the present invention, an inventive concept including, 241. A method for use with nerve tissue of a subject, the nerve tissue conducting endogenous action potentials to an anatomical structure of the subject, the structure being capable of altering a parameter of the subject at least in part responsively to the endogenous action potentials, the method comprising:
during a first period, blocking the endogenous action potentials from propagating through the nerve tissue by applying a non-ablative blocking current to the nerve tissue and, after the start of the application of the non-ablative blocking current, detecting a first value of a factor indicative of the parameter of the subject; and
during a second period, initiating unidirectional action potentials in the nerve tissue by applying an excitatory current to the nerve tissue and, after the start of the application of the excitatory current, detecting a second value of the factor indicative of the parameter of the subject.

242. The method according to inventive concept 241, wherein:
the anatomical structure includes a first anatomical structure of the subject, and the nerve tissue includes a respective first section of nerve tissue that conducts endogenous action potentials to the first anatomical structure; and
blocking the endogenous action potentials comprises (i) blocking the endogenous action potentials from propagating through the first section of nerve tissue, and (ii) blocking endogenous action potentials from propagating through a second section of nerve tissue to a respective second anatomical structure of the subject.

243. The method according to inventive concept 241, further comprising, during a third period, detecting a third value of the factor indicative of the parameter of the subject in the absence of the non-ablative blocking current and the excitatory current.

244. The method according to inventive concept 241, further comprising, responsively to the first and second values, determining a sensitivity of the parameter to action potentials in the nerve tissue.

245. The method according to inventive concept 241, further comprising, responsively to the first and second values, selecting the subject for a treatment comprising ablation of the nerve tissue.

246. The method according to inventive concept 241, wherein detecting the first value after the start of the application of the non-ablative blocking current comprises detecting the first value during the application of the non-ablative blocking current.

247. The method according to inventive concept 241, wherein detecting the first value after the start of the application of the non-ablative blocking current comprises detecting the first value after the application of the non-ablative blocking current.

248. The method according to inventive concept 241, wherein detecting the second value after the start of the application of the excitatory current comprises detecting the second value during the application of the excitatory current.

249. The method according to inventive concept 241, wherein detecting the second value after the start of the application of the excitatory current comprises detecting the second value after the application of the excitatory current.

250. The method according to any one of inventive concepts 241-249, wherein applying the non-ablative blocking current comprises applying the non-ablative blocking current via a plurality of sub-electrodes arranged in a broken arc.

251. The method according to inventive concept 250, wherein applying the non-ablative blocking current comprises applying the non-ablative blocking current simultaneously via the plurality of sub-electrodes.

252. The method according to inventive concept 251, wherein the plurality of sub-electrodes includes a plurality of independently addressable sub-electrodes, and applying the non-ablative blocking current comprises applying the non-ablative blocking current via the plurality of independently addressable sub-electrodes.

253. The method according to inventive concept 251, further comprising balancing the non-ablative blocking current across the plurality of sub-electrodes.

254. The method according to any one of inventive concepts 241-249, wherein the nerve tissue includes nerve tissue of a blood vessel of a subject, and wherein blocking and initiating comprise blocking and initiating using an electrode unit disposed within the blood vessel of the subject.

255. The method according to inventive concept 254, wherein the nerve tissue includes a renal nerve of the subject, the blood vessel includes a renal artery of the subject, and blocking and initiating comprise blocking and initiating using an electrode unit disposed within the renal artery of the subject.

256. The method according to inventive concept 254, wherein the factor includes a factor indicative of a blood pressure of the subject, detecting the first value comprises detecting a first value of the factor indicative of the blood pressure of the subject, and detecting the second value comprises detecting a second value of the factor indicative of the blood pressure of the subject.

257. The method according to any one of inventive concepts 241-249, wherein:

the method further comprises applying ablative energy to a first portion of the nerve tissue of the subject.

initiating the unidirectional action potentials during the second period comprises initiating the unidirectional action potentials in a second portion of the nerve tissue by applying a first application of the excitatory current to the second portion of the nerve tissue prior to the application of ablative energy, and detecting the second value of the factor comprises detecting the second value of the factor prior to the application of ablative energy, and the method further comprises, during a third period, subsequently to the application of ablative energy, initiating unidirectional action potentials in the nerve tissue by applying a second application of the excitatory current to the second portion of the nerve tissue and, after the start of the second application of the excitatory current, detecting a third value of the factor indicative of the parameter of the subject.

258. The method according to inventive concept 257, wherein:

applying ablative energy comprises applying a first application of ablative energy, and the method further comprises, at least in part responsively to the second value and the third value, applying a second application of ablative energy to the first portion of the nerve tissue of the subject.

259. The method according to inventive concept 258, wherein applying the second application of ablative energy comprises applying the second application of ablative energy at least in part responsively to the first value.

260. The method according to inventive concept 258, wherein applying the second application of ablative energy comprises applying a second application of ablative energy that has an intensity different from an intensity of the first application of ablative energy.

There is further provided, in accordance with an application of the present invention, an inventive concept including:

261. A method for use with a renal artery of a subject, the renal artery including nerve tissue, the method comprising:

generating a lesion in the renal artery of the subject;

initiating first unidirectional action potentials on a first side of the lesion, such that the action potentials propagate toward the lesion; and initiating second unidirectional action potentials on a second side of the lesion, such that the action potentials propagate toward the lesion.

There is further provided, in accordance with an application of the present invention, an inventive concept including:

262. A method, comprising:

measuring a first blood pressure value of a subject who does not suffer from hypertension;

subsequently, at least partly ablating nerve tissue of a renal artery of the subject;

subsequently, measuring a second blood pressure value of the subject; and subsequently, at least in part responsively to the first blood pressure value, and at least in part responsively to the second blood pressure value, further ablating the nerve tissue.

There is further provided, in accordance with an application of the present invention, an inventive concept including:

263. A method for facilitating ablation of renal nerve tissue of a renal artery of a subject, the method comprising:

introducing into a subject, a transvascular catheter including (1) at a distal portion thereof, an electrode unit and an ablation unit disposed proximally from the electrode unit, and (2) a pressure sensor disposed proximally from the ablation unit;

transfemorally advancing the transvascular catheter into an operative position in which the distal portion is disposed within the renal artery of the subject, and the pressure sensor is disposed in an aorta of the subject; and while the transvascular catheter is in the operative position, activating a control unit to drive the electrode unit to apply an electrical current to the nerve tissue.

264. The method according to inventive concept 263, wherein the step of introducing comprises introducing into the subject a transvascular catheter including (1) at a distal portion thereof, an electrode unit and an ablation unit disposed proximally from the electrode unit, and (2) a pressure sensor disposed more than 2 cm proximally from the ablation unit.

265. The method according to inventive concept 263, wherein:

the distal portion includes a first distal portion thereof, the transvascular catheter is bifurcated so as to have the first distal portion and a second distal portion, and transfemorally advancing comprises transfemorally advancing the transvascular catheter such that the second distal portion is disposed within another renal artery of the subject.

266. The method according to inventive concept 263, wherein activating the control unit comprises activating a control unit that is coupled to the transvascular catheter, such that the control unit:

drives the electrode unit to apply a non-ablative electrical current to the nerve tissue, subsequently drives the ablation unit to apply a first application of ablative energy to the nerve tissue, receives, from the pressure sensor, (1) a first value of the subject, the first value being indicative of a blood pressure of the subject after a start of the application of the non-ablative electrical current and before the first application of ablative energy, and (2) a second value of the subject, the second value being indicative of the blood pressure of the subject after the first application of ablative energy, and at least in part responsively to a difference between the first value and the second value, drives the ablation unit to apply a second application of ablative energy to the nerve tissue.

267. The method according to any one of inventive concepts 263-266, wherein activating the control unit comprises activating a control unit that is coupled to the transvascular catheter, such that the control unit:

receives, from the pressure sensor, a preliminary blood pressure value of the subject;

iteratively repeats the steps of:

(a) inducing action potentials in the renal nerve tissue by applying an excitatory current to a first portion of the renal nerve tissue, (b) receiving, from the pressure sensor, a detected excited blood pressure value, indicative of a blood pressure of the subject after a start of the application of the excitatory current, and (c) altering a value of at least one property of the excitatory current, until the detected excited blood pressure value crosses a first threshold defined at least in part based on a pre-determined target excited blood pressure value, and subsequently, iteratively repeats the steps of:

(d) applying ablating energy to a second portion of the renal nerve tissue that is further from the kidney than is the first portion of the renal nerve tissue, (e) subsequently, applying, to the first portion of the renal nerve tissue, a selected excitatory current a characteristic of which is at least in part based on the value of the at least one property at which the detected excited blood pressure value crossed the first threshold, and (f) receiving, from the pressure sensor, a detected ablated blood pressure value, indicative of a blood pressure of the subject after a start of the application of the selected excitatory current, until the detected ablated blood pressure value crosses a second threshold defined at least in part based on a target ablated blood pressure value that is generated at least in part based on the preliminary blood pressure value and at least in part based on at least one excited blood pressure value selected from the group consisting of (i) the target excited blood pressure value and (ii) the detected excited blood pressure value.

268. The method according to inventive concept 267, wherein activating the control unit comprises activating the control unit such that the control unit generates the target excited blood pressure value at least in part responsively to the preliminary blood pressure value.

269. The method according to inventive concept 267, further comprising inputting, into an interface of the control unit, the target excited blood pressure value.

270. The method according to inventive concept 267, wherein activating the control unit comprises activating the control unit such that the control unit generates the target ablated blood pressure value at least in part responsively to (1) the preliminary blood pressure value and (2) at least one excited blood pressure value selected from the group consisting of (i) the target excited blood pressure value and (ii) the detected excited blood pressure value.

271. The method according to inventive concept 270, further comprising inputting, into an interface of the control unit, a value indicative of a target degree of ablation of the renal nerve tissue, wherein activating the control unit comprises activating the control unit such that the control unit generates the target excited blood pressure value at least in part responsively to the value indicative of the target degree of ablation.

272. The method according to inventive concept 267, further comprising inputting, into an interface of the control unit, the target ablated blood pressure value.

There is further provided, in accordance with an application of the present invention, an inventive concept including:

273. A method for use with a renal nerve of a subject, the nerve innervating an ipsilateral kidney of the subject, the method comprising:

initiating action potentials at a first site of the nerve by applying a first application of excitatory current to the nerve;

within 60 seconds after a start of the first application, measuring a first blood pressure value of the subject;

after at least 60 seconds from the start of the first application, measuring a second blood pressure value of the subject;

subsequently to applying the first application of excitatory current, applying a first application of ablation energy to a second site of the nerve, a distance between the second site and the ipsilateral kidney being greater than a distance between the first site and the ipsilateral kidney;

subsequently to applying the first application of ablation energy, initiating action potentials at the first site by applying a second application of excitatory current to the nerve;

within 60 seconds after a start of the second application of excitatory current, measuring a third blood pressure value of the subject;

after at least 60 seconds from the start of the second application of excitatory current, measuring a fourth blood pressure value of the subject; and at least in part dependently on a relationship between (1) a difference between the first and third blood pressure values, and (2) a difference between the second and fourth blood pressure values, applying a second application of ablation energy to the nerve.

274. The method according to inventive concept 273, wherein applying the second application of ablation energy comprises applying the second application of ablation energy to the second site of the nerve.

275. The method according to inventive concept 273, wherein applying the second application of ablation energy comprises applying the second application of ablation energy to a third site of the nerve, a distance between the third site and the ipsilateral kidney being smaller than a distance between the first site and the ipsilateral kidney.

276. The method according to inventive concept 275, further comprising:

subsequently to applying the second application of ablation energy, initiating action potentials at the first site by applying a third application of excitatory current to the nerve;

within 60 seconds after the start of the third application of excitatory current, measuring a fifth blood pressure value of the subject; and after at least 60 seconds from the start of the third application of excitatory current, measuring a sixth blood pressure value of the subject.

There is further provided, in accordance with an application of the present invention, an inventive concept including:

277. Apparatus for use with nerve tissue associated with a structure of a body of a subject, the structure having a lumen, the apparatus comprising:

a transvascular catheter, having a distal portion that is configured to be percutaneously advanced to a site in the lumen;

a first ablation unit, disposed at a first longitudinal position of the distal portion, and configured to apply ablation energy to a first portion of the nerve tissue;

a second ablation unit, disposed at a second longitudinal position of the distal portion, and configured to apply ablation energy to a second portion of the nerve tissue;

an electrode unit:

disposed at a third longitudinal position of the distal portion, the third longitudinal position being between the first and second longitudinal positions, and configured to induce action potentials in a third portion of the nerve tissue by applying excitatory current to the third portion of the nerve tissue; and a control unit, configured to drive, independently of each other:
  the electrode unit to apply excitatory current,
  the first ablation unit to apply ablation energy, and
  the second ablation unit to apply ablation energy.
278. The apparatus according to inventive concept 277, further comprising a sensor coupled to the catheter, the sensor configured to detect a factor of the subject, and the control unit configured to receive from the sensor:
  a first value of the factor, detected at a first time after a start of the application of the excitatory current, and
  a second value of the factor, detected at a second time.

There is further provided, in accordance with an application of the present invention, an inventive concept including:
279. A method for use with nerve tissue of a subject, the nerve tissue being associated with a blood vessel of the subject, the method comprising:
  providing a transvascular catheter including a plurality of electrodes at a distal portion of the catheter;
  transluminally advancing the distal portion into the blood vessel such that the plurality of electrodes is distributed along a central longitudinal axis of the blood vessel;
  applying a first application of non-ablating current to the blood vessel by driving the first application of non-ablating current between a first pair of electrodes of the plurality of electrodes;
  after a start of the first application of non-ablating current, detecting a first value of a factor of the subject;
  subsequently, applying a second application of non-ablating current to the blood vessel by driving the second application of non-ablating current between a second pair of electrodes of the plurality of electrodes, a distance between the second pair of electrodes being different to a distance between the first pair of electrodes; and
  after a start of the second application of non-ablating current, detecting a second value of the factor.
280. The method according to inventive concept 279, wherein the first pair of electrodes includes a first electrode and a second electrode, and the second pair of electrodes includes an electrode selected from the group consisting of: the first electrode and the second electrode, and driving the second application comprises driving the second application between the second pair of electrodes that includes the selected electrode.
281. The method according to inventive concept 279, wherein transluminally advancing the distal portion into the blood vessel comprises transluminally advancing the distal portion into the blood vessel such that the plurality of electrodes is arranged parallel to a central longitudinal axis of the blood vessel.
282. The method according to inventive concept 279, further comprising, before the start of the first application and the start of the second application, detecting a third detection of the factor.
283. The method according to inventive concept 279, wherein:
  driving the current between the first pair of electrodes comprises driving the first pair of electrodes to apply the first application of non-ablating current in a first arc subtending a first angular range around the central longitudinal axis of the blood vessel,
  driving the current between the second pair of electrodes comprises driving the second pair of electrodes to apply the second application of non-ablating current in a second arc subtending a second angular range around the central longitudinal axis of the blood vessel, the second angular range at least partly coinciding with the first angular range.
284. The method according to inventive concept 279, wherein:
  driving the current between the first pair of electrodes comprises driving the first pair of electrodes to apply the first application of non-ablating current in a first arc subtending a first angular range around the central longitudinal axis of the blood vessel,
  driving the current between the second pair of electrodes comprises driving the second pair of electrodes to apply the second application of non-ablating current in a second arc subtending a second angular range around the central longitudinal axis of the blood vessel, the second angular range not at all coinciding with the first angular range.
285. The method according to inventive concept 279, wherein:
  the non-ablating current is an excitatory current, configured to induce action potentials in the nerve tissue,
  driving the current between the first pair of electrodes comprises driving the first pair of electrodes to apply a first application of the excitatory current, and
  driving the current between the second pair of electrodes comprises driving the second pair of electrodes to apply a second application of the excitatory current.
286. The method according to inventive concept 279, wherein:
  the non-ablating current is a blocking current, configured to block action potentials in the nerve tissue.
  driving the current between the first pair of electrodes comprises driving the first pair of electrodes to apply a first application of the blocking current, and
  driving the current between the second pair of electrodes comprises driving the second pair of electrodes to apply a second application of the blocking current.
287. The method according to inventive concept 279, wherein advancing the distal portion comprises advancing the distal portion such that the plurality of electrodes is arranged in an arc inside the blood vessel, the arc lying on a transverse plane of the blood vessel at a longitudinal site of the blood vessel.
288. The method according to inventive concept 279, wherein:
  the plurality of electrodes includes a first plurality of electrodes and a second plurality of electrodes,
  advancing the distal portion comprises advancing the distal portion such that (1) the first plurality of electrodes is arranged circumferentially around the central longitudinal axis of the blood vessel at a first longitudinal site of the blood vessel, and (2) the second plurality of electrodes is arranged circumferentially around the central longitudinal axis of the blood vessel at a second longitudinal site of the blood vessel, and
  driving the current between the first pair of electrodes comprises driving the first application of non-ablating current between a first electrode of the first plurality and a first electrode of the second plurality, and driving the current between the second pair of electrodes comprises driving the second application of non-ablating current between a second electrode of the first plurality and a second electrode of the second plurality.
289. The method according to any one of inventive concepts 279-288, further comprising, at least in part dependently on the first value and at least in part dependently on the second value, determining a target site of the blood vessel, the target site being a target site for administration of ablation energy.
290. The method according to inventive concept 289, wherein determining the target site comprises determining an arc for the administration of the ablation energy, the arc subtending an angular range around the central longitudinal axis of the blood vessel.

291. The method according to inventive concept 289, further comprising applying the ablating energy to the target site.

292. The method according to inventive concept 291, wherein applying the ablating energy comprises applying the ablating energy using an ablation unit at a distal portion of the catheter.

293. The method according to inventive concept 292, wherein:
the steps of driving the current between first pair of electrodes, driving the current between the second pair of electrodes, detecting the first value, and detecting the second value are performed by a control unit automatically upon activation of the control unit,
the method further comprises activating the control unit, and
activating the control unit comprises the steps of driving the current between the first pair of electrodes, driving the current between the second pair of electrodes, detecting the first value, and detecting the second value.

294. The method according to inventive concept 293, wherein:
the step of determining the target site is performed by the control unit automatically upon activation of the control unit, and
activating the control unit comprises the step of determining the target site.

295. The method according to inventive concept 294, wherein:
the step of applying the ablating energy is performed by the control unit automatically upon activation of the control unit, and
activating the control unit comprises the step of applying the ablating energy.

296. The method according to any one of inventive concepts 279-288, wherein providing the transvascular catheter comprises providing a transvascular catheter that includes an ablation unit at a distal portion of the catheter, and the method further comprises, at least in part responsively to the first detection and at least in part responsively to the second detection, driving the ablation unit to apply an application of ablation energy to the blood vessel.

297. The method according to inventive concept 296, wherein driving the ablation unit to apply the application of ablation energy comprises driving the ablation unit to apply the application of ablation energy partially circumferentially around the central longitudinal axis of the blood vessel.

298. The method according to inventive concept 296, wherein:
driving the current between the first pair of electrodes comprises driving the first pair of electrodes to apply the first application in a first arc that subtends a first angular range around the central longitudinal axis of the blood vessel,
driving the current between the second pair of electrodes comprises driving the second pair of electrodes to apply the second application in a second arc that subtends a second angular range around the central longitudinal axis of the blood vessel, and
driving the ablation unit to apply the application of ablation energy comprises driving the ablation unit to apply the application of ablation energy in a third arc that subtends a third angular range that at least in part falls within an angular range selected from the group consisting of: the first angular range and the second angular range.

299. The method according to any one of inventive concepts 279-288, wherein:
driving the current between the first pair of electrodes comprises driving the first pair of electrodes to apply the first application in a first arc that subtends a first angular range around the central longitudinal axis of the blood vessel, and
driving the current between the second pair of electrodes comprises driving the second pair of electrodes to apply the second application in a second arc that subtends a second angular range around the central longitudinal axis of the blood vessel.

300. The method according to inventive concept 299, wherein the first arc is a complete circle, and driving the first pair of electrodes to apply the first application in the first arc comprises driving the first pair of electrodes to apply the first application in the complete circle.

301. The method according to any one of inventive concepts 279-288, further comprising driving all the electrodes of the plurality of electrodes to apply a third application of non-ablating current to the blood vessel.

302. The method according to inventive concept 301, wherein driving all the electrodes comprises driving all the electrodes prior to the step of driving the first subset and the step of driving the second subset.

There is further provided, in accordance with an application of the present invention, an inventive concept including:

303. Apparatus for use with nerve tissue associated with a structure of a body of a subject, the structure comprising a wall defining a lumen, the apparatus comprising:
a transluminally-advanceable catheter;
an intravascular device:
coupled to a distal portion of the catheter,
comprising a plurality of needles having a retracted state, being radially-extendable into an extended state, and being configured to penetrate the wall when moved toward the extended state;
a reservoir, configured to contain a liquid comprising ethanol, and in fluid communication with the needles; and
a control unit, configured:
to drive a non-ablative current into the wall via the plurality of needles,
to pump the liquid through the plurality of needles.

304. The apparatus according to inventive concept 303, wherein:
the apparatus is for use with a sensor, configured to detect a factor of the subject,
the control unit is configured:
to sequentially drive respective applications of the non-ablative current via respective subsets of the plurality of needles,
to receive from the sensor a respective value of the factor, the respective value detected by the sensor after a start of the respective application of the non-ablative current, and
to pump the liquid though a selected subset of the plurality of needles, the selected subset being selected at least in part responsively to a relationship between the respective values of the factor.

305. The apparatus according to inventive concept 304, wherein the control unit is configured to automatically select the selected subset.

There is further provided, in accordance with an application of the present invention, an inventive concept including:

306. Apparatus for use with (a) nerve tissue associated with a structure of a body of a subject, the structure comprising a wall defining a lumen, and (b) a sensor, configured to detect a factor indicative of blood pressure of the subject, the apparatus comprising:
a transluminally-advanceable catheter;
an intravascular device:
coupled to a distal portion of the catheter.
comprising a plurality of needles having a retracted state, being radially-extendable into an extended state, and being configured to penetrate the wall when moved toward the extended state;
a control unit, configured, while the needles are in the extended state, to:
during a first period, drive a first application of non-ablative current into the wall via a first subset of the plurality of needles,
during a second period, drive a second application of non-ablative current into the wall via a second subset of the plurality of needles, the second subset being non-identical to the first subset,
receive, from the sensor:
a first value of the factor, detected by the sensor after a start of the first application of the non-ablative current, and
a second value of the factor, detected by the sensor after a start of the second application of the non-ablative current, and
at least in part dependent on a relationship between the first value and the second value, ablate the nerve tissue using at least one of the needles.

307. The apparatus according to inventive concept 306, wherein the control unit is configured to ablate the nerve tissue by driving ablative energy into the wall via at least one of the needles.

308. The apparatus according to inventive concept 306, wherein the control unit is configured to ablate the nerve tissue by pumping a liquid comprising ethanol out of at least one of the needles.

309. The apparatus according to any one of inventive concepts 306-308, wherein the non-ablative current is an excitatory current, configured to induce action potentials in the nerve, and the control unit is configured to drive a first application of the excitatory current during the first period, and to drive a second application of the excitatory current during the second period.

310. The apparatus according to inventive concept 309, wherein the control unit is configured to ablate the nerve tissue using a subset of the needles selected from the group consisting of: the first subset and the second subset, the selected subset of needles being the subset via which the respective application of excitatory current was driven, after the start of which a greatest value of the factor was detected, the greatest value selected from the group consisting of: the first value and the second value.

311. The apparatus according to any one of inventive concepts 306-308, wherein the non-ablative current is a non-ablative blocking current, configured to inhibit propagation of action potentials in the nerve, and the control unit is configured to drive a first application of the non-ablative blocking current during the first period, and to drive a second application of the non-ablative blocking current during the second period.

312. The apparatus according to inventive concept 311, wherein the control unit is configured to ablate the nerve tissue using a subset of the needles selected from the group consisting of: the first subset and the second subset, the selected subset of needles being the subset via which the respective application of non-ablative blocking current was driven, after the start of which a lowest value of the factor was detected, the lowest value selected from the group consisting of: the first value and the second value.

There is further provided, in accordance with an application of the present invention, an inventive concept including:

313. A method for use with nerve tissue of a subject, the nerve tissue being associated with a wall of a blood vessel of the subject, the method comprising:
applying ablation energy to a first site of the wall; and
initiating action potentials in the nerve tissue by applying an application of excitatory current:
from a first electrode in contact with a second site of the wall, the second site being disposed on a first side of the first site,
via the first site, and
to a second electrode in contact with a third site of the wall, the third site being disposed on a second side of the first site.

There is further provided, in accordance with an application of the present invention, an inventive concept including:

314. A method for use with nerve tissue of a subject, the nerve tissue being associated with a wall of a blood vessel of the subject, the method comprising:
increasing a temperature of the wall to less than 45 degrees C. without applying ablating energy to the wall; and
subsequently, ablating the nerve tissue by applying ablating energy to the wall.

There is further provided, in accordance with an application of the present invention, an inventive concept including:

315. A method for use with nerve tissue of a subject, the nerve tissue being associated with a wall of a blood vessel of the subject, the method comprising:
detecting a first value of a factor of the subject;
modifying a temperature of the wall to fall within a range selected from the group consisting of: 10-36 degrees C., 38-42 degrees C., and 42-45 degrees C.;
while the temperature of the wall is within the selected range, inducing action potentials in the nerve tissue by applying an application of excitatory current to the nerve tissue; and
after a start of the application of excitatory current, detecting a second value of the factor.

316. The method according to inventive concept 315, wherein the selected range is 10-36 degrees C.

317. The method according to inventive concept 315, wherein the selected range is 38-42 degrees C.

318. The method according to inventive concept 315, wherein the step of detecting the first value is performed subsequently to the step of modifying the temperature.

319. The method according to any one of inventive concepts 315-318, further comprising, subsequently to the detecting, applying ablative energy to the nerve tissue, at least in part responsively to a relationship between the first value and the second value.

There is further provided, in accordance with an application of the present invention, an inventive concept including:

320. Apparatus for use with (a) nerve tissue associated with a structure of a body of a subject, the structure having a lumen, and (b) a sensor, configured to detect a factor of the subject, the apparatus comprising:
a transvascular catheter, having a distal portion that is configured to be percutaneously advanced to a site in the lumen;
a plurality of electrodes, coupled to the distal portion; and
a control unit, configured to:
during a first period, block endogenous action potentials from propagating through the nerve tissue by driving at least one electrode of the plurality of electrodes to apply a non-ablative blocking current to the nerve tissue, during a second period, initiate action potentials in the nerve tissue by driving at least one electrode of the plurality of electrodes to apply an excitatory current to the nerve tissue, receive, from the sensor:
  a first value of the factor, detected by the sensor after a start of the application of the non-ablative blocking current, and
  a second value of the factor, detected after a start of the application of the excitatory current, and provide at least one output, the at least one output being at least in part dependent on a relationship between the first value and the second value.

321. The apparatus according to inventive concept 320, wherein the apparatus does not comprise an intravascular ablation unit coupled to the catheter.

322. The apparatus according to any one of inventive concepts 320-321, further comprising the sensor.

323. The apparatus according to inventive concept 322, wherein the sensor comprises an intravascular blood-pressure sensor, and is coupled to the catheter.

There is further provided, in accordance with an application of the present invention, an inventive concept including:

324. A method for use with nerve tissue of a subject, the nerve tissue conducting endogenous action potentials to an anatomical structure of the subject, the structure being capable of altering a parameter of the subject at least in part responsively to the endogenous action potentials, the method comprising:

during a first period, performing a first detection of a factor indicative of the parameter of the subject at rest;

during a second period, initiating action potentials in the nerve tissue by applying an excitatory current to the nerve tissue and, after a start of the application of the excitatory current, performing a second detection of the factor indicative of the parameter of the subject; and at least in part responsively to the first detection and to the second detection, selecting the subject for a treatment including ablation of the nerve tissue.

There is further provided, in accordance with an application of the present invention, an inventive concept including:

325. A method for use with nerve tissue of a subject, the nerve tissue conducting endogenous action potentials to an anatomical structure of the subject, the structure being capable of altering a parameter of the subject at least in part responsively to the endogenous action potentials, the method comprising:

during a first period, blocking the endogenous action potentials from propagating through the nerve tissue by applying a non-ablative blocking current to the nerve tissue and, after a start of the application of the non-ablative blocking current, detecting a first value of a factor indicative of the parameter of the subject; and during a second period, initiating unidirectional action potentials in the nerve tissue by applying an excitatory current to the nerve tissue and, after a start of the application of the excitatory current, detecting a second value of the factor indicative of the parameter of the subject.

There is further provided, in accordance with an application of the present invention, an inventive concept including:

326. A method for use with nerve tissue of a subject, the nerve tissue being associated with a blood vessel of a subject, the method comprising:

providing a transvascular catheter including a plurality of electrodes at a distal portion of the catheter;

transluminally advancing the distal portion into the blood vessel such that the plurality of electrodes is arranged around a central longitudinal axis of the blood vessel;

driving a first subset of the plurality of electrodes to apply a first application of non-ablating current to the blood vessel, the first subset including one or more but not all of the electrodes of the plurality of the electrodes;

after a start of the first application of non-ablating current, detecting a first value of a factor of the subject;

subsequently, driving a second subset of the plurality of electrodes to apply a second application of non-ablating current to the blood vessel, the second subset including one or more but not all of the electrodes of the plurality of the electrodes, and being non-identical to the first subset; and after a start of the second application of non-ablating current, detecting a second value of the factor.

327. The method according to inventive concept 326, wherein:

driving the first subset comprises driving the first subset to apply the first application of non-ablating current in a first arc subtending a first angular range around the central longitudinal axis of the blood vessel, driving the second subset comprises driving the second subset to apply the second application of non-ablating current in a second arc subtending a second angular range around the central longitudinal axis of the blood vessel, the second angular range at least partly coinciding with the first angular range.

328. The method according to inventive concept 326, wherein:

driving the first subset comprises driving the first subset to apply the first application of non-ablating current in a first arc subtending a first angular range around the central longitudinal axis of the blood vessel, and driving the second subset comprises driving the second subset to apply the second application of non-ablating current in a second arc subtending a second angular range around the central longitudinal axis of the blood vessel, the second angular range not at all coinciding with the first angular range.

329. The method according to inventive concept 326, further comprising, before the start of the first application and the start of the second application, detecting a third detection of the factor.

330. The method according to inventive concept 326, wherein:

the non-ablating current is an excitatory current, configured to induce action potentials in the nerve tissue, driving the first subset to apply the first application comprises driving the first subset to apply a first application of the excitatory current, and driving the second subset to apply the second application comprises driving the second subset to apply a second application of the excitatory current.

331. The method according to inventive concept 326, wherein:

the non-ablating current is a blocking current, configured to block action potentials in the nerve tissue, driving the first subset to apply the first application comprises driving the first subset to apply a first application of the blocking current, and driving the second subset to apply the second application comprises driving the second subset to apply a second application of the blocking current.

332. The method according to inventive concept 326, wherein advancing the distal portion comprises advancing the distal portion such that the plurality of electrodes is arranged in an arc inside the blood vessel, the arc lying on a transverse plane of the blood vessel at a longitudinal site of the blood vessel.

333. The method according to inventive concept 326, wherein:
the plurality of electrodes includes a first plurality of electrodes,
the catheter includes a second plurality of electrodes at the distal portion,
advancing the distal portion comprises advancing the distal portion such that (1) the first plurality of electrodes is disposed at a first longitudinal site of the blood vessel, and (2) the second plurality of electrodes is arranged circumferentially around the central longitudinal axis of the blood vessel at a second longitudinal site of the blood vessel, and
driving the first subset comprises applying the first application of non-ablating current between the first subset of the first plurality of electrodes and a respective first subset of the second plurality of electrodes, the first subset of the second plurality of electrodes including one or more but not all of the electrodes of the second plurality of the electrodes.

334. The method according to any one of inventive concepts 326-333, further comprising, at least in part dependently on the first value and at least in part dependently on the second value, determining a target site of the blood vessel, the target site being a target site for administration of ablation energy.

335. The method according to inventive concept 334, wherein determining the target site comprises determining an arc for the administration of the ablation energy, the arc subtending an angular range around the central longitudinal axis of the blood vessel.

336. The method according to inventive concept 334, further comprising applying the ablating energy to the target site.

337. The method according to inventive concept 336, wherein applying the ablating energy comprises applying the ablating energy using an ablation unit at a distal portion of the catheter.

338. The method according to inventive concept 337, wherein:
the steps of driving the first subset, driving the second subset, detecting the first value, and detecting the second value are performed by a control unit automatically upon activation of the control unit,
the method further comprises activating the control unit, and
activating the control unit comprises the steps of driving the first subset, driving the second subset, detecting the first value, and detecting the second value.

339. The method according to inventive concept 338, wherein:
the step of determining the target site is performed by the control unit automatically upon activation of the control unit, and
activating the control unit comprises the step of determining the target site.

340. The method according to inventive concept 339, wherein:
the step of applying the ablating energy is performed by the control unit automatically upon activation of the control unit, and
activating the control unit comprises the step of applying the ablating energy.

341. The method according to any one of inventive concepts 326-333, wherein providing the transvascular catheter comprises providing a transvascular catheter that includes an ablation unit at a distal portion of the catheter, and the method further comprises, at least in part responsively to the first detection and at least in part responsively to the second detection, driving the ablation unit to apply an application of ablation energy to the blood vessel.

342. The method according to inventive concept 341, wherein driving the ablation unit to apply the application of ablation energy comprises driving the ablation unit to apply the application of ablation energy partially circumferentially around the central longitudinal axis of the blood vessel.

343. The method according to inventive concept 341, wherein:
driving the first subset comprises driving the first subset to apply the first application in a first arc that subtends a first angular range around the central longitudinal axis of the blood vessel,
driving the second subset comprises driving the second subset to apply the second application in a second arc that subtends a second angular range around the central longitudinal axis of the blood vessel, and
driving the ablation unit to apply the application of ablation energy comprises driving the ablation unit to apply the application of ablation energy in a third arc that subtends a third angular range that at least in part falls within an angular range selected from the group consisting of: the first angular range and the second angular range.

344. The method according to any one of inventive concepts 326-333, wherein:
driving the first subset comprises driving the first subset to apply the first application in a first arc that subtends a first angular range around the central longitudinal axis of the blood vessel, and
driving the second subset comprises driving the second subset to apply the second application in a second arc that subtends a second angular range around the central longitudinal axis of the blood vessel.

345. The method according to inventive concept 344, wherein the first arc is a complete circle, and driving the first subset to apply the first application in the first arc comprises driving the first subset to apply the first application in the complete circle.

346. The method according to any one of inventive concepts 326-333, further comprising driving all the electrodes of the plurality of electrodes to apply a third application of non-ablating current to the blood vessel.

347. The method according to inventive concept 346, wherein driving all the electrodes comprises driving all the electrodes prior to the step of driving the first subset and the step of driving the second subset.

There is further provided, in accordance with an application of the present invention, an inventive concept including:

348. Apparatus for use with nerve tissue associated with a blood vessel of a subject, the apparatus comprising:
a transvascular catheter comprising a plurality of electrodes arranged around a central longitudinal axis of a distal portion of the catheter, the distal portion of the catheter being configured to be transluminally advanced into the blood vessel;
a sensor, configured to detect a factor of the subject; and
a control unit, configured to:
drive a first subset of the plurality of electrodes to apply a first application of non-ablating current to the blood vessel, the first subset comprising one or more but not all of the electrodes of the plurality of the electrodes, receive from the sensor a first value of the factor, detected after a start of the first application of non-ablating current, subsequently, drive a second subset of the plurality of electrodes to apply a second application of non-ablating current to the blood vessel, the second subset comprising one or more but not all of the electrodes of the plurality of the electrodes, and being non-identical to the first subset, and receive from the sensor a second value of the factor, detected after a start of the second application of non-ablating current.

The present invention will be more fully understood from the following detailed description of applications thereof, taken together with the drawings, in which:

BRIEF DESCRIPTION OF THE DRAWINGS

FIGS. 2A-H are schematic illustrations of a technique for facilitating ablation of nerve tissue of the blood vessel of the subject, in accordance with some applications of the invention;

FIG. 4 is a flow diagram of at least some steps in the techniques described with reference to FIGS. 2A-H and 3;

FIGS. 5A-B are schematic illustrations of systems for ablating nerve tissue of at least one renal artery of a subject, in accordance with some applications of the invention;

FIGS. 6-8 are schematic illustrations of systems for ablating nerve tissue of a blood vessel of a subject, in accordance with some applications of the invention;

FIGS. 9A-B are schematic illustrations of electrodes, in accordance with some applications of the invention;

FIG. 10 is a now diagram, illustrating at least some steps in ablating nerve tissue of the renal artery of the subject, in accordance with some applications of the invention;

FIGS. 15A-F are schematic illustrations of a system and technique for facilitating ablation of nerve tissue of a subject, in accordance with some applications of the invention;

FIGS. 16A-G are schematic illustrations of a system and technique for facilitating ablation of nerve tissue of a subject, in accordance with some applications of the invention;

FIGS. 17B-E are schematic illustrations of stimulating electric currents being driven into a wall of a blood vessel, in accordance with some applications of the present invention;

FIG. 18 is a flow chart showing at least some steps of a technique for facilitating ablation of nerve tissue of a subject, in accordance with some applications of the invention;

FIGS. 19, 20, and 21A-B are a schematic illustration of a system for facilitating ablation of nerve tissue of a subject, a flow chart showing at least some steps of a technique for use with the system, and graphs relating to the technique, in accordance with some applications of the invention;

FIG. 30 is a schematic illustration showing data used to decide whether to perform an ablation, in accordance with some applications of the present invention.

DETAILED DESCRIPTION OF APPLICATIONS

Figure 1:
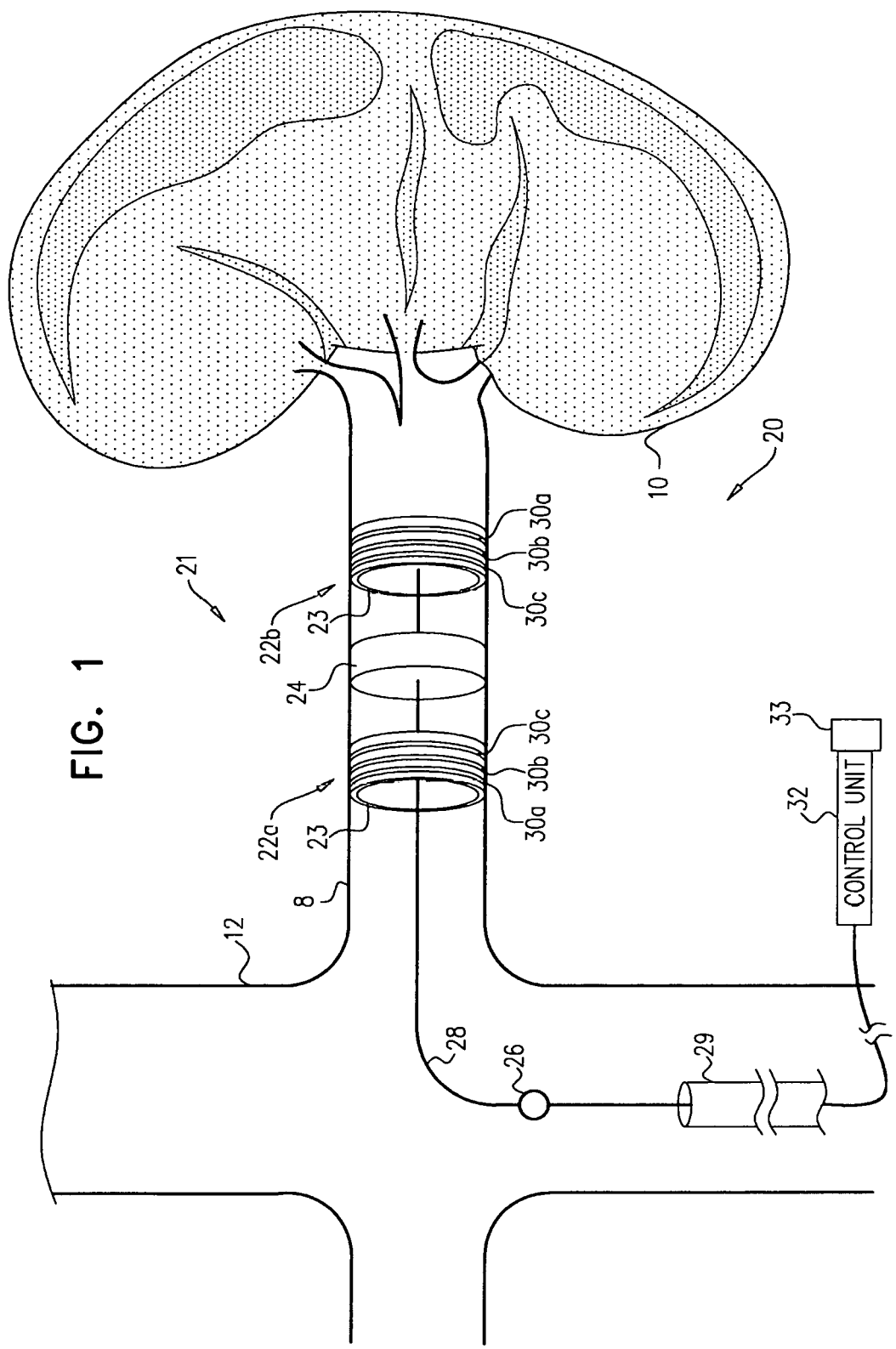
FIG. 1 is a schematic illustration of a system for ablating nerve tissue of a blood vessel of a subject, in accordance with some applications of the invention.

Reference is made to FIG. 1, which is a schematic illustration of a system 20 for ablating nerve tissue of a blood vessel of a subject, in accordance with some applications of the invention. System 20 comprises an intravascular device 21 that comprises at least one electrode unit 22, an ablation unit 24, and a sensor 26. Sensor 26 is configured to detect a factor of the subject, such as a factor indicative of blood pressure, heart rate, heart rate variability, and/or blood flow. Ablation unit 24 is configured to ablate the nerve tissue of the blood vessel by applying ablation energy thereto, so as to block endogenous action potentials from propagating through the nerve tissue (e.g., to ablate nerve tissue in a first portion of the nerve tissue, so as to permanently block pathogenic action potentials from propagating past the first portion of the nerve tissue). Electrode unit 22 is configured to apply a non-ablative electrical current to the nerve tissue, typically so as to initiate and/or block action potentials in the nerve tissue (e.g., to apply the non-ablative electrical current to a second portion of the nerve tissue, so as to initiate and/or temporarily block action potentials in the second portion of the nerve tissue).

Typically, when electrode unit 22 is configured to initiate action potentials in the nerve tissue, it is configured to initiate action potentials that have similar characteristics and/or effects as the endogenous action potentials that the ablation unit is configured to block by ablating the nerve tissue. The parameter that sensor 26 is configured to detect is typically a parameter that changes in response to action potentials in the nerve tissue (e.g., in response to the endogenous action potentials and the induced action potentials, and in response to the blocking of the endogenous action potentials). That is, sensor 26 is configured to detect a physiological response to electrode unit 22 blocking the endogenous action potentials and/or initiating the induced action potentials, and/or to ablation unit 24 ablating the nerve tissue, and thereby blocking the action potentials.

Although units 22a, 22b and 24 are shown as distinct elements, for some applications intravascular device 21 is an integrated unit that comprises and/or defines units 22a, 22b and 24 (e.g., disposed on a single body 23). For example, device 21 may define units 22a, 22b and 24 by comprising the components (e.g., electrodes) of units 22a, 22b and 24 (e.g., device 21 may comprise a stent-like body and a plurality of electrodes, distributed along the length of the body).

Typically, at least electrode unit 22 and ablation unit 24 are coupled to a single longitudinal member, such as a catheter 28, and the longitudinal member, electrode unit 22, and ablation unit 24 are advanceable together, such as within and/or through a sheath 29. For some applications, and as shown in FIG. 1, sensor 26 is also coupled to catheter 28 and is advanceable therewith.

For some applications, and as shown in FIG. 1, system 20 comprises two electrode units 22 (e.g., electrode unit 22a and electrode unit 22b). Electrode unit 22a is disposed proximally from ablation unit 24, and electrode unit 22b is disposed distally from ablation unit 24. Typically, each electrode unit 22 is configured to initiate unidirectional action potentials in the nerve tissue, such as by providing an excitatory current adjacent to a non-ablative blocking current, e.g., as is known in the nerve cuff art, such as a cathodic or anodic DC blocking current, or a high-frequency (HF) blocking current (e.g., an HF blocking current having a frequency of greater than 4 kHz, less than 6 kHz and/or between 4 and 6 kHz). For example, each electrode unit 22 may comprise one or more (e.g., three or more) electrodes 30 (e.g., electrodes 30a, 30b, and 30c), electrodes 30a and 30b being driven (e.g., by a control unit 32) to apply a non-ablative blocking current, and electrode 30c being driven to apply an excitatory current that initiates action potentials that thereby propagate only in the direction away from the other two electrodes (i.e., the action potentials are blocked from propagating past the other two electrodes). Typically, the excitatory current has a lower frequency than the non-ablative blocking current. Further typically, the excitatory current has a frequency of greater than 1 Hz and/or less than 100 Hz, such as between 1 and 100 Hz, e.g., between 10 and 100 Hz. When each electrode unit 22 is configured to initiate unidirectional action potentials, the electrode units are oriented on catheter 28 such that the unidirectional action potentials initiated by each electrode unit propagate toward the nerve tissue that is adjacent to ablation unit 24 (e.g., toward the first portion of the nerve tissue).

For applications in which system 20 comprises two electrode units, the electrode units are thereby also oriented such that the unidirectional action potentials initiated by each electrode unit propagate toward the other electrode unit. For applications in which system 20 comprises only one electrode unit, that electrode unit may comprise electrode unit 22a or 22b (e.g., that electrode unit may be disposed in the position and/or orientation described for electrode unit 22a or 22b). It should be noted that, although control unit 32 is shown in FIG. 1 as being outside of the blood vessel(s) in which the electrode units and ablation unit are disposed (e.g., outside the body of the subject), for some applications, control unit 32 and/or other controllers are configured to be intracorporal (e.g., to be disposed within the blood vessel(s) in which the electrode units and ablation unit are disposed).

For some applications, ablation unit 24 comprises one or more electrodes, and is configured to ablate the nerve tissue by applying radio frequency (RF) current to the nerve tissue (e.g., ablation unit 24 comprises an RF ablation unit that is configured to be driven by control unit 32 to apply the RF current). For some applications, the RF current has a frequency of above 5 kHz and/or below 1 GHz, such as between 5 kHz and 1 GHz (e.g., 10 kHz-10 MHz. e.g., 50 kHz-1 MHz, e.g., 300 kHz-1 MHz. e.g., 300 kHz-500 kHz). For some such applications, ablation unit 24 comprises a plurality of electrodes arranged at different positions along the axis of catheter 28 (e.g., at different distances from the electrode unit), such that when disposed within renal artery 8, each of the plurality of electrodes of the ablation unit is disposed adjacent to a different site of the nerve tissue of the renal artery. Typically, for such applications, a different one of the plurality of electrodes is used for each application of ablation energy (described hereinbelow), such that a different site of nerve tissue is ablated by each application of ablation energy.

For some applications, ablation unit 24 comprises one or more ultrasound transducers, and is configured to ablate the nerve tissue by applying ultrasound energy to the nerve tissue (e.g., ablation unit 24 comprises an ultrasound ablation unit that is configured to be driven by control unit 32 to apply the ultrasound energy). Ablation unit 24 may alternatively or additionally be configured to ablate the nerve tissue cryogenically, using laser, using resistive heating, using chemical ablation, or via another ablation mechanism.

Reference is now made to FIGS. 1 and 2A-H, FIGS. 2A-H being schematic illustrations of a technique for facilitating ablation of nerve tissue of the blood vessel of the subject using system 20, in accordance with some applications of the invention. In FIGS. 1 and 2A-H, the blood vessel comprises a renal artery 8 of the subject, disposed between a kidney 10 and the aorta 12 (e.g., the abdominal aorta) of the subject, and system 20 is configured to ablate nerve tissue of the renal artery, so as to treat hypertension. However, for other applications, system 20 may be used to ablate nerve tissue of another blood vessel, such as the carotid artery (e.g., the carotid sinus) or the aortic arch. For example, hypertension may alternatively or additionally be treated by ablation of chemoreceptors and/or baroreceptors in the carotid sinus, and/or nerve tissue associated therewith, and/or ablation of sympathetic nerve tissue of the aortic arch.

Furthermore, system 20 may be used to ablate nerve tissue at other sites, such as at a pulmonary vein ostium.

System 20 is advanced percutaneously (e.g., transluminally, such as transfemorally) such that at least electrode units 22a and 22b, and ablation unit 24 are disposed within renal artery 8. Thereby, electrode units 22a and 22b, and ablation unit 24 are adjacent to respective portions of the nerve tissue of the renal artery. Typically, sensor 26 is configured to detect a parameter indicative of blood pressure of the subject (e.g., sensor 26 may comprise a pressure sensor). Typically, sensor 26 is coupled to catheter 28 such that when the electrode units and ablation unit are disposed in renal artery 8, the sensor is disposed in aorta 12 (or alternatively in the femoral artery). For example, sensor 26 may be disposed greater than 2 cm and/or less than 70 cm (e.g., between 2 and 50 cm, such as between 2 and 30 cm, or between 5 and 40 cm) proximally from intravascular device 21 and/or one or more components thereof. Alternatively, system 20 may be configured such that sensor 26 is disposed in renal artery 8. Sensor 26 may alternatively be configured to detect a parameter indicative of blood flow of the subject. For example, sensor 26 may comprise an ultrasound transceiver, configured to detect the blood flow using Doppler ultrasound. For some such applications, sensor 26 may be extracorporeal (e.g., not coupled to catheter 28).

Following delivery to renal artery 8, electrode units 22a and 22b are typically expanded from a compressed delivery state, to an expanded state in which electrodes 30 are placed in contact with the wall of the renal artery, typically in a manner in which at least some (e.g., most) fluid communication is maintained between the aorta 12 and kidney 10 (i.e., the intravascular device is generally non-occlusive). For example, and as shown in FIGS. 1 and 2A-H, each electrode unit may comprise a body 23 (e.g., a support structure), such as a balloon (e.g., a tubular balloon that defines a lumen therethrough), a "basket", a stent, or a longitudinal structure configured to assume a helix within the renal artery, on which electrodes 30 are disposed. Alternatively, the ablation and electrode units may be integrated on a single body. For some applications, each electrode unit may comprise discrete "lasso"-type electrodes that are not coupled to a tubular element. However, for simplicity, throughout most of this application the body on which the electrodes are disposed is shown as generally tubular, as shown in FIG. 1. Alternatively, the intravascular device may in fact be generally occlusive (e.g., may comprise a balloon that generally occludes the renal artery when inflated). Various embodiments of bodies on which electrodes may be disposed are described with reference to FIGS. 23A-26.

For some applications (e.g., for applications in which ablation unit 24 comprises an RF ablation unit), ablation unit 24 is also expanded from a compressed delivery state to an expanded state thereof. For some such applications, electrode units 22 and ablation unit 24 are disposed on a single body, and/or comprise an integrated device. Alternatively (e.g., for applications in which ablation unit 24 comprises an ultrasound ablation unit), ablation unit 24 is not expanded (e.g., does not require contact with the wall of renal artery 8).

FIGS. 2A-H show sequential steps in a technique of ablating nerve tissue of renal artery 8, using system 20, in accordance with some applications of the invention. Each of FIGS. 2A-H shows a state of system 20 for a respective step, and a corresponding illustrative chart of blood pressure detected up until, and including, the respective step.

Following placement of system 20 in the body of the subject (e.g., as described hereinabove), sensor 26 detects a blood pressure p_A of the subject (FIG. 2A). For some applications, detected blood pressure p_A represents an "untreated" blood pressure. Endogenous efferent action potentials 40 and endogenous afferent action potentials 42 are shown propagating along nerve tissue of renal artery 8 (e.g., between kidney 10 and the central nervous system (CNS) of the subject). It is to be noted that blood pressure p_A, and the other detected blood pressures described herein, are typically each detected while the subject is in the same state (e.g., reclining and/or sedated), so as to reduce variability.

FIG. 2B shows electrode units 22a and 22b each applying a non-ablative blocking current to the nerve tissue of renal artery 8. It is to be noted that throughout the specification, the blocking current is referred to as the "non-ablative blocking current," so as to be distinct from any current of ablative energy applied by the ablation unit, which may otherwise be considered a "blocking current" because of the blocking effect of the resulting ablation. It is to be further noted that, although the excitatory current applied by the electrode units is also non-ablative, it is generally referred to as the "excitatory current".

As described hereinabove, for some applications, the electrode units drive the non-ablative blocking current via electrodes 30a and 30b. For some applications, only one of the electrode units applies the non-ablative blocking current. Endogenous efferent action potentials 40 and endogenous afferent action potentials 42 are shown being blocked from propagating along nerve tissue of renal artery 8, by the non-ablative blocking current. It is hypothesized that this blocking of endogenous action potentials has similar effects to ablation of nervous tissue of the renal artery (e.g., to decrease systemic blood pressure), as is known in the art.

After the start of the application of the non-ablative blocking current (e.g., while the non-ablative blocking current is being applied, or after it has stopped being applied) sensor 26 detects a blood pressure p_B of the subject. (In general, sensing may also be performed at any other time, e.g., continuously.) For example, the blood pressure may be detected after a duration in which blood pressure is allowed to respond to the reduction in renal nerve activity. The non-ablative blocking current may be calibrated in real-time (e.g., by adjusting amplitude, frequency and/or duty cycle), so as to establish the current that results in the lowest blood pressure in the subject. In general, p_B represents a hypothetical lowest blood pressure achievable by a hypothetical perfect ablation of the nerve tissue of renal artery 8, that blocks all action potentials from propagating therealong.

FIG. 2C shows electrode units 22a and 22b initiating respective action potentials 50 and 52 (i.e., induced action potentials) in the nerve tissue of renal artery 8, by applying an excitatory current to the nerve tissue. As described hereinabove, for some applications, each electrode unit drives the excitatory current via electrode 30c. As also described hereinabove, the electrode units are typically configured to initiate unidirectional action potentials, and are oriented such that the unidirectional action potentials propagate toward the nerve tissue adjacent to ablation unit 24 and toward the other electrode unit. That is, (1) action potentials 50, initiated by electrode unit 22a are typically efferent, and propagate from unit 22, past ablation unit 24, and toward kidney 10, and (2) action potentials 52, initiated by electrode unit 22b are typically afferent, and propagate from unit 22, past ablation unit 24, and toward aorta 12 and the CNS of the subject.

It is hypothesized that, by contrast to the blocking of endogenous action potentials, initiation of action potentials 50 and 52 has similar effects to increased endogenous action potentials (e.g., to increase systemic blood pressure). For example, it is hypothesized that action potentials 50 induce kidney 10 to increase systemic blood pressure via the sympathetic pathway, and action potentials 52 induce the CNS to increase systemic blood pressure via the sympathetic pathway. It is further hypothesized that the magnitude of the effects of action potentials 50 and 52 may be greater than those of the endogenous action potentials, and/or that action potentials 50 and 52 are configurable to have such greater effects.

After the start of the application of the excitatory current (e.g., while the excitatory current is being applied, or after it has stopped being applied), sensor 26 detects a blood pressure p_C of the subject. For example, the blood pressure may be detected after a duration in which blood pressure is allowed to respond to the increase in renal nerve activity. The excitatory current may be calibrated in real-time (e.g., by adjusting amplitude, frequency and/or duty cycle), so as to establish the current that results in the highest blood pressure in the subject. For some applications, p_C represents a hypothetical highest blood pressure achievable by a high-level (e.g., hypothetical maximum) renal nerve activity (e.g., the highest blood pressure achievable by the body of the subject via renal nerve activity).

Although FIG. 2C shows two opposite-facing unidirectional electrode units, it is noted that for some applications, only one electrode unit is used, and for some applications, the electrode unit(s) are not unidirectional. For applications in which two electrode units are used, the operation of the electrode units may be temporally offset with respect to each other, so as to reduce interference therebetween. For example, although on a relatively large timescale, electrode unit 22a may initiate induced action potentials 50 at generally the same time as electrode unit 22b initiates induced action potentials 52, nevertheless, on a relatively small timescale, the action potentials are typically alternated (e.g., as indicated by action potentials 50 and 52 being labeled as being applied at "time=t" and "time=t+delta t", respectively).

Figure 2H:
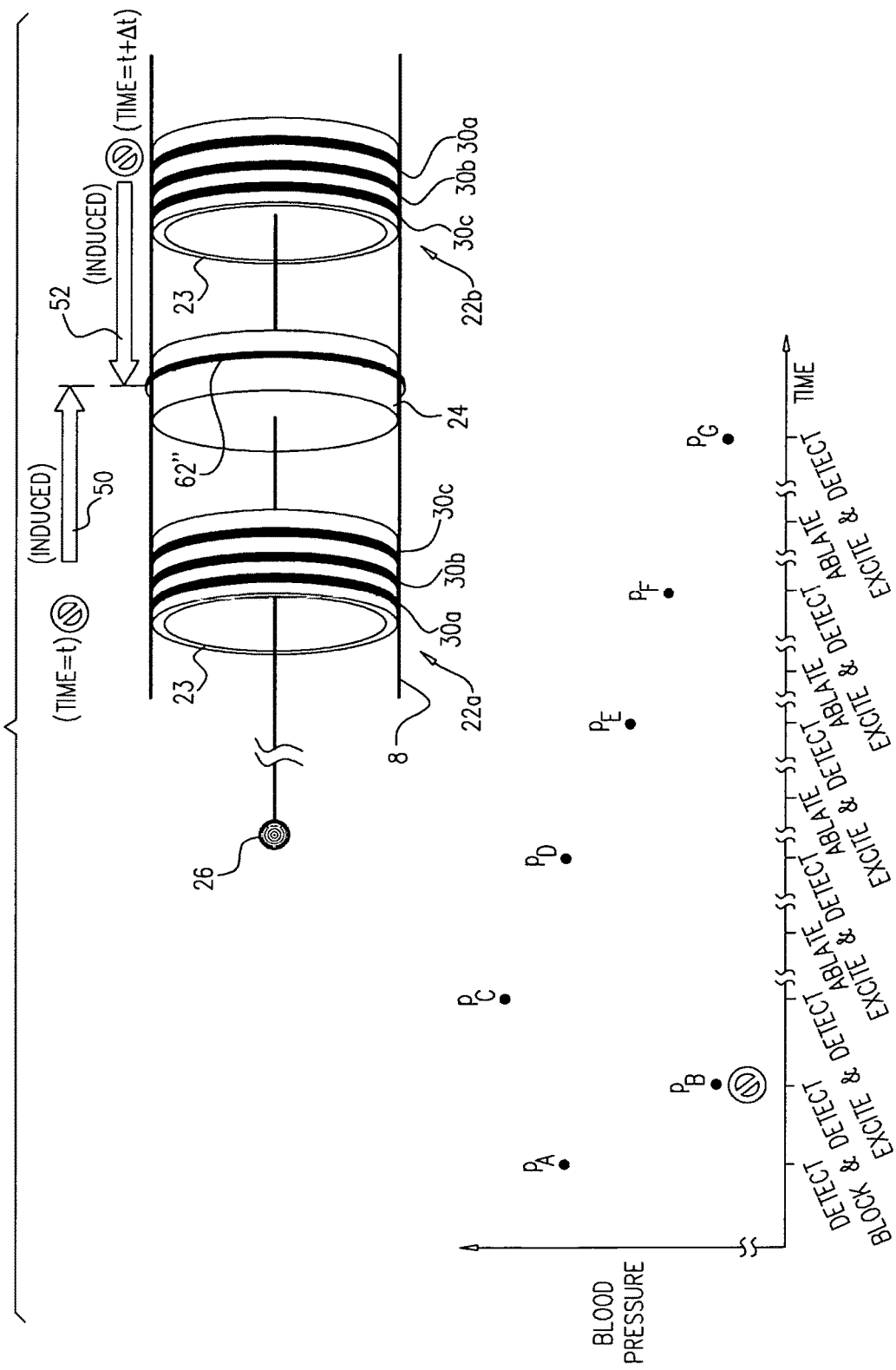

It is to be noted that, although FIGS. 2A-H show sequential steps, the steps described with reference to FIGS. 2A-C may be performed in a different order (e.g., the step described with reference to FIG. 2C may be performed before the step described with reference to FIG. 2B).

FIG. 2D shows ablation unit 24 applying a first application of ablative energy 60 (e.g., ablating RF energy) to the nerve tissue of renal artery 8. It is desirable to ablate renal artery tissue to a degree that is sufficient to achieve a desired decrease of renal nerve activity, but not to a greater degree. The first application of ablative energy 60 is typically configured to be insufficient to ablate the nerve tissue to the desired degree (e.g., insufficient to completely ablate the nerve tissue). For example, first application 60 may be configured to be sufficient to fully ablate nerve tissue in less than 50% (e.g., less than 20%, such as less than 10%) of the general population. That is, first application 60 generates, in the wall of renal artery 8, a lesion 62 (e.g., a circumferential lesion) that is sufficient to completely block renal nerve activity in less than 50% (e.g., less than 20%, such as less than 10%) of the general population.

FIG. 2D does not show the non-ablative blocking current being applied by electrode units 22a and 22b during the application of the ablative energy by ablating unit 24. However, for some applications, the non-ablative blocking current is applied at this time. For some such applications, the application of the non-ablative blocking current during the application of the ablative energy reduces pain experienced by the subject, e.g., by inducing local paresthesia and/or anesthesia. The non-ablative blocking current that is used to induce this pain relief may have the same characteristics as, or different characteristics from, the non-ablative blocking current used to block endogenous signals in the nerve tissue being ablated. For some applications, a distinct electrode unit is used for application of the pain-relieving non-ablative blocking current. For some applications, another pain-relief method (e.g., providing an analgesic drug) is alternatively or additionally used.

Subsequent to first application 60, electrode units 22a and 22b again initiate induced action potentials 50 and 52, by again applying the excitatory current (FIG. 2E). Action potentials 50 and 52 are at least in part blocked from propagating past lesion 62 in the nerve tissue (illustrated by the portions of the arrows of the action potentials that are disposed past lesion 62 being broken). After the start of the application of the excitatory current (e.g., while the excitatory current is being applied, or after it has stopped being applied) sensor 26 detects a blood pressure p_D of the subject. For example, the blood pressure may be detected after a duration in which blood pressure is allowed to respond to action potentials 50 and 52. Detected blood pressure p_D may thereby represent a hypothetical highest blood pressure achievable by a high-level (e.g., hypothetical maximum) renal nerve activity, following first application of ablative energy 60 (e.g., a high-level (e.g., hypothetical maximum) renal nerve activity in the presence of lesion 62). Due to the reduced propagation of induced action potentials 50 and 52 caused by lesion 62, detected blood pressure p_D is typically lower than detected blood pressure p_C. Pressure p_D is typically greater than pressure p_B (e.g., due to the typical configuration of first application of ablative energy 60 to be typically insufficient to completely ablate the nerve tissue).

Subsequently, ablation unit 24 typically applies a second application of ablative energy 60' to the nerve tissue of renal artery 8, thereby increasing the degree of ablation of the lesion (now designated 62' (FIG. 2F)). Second application 60' may have the same characteristics (e.g., intensity) as first application 60, or may be different (e.g., may have a greater or lower intensity). For example, if sensor 26 determines that the reduction in systemic blood pressure due to first application of ablative energy 60 is significantly less than is desired, then second application of ablative energy 60' may be set to have a higher intensity than first application of ablative energy 60. Similarly, if sensor 26 determines that the reduction in systemic blood pressure due to first application of ablative energy 60 is close to a target level (e.g., a desired level), then second application of ablative energy 60' may be set to have an equal or lower intensity than first application of ablative energy 60. (In general, the intensity of applied energy may be varied using techniques known in the art, such as by varying amplitude, pulse width, frequency, duration of energy application, or duty cycle of energy application.)

Subsequent to second application of ablative energy 60', electrode units again initiate action potentials 50 and 52 by applying the excitatory current (FIG. 2G). Due to the increased ablation of the lesion, action potentials 50 and 52 are blocked from propagating past lesion 62', to a greater degree than they were from propagating past lesion 62 (illustrated by the broken portions of the arrows of the action potentials in FIG. 2G, being more broken than the same portions in FIG. 2G). After the start of the application of the excitatory current (e.g., while the excitatory current is being applied, or after it has stopped being applied) sensor 26 detects a blood pressure p_E of the subject. For example, the blood pressure may be detected after a duration in which blood pressure is allowed to respond to action potentials 50 and 52. Detected blood pressure p_D may thereby represent a hypothetical highest blood pressure achievable by a high-level (e.g., hypothetical maximum) renal nerve activity, following second application of ablative energy 60' (e.g., a high-level (e.g., hypothetical maximum) renal nerve activity in the presence of lesion 62'). Due to the further reduced propagation of induced action potentials 50 and 52 caused by lesion 62', detected blood pressure p_E is typically lower than detected blood pressure p_D.

The cycle of ablating nerve tissue, initiating action potentials, and detecting blood pressure (e.g., as described with reference to FIGS. 2D-E, and FIGS. 2F-G) may be repeated as necessary. FIG. 2H shows an example in which a further two such cycles have been performed, and respective detected blood pressures p_F and p_G have been obtained. Induced action potentials 50 and 52 are completely blocked from propagating past the lesion, which is now designated 62". It is to be noted that, for some applications and/or for some subjects, fewer or more cycles may be useful to achieve a desired degree of blocking (e.g., complete blocking). For example, for some subjects, only one application of ablation energy is applied.

Reference is again made to FIGS. 2A-H. For some applications, impedance between electrode units 22a and 22b is measured at each cycle, so as to further facilitate the determination of the achieved degree of ablation.

Figure 3:
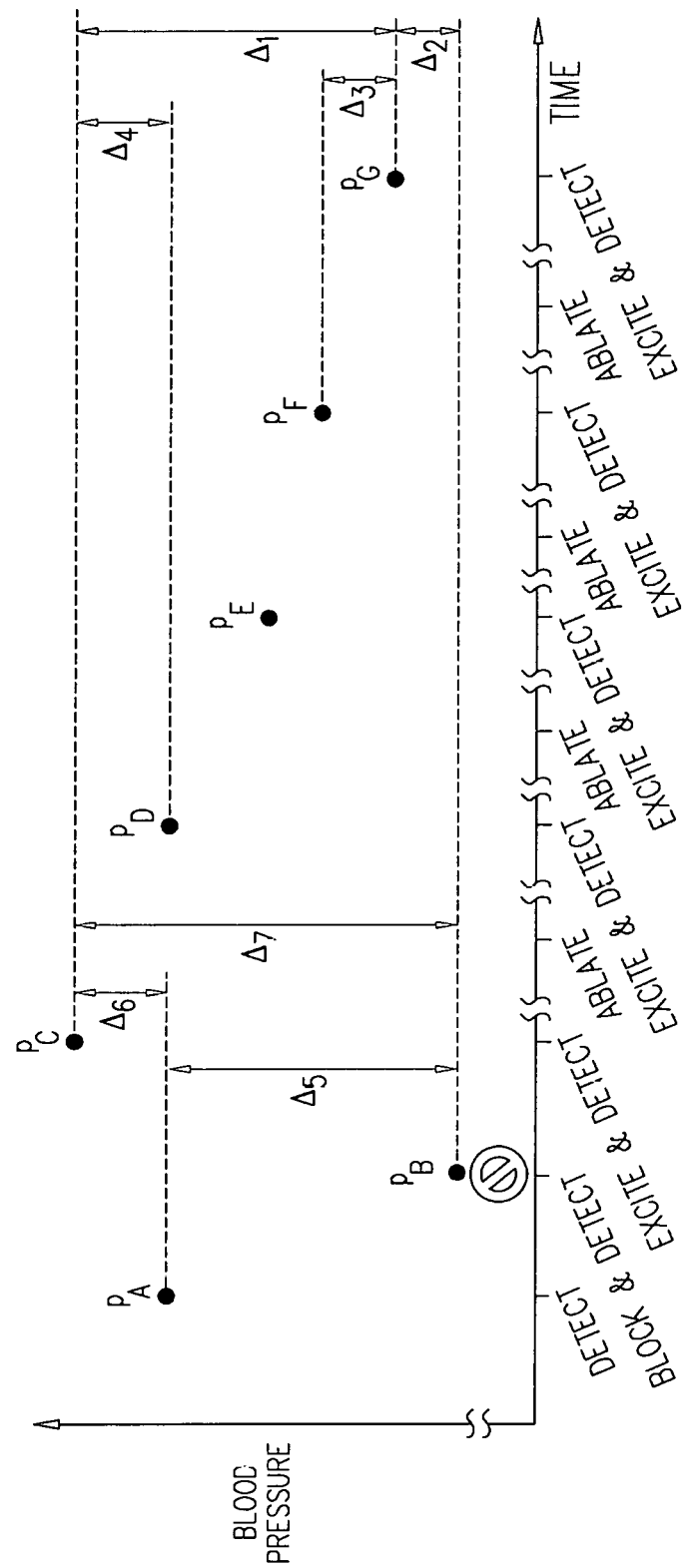
FIG. 3 is a schematic illustration of some techniques for facilitating ablation of nerve tissue of the renal artery, in accordance with some applications of the invention.

Reference is made to FIG. 3, which is a schematic illustration of some techniques for facilitating ablation of nerve tissue of the renal artery, in accordance with some applications of the invention. FIGS. 2A-H show a technique of using system 20 to repeatedly (e.g., cyclically) initiate induced action potentials in, and ablate, nerve tissue of the renal artery, and to repeatedly detect blood pressure of the subject (1) in the presence and absence of the induced action potentials, and (2) before and after the ablations. As described with reference to FIGS. 2A-H, this ablate-excite-detect cycle may be repeated as necessary to achieve a desired degree of ablation. FIG. 3 shows several techniques by which a suitable number of repetitions may be determined. Typically, this determination is performed after each detection of blood pressure subsequent to detection of blood pressure p_A. For illustrative purposes, FIG. 3 shows this determination being performed after four ablations and four respective blood pressure detections (p_D, p_E, p_F, and p_G).

For some applications, the ablate-excite-detect cycle is stopped at least in part responsively to the difference delta_1 between detected blood pressure p_G and detected blood pressure p_C. For example, difference delta_1 may be the difference between (1) the blood pressure detected after the most recent application of ablation energy, and (2) the highest blood pressure achievable by the high-level (e.g., hypothetical maximum) renal nerve activity.

For some applications, the ablate-excite-detect cycle is stopped at least in part responsively to the difference delta_2 between detected blood pressure p_G and detected blood pressure p_B. For example, difference delta_2 may be the difference between (1) the blood pressure detected after the most recent application of ablation energy, and (2) the hypothetical lowest blood pressure achievable by the hypothetical perfect ablation of the nerve tissue of the renal artery. For some such applications, the cycle is stopped at least in part responsively to a difference in magnitude between difference delta_1 and difference delta_2. For example, if delta_1 is significantly greater (e.g., more than a threshold magnitude greater) than delta_2, the cycle may be stopped because a threshold proportion of a hypothetical possible effect on blood pressure is deemed to have already been induced.

It is hypothesized that delta_1 and delta_2 are indicative of the cumulative effect of the ablations up to, and including, the most recent ablation, on the maximum possible contribution by renal nerve activity to blood pressure.

For some applications, the ablate-excite-detect cycle is stopped at least in part responsively to the difference delta_3 between detected blood pressure p_G and detected blood pressure p_F. For example, difference delta_3 may be the difference between (1) the blood pressure detected after the most recent application of ablation energy, and (2) the blood pressure detected after the immediacy-prior application of ablation energy. For some such applications, the cycle is stopped at least in part responsively to the difference delta_4 between detected blood pressure p_D and detected blood pressure p_C. For example, difference delta_4 may be the difference between (1) the blood pressure detected after the first application of ablation energy, and (2) the blood pressure detected before the first application of ablation energy. For some such applications, the cycle is stopped at least in part responsively to a difference in magnitude between difference delta_3 and difference delta_4. For example, if delta_3 is significantly smaller (e.g., more than a threshold magnitude smaller) than delta_4, the cycle may be stopped because it is deemed that the most recent application of ablative energy (i.e., that which resulted in difference delta_4) was significantly less effective in reducing blood pressure than was the first application of ablative energy, and thereby further applications of ablative energy are also unlikely to be significantly effective.

It is hypothesized that delta_3 and delta_4 are indicative of the effect of the most recent ablation, and the first ablation, respectively, on the maximum possible contribution by renal nerve activity to blood pressure. It is thereby hypothesized that delta_4 alone, and when compared to delta_3, is indicative of the efficacy of the most recent application of ablation energy.

For some applications, at least in part responsively to one or more blood pressure detections, no ablation is performed. For example, if, in a given subject, a difference delta_5 between detected "untreated" blood pressure p_A and the hypothetical lowest blood pressure achievable by the hypothetical perfect ablation of the nerve tissue p_B, is lower than a threshold difference, it may be determined that renal nerve ablation is not an appropriate treatment for that subject. A similar determination may be made alternatively or additionally in response to (1) a difference delta_6 between blood pressure p_A and blood pressure p_C, and/or (2) a difference delta_7 between blood pressure p_C and blood pressure p_B. It is hypothesized that differences delta_5, delta_6, and/or delta_7 are indicative of the potential efficacy of renal nerve ablation on hypertension for the given subject, and thereby, at least in part responsively to these differences, patient selection may be performed. For example, a high value of delta_7 may be indicative of a relatively high sensitivity of blood pressure to renal nerve activity in the given subject, and therefore the given subject is more likely to be selected for renal nerve ablation.

It is to be noted that, for some applications, one or more of the blood pressure measurements described hereinabove may be omitted from the procedure. For example, if it is known in advance which of differences delta_1 through delta_7 are to be used to determine when to stop the ablate-excite-detect cycle, a measurement that is not to be used may be omitted. Typically, however, only a maximum of two of the pre-ablation blood pressures (e.g., p_A, p_B, and p_C) are omitted, and none of the post-ablation blood pressures (e.g., p_D, p_E, p_F, and p_G) are omitted. For some applications, the determination of when to stop the ablate-excite-detect cycle is based solely on the blood pressure achieved following the most recent ablation.

Reference is made to FIG. 4, which is a flow diagram, illustrating at least some steps in the techniques described with reference to FIGS. 2A-H and 3. Step 102 comprises detecting a preliminary value of a parameter indicative of blood pressure, e.g., as described with reference to FIG. 2A.

Step 104 comprises (1) blocking endogenous action potentials in the nerve by applying a non-ablative blocking current to the nerve and (2) after the start of the application of the non-ablative blocking current, detecting a value of the parameter (i.e., a "blocked" value), e.g., as described with reference to FIG. 2B. The "blocked" value may be greater or smaller than the preliminary value, depending on the parameter and nerve being ablated. For example, for applications in which the renal nerve is being ablated so as to treat hypertension, blocking of endogenous action potentials in the renal nerve typically reduces blood pressure. As also described with reference to FIG. 2B, a calibration step 106 is optionally performed, so as to establish the characteristics of the non-ablative blocking current that will have the greatest effect on the detected parameter.

Step 108 comprises (1) initiating action potentials in the nerve by applying an excitatory current to the nerve and (2) after the start of the application of the excitatory current, detecting a value of the parameter (i.e., an "excited" value), e.g., as described with reference to FIG. 2C. Similarly to the "blocked" value, the "excited" value may be greater or smaller than the preliminary value, depending on the parameter and nerve being ablated. As also described with reference to FIG. 2C, a calibration step 110 is optionally performed, so as to establish the characteristics of the excitatory current that will have the greatest effect on the detected parameter.

As described hereinabove, steps 102, 104, and 106 may be performed in a different order from that shown in FIG. 4. However, step 102 is typically performed subsequent to the delivery of the apparatus (e.g., system 20) into the subject, and prior to steps 104 and 106.

Step 112 comprises ablating the nerve tissue by applying ablative energy, e.g., as described with reference to FIG. 2D (and as subsequently described with reference to FIG. 2F). Subsequently, step 114 is performed, which comprises (1) initiating action potentials in the nerve by applying an excitatory current to the nerve and (2) after the start of the application of the excitatory current, detecting a value of the parameter, e.g., as described with reference to FIG. 2E. For some applications, step 114 is identical to step 108, except that the nerve tissue in which the action potentials are being initiated has been at least in part ablated. The value detected in step 114 is thereby an "ablated" value.

Subsequently, the "ablated" value is compared to at least one of: the preliminary value, the "blocked" value, and the "excited" value (step 116), and a decision 118 to continue ablating, or to stop, is made, e.g., as described with reference to FIG. 3. If it is decided to continue ablating, steps 112, 114, 116, and 118 are repeated, optionally after an adjustment step 120 in which one or more characteristics (e.g., the intensity) of the ablation energy is adjusted. This part of the technique thereby represents an iterative routine 122 (e.g., a cycle), which may comprise the ablate-excite-detect cycle described hereinabove (e.g., with reference to FIGS. 2A-H and 3).

For some applications, the initiation of action potentials and the ablation steps shown in FIG. 4 (e.g., within steps 108 and 114) may be performed using a single electrode unit. For example, a single electrode unit may be moved back and forth through a blood vessel, alternating between applying an excitatory current and applying ablative energy (e.g., an ablating RF current). The single electrode unit may also be used to perform the blocking of endogenous action potentials (e.g., within step 104), by applying a non-ablating blocking current.

Reference is again made to FIGS. 2A-4. System 20, and the techniques described herein, may be performed with varying degrees of automation, in accordance with various applications of the invention. For example:

System 20 may display the blood pressures detected by sensor 26 (e.g., on a display, in numerical and/or graphical format), such that an operating physician (or another healthcare provider) may determine when to stop the ablate-excite-detect cycle. For example, a graph similar to that shown in FIG. 3 may be displayed.

System 20, at least in part based on the detected blood pressures, may display an instruction or suggestion to the physician, as to whether to continue or stop the ablate-excite-detect cycle. Similarly, audio instructions/suggestions may be provided by system 20.

System 20 (e.g., control unit 32 thereof) may automatically control the electrode units and ablation unit, at least in part based on the detected blood pressures. For example, control unit 32 may receive, from sensor 26, information indicative of the detected blood pressures, and responsively control (e.g., stop) the ablate-excite-detect cycle.

Reference is again made to FIGS. 2A-4. For some applications of the invention, one or more drugs may be administered to the subject so as to modulate the blood pressure of the subject, in order to facilitate one or more of the steps described hereinabove. For example, a blood pressure-reducing drug may be administered to the subject throughout the entire procedure, so as to reduce all the detected values of blood pressure (e.g., p_A, p_B, etc., shown in FIG. 3). For some such applications, the differences between these detected values (e.g., delta_5, delta_6, etc., shown in FIG. 3) remain relatively constant (i.e., shift, but generally do not change in magnitude) as the detected values change. It is hypothesized that, for some such applications, administering such a blood pressure-reducing drug allows the determination of the hypothetical highest blood pressure achievable by a high-level (e.g., hypothetical maximum) renal nerve activity (e.g., p_C) without increasing the blood pressure of the subject to more than a desired (e.g., safe) threshold. Similarly, a blood pressure-increasing drug may be administered to increase the detected values of blood pressure, such as to allow the determination of the hypothetical lowest blood pressure achievable by a hypothetical perfect ablation of the nerve tissue (e.g., p_B, shown in FIG. 3), without reducing the blood pressure of the subject to below a desired (e.g., safe) threshold.

Figure 5A:
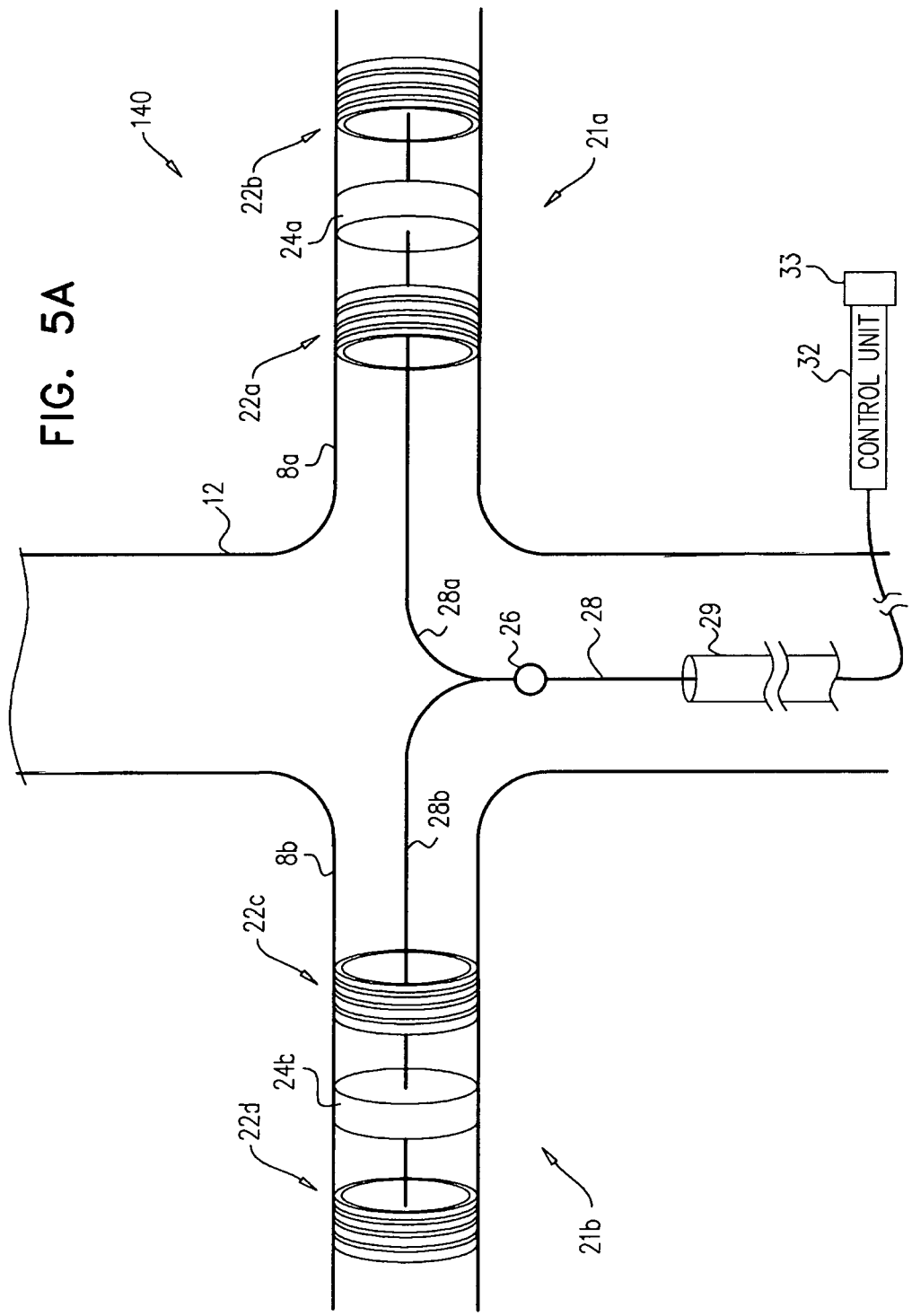

Reference is made to FIGS. 5A-B, which are schematic illustrations of systems for ablating nerve tissue of at least one renal artery of a subject, in accordance with some applications of the invention. For some applications, it is desirable to ablate nerve tissue of both renal arteries 8a and 8b of the subject. For example, it is hypothesized that, for some applications, it is advantageous to ablate the nerve tissue incompletely in both renal arteries (e.g., as opposed to completely ablating the nerve tissue in only one renal artery), so as to retain at least some nerve activity in each renal nerve, e.g., such that each kidney retains at least some blood pressure control. FIG. 5A shows a system 140, comprising two intravascular devices 21 (e.g., intravascular device 21a and intravascular device 21b), each comprising a respective ablation unit 24 (i.e., ablation unit 24a and ablation unit 24b), and a respective pair of electrode units 22 (i.e., one pair comprising electrode units 24a and 24b, and another pair comprising electrode units 24c and 24d). One intravascular device 21 (i.e., one ablation unit and one pair of electrode units) is disposed in each renal artery, and is configured to ablate a respective section of nerve tissue of the respective renal artery. For some applications (e.g., as shown in FIG. 5A for system 140) intravascular device 21b is identical to (i.e., separate from but identical to) intravascular device 21*a*. That is, the two distal portions of system 140 are separate from but identical to each other. For some applications (e.g., as shown in FIG. 5B for system 160), the two intravascular devices and/or the two distal portions of the system are not identical to each other.

For some applications of the invention, when initiating induced action potentials in nerve tissue of one renal artery, the endogenous action potentials in the nerve tissue of the other renal artery are blocked using the non-ablative blocking current, e.g., so as to reduce obfuscation of any effect seen. Alternatively, induced action potentials are initiated in the nerve tissue of both renal arteries (e.g., simultaneously). For some applications, it is desirable to perform this blocking and/or initiating in the nerve tissue of the other renal artery even when the nerve tissue of the other renal artery is not to be ablated. For some applications, the non-ablative blocking current is applied to nerve tissue of both renal arteries (i.e., bilaterally) at substantially the same time, e.g., so as to determine a lowest blood pressure achievable by a hypothetical perfect ablation of the nerve tissue of both renal arteries. For some applications, such a lowest blood pressure is used in place of, or in addition to, p_B, described with reference to FIGS. 2A-4. For some such applications, system 160 (shown in FIG. 5B), system 220 (described hereinbelow with reference to FIG. 6), system 320 (described hereinbelow with reference to FIG. 7), and/or system 420 (described hereinbelow with reference to FIG. 8) is used in place of system 160, mutatis mutandis. System 160 comprises a third electrode unit 162 (which may comprise electrode unit 22*c*), but typically does not comprise electrode unit 22*d* or ablating unit 24*b*. Systems 140 and 160 are typically used as described hereinabove for system 20, mutatis mutandis.

For some applications, catheter 28 of systems 140 and 160 has two distal portions thereof: longitudinal member first distal portion 28*a*, and longitudinal member second distal portion 28*b*. That is, for some applications, the distal portion of catheter 28 is bifurcated into distal portions 28*a* and 28*b*, each of the distal portions being configured to be advanced into a respective renal artery, as shown in FIGS. 5A-B.

Reference is made to FIG. 6, which is a schematic illustration of a system 220 for ablating nerve tissue of a blood vessel of a subject, in accordance with some applications of the invention. System 220 is typically used in a similar manner to system 20 described hereinabove, mutatis mutandis, and elements of system 220 are typically identical to identically-named elements of system 20, except where otherwise described. For example, system 220 may be used in combination with the steps described with reference to FIG. 4, mutatis mutandis. System 220 comprises an intravascular device 221 that comprises a first electrode unit 222*a* and a second electrode unit 222*b*, and ablation unit 24 (described hereinabove) disposed therebetween. Although units 222*a*, 222*b* and 24 are shown as distinct elements, for some applications intravascular device 221 is an integral unit that comprises and/or defines units 222*a*. 222*b* and 24 (e.g., disposed on a single body 23). For example, for applications in which ablation unit 24 comprises an RF ablation unit that comprises one or more electrodes, device 221 may define units 222*a*, 222*b* and 24 by comprising the electrodes of units 222*a*, 222*b* and 24 (e.g., device 221 may comprise a stent-like body and four electrodes, distributed along the length of the body).

Second electrode unit 222*b* is configured to initiate action potentials in a portion of the nerve tissue of the blood vessel that is adjacent to unit 222*b*. In contrast to electrode unit 22*b* of system 20, electrode unit 222*b* is typically not unidirectional, but instead typically initiates bidirectional action potentials. Furthermore, electrode unit 222*b* is typically not configured to block action potentials. For some applications, and as shown in FIG. 6, electrode unit 222*b* comprises a single electrode 230*c*, and another electrode (e.g., an electrode of electrode unit 222*a*, an electrode of ablation unit 24, or an extracorporeal electrode) may serve as the return electrode.

First electrode unit 222*a* is configured to block action potentials in a portion of the nerve tissue of the blood vessel that is adjacent to unit 222*a*, such as action potentials propagating past unit 222*a*. In contrast to electrode unit 22*a* of system 20, electrode unit 222*a* is typically not configured to induce action potentials. For some applications, and as shown in FIG. 6, electrode unit 222*a* comprises two electrodes 230*a* and 230*b*, and control unit 32 is configured to drive the non-ablative blocking current between electrodes 230*a* and 230*b* (e.g., the control unit may be configured to drive the non-ablative blocking current via electrode 230*a*, with electrode 230*b* serving as a return electrode for the non-ablative blocking current). Alternatively, electrode unit 222*a* may comprise only one electrode, and another electrode (e.g., an electrode of electrode unit 222*b*, an electrode of ablation unit 24, or an extracorporeal electrode) may serve as the return electrode.

As described hereinabove, system 20 (as described hereinabove with reference to FIGS. 1-2H) is configured to initiate (1) unidirectional action potentials that propagate past ablation unit 24 and toward the kidney, and independently (2) unidirectional action potentials that propagate past ablation unit 24 and toward the CNS. Because all the initiated unidirectional action potentials must propagate past ablation unit 24, they must propagate through the portion of the nerve tissue that is subjected to ablation, and therefore the resulting increase in systemic blood pressure is indicative of the degree of ablation of that portion of the nerve tissue.

It will be observed that system 220 typically comprises fewer electrodes than does system 20. That is, system 220 is typically simpler than system 20. It will further be observed that, because action potentials induced by electrode unit 222*b* are not unidirectional, they also typically propagate toward kidney 10 without passing through the portion of the nerve tissue that is subjected to ablation. It has been noted by the inventors that the effect on systemic blood pressure resulting from stimulation of the CNS is more immediate than that resulting from stimulation of the kidney. It is hypothesized that similar techniques to those described hereinabove as performed with system 20 may be performed using system 220 because, although some initiated action potentials propagate toward the kidney without passing though the portion of the nerve tissue that is subjected to ablation, the detection of systemic blood pressure during the "excite & detect" steps described hereinabove (e.g., with reference to FIGS. 2A-4) typically involves detection of the more immediate changes caused by CNS stimulation, rather than the slower effects caused by kidney stimulation. For some applications, detection of a particular pattern of changes in parameters of the subject (e.g., heart rate and blood pressure) may be used to identify and/or distinguish effects caused by action potentials initiated by system 220.

For some applications, system 220 comprises a single intravascular device 221. For some applications, system 220 comprises two intravascular devices 221, each intravascular device being configured to be placed in a respective renal artery, in a manner similar to that described with reference to FIG. 5A for system 140, mutatis mutandis. FIG. 6 illustrates the option of system 220 comprising two intravascular devices, by showing in phantom second distal portion 28b of catheter 28, described hereinabove with reference to FIGS. 5A-B, to which a second intravascular device would be coupled.

Reference is made to FIG. 7, which is a schematic illustration of a system 320 for ablating nerve tissue of a blood vessel of a subject, in accordance with some applications of the invention. System 320 is typically used in a similar manner to systems 20 and 220 described hereinabove, mutatis mutandis, and elements of system 320 are typically identical to identically-named elements of system 20, except where otherwise described. For example, system 320 may be used in combination with the steps described with reference to FIG. 4, mutatis mutandis.

System 320 comprises an intravascular device 321 that comprises (1) a first electrode unit 322a comprising an electrode 330a, (2) a second electrode unit 322b comprising an electrode 330b, and ablation unit 24 (described hereinabove) disposed therebetween. Although units 322a, 322b and 24 are shown as distinct elements, for some applications intravascular device 321 is an integrated unit that comprises and/or defines units 322a, 322b and 24, e.g., as described hereinabove for device 221, mutatis mutandis.

As described hereinabove, electrode unit 222a of system 220 may comprise only one electrode. For some applications, system 320 comprises or is an embodiment of system 220 when electrode unit 222a of system 220 comprises only one electrode.

For some applications, control unit 32 is configured to drive the excitatory current via electrode 330b, with another electrode (e.g., an electrode of ablation unit 24, electrode 330a, and/or an extracorporeal electrode) serving as a return electrode for the excitatory current. That is, for some applications, control unit 32 drives electrodes 330b and 330a to apply the excitatory current between them, across the ablation site. For some applications, control unit 32 is configured to drive the non-ablative blocking current via electrode 330a, with another electrode (e.g., an electrode of ablation unit 24, electrode 330b, and/or an extracorporeal electrode) serving as a return electrode for the non-ablative blocking current. For some applications in which ablation unit 24 comprises an RF ablation unit, electrode 330a, electrode 330b, and/or an extracorporeal electrode may serve as return electrodes for the ablating RF energy (i.e., RF current).

For some applications, system 320 comprises a single intravascular device 321. For some applications, system 320 comprises two intravascular devices 321, each intravascular device being configured to be placed in a respective renal artery, in a manner similar to that described with reference to FIG. 5A for system 140, mutatis mutandis. FIG. 7 illustrates the option of system 320 comprising two intravascular devices, by showing in phantom second distal portion 28b of catheter 28, described hereinabove with reference to FIGS. 5A-B, to which a second intravascular device would be coupled.

Figure 8:
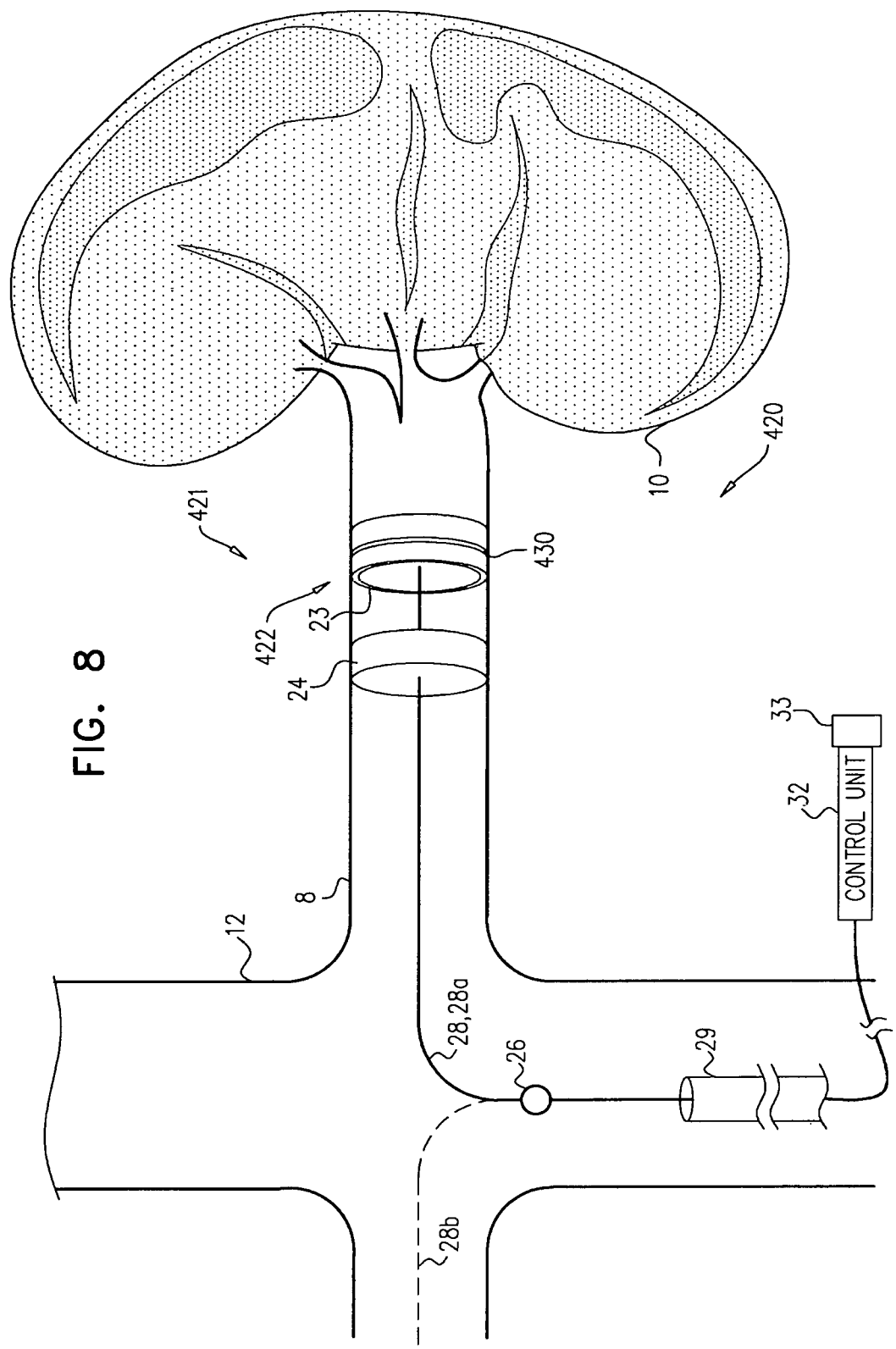

Reference is made to FIG. 8, which is a schematic illustration of a system 420 for ablating nerve tissue of a blood vessel of a subject, in accordance with some applications of the invention. System 420 is typically used in a similar manner to systems 20, 220 and 320 described hereinabove, mutatis mutandis, and elements of system 420 are typically identical to identically-named elements of system 20, except where otherwise described. For example, system 420 may be used in combination with the steps described with reference to FIG. 4, mutatis mutandis.

System 420 comprises an intravascular device 421 that comprises (1) an electrode unit 422 comprising an electrode 430, and (2) ablation unit 24 (described hereinabove). Although units 422 and 24 are shown as distinct elements, for some applications intravascular device 421 is an integrated unit that comprises and/or defines units 422a and 24, e.g., as described hereinabove for devices 221 and 321, mutatis mutandis.

For some applications, control unit 32 is configured to drive the excitatory current via electrode 430, with another electrode (e.g., an electrode of ablation unit 24, and/or an extracorporeal electrode) serving as a return electrode for the excitatory current. For some applications, control unit 32 is configured to also drive the non-ablative blocking current via electrode 430, with another electrode (e.g., an electrode of ablation unit 24, and/or an extracorporeal electrode) serving as a return electrode for the non-ablative blocking current. For applications in which ablation unit 24 comprises an RF ablation unit, control unit 32 may alternatively be configured to drive the non-ablative blocking current via an electrode of the RF ablation unit, with electrode 430 and/or an extracorporeal electrode serving as a return electrode for the non-ablative blocking current. For some applications in which ablation unit 24 comprises an RF ablation unit, electrode 430 and/or an extracorporeal electrode may serve as return electrodes for the ablating RF energy (i.e., RF current).

For some applications, system 420 comprises a single intravascular device 421. For some applications, system 420 comprises two intravascular devices 421, each intravascular device being configured to be placed in a respective renal artery, in a manner similar to that described with reference to FIG. 5A for system 140, mutatis mutandis. FIG. 8 illustrates the option of system 420 comprising two intravascular devices, by showing in phantom second distal portion 28b of catheter 28, described hereinabove with reference to FIGS. 5A-B, to which a second intravascular device would be coupled.

Reference is again made to FIGS. 6-8. It is to be noted that in systems 220, 320 and 420, action potentials are initiated on the side of ablation unit 24 that is closer to kidney 10, such that the action potentials must propagate past the ablation unit (i.e., through the portion of the nerve tissue that is subject to ablation) before reaching the CNS, and therefore effects (e.g., on systemic blood pressure) induced by the CNS in response to the initiated action potentials are indicative of the degree of ablation of that portion of the nerve tissue.

Reference is made to FIGS. 9A-B, which are schematic illustrations of electrodes for use with the present invention, in accordance with some applications of the invention. FIG. 9A shows an electrode 240, which comprises a generally circular electrode that is placeable against (or close to) the inner wall of renal artery 8 such that the electrode traces the inner wall of the artery, e.g., forming a complete circle. For some applications, electrode 240 comprises a "lasso"-type electrode that almost forms a complete circle. FIG. 9B shows an electrode 242, which comprises a plurality of sub-electrodes 244 that are placeable against (or close to) the inner wall of renal artery 8. Electrode 242 traces the inner wall of artery 8 generally in an arc (e.g., a generally 360 degree arc (i.e., a complete circle)) but with small gaps between sub-electrodes 244 (e.g., electrode 242 forms a broken arc, e.g., a broken ring). Typically, sub-electrodes 244 are configured to be driven simultaneously, but at least partly independently of each other (e.g., the sub-electrodes are independently addressable by the control unit), and are further typically configured (e.g., electrically coupled to a control unit, such as control unit 32) such that current is balanced (e.g., spread evenly) among the sub-electrodes, e.g., via separate wires leading from the control unit. It is hypothesized that for some applications, the use of electrode 242 comprising sub-electrodes 244 advantageously reduces variances in the distribution of current around the circumference of artery 8 that may otherwise be caused by variances in conductivity of tissue around the circumference.

For some applications, one or more of the electrodes described hereinabove may comprise electrode 242. For example, electrodes of an electrode unit (for application of blocking and/or excitatory current) and/or, for applications in which ablation unit 24 comprises an RF ablation unit, the ablating electrode of the ablation unit may comprise electrode 242.

Reference is made to FIG. 10, which is a flow diagram, illustrating at least some steps in ablating nerve tissue of renal artery 8 of the subject, in accordance with some applications of the invention. For some applications, it is desirable to ablate the nerve tissue incompletely, e.g., to a known degree. For such applications, blood pressure may be used as an indicator of such ablation. The steps shown in FIG. 10 are described herein as being performed using system 420, described with reference to FIG. 8, but it is to be noted that the steps may alternatively be performed using other apparatus, such as other systems described herein, mutatis mutandis.

A preliminary value of blood pressure (e.g., at rest) of the subject is detected 502, e.g., using sensor 26. A detected excited blood pressure value is determined 504 by applying an excitatory current (e.g., using electrode 430) that induces action potentials in the renal nerve, and detecting a detected excited blood pressure value after the start of the application of the excitatory current (e.g., while the excitatory current is being applied, or after it has stopped being applied). For example, the blood pressure may be detected after a duration in which blood pressure is allowed to respond to the increase in renal nerve activity.

The detected excited blood pressure value is compared 506 (e.g., by control unit 32) with a target excited blood pressure value (described hereinbelow with reference to step 508). If the detected excited blood pressure value does not cross a threshold defined at least in part based on the target excited blood pressure value, the value of at least one property (such as, but not limited to, frequency or amplitude) of the excitatory current is altered 510, and the detected excited blood pressure value is determined again 504, until the detected excited blood pressure value does cross the threshold defined at least in part based on the target excited blood pressure value. This iterative routine is indicated by box 512. For some applications, this iterative routine is automatically performed by control unit 32. For example, the operating physician (or another healthcare provider) may press a single button on control unit 32, and the control unit iteratively (1) applies 504 the excitatory current and detects 504 the detected excited blood pressure value, (2) compares 506 the detected excited blood pressure value to the target excited blood pressure value, and (3) alters the value of the at least one property of the excitatory current, until the detected excited blood pressure value crosses the threshold defined at least in part based on the target excited blood pressure value.

It is to be noted that throughout this patent application, including the specification and the claims, a "threshold defined at least in part based on" a given, value may be:

equal to the given value (e.g., with reference to the above paragraph, the detected excited blood pressure value crosses the threshold by becoming equal to or greater than the target excited blood pressure value), or different from the given value by a fixed value, by a fixed multiple of the given value, and/or by a linear or non-linear function determined at least in part based on the given value (e.g., with reference to the above paragraph, the detected excited blood pressure value crosses the threshold by becoming equal to or greater than a value that is different from the target excited blood pressure value by a fixed value, by a fixed multiple of the target excited blood pressure value, and/or by a linear or non-linear function determined at least in part based on the target excited blood pressure value).

For some applications, the target excited blood pressure value is provided 508 (e.g., generated) by control unit 32 at least in part responsively to the preliminary blood pressure value. For example, control unit 32 may set the target excited blood pressure value to be a given amount or percentage greater than the preliminary blood pressure value. Alternatively, the target excited blood pressure value may be provided 508 manually, such as by the operating physician (or another healthcare provider) entering the target excited blood pressure value into control unit 32.

Once the detected excited blood pressure value crosses the threshold defined at least in part based on the target excited blood pressure value, ablating energy is applied 514 (e.g., using ablation unit 24) to the nerve tissue of renal artery 8.

Subsequently, action potentials are again induced 516 in the nerve tissue by applying (e.g., using electrode 430) a selected excitatory current (e.g., a characteristic thereof) that is at least in part based on the excitatory current at which the detected excited blood pressure value crossed threshold defined at least in part based on the target excited blood pressure value (in step 506). For example, the value of at least one characteristic (e.g., frequency and/or amplitude) of the selected excitatory current may be equal to the value of the same property of the excitatory current at which the detected excited blood pressure value crossed the threshold (e.g., the excitatory current that induced the detected excited blood pressure value to cross the threshold) is "selected" (e.g., by control unit 32) as the selected excitatory current. For some applications, the selected excitatory current may be identical to the excitatory current at which the detected excited blood pressure value crossed the threshold defined at least in part by the target excited blood pressure value.

A detected ablated blood pressure value is detected 516 (e.g., by sensor 26) after the start of the application of the selected excitatory current (e.g., while the selected excitatory current is being applied, or after it has stopped being applied). For example, the blood pressure may be detected after a duration in which blood pressure is allowed to respond to the increase in renal nerve activity.

The detected ablated blood pressure value is compared 518 (e.g., by control unit 32) with a target ablated blood pressure value (described hereinbelow with reference to step 520). If the detected ablated blood pressure value does not cross a threshold defined at least in part based on the target ablated blood pressure value, ablation energy is applied again 514, and the detected ablated blood pressure value is determined again 516 until the detected ablated blood pressure value does cross the threshold defined at least in part based on the target ablated blood pressure value. This iterative routine is indicated by box 522. For some applications, this iterative routine is automatically performed by control unit 32. For example, the operating physician (or another healthcare provider) may press a single button on control unit 32, and the control unit iteratively (1) applies 514 the ablation energy, (2) applies 516 the selected excitatory current and detects 516 the detected ablated excited blood pressure value, and (3) compares 518 the detected ablated blood pressure value to the target ablated blood pressure value, until the detected ablated blood pressure value crosses the threshold defined at least in part based on the target ablated blood pressure value.

It is to be noted that the threshold defined at least in part based on the target ablated blood pressure value may be:
- equal to the target ablated blood pressure value (e.g., the detected ablated blood pressure value crosses the threshold by becoming equal to or lower than the target ablated blood pressure value), or
- different from the target ablated blood pressure value by a fixed value, by a fixed multiple of the target ablated blood pressure value, and/or by a linear or non-linear function determined at least in part based on the target ablated blood pressure value (e.g., the detected ablated blood pressure value crosses the threshold by becoming equal to or lower than a value that is different from the target ablated blood pressure value by a fixed value, by a fixed multiple of the target ablated blood pressure value, and/or by a linear or non-linear function determined at least in part based on the target ablated blood pressure value).

For some applications, during each iteration, the ablation energy retains the same characteristics (e.g., control unit 32 drives ablation unit 24 to apply ablation energy having the same characteristics). For some applications, a characteristic of the ablation energy is altered 524 (e.g., by control unit 32) prior to each subsequent application of the ablation energy. For example, the intensity of the ablation energy may be increased or decreased by control unit 32.

For some applications, the target ablated blood pressure value is provided 520 (e.g., generated) by control unit 32 at least in part responsively to (1) the preliminary blood pressure value (as described with reference to step 502), and (2) the target excited blood pressure value and/or the detected excited blood pressure value (as described with reference to steps 506 and 508), and optionally at least in part responsively to a target level (e.g., a desired level) of ablation which may be provided 526 to the control unit. For example, an operating physician (or another healthcare provider) may input into control unit 32 (e.g., via an interface 33 thereof, such as a dial or a keypad) the target degree of ablation (e.g., based on one or more parameters of the subject and/or the condition being treated), and the control unit calculates, at least in part responsively to (1) the preliminary blood pressure value, and (2) the target excited blood pressure value and/or the detected excited blood pressure value, the target ablated blood pressure value that corresponds to the target degree of ablation. Purely for illustrative purposes, for example, if the target degree of ablation is 50%, the target ablated blood pressure value may be calculated as being midway between (1) the preliminary blood pressure value, and (2) the target excited blood pressure value and/or the detected excited blood pressure value. The target ablated blood pressure value may alternatively be provided 520 manually, such as by the operating physician (or another healthcare provider) entering the target ablated blood pressure value into control unit 32.

Figure 11:
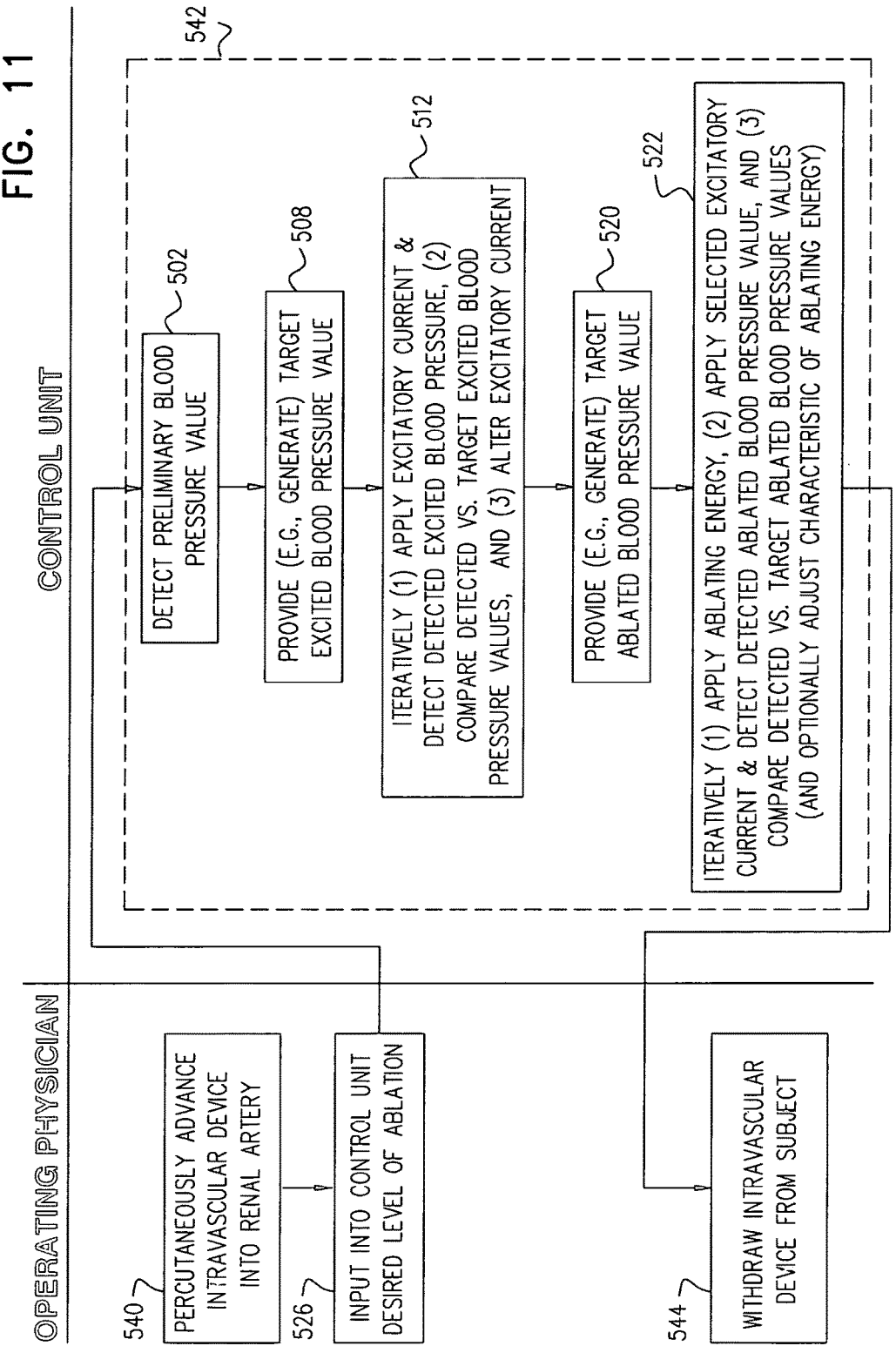
FIG. 11 is a flow diagram, illustrating automation of at least some of the steps described with reference to FIG. 10, in accordance with some applications of the invention.

Reference is made to FIG. 11, which is a flow diagram illustrating automation of at least some of the steps described with reference to FIG. 10, in accordance with some applications of the invention. As described with reference to FIG. 10, for some applications, generation of target excited blood pressure values and/or ablated blood pressure values is performed by control unit 32. Similarly, for some applications, iterative step 512 and/or iterative step 522 is performed (e.g., automatically) by control unit 32. FIG. 11 illustrates, for some applications of the invention, which steps are performed (e.g., manually) by the operating physician (or another healthcare provider), and which steps are performed (e.g., automatically) by control unit 32.

The operating physician percutaneously advances 540 the intravascular device (e.g., intravascular device 421 of system 420) into renal artery 8 of the subject, inputs 526 the target degree of ablation into control unit 32 (e.g., via an interface thereof), and activates the control unit. It is to be noted that steps 540 and 526 may alternatively be performed in reverse order, and that another healthcare provider may perform step 526. Subsequently, control unit 32 automatically performs the steps indicated by box 542, and indicates that the procedure (e.g., the ablation procedure) is complete, at which point the operating physician withdraws 544 the intravascular device from the subject. The steps contained by box 542 are described with reference to FIG. 10, using the same reference numerals. It is to be noted that step 512 of FIG. 11 corresponds to box 512 of FIG. 10, which contains steps 504, 506 and 510, and that step 522 of FIG. 11 corresponds to box 522 of FIG. 10, which contains steps 514, 516, 518 and 524.

Although the techniques described with reference to FIGS. 10-11 are generally described as being performed using system 420 (which is described with reference to FIG. 8), it is to be noted that the techniques may alternatively be performed using other apparatus, such as other systems described herein, mutatis mutandis. For example, the techniques described with reference to FIGS. 10-11 may be performed using system 20, system 140, system 160, system 220, or system 320, mutatis mutandis.

Reference is again made to FIGS. 1-11. The techniques described hereinabove utilize blood pressure (typically during application of the excitatory current) as an indicator of ablation of nerve tissue of the renal artery. The resulting controlled ablation of this nerve tissue is useful in treating hypertension, including mild hypertension in subjects for whom full renal nerve ablation is not necessary, and hypertension in subjects who also suffer from renal failure for whom full renal nerve ablation may be deleterious. It is to be noted, however, that these techniques may also be used to facilitate controlled ablation of this nerve tissue for treating other conditions, such as congestive heart failure, sleep apnea, and decreased insulin sensitivity in diabetic subjects. That is, blood pressure can be used to indicate and/or control a degree of ablation of nerve tissue of the renal artery even in subjects without hypertension and/or not being treated for hypertension.

Figure 12:
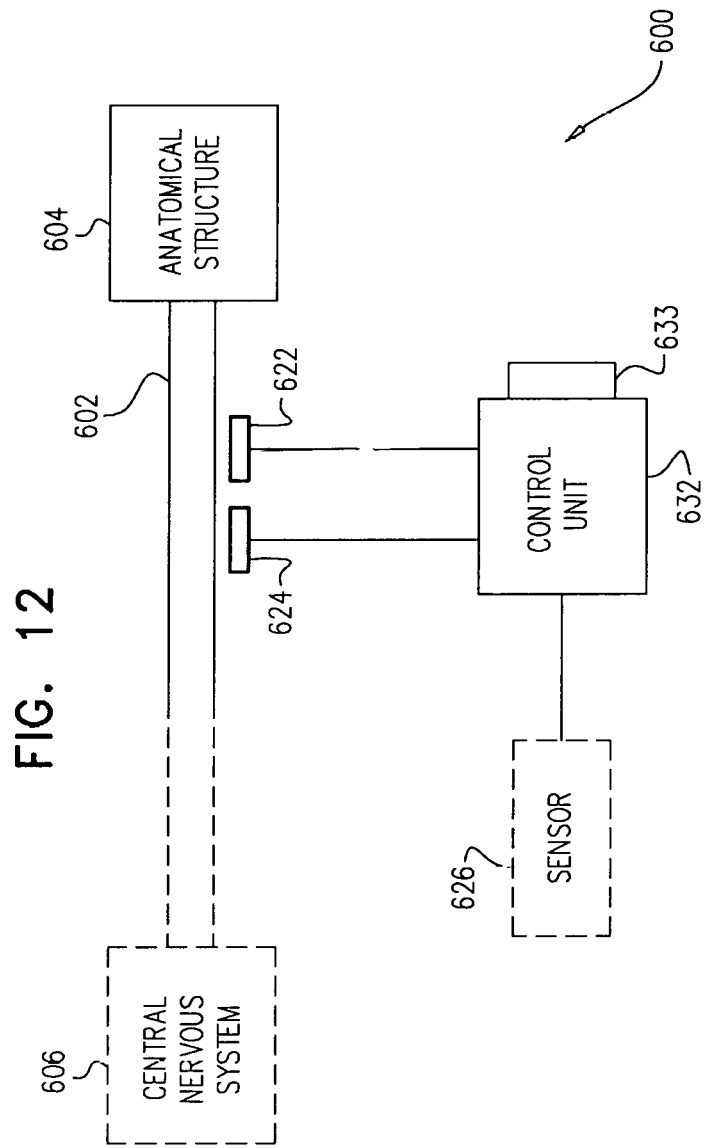
FIG. 12 is a schematic illustration of a system and technique for use thereof, for controlled ablation of nerve tissue of a subject, in accordance with some applications of the invention.
Figure 13:
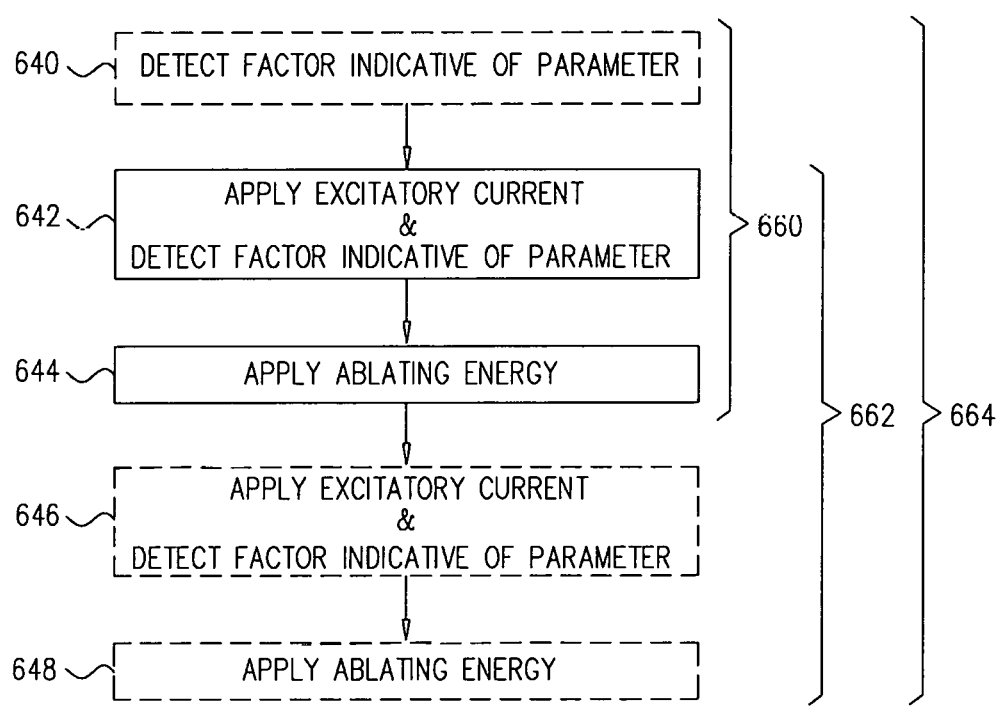
FIG. 13 is a flow chart showing at least some steps in one or more techniques for use with the system of FIG. 12, in accordance with some applications of the invention.

Reference is made to FIGS. 12-13, which are schematic illustrations of a system 600 and techniques for use thereof, for controlled ablation of nerve tissue 602 of a subject, in accordance with some applications of the invention. FIG. 12 is a schematic illustration of system 600, in accordance with some applications of the invention. Nerve tissue 602 typically directly or indirectly innervates an anatomical structure 604 of a subject (e.g., carries action potentials to and/or from the anatomical structure). For some applications, nerve tissue 602 carries action potentials between anatomical structure 604 and a central nervous system 606 of the subject. Typically, the action potentials are capable of altering a parameter of the subject, and thereby anatomical structure 604 is typically capable of altering the parameter of the subject. For some applications, nerve tissue 602 comprises a postganglionic neuron of the subject.

System 600 comprises at least one electrode unit 622, an ablation unit 624, and a control unit 632, configured to drive and/or control the electrode unit and/or the ablation unit. For some applications, control unit 632 comprises an interface 633. Typically, system 600 further comprises a sensor 626, configured to detect a factor indicative of the parameter of the subject. For some applications, system 600 does not comprise a sensor, and the parameter is detected by a sensor that is not a component of system 600, and/or is detected by a medical professional. For such applications, information relating to the factor (e.g., a value of the factor) may be inputted manually or automatically via interface 633.

Electrode unit 622 and ablation unit 624 are advanced to a vicinity of nerve tissue 602, e.g., to within 1 cm of the nerve tissue (e.g., within 1 mm of the nerve tissue, such as to be in contact with the nerve tissue). For some applications, nerve tissue 602 comprises nerve tissue associated with a blood vessel of the subject (e.g., disposed within the adventitia layer of the blood vessel wall), and electrode unit 622 and ablation unit 624 are advanced toward the nerve tissue via the blood vessel, typically remaining within the blood vessel for the duration of the procedure (e.g., as described hereinabove with reference to FIGS. 1-11, mutatis mutandis). It is to be noted that although FIG. 12 shows electrode unit 622 disposed closer to anatomical structure 604 than is ablation unit 624, for some applications the electrode unit is disposed further from the anatomical structure than is the ablation unit. For some applications, electrode unit 622, ablation unit 624, control unit 632 and/or sensor 626 of system 600 comprise a respective identically-named corresponding component of one or more other systems described hereinabove. For some applications, electrode unit 622, ablation unit 624, control unit 632 and sensor 626 of system 600 are arranged (e.g., coupled to each other) as described for identically-named corresponding components of one or more other systems described hereinabove. For example, electrode unit 622, ablation unit 624, control unit 632 and sensor 626 may be coupled to and disposed along a longitudinal member, such as catheter 28 (not shown in FIG. 12).

FIG. 13 is a flow chart showing at least some steps in one or more techniques for use with system 600, in accordance with some applications of the invention. Action potentials are initiated in a first portion of nerve tissue 602 by electrode unit 622 applying an excitatory current to the first portion of the nerve tissue (step 642). The excitatory current typically has a frequency of greater than 1 Hz and/or less than 100 Hz, such as between 1 and 100 Hz, e.g., between 10 and 100 Hz. After a start of the application of the excitatory current, a detection of the factor indicative of the parameter of the subject is performed, e.g., using sensor 626 (step 642). For some applications, the detection is performed during the application of the excitatory current. For some applications, the detection is performed after the excitatory current has stopped being applied.

At least in part in response to the detection of the factor, ablating energy is applied to a second portion of nerve tissue 602 by ablation unit 624 (step 644). For some applications, ablation unit 624 comprises an RF ablation unit, and applies an RF current having a frequency of above 5 kHz and/or below 1 GHz, such as between 5 kHz and 1 GHz (e.g., 10 kHz-10 MHz, e.g., 50 kHz-1 MHz, e.g., 300 kHz-1 MHz, e.g., 300 kHz-500 kHz). As described hereinabove for ablation unit 24, mutatis mutandis, ablation unit 624 may alternatively or additionally be configured to ablate nerve tissue 602 using ultrasound energy, laser energy, resistive heating, cryogenically, using chemical ablation, or via another ablation mechanism.

For some applications, before application of the excitatory current in step 642, a detection of the factor is performed (e.g., while the subject is at rest and/or untreated) (step 640). Reference numeral 660 indicates a technique in which a first detection is performed before application of the excitatory current, a second detection of the factor is performed after the start of the application of the excitatory current, and subsequently ablating energy is applied. For some applications of technique 660, ablating energy is applied 644 at least in part responsively to the detection in step 640 and at least in part responsively to the detection in step 642. For example, ablating energy may be applied in response to a comparison of the first detection and the second detection, e.g., in response to a difference between a first detected value of the factor and a second detected value of the factor. For example, technique 660 may be used to screen subjects likely to be responsive to a treatment comprising ablation of nerve tissue 602 (e.g., by determining a sensitivity of the parameter to action potentials in nerve tissue 602).

For some applications, subsequent to the application of ablating energy in step 644, another application of excitatory current and detection of the factor are performed (step 646). Typically, step 646 is identical in nature to step 642. For such applications, at least in part in response to the detection in step 646 (and typically also at least in part in response to previous detection(s) of the factor), ablating energy is applied to a second portion of nerve tissue 602 by ablation unit 624 (step 648). Reference numeral 662 indicates a technique in which steps 646 and 648 are performed after step 644. Ablating energy of step 648 may be applied in response to a difference between a value of the factor detected in step 646 and a value of the factor detected in step 642. For example, this difference may indicate a degree of ablation achieved by the application of ablating energy, as described hereinabove.

Reference numeral 664 indicates a technique in which, in addition, step 640 is performed before step 642. For such a technique, ablating energy may be applied in response to one or more differences between respective values of the factor detected in steps 640, 642, and 646.

For some applications, the techniques described with reference to FIGS. 12-13 may be combined with those described with reference to other figures, and one or more steps described with reference to FIGS. 12-13 may comprise, or correspond to, steps or values described hereinabove with reference to other figures. For example:

The detection of the factor in step 640 may comprise, or correspond to:
  detecting value p_A described with reference to FIGS. 2A-3, mutatis mutandis;
  step 102 described with reference to FIG. 4, mutatis mutandis; and/or
  step 502 described with reference to FIG. 5, mutatis mutandis.

The detection of the factor in step 642 may comprise, or correspond to:
  detecting value p_C described with reference to FIGS. 2A-3, mutatis mutandis;
  step 114 described with reference to FIG. 4, mutatis mutandis; and/or step 516 described with reference to FIG. 5, mutatis mutandis.

The application of ablating energy in step 644 may comprise, or correspond to:
- the application of ablating energy between the detection of value p_C and the detection of value p_D, described with reference to FIGS. 2A-3, mutatis mutandis;
- step 112 described with reference to FIG. 4, mutatis mutandis; and/or
- step 514 described with reference to FIG. 5, mutatis mutandis.

A difference between a value detected in step 640 and a value detected in step 642 may comprise, or correspond to, difference delta_6, described with reference to FIGS. 2A-3.

A difference between a value detected in step 642 and a value detected in step 646 may comprise, or correspond to, difference delta_4, described with reference to FIGS. 2A-3.

For some applications, steps 644, 646, and 648 represent an iterative routine in which ablative energy is repeatedly applied until a desired detection of the factor is achieved (e.g., until a threshold defined at least in part based on a target ablated value of the factor is crossed). For some applications, this iterative routine comprises, or corresponds to, iterative routine 122 described with reference to FIG. 4, and/or the iterative routine indicated by box 522 described with reference to FIG. 10, mutatis mutandis.

For some applications, step 642 comprises, or represents, an iterative routine in which the excitatory current is applied and adjusted until a desired detection of the factor is achieved (e.g., until a threshold defined at least in part based on a target excited value of the factor is crossed). For some applications, this iterative routine comprises, or corresponds to, steps 108 and 110 described with reference to FIG. 4, and/or the iterative routine indicated by box 512 described with reference to FIG. 10, mutatis mutandis.

For some applications, FIGS. 12-13 and the descriptions thereof are a generalized representation of techniques described with reference to other figures (including those hereinabove and those hereinbelow). Furthermore, the techniques described with reference to FIGS. 12-13 may be used with subjects suffering from conditions other than hypertension, and/or for ablation of nerve tissue other than that of the renal artery. Typically, the techniques described with reference to FIGS. 12-13 are used to facilitate controlled ablation of autonomic nerve tissue (e.g., tissue of an autonomic nerve) of a subject.

For some applications, the techniques described with reference to FIGS. 12-13 are used to treat a subject who suffers from overactivity of the sympathetic nervous system and/or underactivity of the parasympathetic nervous system (e.g. excess activity of the sympathetic nervous system compared to that of the parasympathetic nervous system). For example, nerve tissue 602 may comprise a sympathetic nerve of the subject.

For some applications, the techniques described with reference to FIGS. 12-13 are used to treat a subject who suffers from overactivity of the parasympathetic nervous system and/or underactivity of the sympathetic nervous system (e.g. excess activity of the parasympathetic nervous system compared to that of the sympathetic nervous system). For example, nerve tissue 602 may comprise a parasympathetic nerve of the subject.

For some applications, the techniques described with reference to FIGS. 12-13 are used to treat a subject who suffers from hypertension. For example, anatomical structure 604 may comprise a kidney of the subject, and/or nerve tissue 602 may comprise nerve tissue of the renal artery of the subject, e.g., as described hereinabove with reference to FIGS. 1-11, mutatis mutandis. Alternatively, anatomical structure 604 may comprise a carotid body of the subject, and/or nerve tissue 602 may comprise a glossopharyngeal nerve of the subject and/or a branch thereof that innervates the carotid body (e.g., the Nerve of Hering). For some such applications, detecting the factor indicative of the parameter of the subject comprises detecting blood pressure of the subject (e.g., sensor 626 may comprise a blood pressure sensor), e.g., as described hereinabove with reference to FIGS. 1-11, mutatis mutandis. Alternatively or additionally, ablating nerve tissue of the renal artery may be performed to treat a condition other than hypertension, e.g., as described hereinabove.

For some applications, the techniques described with reference to FIGS. 12-13 are used to treat a subject who suffers from premature ejaculation. For example, anatomical structure 604 may comprise the scrotum and/or the penis of the subject, and/or nerve tissue 602 may comprise the dorsal nerve, the pudendal nerve, and/or a sacral nerve of the subject. For some such applications, detecting the factor indicative of the parameter of the subject comprises detecting an ejaculation of the subject. For some such applications, detecting the factor indicative of the parameter of the subject comprises detecting an electromyographic (EMG) value (e.g., sensor 626 may comprise an EMG sensor comprising EMG electrodes). For example, EMG may be performed on a perineal muscle of the subject.

For some applications, the techniques described with reference to FIGS. 12-13 are used to treat a subject who suffers from erectile dysfunction. For example, anatomical structure 604 may comprise the penis of the subject, and/or nerve tissue 602 may comprise the dorsal nerve of the subject. For some such applications, detecting the factor indicative of the parameter of the subject comprises detecting blood pressure in the corpus cavernosum penis of the subject (e.g., sensor 626 may comprise a blood pressure sensor). For some such applications, detecting the factor indicative of the parameter of the subject comprises detecting an EMG value, such as of tissue of the penis of the subject. For some applications, controlled stimulation of the penis is performed to facilitate the detection.

For some applications, the techniques described with reference to FIGS. 12-13 are used to treat a subject who suffers from overactive bladder (e.g., urge incontinence). For example, anatomical structure 604 may comprise the bladder of the subject, and/or nerve tissue 602 may comprise a hypogastric nerve of the subject or a sacral nerve of the subject. For some such applications, detecting the factor indicative of the parameter of the subject comprises detecting urinary urgency (e.g., the subject may provide feedback). For some such applications, detecting the factor indicative of the parameter of the subject comprises detecting pressure in the bladder of the subject (e.g., sensor 626 may comprise a pressure sensor). For some such applications, detecting the factor indicative of the parameter of the subject comprises detecting an EMG value, such as of the bladder of the subject.

For some applications, the techniques described with reference to FIGS. 12-13 are used to treat a subject who suffers from chronic obstructive pulmonary disease. For example, anatomical structure 604 may comprise a lung of the subject, and/or nerve tissue 602 may comprise the vagal nerve of the subject, and/or a branch thereof that innervates the lung. For some such applications, detecting the factor indicative of the parameter of the subject comprises detecting a breathing-related factor of the subject, such as airflow, breathing-related movement, a dimension of an airway of the subject (e.g., sensor 626 may comprise a breathing sensor or an imaging device, such as an ultrasound transceiver). For some such applications, detecting the factor indicative of the parameter of the subject comprises detecting blood chemistry of the subject (e.g., O2, CO2, or pH level).

For some applications, the techniques described with reference to FIGS. 12-13 are used to treat a subject who suffers from congestive heart failure. For example, anatomical structure 604 may comprise the heart of the subject, and/or nerve tissue 602 may comprise a sympathetic nerve that innervates the heart of the subject. For some such applications, detecting the factor indicative of the parameter of the subject comprises detecting a heart rate of the subject. For some such applications, detecting the factor indicative of the parameter of the subject comprises detecting a blood pressure of the subject.

For some applications, the techniques described with reference to FIGS. 12-13 are used to treat a subject who suffers from uterine bleeding. For example, anatomical structure 604 may comprise the uterus of the subject, and/or nerve tissue 602 may comprise a lumbar splancnic nerve of the subject and/or a nerve that extends from a hypogastric plexus of the subject. For some such applications, detecting the factor indicative of the parameter of the subject comprises detecting a dimension of a blood vessel associated with the uterus (e.g., using ultrasound). For some such applications, detecting the factor indicative of the parameter of the subject comprises detecting blood pressure in a blood vessel associated with the uterus. For some such applications, detecting the factor indicative of the parameter of the subject comprises detecting bleeding (e.g., using a camera).

For some applications, the techniques described with reference to FIGS. 12-13 are used to treat a subject who suffers from nervous stomach. For example, anatomical structure 604 may comprise the stomach of the subject, and/or nerve tissue 602 may comprise vagus nerve tissue of the subject. For some such applications, detecting the factor indicative of the parameter of the subject comprises detecting gastric pH (e.g., sensor 626 may comprise a pH sensor). For some such applications, detecting the factor indicative of the parameter of the subject comprises detecting gastric movement.

For some applications, the techniques described with reference to FIGS. 12-13 are used to treat a subject who suffers from primary hyperhidrosis. For example, anatomical structure 604 may comprise one or more sweat glands of the subject, and/or nerve tissue 602 may comprise a superficial sympathetic nerve that innervates the sweat glands, e.g., a cholinergic sympathetic nerve and/or an adrenergic nerve of the subject. For some such applications, detecting the factor indicative of the parameter of the subject comprises detecting transepidermal water loss. For some such applications, detecting the factor indicative of the parameter of the subject comprises detecting perspiration (e.g., by detecting conduction of an electrical current between electrodes placed on the skin of the subject, e.g., sensor 626 may comprise electrodes and a current meter).

Typically, treatment is targeted to one or more areas of the body of the subject in which excess sweating is considered (e.g., by the subject and/or physician) to be particularly problematic. That is, typically, nerve tissue 602 comprises one or more nerves that innervate the sweat glands in these one or more areas. Typically, detection of perspiration and/or transepidermal water loss is performed in the same one or more areas.

For some applications, the techniques described with reference to FIGS. 12-13 are used to treat a subject who suffers from an inflammatory condition such as, but not limited to: fibrosis of the heart, inflammation of the heart, an autoimmune disease, an autoimmune inflammatory disease, multiple sclerosis, encephalitis, myelitis, immune-mediated neuropathy, myositis, dermatomyositis, polymyositis, inclusion body myositis, inflammatory demyelinating polyradiculoneuropathy, Guillain-Barre syndrome, myasthenia gravis, inflammation of the nervous system, inflammatory bowel disease, Crohn's disease, ulcerative colitis. SLE (systemic lupus erythematosus), rheumatoid arthritis, vasculitis, polyarteritis nodosa, Sjogren syndrome, mixed connective tissue disease, glomerulonephritis, thyroid autoimmune disease, sepsis, meningitis, a bacterial infection, a viral infection, a fungal infection, sarcoidosis, hepatitis, portal vein hypertension, appendicitis, peptic, gastric and duodenal ulcers, peritonitis, pancreatitis, pseudomembranous, acute and ischemic colitis, diverticulitis, epiglottitis, achalasia, cholangitis, coeliac disease, cholecystitis, enteritis, Whipple's disease, asthma, allergy, anaphylactic shock, immune complex disease, organ ischemia, reperfusion injury, organ necrosis, hay fever, septicemia, endotoxic shock, cachexia, hyperpyrexia, cosinophilic granuloma, granulomatosis, septic abortion, epididymitis, vaginitis, prostatitis, urethritis, diseases involving the respiratory system and associated tissues (such as bronchitis, emphysema, rhinitis, cystic fibrosis, adult respiratory distress syndrome, pneumonitis, pneumoultramicroscopicsilicovolcanoconiosis, alvealitis, bronchiolitis, pharyngitis, pleurisy, and sinusitis), diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts), dermatological diseases and conditions of the skin (such as burns, dermatitis, sunburn, urticaria warts, and wheals), diseases involving the cardiovascular system and associated tissues (such as vasulitis, angiitis, endocarditis, arteritis, atherosclerosis, thrombophlebitis, pericarditis, myocarditis, myocardial ischemia, congestive heart failure, periarteritis nodosa, and rheumatic fever), diseases involving the central or peripheral nervous system and associated tissues (such as Alzheimer's disease, cerebral infarction, cerebral embolism, neuritis, neuralgia, spinal cord injury, paralysis, and uveitis), diseases of the bones, joints, muscles and connective tissues (such as the various arthritides and arthralgias, osteomyelitis, fascitis, Paget's disease, gout, periodontal disease, and synovitis), other autoimmune and inflammatory disorders (such as thryoiditis, systemic lupus erythematosus, Goodpasture's syndrome, Behcets's syndrome, allograft rejection, graft-versus-host disease, Type I diabetes, ankylosing spondylitis, Berger's disease, and Retier's syndrome), diabetes, cancer, septic shock, acute respiratory distress syndrome (ARDS), bacterial meningitis, acute pancreatitis, multiple organ failure (MOF), post-ischemic reperfusion, acute cellulitis, abdominal aortic aneurysm, septic or bacterial pyelonephritis, septic arthritis, uveitis, periodontitis, psoriasis, severe burns, skin ulceration, acute lung injury, pneumonia, trauma, severe early graft dysfunction, brochiocactasis, chronic obstructive pulmonary disease (COPD), complications with hemodialysis, hypersensitivity pneumonitis, lung fibrosis, herpes stromal keratitis, vascular restenosis, hypersensitivity, cardiac rupture arising as a complication with myocardial infarction, stroke or cerebral ischemia, and traumatic brain injury, arthritis (bursitis, gouty arthritis, polymyalgia rheumatic, etc.), autoimmune diseases, chronic inflammation, chronic prostatitis, nephritis, pelvic inflammatory disease, transplant rejection, and myocarditis. For example, anatomical structure 604 may comprise the spleen of the subject, and/or nerve tissue 602 may comprise tissue of the splenic nerve of the subject. For some such applications, detecting the factor indicative of the parameter of the subject comprises detecting an inflammatory cytokine, such as tumor-necrosis factor alpha (TNF-alpha), in the blood of the subject.

For some applications, the techniques described with reference to FIGS. 12-13 are used to treat a subject who suffers from obesity. For example, anatomical structure 604 may comprise an organ of the gastrointestinal system of the subject, such as the stomach or duodenum of the subject, and/or nerve tissue 602 may comprise a nerve that conducts action potentials between the organ of the gastrointestinal system and another part of the body of the subject, such as the celiac plexus of the subject. For example, nerve tissue 602 may comprise a vagus nerve or a branch thereof. For some such applications, detecting the factor indicative of the parameter of the subject comprises detecting an EMG value (e.g., of a muscle associated with the gastrointestinal system). For some such applications, detecting the factor indicative of the parameter of the subject comprises detecting the factor using ultrasound (e.g., sensor 626 may comprise an ultrasound transceiver).

For some applications of the invention the nerve tissue being treated (e.g., excited and ablated) is accessed transluminally, and the excitatory current and ablation energy are applied from within a blood vessel. For example, as described hereinabove, nerve tissue associated with the renal artery (i.e., the renal nerve) is accessed via the renal artery. Other nerves which may be treated as described hereinabove via transluminal access include, but are not limited to nerves which are associated with: the superior mesenteric vein, posterior, anterior, inferior pancreaticoduodenal veins, middle colic vein, right colic vein, ileocolic vein, anterior, posterior cecal veins, hepatic portal vein, posterior superior pancreaticoduodenal vein, prepyloric vein, anterior superior pancreaticoduodenal vein, hepatic portal vein, posterior superior pancreaticoduodenal vein, superior mesenteric vein, anterior superior pancreaticoduodenal vein, anterior inferior pancreaticoduodenal vein, posterior inferior pancreaticoduodenal vein, a vein that vascularizes the duodenum.

The apparatus and techniques described throughout this patent application, including those described hereinbelow, may be used to facilitate screening and/or ablation in the example conditions, anatomical sites and nerves provided hereinabove.

Figure 14:
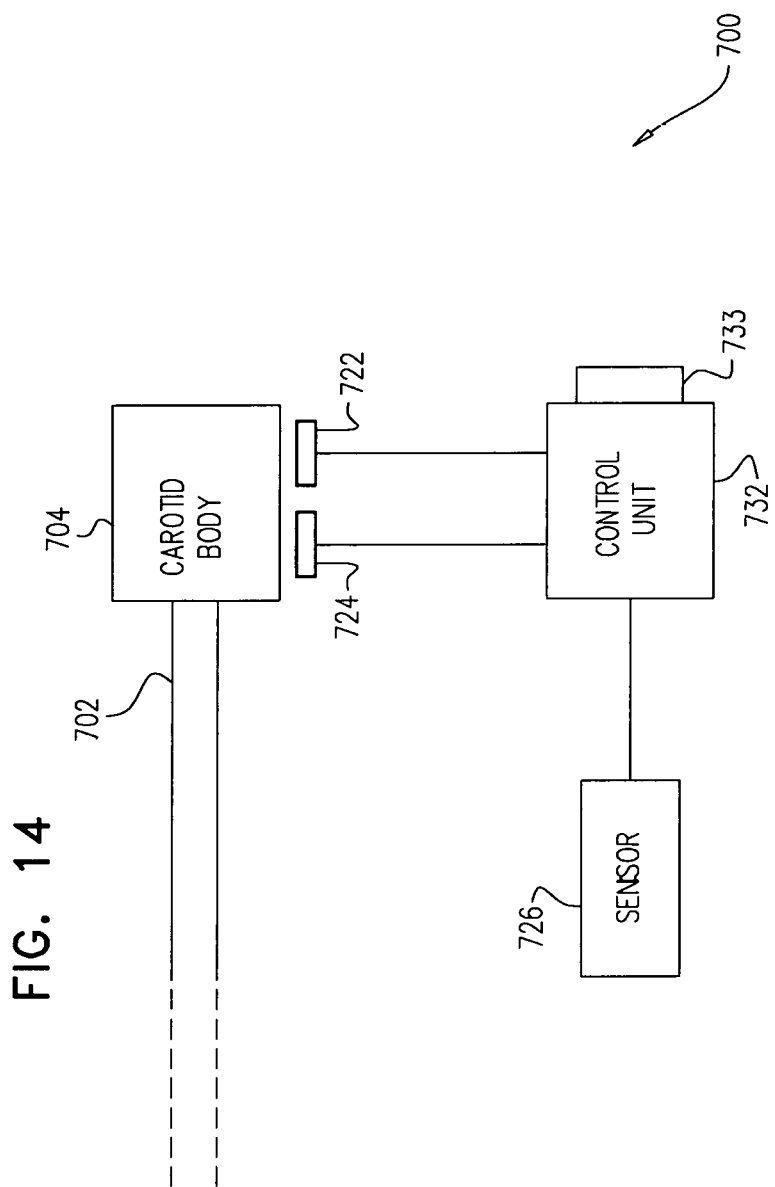
FIG. 14 is a schematic illustration of a system for controlled ablation of tissue of a carotid body of a subject, in accordance with some applications of the invention.

Reference is made to FIG. 14, which is a schematic illustration of a system 700 for controlled ablation of tissue of a carotid body 704 of a subject, such as chemoreceptors and/or glomus cells, e.g., to treat a subject who suffers from hypertension, in accordance with some applications of the invention. Carotid body 704 is capable of modulating blood pressure of the subject by inducing action potentials in a nerve 702 of the subject in response to detected levels of oxygen partial pressure, carbon dioxide partial pressure, pH, and temperature, as well as detecting changes in blood pressure. Nerve 702 may comprise a glossopharyngeal nerve of the subject and/or a branch thereof that innervates the carotid body (e.g., the Nerve of Hering).

System 700 comprises at least one electrode unit 722, an ablation unit 724, and a control unit 732, configured to drive and/or control the electrode unit and/or the ablation unit. For some applications, control unit 732 comprises an interface 733. Typically, system 700 further comprises a sensor 726, configured to detect a factor indicative of the parameter of the subject (e.g., the sensor is configured to detect blood pressure of the subject). For some applications, system 700 does not comprise a sensor, and the parameter is detected by a sensor that is not a component of system 700, and/or is detected by a medical professional. For such applications, information relating to the factor (e.g., a value of the factor, such as a blood pressure value) may be inputted manually or automatically via interface 733.

Electrode unit 722 and ablation unit 724 are advanced to a vicinity of carotid body 704 (e.g., to within 1 cm of the carotid body (e.g., to within 1 mm of the carotid body, such as to be in contact with the carotid body)). For some applications, electrode unit 722 and ablation unit 724 are advanced toward the carotid body transluminally, typically remaining within a blood vessel (e.g., the carotid artery) for the duration of the procedure. For some applications, electrode unit 722, ablation unit 724, control unit 732 and/or sensor 726 of system 700 comprise a respective identically-named corresponding component of one or more other systems described hereinabove. For some applications, electrode unit 722, ablation unit 724, control unit 732 and sensor 726 of system 700 are arranged (e.g., coupled to each other) as described for identically-named corresponding components of one or more other systems described hereinabove. For example, electrode unit 722, ablation unit 724, control unit 732 and sensor 726 may be coupled to and disposed along a longitudinal member, such as catheter 28 (not shown in FIG. 14).

For some applications, system 700 does not comprise distinct electrode and ablation units, but rather comprises one effector unit that functions, under control of control unit 732, as both electrode unit 722 and ablation unit 724. The effector unit may, for some applications, comprise a single electrode. That is, for some applications, control unit 732 drives the effector unit (e.g., an electrode thereof) to apply, as appropriate, the excitatory current and the ablating energy.

System 700 is typically used in combination with techniques described hereinabove, mutatis mutandis. For example, with reference to the steps shown in FIG. 13, mutatis mutandis:

Carotid body 704 is stimulated by electrode unit 722 applying an excitatory current to the carotid body (step 642). The excitatory current typically has a frequency of greater than 1 Hz and/or less than 100 Hz, such as between 1 and 100 Hz, e.g., between 10 and 100 Hz. After a start of the application of the excitatory current, a detection of a factor indicative of the parameter of the subject is performed, e.g., using sensor 726 (step 642). For some applications, the detection is performed during the application of the excitatory current. For some applications, the detection is performed after the excitatory current has stopped being applied. At least in part in response to the detection of the factor, ablating energy is applied to carotid body 704 by ablation unit 724 (step 644). Typically, the ablating energy has characteristics similar to (e.g., the same as) those of ablating energy described elsewhere hereinabove.

For some applications, before application of the excitatory current in step 642, a detection of the factor is performed (e.g., while the subject is at rest and/or untreated) (step 640). Reference numeral 660 indicates a technique in which a first detection is performed before application of the excitatory current, a second detection of the factor is performed after the start of the application of the excitatory current, and subsequently ablating energy is applied. For some applications of technique 660, ablating energy is applied 644 at least in part responsively to the detection in step 640 and at least in part responsively to the detection in step 642. For example, ablating energy may be applied in response to a comparison of the first detection and the second detection, e.g., in response to a difference between a first detected value of the factor and a second detected value of the factor. For example, technique 660 may be used to screen subjects likely to be responsive to a treatment comprising ablation of carotid body 704 (e.g., by determining a sensitivity of the parameter to action potentials initiated by the carotid body).

For some applications, subsequent to the application of ablating energy in step 644, another application of excitatory current and detection of the factor are performed (step 646). Typically, step 646 is identical in nature to step 642. For such applications, at least in part in response to the detection in step 646 (and typically also at least in part in response to previous detection(s) of the factor), ablating energy is applied to carotid body 704 by ablation unit 724 (step 648). Reference numeral 662 indicates a technique in which steps 646 and 648 are performed after step 644. Ablating energy of step 648 may be applied in response to a difference between a value of the factor detected in step 646 and a value of the factor detected in step 642. For example, this difference may indicate a degree of ablation achieved by the application of ablating energy, as described hereinabove.

Reference is made to FIGS. 15A-F, which are schematic illustrations of a system 740 and techniques for facilitating ablation of nerve tissue of a subject, in accordance with some applications of the invention. System 740 comprises a plurality of stimulating electrodes coupled to transvascular catheter 28, which is advanced to at least one location within the blood vessel. For example, an intravascular device 741 at a distal portion of the system may be coupled to catheter 28, device 741 comprising at least two pluralities (or "rings") of electrodes 750 and 752, disposed at respective longitudinal positions of the intravascular device. It is noted that in the context of the claims and description of the present application, the terms "catheter" and "intravascular device" may be used interchangeably, such that a statement relating to one of these terms (e.g., "electrodes coupled to a catheter") includes within its scope a parallel statement relating to the other one of these terms (e.g., "electrodes coupled to an intravascular device, which may be coupled to a catheter").

System 740 typically further comprises sensor 26 and control unit 32, as described hereinabove (with control unit 32 configured to execute the steps described with reference to system 740). The electrodes of each plurality of electrodes are arranged (e.g., distributed) around a central longitudinal axis ax1 of the distal portion of the device (e.g., circumferentially around a central longitudinal axis of intravascular device 741). That is, the electrodes are disposed in a circumferential arc (e.g., a circle) such that each electrode is disposed at a respective circumferential position on the arc. As shown, when intravascular device 741 is disposed within a blood vessel (e.g., renal artery 8), the electrodes of each plurality of electrodes are arranged around a central longitudinal axis of the blood vessel. Although each plurality of electrodes is shown as being arranged in a respective ring at a respective distinct longitudinal site of the intravascular device (e.g., on a transverse plane thereof), each plurality of electrodes may have a different arrangement, such as a helical arrangement.

FIGS. 15A-F show renal artery 8 (e.g., the wall thereof) in more detail than do earlier figures, but it is to be noted that the position of intravascular device 741 is typically generally the same as the position of the intravascular devices described hereinabove. The innermost layer of the renal artery is intima 762 (also known as the tunica intima), which is covered with endothelium 760 (i.e., the inner surface of the artery is lined with endothelium). Disposed circumferentially around intima 762 is media 764 (also known as the tunica media) which comprises, inter alia, smooth muscle. The outer layer of the renal artery is adventitia 766 (also known as the tunica adventitia, which comprises mainly collagen fibers. The nerve tissue of the renal artery (e.g., renal nerve 770) is disposed within adventitia 766. For illustrative purposes and simplicity, nerve 770 is shown at the bottom side of artery 8.

Typically, each electrode of each plurality of electrodes is paired with a corresponding electrode of the other plurality of electrodes, the pair of electrodes being disposed at a particular rotational position around central longitudinal axis ax1. For example, and as shown, a first electrode 750a of plurality 750 may be paired with a first electrode 752a of plurality 752, the pair of electrodes being disposed at a particular rotational position around axis ax1. Other pairs of electrodes (e.g., second electrodes 750b and 752b, third electrodes 750c and 752c, and fourth electrodes 750d and 752d) are disposed at other respective rotational positions around axis ax1.

A preliminary (e.g., baseline) blood pressure value q_A is detected (e.g., by sensor 26) in the absence of any current applied by the electrodes of device 741 (FIG. 15A). Typically, value q_A is detected while the subject is at rest. Value q_A is typically detected following introduction of intravascular device 741 into artery 8, but may be additionally or alternatively detected prior to the introduction of the intravascular device. For some applications, value q_A corresponds to, or is analogous to, value p_A, described hereinabove, mutatis mutandis.

Figure 15B:
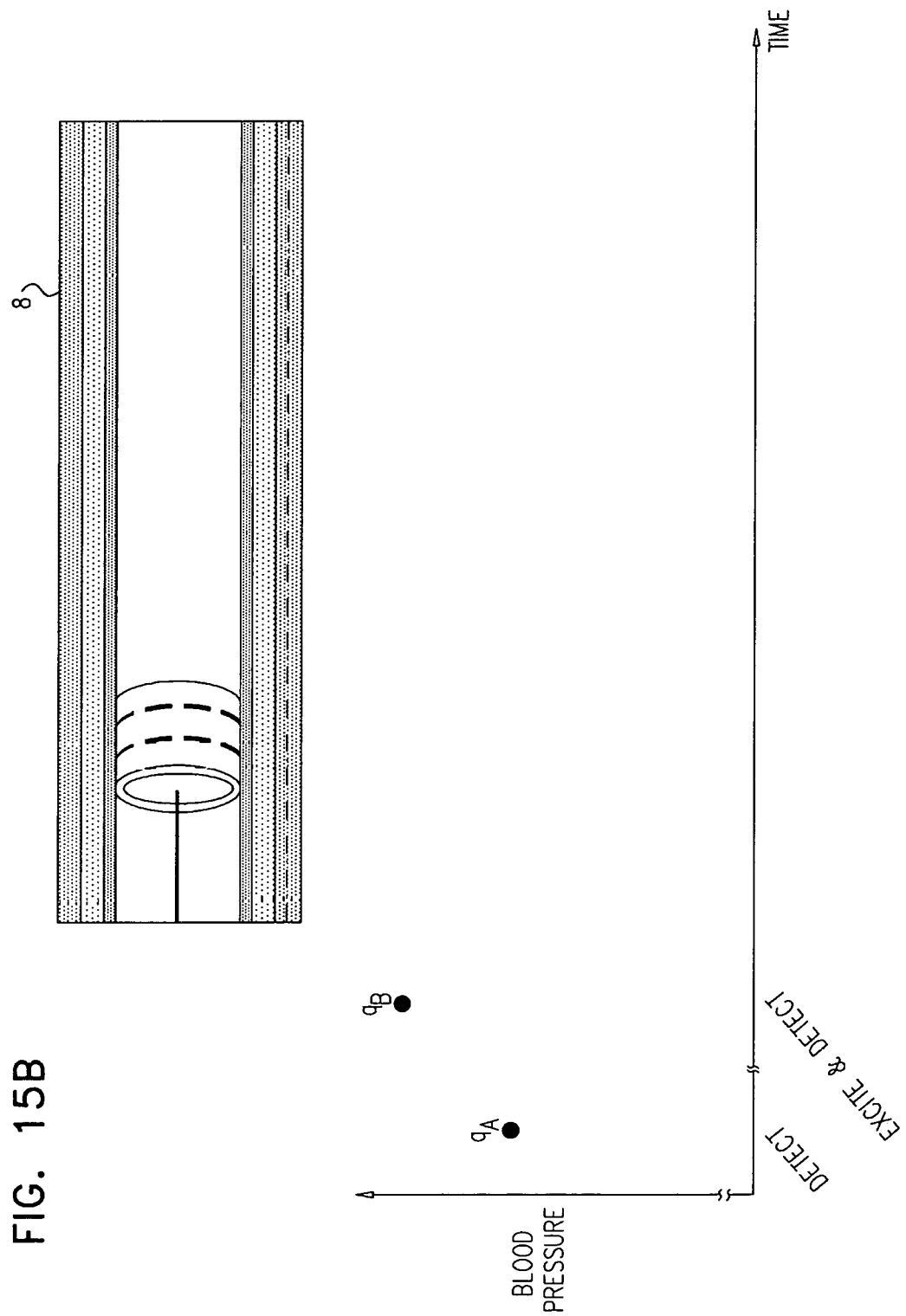

For some applications, excitatory current is subsequently applied by all the electrodes of pluralities 750 and 752 (e.g., by driving the current from all the electrodes of plurality 750 to all the electrodes of plurality 752) and a blood pressure value q_B is detected after the start of the application of the excitatory current (FIG. 15B). As described hereinabove, the excitatory current is configured to induce action potentials in the renal nerve (or the nerve associated with any other blood vessel in which the techniques described herein are used). For some applications, value q_B represents a hypothetical highest blood pressure achievable by a high-level (e.g., hypothetical maximum) renal nerve activity (e.g., the highest blood pressure achievable by the body of the subject via renal nerve activity). For some applications, value q_B corresponds to, or is analogous to, value p_C, described hereinabove, mutatis mutandis.

Figure 15C:
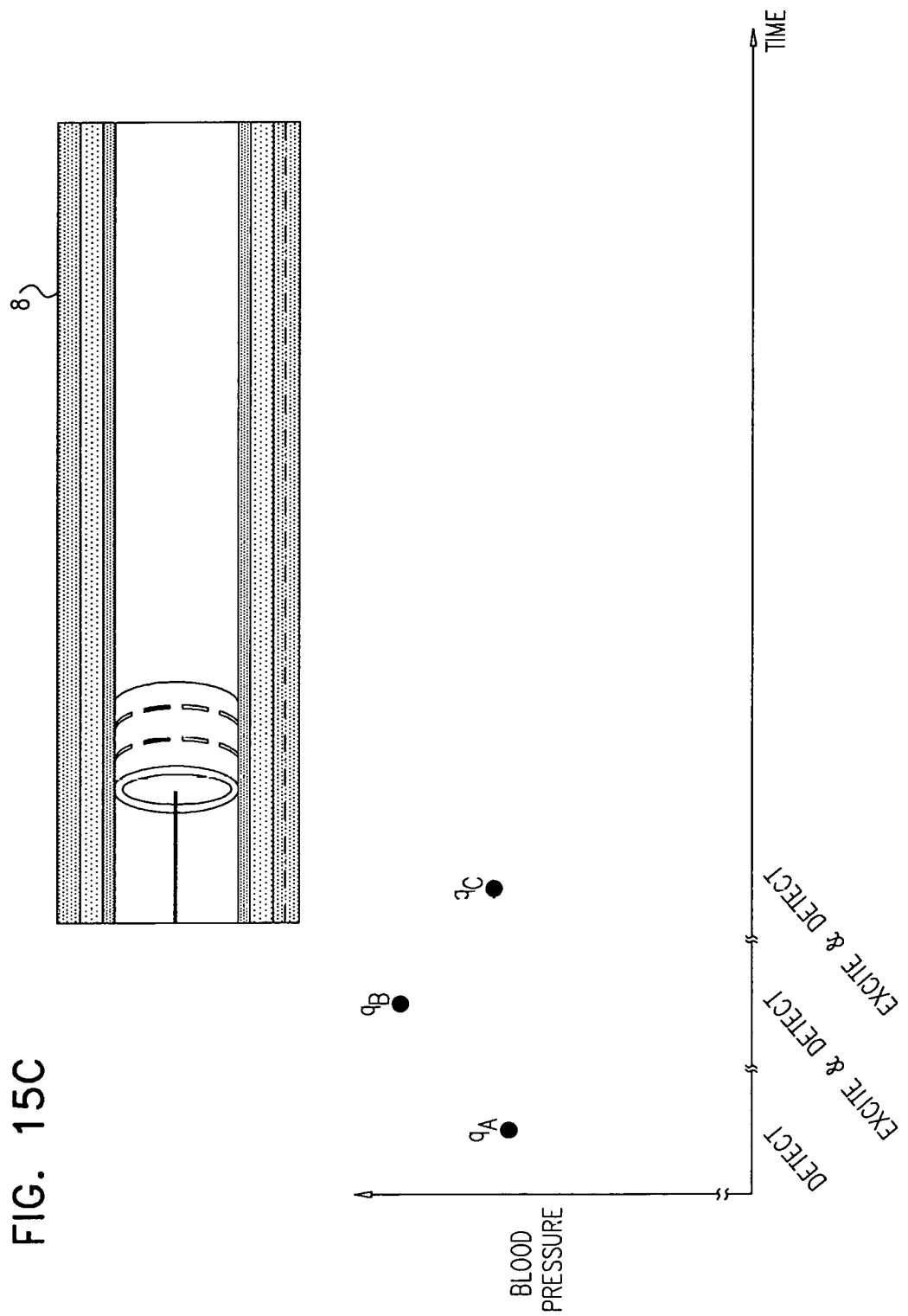
Figure 15F:
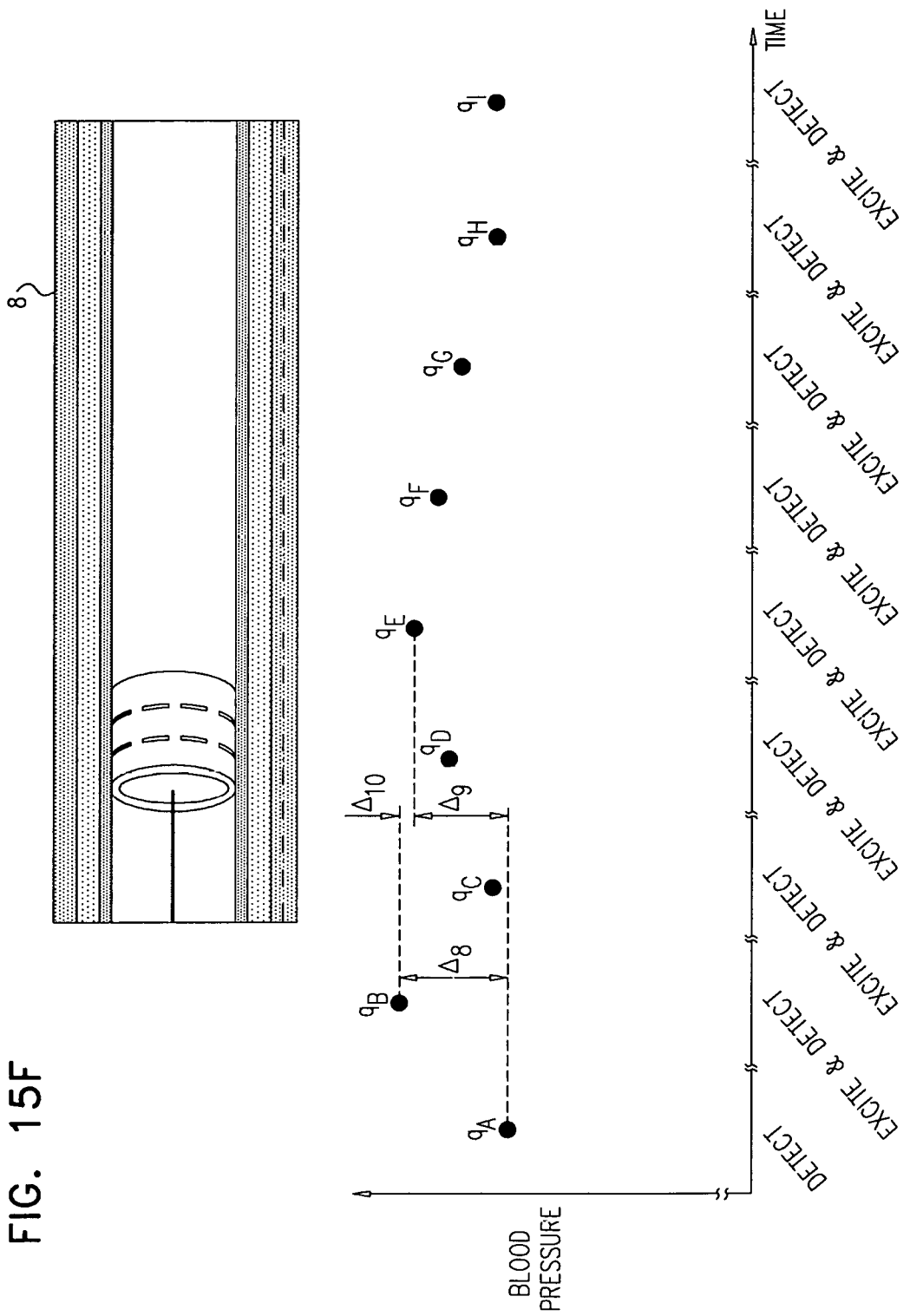

Subsequently, excitatory current is applied by driving the excitatory current between the electrodes of each pair of electrodes consecutively (although not necessarily in the order shown, nor necessarily in any particular order). After the start of each application, a respective blood pressure value is detected. FIG. 15C shows the excitatory current being applied by (e.g., between) electrodes 750b and 752b, and blood pressure value q_C being detected subsequently to the start of the application of the current. FIG. 15D shows the same for electrodes 750c and 752c, mutatis mutandis (detecting value q_D), and FIG. 15E shows the same for electrodes 750d and 752d, mutatis mutandis (detecting value q_E). FIG. 15F shows the same for electrodes 750a and 752a, mutatis mutandis (detecting value q_I), the procedure having been previously performed for all the other electrode pairs, mutatis mutandis (detecting values q_F. q_G, and q_H).

The measured blood pressure values for FIGS. 15A-F appear respectively on the graph of these figures, and their relative magnitudes are purely exemplary for illustrative purposes. A difference delta_8 between values q_A and q_B may be used to determine whether the subject is a good candidate for renal nerve ablation treatment (e.g., a higher value delta_8 may indicate a higher suitability of the subject for renal nerve ablation treatment), and thereby to screen/select subjects for such treatment (e.g., as described hereinabove for difference delta_6, mutatis mutandis). At least in part responsively to one or more (typically at least two) of the detected values, at least one electrode pair is selected for subsequent application of ablation energy. For example, each of values q_C-q_I may be compared to one or more others of these values, and/or to values q_A and/or q_B. The at least one electrode pair selected for subsequent application of ablation energy typically comprises at least those electrodes via which the excitatory current produced the greatest increase in blood pressure. In the example shown, the pair of electrodes 750d and 752d might be selected (of values q_C-q_I, value q_E is greatest, being furthest from value q_A (difference delta_9) and closest to value q_B (difference delta_10)).

Typically, the selected electrode pair is that which is closest to renal nerve 770 (and/or which has the best conductive path to the nerve). This is illustrated in FIGS. 15A-F by electrodes 750d and 752d being closest to nerve 770. Ablation energy (typically RF energy) is applied to the nerve using the selected electrode pair (not shown). That is, at least in part dependently on at least two of the detected blood pressure values, a target site of the renal nerve is determined, and the ablation energy is applied to the target site.

Although FIGS. 15C-F show application of current by sequential individual electrode pairs, it is to be noted that similar steps may be alternatively or additionally performed using application of current by more than one electrode pair. For example, an intervening step in which more than one electrode pair is used may increase the efficiency of the technique, e.g., using a binary search technique. An illustrative but non-limiting example of such a use of a binary search technique includes (1) testing blood pressure responsiveness to (a) excitatory current applied by one half of the electrode pairs, and (b) excitatory current applied by the other half of the electrode pairs, (2) selecting the half that provided the greatest change in blood pressure, sub-dividing that half into half again (i.e., into quarters), and testing blood pressure responsiveness to (a) excitatory current applied by one of the quarters, and (h) excitatory current applied by the other one of the quarters, and (3) repeating the division and testing until a desired resolution (i.e., precision) is achieved (e.g., until a single electrode pair is identified that produces the greatest blood pressure change).

Figure 28:
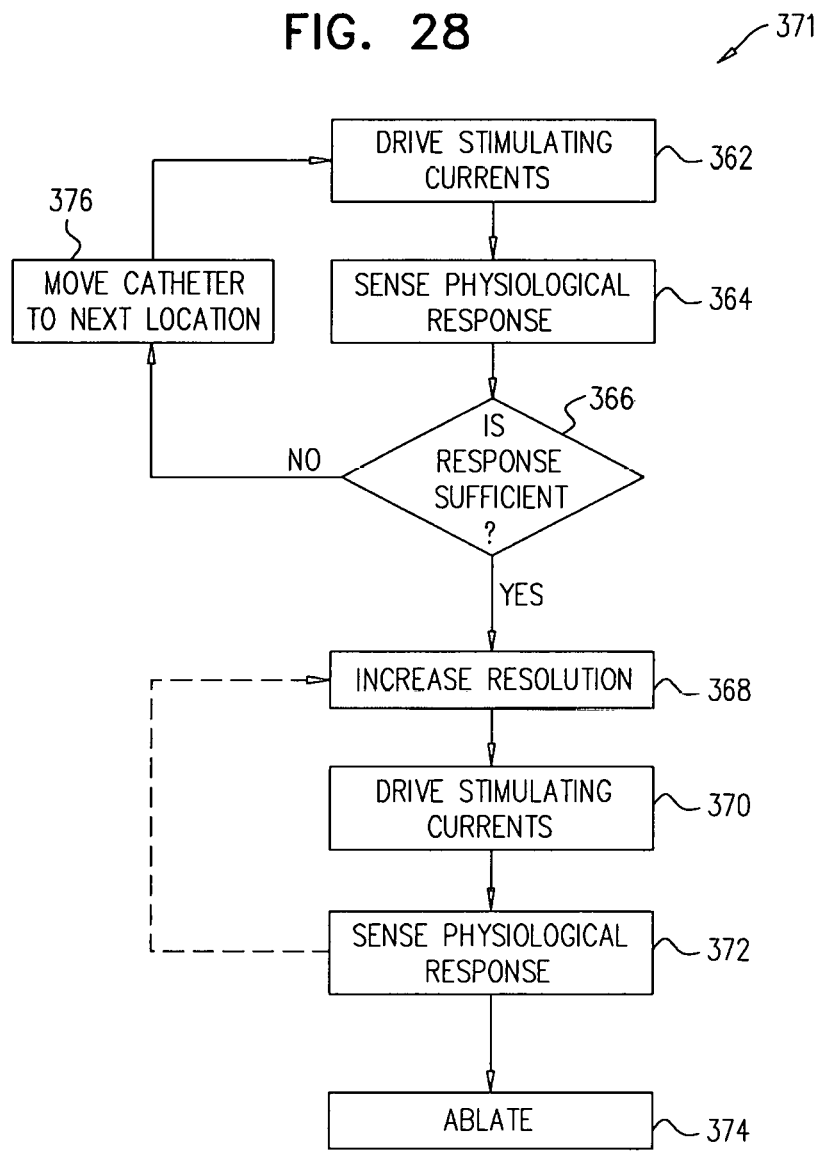
FIG. 28 shows a flow chart for a method for locating and ablating a nerve, in accordance with some applications of the present invention.

Reference is now additionally made to FIG. 28, which shows a flow chart for a method 371 for locating and ablating a nerve passing longitudinally within a wall of a blood vessel of a subject, in accordance with some applications of the present invention. The binary search technique described immediately hereinabove is an instance of method 371, the steps of which are as follows:

(i) At a first stimulating step 362, the stimulating electrodes are used to drive one or more first-precision-locating stimulating electric currents into the wall of the blood vessel, at a first location.

(ii) Using a physiological sensor, at a first sensing step 364, the physiological response of the subject to the first-precision-locating stimulating electric currents (e.g., a change in blood pressure) is sensed.

(iii) At a response-assessing step 366, the physiological response of the subject is assessed. If the response is deemed to be sufficient (e.g., a significant increase in blood pressure, e.g., an increase of 3.2 mmHg, is sensed), the nerve is located to a first degree of precision.

(iii) In response to locating the nerve to the first degree of precision, the resolution of the search is increased at a resolution-increasing step 368, e.g., as further described hereinbelow with reference to FIGS. 17A-E. (Resolution-increasing step 368 is generally a "configuration" step, in which the stimulation parameters are set.) Subsequently, at a second stimulating step 370, the stimulating electrodes are used to drive one or more sets of one or more second-precision-locating stimulating electric currents into the wall of the blood vessel.

(iv) Using the physiological sensor, at a second sensing step 372, the physiological response of the subject (e.g., a change in blood pressure) to each of the sets of second-precision-locating stimulating electric currents is sensed, and in response to the physiological response, the nerve is located to a second degree of precision that is greater than the first degree of precision.

(v) In response to locating the nerve to the second degree of precision, the nerve is ablated, at an ablating step 374.

If, at response-assessing step 366, the physiological response of the subject to the first-precision-locating stimulating electric currents is deemed to be insufficient (e.g., the sensed increase in blood pressure was relatively insignificant), the catheter may be moved, at a catheter-moving step 376, from the first location to a second location within the blood vessel. Step 362 is then repeated, i.e., the stimulating electrodes are used to drive one or more first-precision-locating stimulating electric currents into the wall of the blood vessel at the second location. Subsequently, the physiological response of the subject is assessed at first sensing step 364, and the physiological response is assessed, at response-assessing step 366. If the physiological response was sufficient, the nerve may be located to the first degree of precision, by identifying that the nerve is more likely to be located at the second location than at the first location. If the physiological response was insufficient, catheter-moving step 376 may be repeated one or more times, until the nerve is located to the first degree of precision. (If, after stimulating the tissue at multiple locations, a sufficient response is not sensed, method 371 may terminate, such that no ablation is performed.)

Various parts of method 371 may be performed in an iterative manner. For example, as described hereinabove, steps 362, 364, 366, and 376 may be performed in sequence multiple times, until the nerve is located to the first degree of precision. Alternatively or additionally, steps 368, 370, and 372 may be performed in sequence multiple times. Each iteration of steps 368, 370, and 372 increases the precision to which the nerve is located.

In some applications, a variation of method 371 is performed, in order to "map" the area of the blood vessel, i.e., identify "hot spots" for a subsequent ablation routine. In such a variation of method 371, the first-precision-locating stimulating electric currents are driven into the wall of the blood vessel at a plurality of locations. For each of the locations, the physiological response of the subject is assessed, and, if the response is sufficient, the sets of second-precision-locating stimulating electric currents are applied at the location. (Thus, the hot spots are more precisely located.) Subsequent to the mapping, ablating step 374 is performed for the hot spots that were identified.

Method 371 is further described hereinbelow, with reference to FIGS. 17A-E.

Whether a given application of excitatory current shown in FIGS. 15C-F is performed using an individual electrode pair or more than one electrode pair, the application of excitatory current shown in these figures is performed via a subset of each plurality of electrodes. That is, the subset may include one or more electrodes from each plurality 150 and 152. Whether each subset includes one electrode pair or more than one electrode pair, it is to be noted that the subset via which each application of excitatory current is applied is non-identical to the other subsets. Similarly, ablation energy is typically applied by a subset of electrodes. Whether each subset of each plurality of electrodes comprises a single electrode or more than one electrode, each application of the excitatory current and/or ablation energy may be considered to be applied in an arc that subtends an angular range around central longitudinal axis ax. For some applications, the angle subtended by one of the applications at least in part coincides with that subtended by another of the applications. For some applications, the angle subtended by one of the applications does not at all coincide with that subtended by another of the applications.

It is to be noted that the order of FIGS. 15A-F is illustrative, and other orders may be used.

For some applications, control unit 32 automatically performs the steps shown in FIGS. 15A-F. For example, a user (e.g., an operating physician) may activate control unit 32, which automatically performs the consecutive applications of excitatory current (via the electrodes) and detection of the blood pressure values (via the sensor). For some applications, control unit 32 further automatically drives the selected electrodes to apply the ablation energy.

It is hypothesized that the apparatus and techniques described with reference to FIGS. 15A-F may facilitate effective renal nerve ablation without creation of a lesion that completely circumscribes the renal artery, thereby reducing narrowing of the lumen of the artery that may otherwise result from such circumferential ablation.

Because the electrodes of device 741 are used to apply both the excitatory current and the ablation energy, device 741 may be considered to serve as both an electrode unit (e.g., corresponding to one or more of the electrode units described hereinabove) and as an ablation unit (e.g., corresponding to one or more of the ablation units described hereinabove). In this way, device 741 may be considered to be a modified embodiment of intravascular device 421 (described with reference to FIG. 8), in which the electrodes of electrode unit 422 and ablation unit 24 are replaced with pluralities of electrodes 750 and 752. For some applications, pluralities of electrodes 750 and 752 correspond to sub-electrodes 244, described hereinabove with reference to FIGS. 9A-B, mutatis mutandis.

For some applications, intravascular device 741 and/or the electrode pluralities thereof may replace another intravascular device and/or the electrodes thereof, described elsewhere herein, mutatis mutandis. For some applications, the apparatus and techniques described with reference to FIGS. 15A-F may be used in combination with those described elsewhere herein, mutatis mutandis. For example, any of the techniques described hereinabove may be augmented by determining a rotational position of a target site for application of ablation energy).

It is to be noted that for some applications the apparatus and techniques described with reference to FIGS. 15A-F may be modified to determine the target site by applying a non-ablative blocking current (as described hereinabove, mutatis mutandis) in place of the excitatory current. For some such applications, the target site is determined (and the electrode pairs are selected) according to the electrode pair(s) that provide the greatest reduction in blood pressure. Alternatively, a non-ablative blocking current may be used in addition to the excitatory current (e.g., in separate steps) to provide greater information about the potential responsiveness of the subject to nerve ablation (e.g., as described with reference to FIGS. 2B and 3, mutatis mutandis).

Reference is made to FIGS. 16A-G, which are schematic illustrations of a system 780 and techniques for facilitating ablation of nerve tissue of a subject, e.g., by determining an approximate distance of a nerve from a wall of a blood vessel of a subject, in accordance with some applications of the invention. System 780 comprises a plurality of stimulating electrodes 790 coupled to catheter 28. For example, in some applications, system 780 comprises an intravascular device 781 at a distal portion of the system, coupled to catheter 28, and electrodes 790 are arranged (e.g., distributed) along a central longitudinal axis of device 781. (Alternatively, in some applications, intravascular device 781 is not coupled to catheter 28, and/or the electrodes are arranged along a central longitudinal axis of a distal portion of system 780 that is not device 781.) System 780 typically further comprises sensor 26 and control unit 32, as described hereinabove (with control unit 32 configured to execute the steps described with reference to system 780). As shown, when intravascular device 781 is disposed within a blood vessel (e.g., renal artery 8), the plurality of electrodes is arranged along a central longitudinal axis of the blood vessel. For some applications, each electrode is separated from its neighbors by more than 1 mm, less than 5 mm, and/or 1-5 mm (e.g., 1-3 mm, such as about 1.5 mm). Each electrode 790 is shown as ring-shaped purely as an illustrative example, and may assume a different shape. The anatomy of artery 8 is described with reference to FIGS. 15A-F.

Figure 16A:
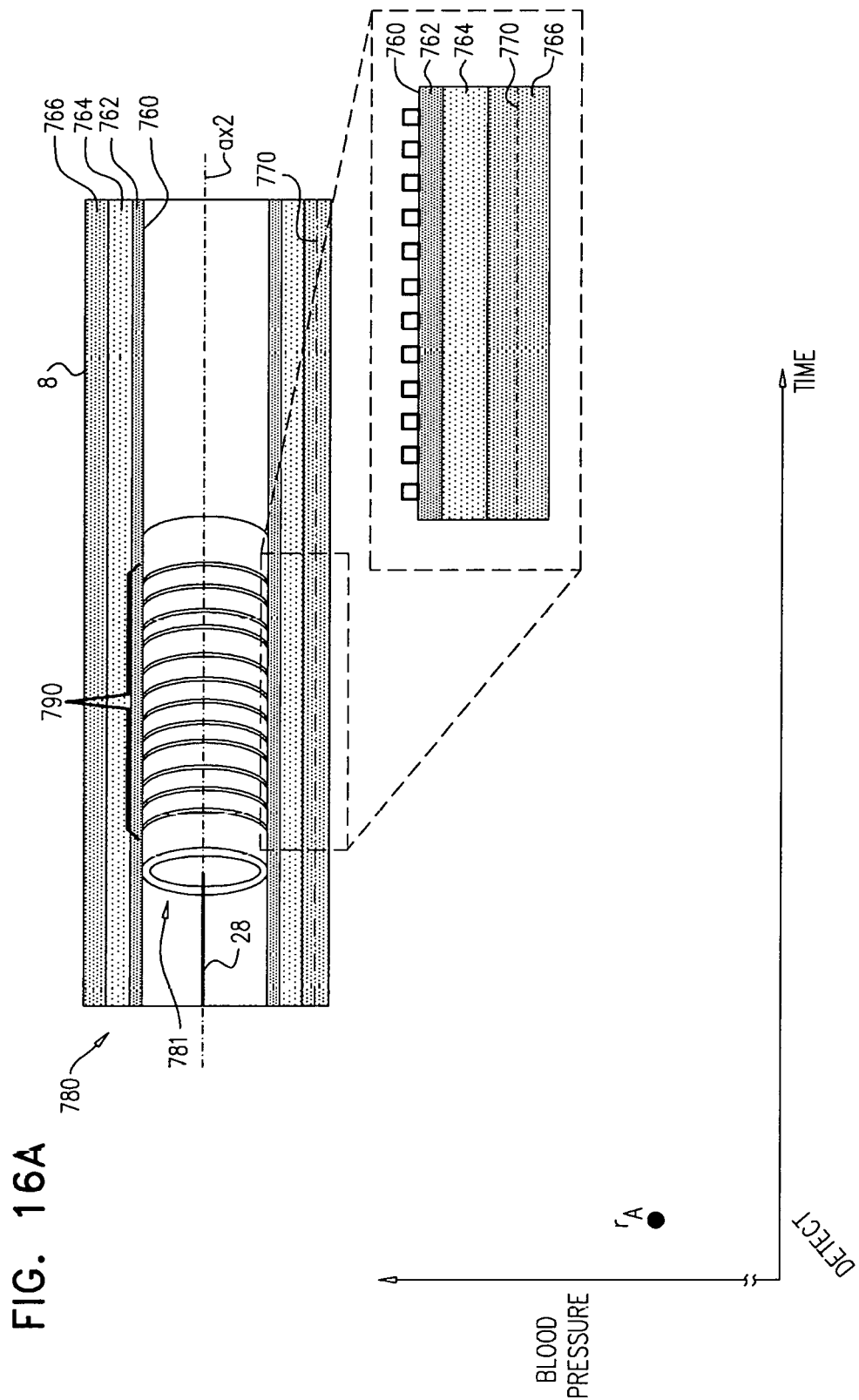

A preliminary (e.g., baseline) blood pressure value $r \ldots A$ is detected (e.g., by sensor 26) in the absence of any current applied by the electrodes of device 781 (FIG. 16A). Typically, value $r\_A$ is detected while the subject is at rest. Value $r\_A$ is typically detected following introduction of intravascular device 781 into artery 8, but may be additionally or alternatively detected prior to the introduction of the intravascular device. For some applications, value $r\_A$ corresponds to, or is analogous to, value $p\_A$ and/or value $q\_A$, described hereinabove, mutatis mutandis.

If not already done prior to detecting value $r\_A$, the catheter, and/or device 781, is advanced to a location of interest within the blood vessel. Subsequently, excitatory current (i.e., non-ablating, stimulating current) is applied by driving the excitatory current between various pairs of electrodes 790 consecutively (although not necessarily in the order shown, nor necessarily in any particular order). After the start of each application, a physiological sensor is used to sense a physiological response of the subject to the non-ablating current. For example, respective blood pressure values may be detected (i.e., respective changes in blood pressure may be sensed), using a blood-pressure sensor.

Figure 16B:
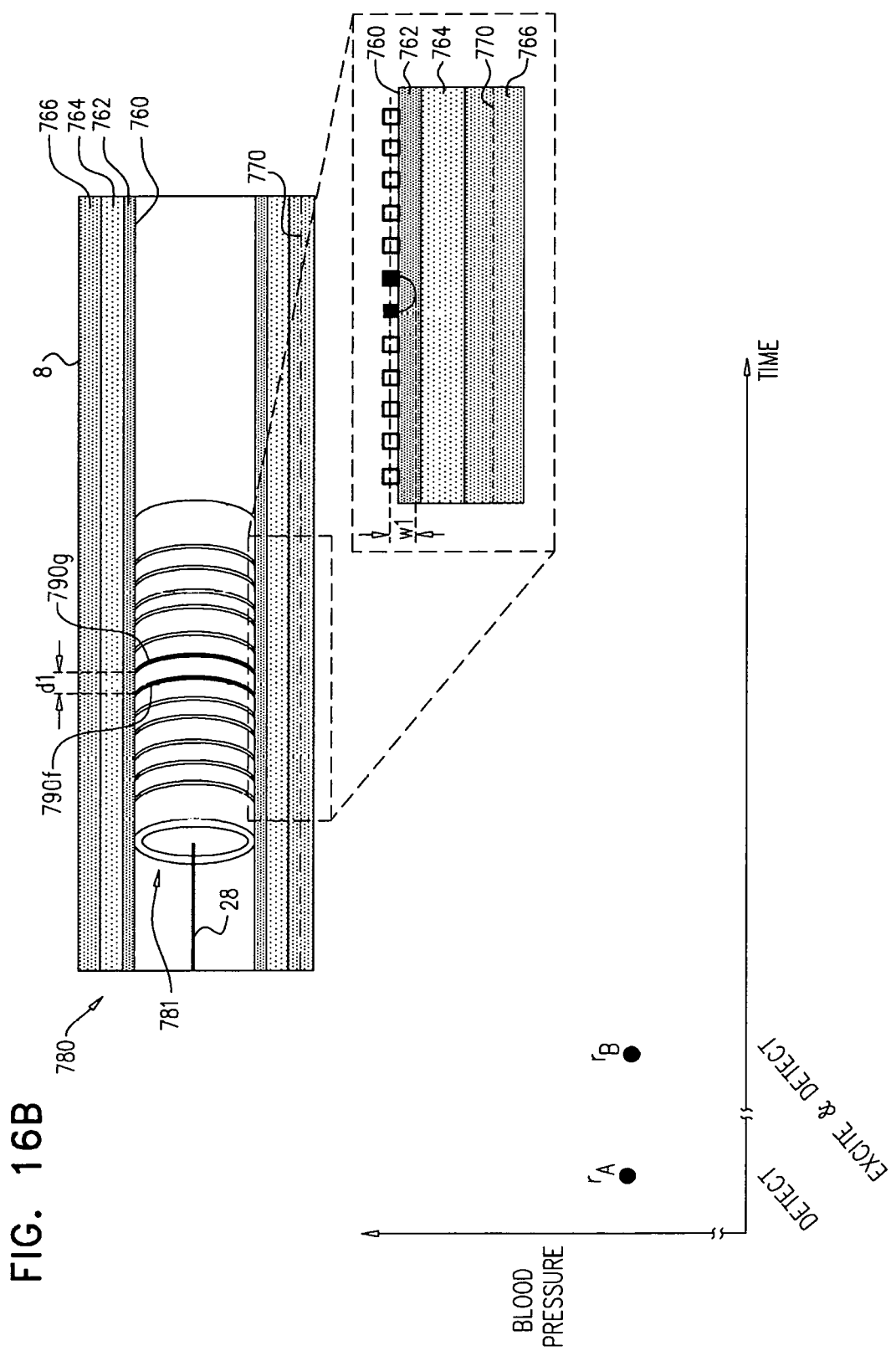
Figure 16F:
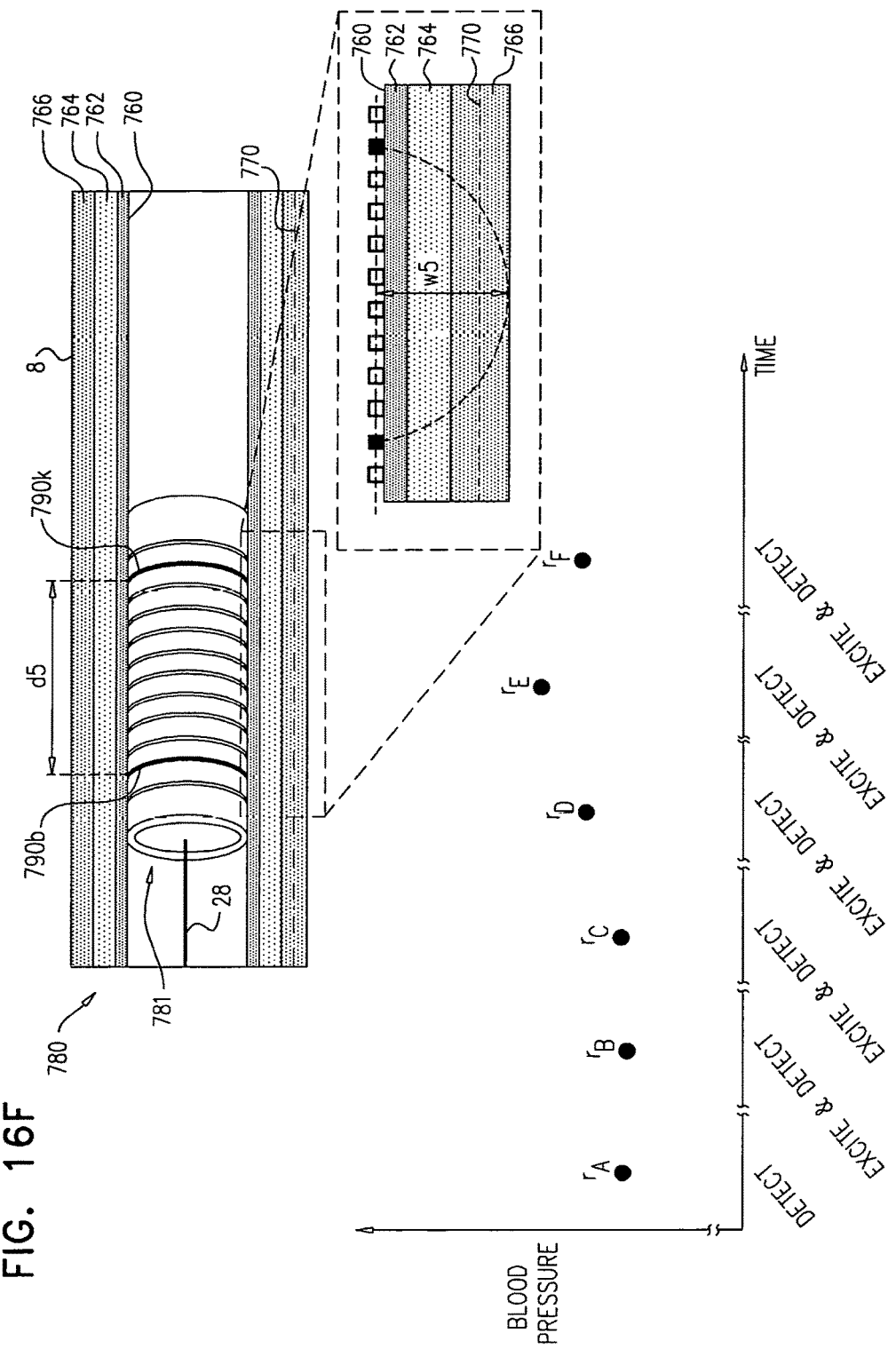
Figure 16G:
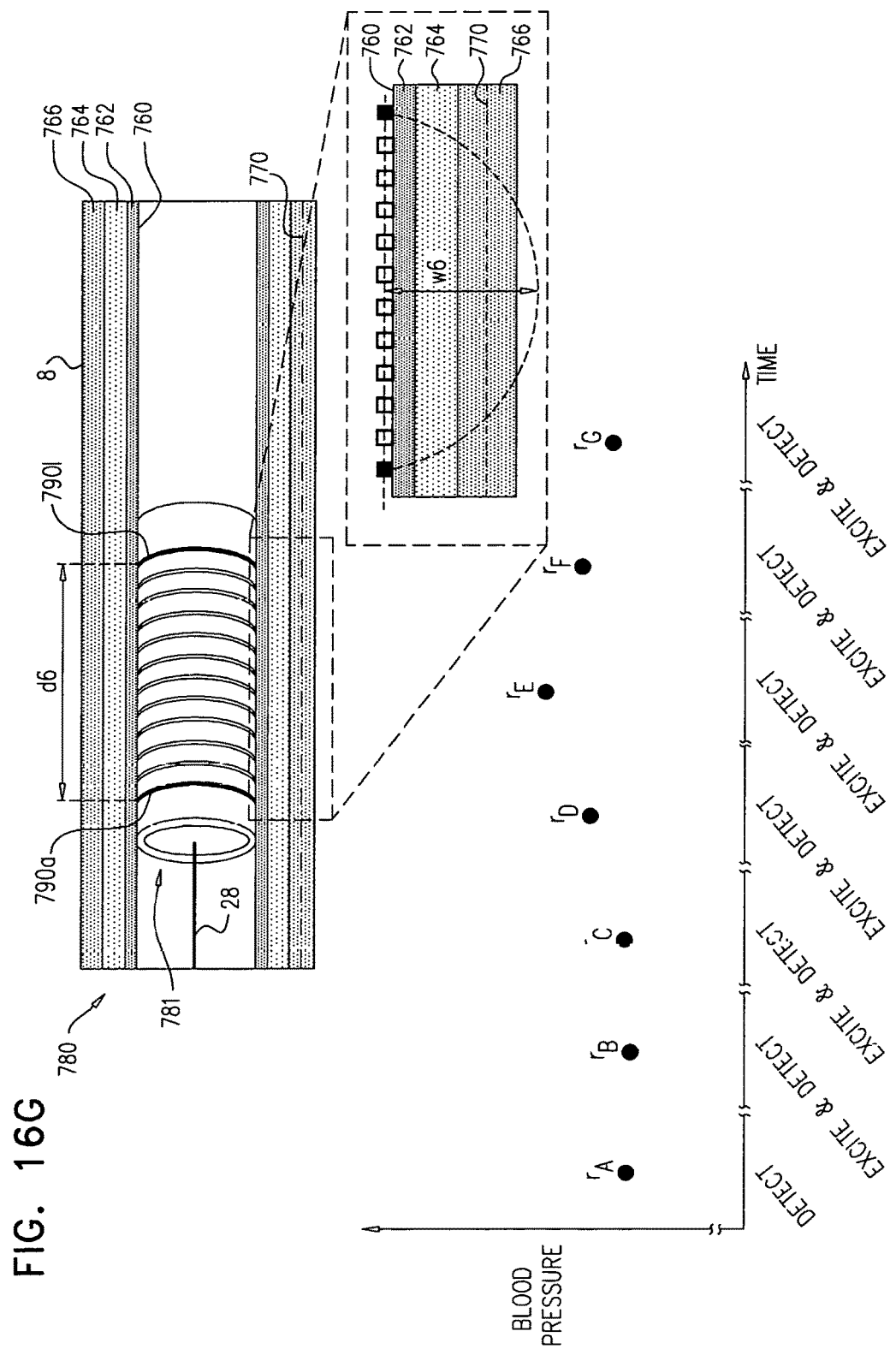

FIG. 16B shows the excitatory current being applied by (e.g., between) electrodes 790f and 790g, and blood pressure value r_B being detected subsequently to the start of the application of the current. Electrodes 790f and 790g are disposed a distance d1 apart. FIG. 16C shows the same for electrodes 790e and 790h, mutatis mutandis (distance d2; value r_C). FIG. 16D shows the same for electrodes 790d and 790i, mutatis mutandis (distance d3; value r_D). FIG. 16E shows the same for electrodes 790c and 790j, mutatis mutandis (distance d4; value r_E). FIG. 16F shows the same for electrodes 790b and 790k, mutatis mutandis (distance d5; value r_F). FIG. 16G shows the same for electrodes 790a and 790l, mutatis mutandis (distance d6; value r_G).

For a given current (e.g., a current having given characteristics), a characteristic depth "w" of the electrical field generated when the current is driven between two electrodes (as measured from, and orthogonally to, an axis between the two electrodes) increases with an increase in distance between the two electrodes. For example, for electrodes 790f and 790g, disposed distance d1 apart, the electrical field generated has a depth w1, and just as distances d2, d3, d4, d5, and d6 are progressively greater, so are respective depth w2, w3, w4, w5, and w6. By applying the excitatory current between electrodes of different distances from each other, and detecting the resulting blood pressure, the electrode pair that results in the greatest blood pressure increase compared to value r_A may be identified. Typically, the characteristic depth of the electric field that causes the greatest increase in blood pressure will correspond to the approximate distance of the nerve from the wall of the blood vessel; thus, by identifying the "maximum stimulation" electrode pair, the approximate distance of the nerve may be determined.

In some applications, the characteristic depth of the electric field is varied by varying the amplitude of the non-ablating current, alternatively or additionally to using different pairs of electrodes to apply the non-ablating current, as described above. In other words, at least one of the stimulating electrodes may be used to drive a plurality of non-ablating currents into the wall of the blood vessel, the non-ablating currents having respective amplitudes that are different from each other. In general, a current having a greater amplitude will generate an electric field having a greater characteristic depth, relative to a current having a lesser amplitude. Thus, by varying the amplitude of the stimulating current, the approximate distance of the nerve may be determined. (The varying of the amplitude of the non-ablating current, as described immediately above, is generally analogous to calibration step 110, described hereinabove with reference to FIG. 4.)

In response to the approximate distance of the nerve, a pair of ablating electrodes may be identified. Subsequently, an ablation signal may be passed through the nerve, i.e., ablation energy may be applied to the nerve, by driving an ablating current (e.g., RF current) between the pair of ablating electrodes. In some applications, each electrode of the pair of the ablating electrodes is also one of the stimulating electrodes, e.g., the identified "maximum stimulation" electrode pair is selected (e.g., by control unit 32) for application of the ablation energy. Alternatively, due to known differences for one or more characteristics between the excitation current and the ablation energy, a different electrode pair may be used for application of the ablation energy, the different electrode pair being selected at least in part based on the identified "maximum stimulation" electrode pair. Alternatively or additionally to identifying the pair of ablating electrodes in response to the approximate distance of the nerve, the power of the ablation signal, and/or another parameter (e.g., a frequency) of the ablation signal, may be set in response to the approximate distance. (In general, a higher-power signal will ablate at a larger distance from the blood vessel, relative to a lower-power signal.)

In some cases, ablation modalities other than RF ablation, such as ultrasound ablation, chemical ablation, and cryoablation, may be used via the portion of system 780 that is disposed within the blood vessel. (For example, an ultrasound transducer may be coupled to intravascular device 781, the ultrasound transducer being used to apply ablating energy using an ultrasound signal.) Some modalities (e.g., ultrasound) are relatively "controllable," such that using these modalities, an ablation may be performed at a desired ablation site, while generally limiting "collateral damage" caused to tissue other than the tissue that is targeted for ablation. For example, using ultrasound ablation, it is generally possible to ablate the nerve while generally not causing damage to tissue that is between the nerve and blood vessel. Other modalities (e.g., RF) are relatively less controllable. Typically, however, a modality that is more controllable is more expensive, and/or less practical, to use, than a less controllable modality. Hence, it is generally preferable to use a less-controllable modality, as long as the nerve is close enough to the blood vessel such that relatively little collateral damage is anticipated. It is thus generally advantageous to know the approximate distance of the nerve, in that an appropriate ablation modality may be selected in response to knowing the approximate distance.

In some applications, in response to the approximate distance of the nerve, an ablation modality is selected from a plurality of distinct (i.e., non-identical) ablation modalities, the selected ablation modality then being used to ablate the nerve. For example, an ablation modality may be selected from (a) RF ablation, and (b) an ablation modality that is not RF ablation (e.g., ultrasound). Typically, if the approximate distance of the nerve is less than a threshold, RF ablation is selected, whereas, if the approximate distance is not less than the threshold, the other modality is selected. In some applications, unipolar RF ablation is used if the approximate distance is greater than a threshold, whereas bipolar RF ablation is used otherwise.

For some applications, the excitatory current is increased (e.g., manually by the operator, or automatically by the control unit) as distance d between electrodes is increased, e.g., so as to compensate for increased overall resistance due to the increased distance through tissue that the current must pass.

It is to be noted that properties of the tissue (e.g., spatial variations in such properties) may also affect the depth of the field between each electrode pair. Therefore for some applications there may not be a direct relationship between distance d and depth w. However, the apparatus and techniques described hereinabove nevertheless facilitate identification of the electrode pair that is most effective for application of excitatory current, and thereby identification/selection of an electrode pair that is appropriate for the application of ablation energy.

In the example shown in FIGS. 16A-G, value r_E, corresponding to electrodes 790c and 790j, is greatest, thereby field depth w4 provides the greatest excitation (i.e., initiation of action potentials). This is schematically illustrated by depth w4 corresponding to the distance between electrodes 790 and nerve 770. It is to be noted that the line indicating field depth w does not necessarily indicate the limit of the field; rather it indicates the "effective" field depth i.e., the depth of the portion of the field that has a tangible and/or desired effect. For example, although the field generated by driving the excitatory current between electrodes 790d and 790i (FIG. 16D) may have a total depth that is greater than depth w3, the depth of the portion of the field that is capable of inducing action potentials in nerve 770 is smaller than this total depth, and is indicated by reference numeral w3.

Therefore, system 780 may be used to apply ablation energy having a field depth that has been identified as suitable for a particular subject, and/or for a particular site within renal artery 8 of the subject. For some applications, this advantageously facilitates application of an amount of ablation energy (e.g., an amplitude and/or duration) that is sufficient for successful nerve ablation treatment but that is not excessive, thereby avoiding unnecessary tissue damage.

FIGS. 16A-G show each pair of electrodes including an electrode that is not included by another pair of electrodes. That is, there is no overlap between the electrode pairs shown. For some applications, a pair of electrodes includes an electrode that is also included by another pair of electrodes. For example, such a pair of electrodes may include electrodes 790e and 790g. It is hypothesized that such a configuration may provide more pairing options, thereby potentially facilitating identification of an even more preferable electrode pair.

Figure 17A:
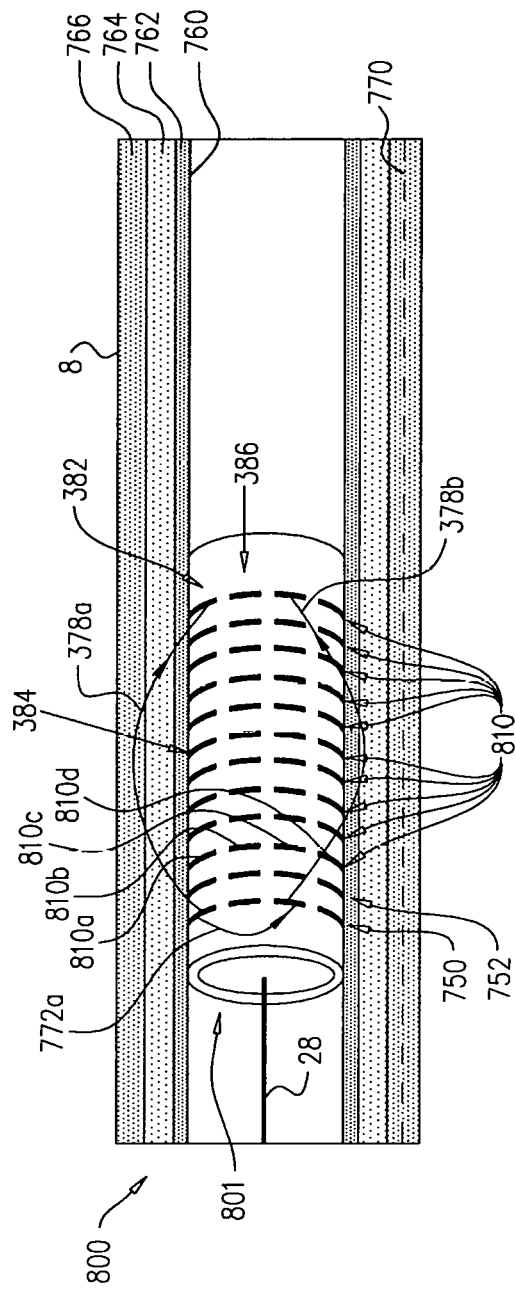
FIG. 17A is a schematic illustration of a system for facilitating ablation of nerve tissue of a subject, in accordance with some applications of the invention.

Reference is made to FIG. 17A, which is a schematic illustration of a system 800 for facilitating ablation of nerve tissue of a subject, in accordance with some applications of the invention. For some applications, an intracorporal device of a system for facilitating ablation of nerve tissue combines the circumferentially-distributed electrodes of system 740 with the longitudinally-distributed electrodes of system 780, thereby enabling the identification (and optionally ablation) of regions of artery tissue whose ablation is more likely to affect systemic blood pressure. System 800 is an example of such a combination. System 800 comprises an intravascular device 801 at a distal portion of the system, typically coupled to catheter 28. System 800 typically further comprises sensor 26 and control unit 32, as described hereinabove (with control unit 32 configured to execute the steps described with reference to system 800). System 800 comprises plurality of electrodes 750 and plurality of electrodes 752 (described hereinabove with reference to FIGS. 15A-F), and further comprises one or more additional pluralities (or "rings") of electrodes 810 (each comprising respective electrodes 810a, 810b, 810c and 810d), which are typically identical to pluralities 750 and 752. System 800 is shown with several more such pluralities of electrodes.

In general, the arrangement of electrodes shown in FIG. 17A, in which the electrodes are arranged both longitudinally and circumferentially, facilitates the determination of both (a) the approximate distance of the nerve from the wall of the blood vessel (as in FIGS. 16A-G), and (b) the angular position of the nerve with respect to the circumference of the blood vessel (as in FIGS. 15A-F). For example, it may be determined that the nerve is at a distance of 3 cm from the wall of the renal artery, at "4 o'clock" with respect to the circumference of the artery. In response to the angular position of the nerve, a pair of ablating electrodes may be identified. For example, the pair of electrodes that caused the greatest amount of stimulation may be used for ablation. Alternatively or additionally, the power of the ablation signal may be set in response to the angular position of the nerve.

Furthermore, system 800 may perform the steps described with reference to FIGS. 15A-F and 16A-G in any order, and may use efficiency-increasing methods such as method 371 (e.g., a binary search technique), as described hereinabove, mutatis mutandis. Examples of applications of method 371, using system 800, are hereby further described, with reference additionally being made to (i) FIGS. 17B-E, which are schematic illustrations of stimulating electric currents being driven into a wall of a blood vessel, in accordance with some applications of the present invention, and (ii) FIG. 28. (FIGS. 17B-E show a cross-section of the blood vessel, intravascular device 801 being situated within the blood vessel such that the electrodes are very close to, e.g., in contact with, the inner wall of the blood vessel.)

Figure 17B:
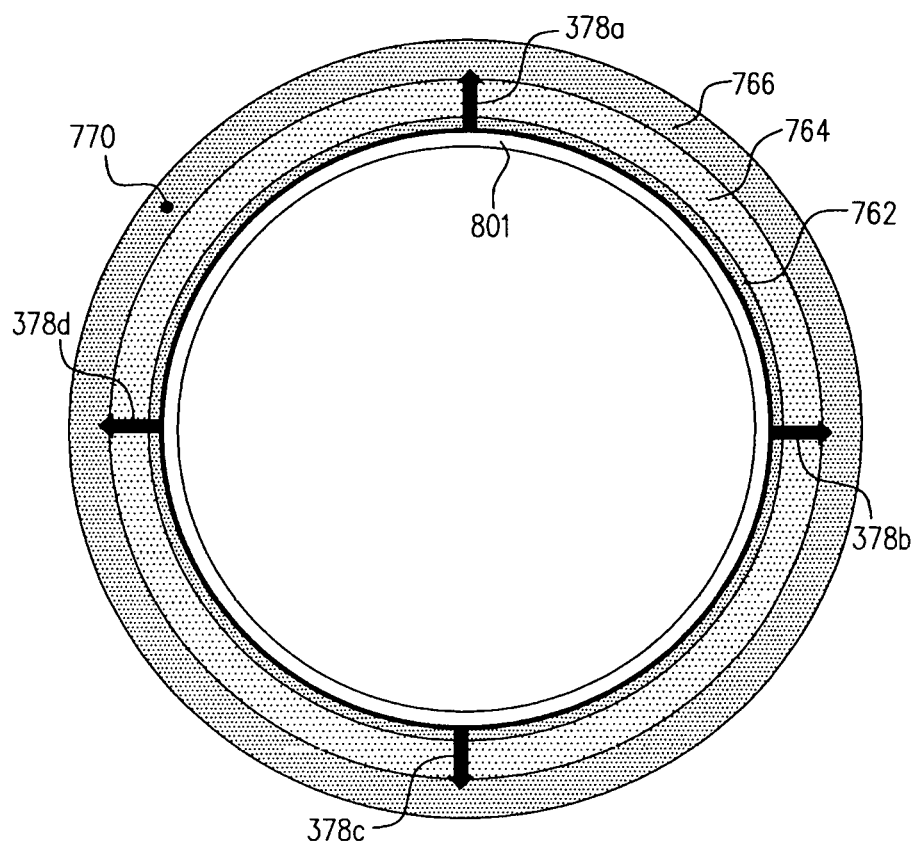

At first stimulating step 362, each of the first-precision-locating stimulating electric currents may be driven into the wall of the blood vessel by being driven between (a) a first one of the stimulating electrodes, and (b) a second one of the stimulating electrodes that is longitudinally separated from the first one of the stimulating electrodes. For example, FIG. 17A shows two first-precision-locating stimulating electric currents 378a and 378b, each of which is driven longitudinally (at approximately "12 o'clock" and "3 o'clock", respectively) between (a) a first electrode belonging to ring 750, and (h) a second electrode belonging to a ring 382 (which is one of the pluralities 810 of electrodes). FIG. 17B shows currents 378a and 378b from a longitudinally-facing perspective, and further shows an additional two currents 378c and 378d being driven at approximately "6 o'clock" and "9 o'clock", respectively.

Typically, a plurality of first-precision-locating stimulating electric currents are driven into the wall of the blood vessel at a plurality of positions along the circumference of the wall in rapid succession, e.g., with a time interval of 100 microseconds between each pair of successive currents. (Since the first-precision-locating stimulating electric currents are applied rapidly in sequence, the first-precision-locating stimulating electric currents effectively apply stimulation to the tissue at roughly the same time. Thus, FIG. 17B depicts the first-precision-locating stimulating electric currents as being applied simultaneously.) The first-precision-locating stimulating electric currents are driven into the wall such that they span a first range of the circumference of the wall. For example, as shown in FIG. 17B, the first-precision-locating stimulating electric currents may span the full circumference of the wall. (In other words, a 360 degree stimulation may be performed.)

Following first stimulating step 362, first sensing step 364 and response-assessing step 366 are performed. If the physiological response of the subject was not sufficient, intravascular device 801 is moved to another longitudinal location, at catheter-moving step 376, and first stimulating step 362 is repeated. Upon sensing a sufficient physiological response, method 371 continues with resolution-increasing step 368. Two examples of how resolution-increasing step 368 may be performed are hereby provided.

EXAMPLE 1 (FIG. 17C)

At resolution-increasing step 368, the resolution of the search may be increased, by setting the stimulation parameters such that the circumferential span of the stimulating is reduced. Subsequently, at second stimulating step 370, one or more sets 772 of one or more second-precision-locating stimulating electric currents having the reduced circumferential span are driven into the wall of the blood vessel. (In other words, each of the sets of second-precision-locating stimulating electric currents spans a second range of the circumference that is smaller than the first range.) For example, as shown in FIG. 17C, four generally non-overlapping 90-degree stimulations may be sequentially applied to the blood vessel, by driving a set 772 of one or more second-precision-locating stimulating electric currents at each of "12 o'clock", "3 o'clock", "6 o'clock", and "9 o'clock". (Thus, the tissue at "3 o'clock" is stimulated only after the tissue at "12 o'clock" is generally no longer stimulated, the tissue at "6 o'clock" is stimulated only after the tissue at "3 o'clock" is generally no longer stimulated, and the tissue at "9 o'clock" is stimulated only after the tissue at "6 o'clock" is generally no longer stimulated.)

In response to, at second sensing step 372, sensing the physiological response of the subject to each of the stimulations, the nerve may be located to a second degree of precision that is greater than the first. (The second degree of precision is greater than the first, in that the first degree of precision includes only longitudinal precision, whereas the second degree of precision includes additional circumferential precision.) For example, with reference to the position of nerve 770 as shown in FIG. 17C, it may be determined that the angular position of the nerve with respect to the circumference of the blood vessel is between "9 o'clock" and "12 o'clock".

Subsequently, the nerve may be ablated at the identified location. Alternatively, the resolution of the search may be further increased by further reducing the span of each of the sets of second-precision-locating stimulating electric currents. For example, if the location of the nerve was identified as being somewhere within a particular 90 degree span, the particular 90 degree span may then be divided into two 45 degree spans, per the binary search technique described hereinabove.

EXAMPLE 2 (FIG. 17D)

Figure 17D:
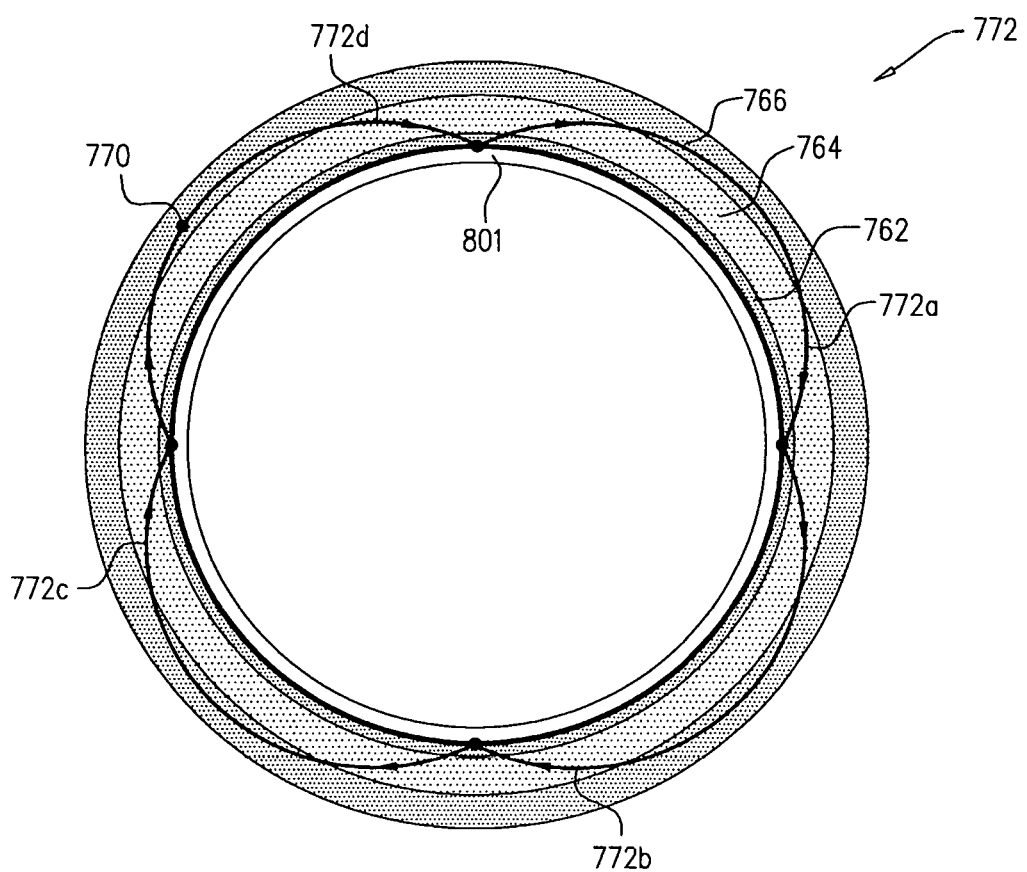

At resolution-increasing step 368, the resolution of the search may be increased, by setting the stimulation parameters such that the "longitudinal span" of the stimulating, i.e., the longitudinal distance over which the current is driven, is reduced. For example, at least two sets 772 of second-precision-locating stimulating electric currents may be driven into the wall of the blood vessel at respective longitudinal locations, i.e., a first one of the sets may be driven into the wall at a first location, and a second one of the sets may be driven into the wall at a second location that is longitudinally separated from the first location. (In this manner, the nerve is located to a second degree of longitudinal precision that is greater than the first degree of precision.) FIG. 17D shows a set 772 of second-precision-locating stimulating electric currents for one such longitudinal location.

Typically, for each of the sets of second-precision-locating stimulating electric currents, at least one second-precision-locating stimulating electric current is driven between two electrodes that are separated circumferentially (and typically not also longitudinally) from one another along the catheter. For example, FIG. 17A shows a current 772*a* that is passed between two circumferentially-separated electrodes on ring 750. FIG. 17D shows circumferentially-driven current 772*a* from a longitudinally-facing perspective, and further shows additional circumferentially-driven currents 772*b*, 772*c*, and 772*d*. Typically, a plurality of circumferentially-driven currents, such as the plurality shown in FIG. 17D, are applied in rapid succession, such that, effectively, a full "circular" stimulation is applied to the surrounding tissue, i.e., the entire circumference of the blood vessel is stimulated at the particular longitudinal location.

(FIG. 17D thus depicts currents 772*a*, 772*b*, 772*c*, and 772*d* as being applied simultaneously.) A circular stimulation such as depicted in FIG. 17D may be applied, sequentially, at several longitudinal locations, e.g., at each of rings 750, 384, and 382. (In other words, the tissue surrounding ring 384 may be stimulated only after the tissue surrounding ring 750 is generally no longer stimulated, and the tissue surrounding ring 382 may be stimulated only after the tissue surrounding ring 750 is generally no longer stimulated.) In response to the physiological response of the subject to each of the circular stimulations, it may be identified whether the nerve is closer to ring 750, ring 384, or ring 382.

(More broadly, in the context of the claims and description of the present application, "locating" the nerve at a particular location generally means identifying the particular location as being more suitable as an ablation site than another location. For example, in some cases, the nerve may be generally equidistant from the blood vessel at each of rings 750, 384, and 382, but may be less covered by ablation-inhibiting tissue at ring 750 than at rings 384 or 382. In such cases, the nerve may be said to be (i) located to a first degree of precision at the full longitudinal span of rings 750, 384, and 382, and (ii) located to a second, higher, degree of precision at ring 750.)

Subsequently, at ablating step 374, the nerve is ablated at the identified location. Alternatively, the resolution of the search may be further increased, e.g., by implementing the binary search technique described hereinabove.

In general, aspects of Example 1 may be combined with aspects of Example 2. For example, at resolution-increasing step 368, both the longitudinal and circumferential span of the stimulating currents may be decreased. e.g., by applying "quarter-circle" stimulations, sequentially, at each of several longitudinal positions. FIG. 17E shows such an application of "quarter-circle" stimulations for a particular longitudinal location. In FIG. 17E, currents 772*a*, 772*b*, 772*c*, and 772*d* are applied sequentially, rather than at effectively the same time, as was shown in FIG. 17D.

In some applications, at least one second-precision-locating stimulating electric current is driven between (a) one of the plurality of stimulating electrodes, and (b) an electrode that is disposed outside the subject's body.

In some applications, a "high resolution scanning" may be performed even without a prior performance of a "low resolution scanning". For example, sets 772 of second-precision-locating stimulating electric currents may be applied as generally shown in FIG. 17C, FIG. 17D, or FIG. 17E, even without first applying first-precision-locating stimulating electric currents as shown in FIG. 17B.

Reference is made to FIG. 18, which is a flow chart showing at least some steps of a technique 820 for facilitating ablation of nerve tissue of a subject, in accordance with some applications of the invention. As described with reference to FIG. 7, electrode unit 222*a* of system 220 may comprise only one electrode, and for some applications, system 320 comprises or is an embodiment of system 220 when electrode unit 222*a* of system 220 comprises only one electrode. As also described with reference to FIG. 7, for some applications, electrode 330*a* may serve as a return electrode for excitatory current applied by electrode 330*b*. That is, the excitatory current may be applied between electrodes 330*a* and 330*b*, which are disposed on either side of ablation unit 24 (and thereby on either side of the ablation site, e.g., the lesion). That is, the excitatory current may be applied across the ablation site.

It is hypothesized that, advantageously, for applications in which the excitatory current is applied across the ablation site (e.g., the lesion), a reduced ability of the excitatory current to induce action potentials that result in increased blood pressure is indicative of the degree of ablation achieved. Technique 820 utilizes this hypothesized advantage. It is further hypothesized that for some applications, compared to the application of the excitatory current by the same electrodes that apply the ablation energy, application of the excitatory current across the ablation site using electrodes disposed on either side of the ablation site advantageously avoids application of the excitatory current at the interface between the ablation unit and the tissue (e.g., the surface of the tissue in contact with electrodes of the ablation unit); ablation may cause the interface to become electrically insulating, thereby otherwise inhibiting the excitatory current from reaching the renal nerve.

Step 822 comprises detecting a preliminary value of a parameter indicative of blood pressure, e.g., as described hereinabove.

Step 824 comprises (1) initiating action potentials in the nerve by applying the excitatory current between electrodes 330a and 330b, and (2) after the start of the application of the excitatory current, detecting a value of the parameter (i.e., an "excited" value), e.g., as described hereinabove, mutatis mutandis.

Step 826 comprises applying ablation energy to the ablation site using ablation unit 24, e.g., as described hereinabove, mutatis mutandis.

Step 828 comprises (1) by applying the excitatory current between electrodes 330a and 330b again, and (2) after the start of the application of the excitatory current, detecting a value of the parameter (i.e., an "ablated" value), e.g., as described hereinabove, mutatis mutandis. (This corresponds to the variant of step 828 that appears above the divider; the variant of step 828 that is below the divider is described hereinbelow.)

Subsequently, the "ablated" value is compared to the preliminary value and/or the "excited" value (step 830). (This corresponds to the variant of step 828 that appears above the divider; the variant of step 828 that is below the divider is described hereinbelow.) A decision 832 to continue ablating, or to stop, is made (for example, by control unit 32), e.g., as described hereinabove, mutatis mutandis. If subsequent ablation is performed, then subsequent iterations of step 830 may alternatively or additionally comprise comparing the subsequent "ablated" value to another (e.g., a previous) "ablated" value.

As described with reference to FIGS. 16A-G, for some applications, excitatory current is applied between more than one pair of electrodes, each pair having a respective different distance between the electrodes of the pair. This technique may be used in combination with that described with reference to FIG. 18. That is, more than one pair of excitatory electrodes may be used, with one electrode of each pair being disposed on one side of ablation unit 24, and the other electrode of each pair being disposed on the other side of the ablation unit. The variants of steps 828 and 830 that appear below the dividers relate to such a combination of the technologies from FIGS. 16A-G and 18. The excitatory current is applied between electrodes of more than one pair of electrodes, and the "ablated" value of the parameter is detected after the start of the application of each application of the excitatory current (step 828). The "ablated" value is compared to "ablated" values from other electrode pairs, the "excited" value, and/or the preliminary value (step 830). If subsequent ablation is performed, then subsequent iterations of step 830 may alternatively or additionally comprise comparing the subsequent "ablated" value to another (e.g., a previous) "ablated" value.

Reference is made to FIGS. 19, 20, and 21A-B, which are, respectively, a schematic illustration of a system 840 for facilitating ablation of nerve tissue of a subject, a flow chart showing at least some steps of a technique for use with the system, and charts relating to the technique, in accordance with some applications of the invention.

Figure 19:
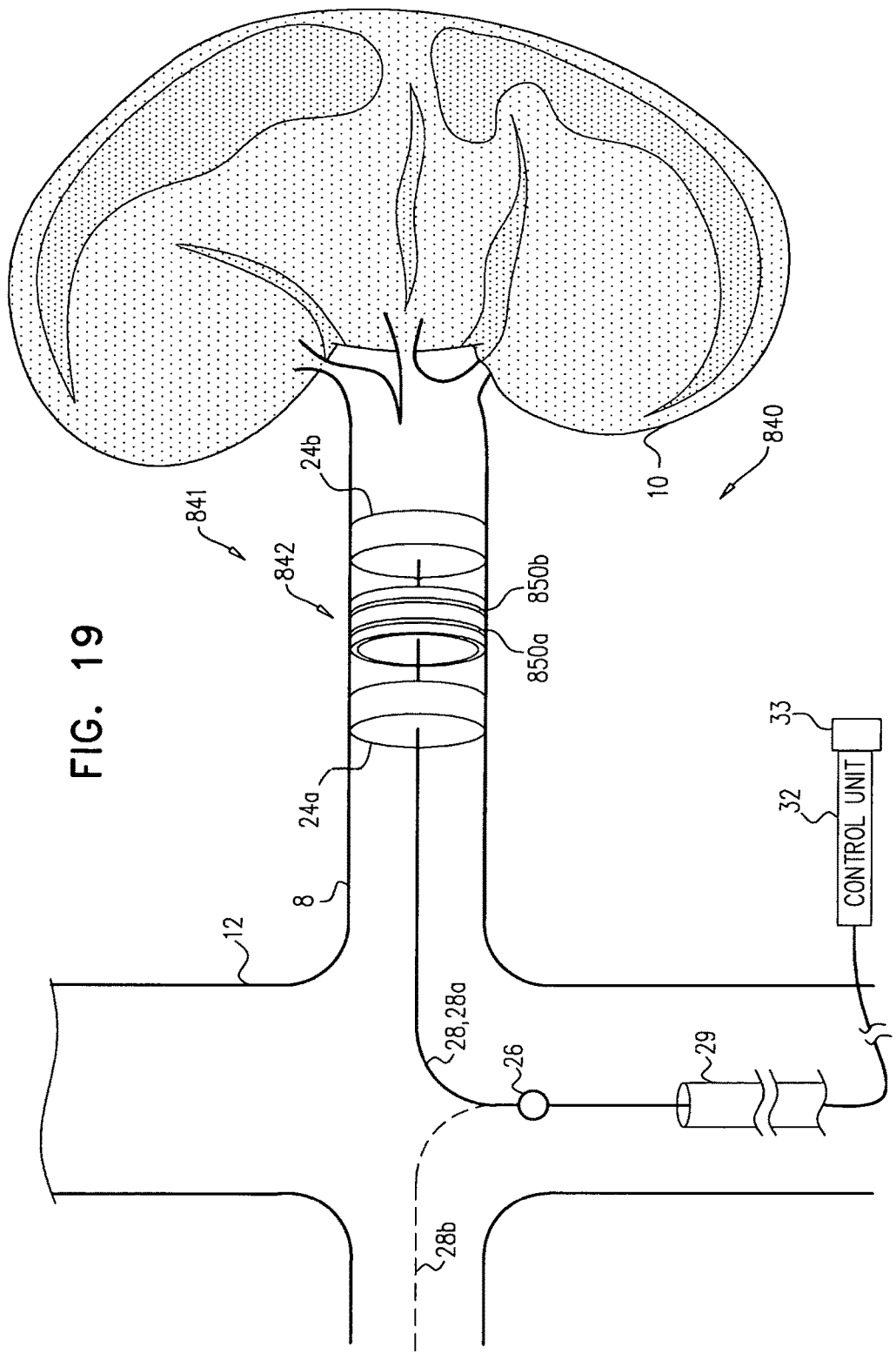

FIG. 19 shows system 840, which comprises an intravascular device 841 at a distal portion of the system, typically coupled to catheter 28. System 840 typically further comprises sensor 26 and control unit 32, as described hereinabove (with control unit 32 configured to execute the steps described with reference to system 840). Device 841 comprises two ablation units 24a and 24b, and an electrode unit 842 disposed therebetween (i.e., proximal to electrode unit 24b and distal to electrode unit 24a). Electrode unit 842 typically comprises at least two electrodes 850a and 850b, and control unit 32 is configured to drive these electrodes to apply excitatory current to the renal artery. It will be understood that action potentials initiated by the excitatory current will propagate past both ablation units.

As described with reference to FIG. 6, the effect on systemic blood pressure resulting from stimulation of the CNS is more immediate than that resulting from stimulation of the kidney. As also described with reference to FIG. 6, for some applications, detection of a particular pattern of changes in the detected parameter may be used to identify and/or distinguish effects caused by action potentials propagating toward the CNS and those caused by action potentials propagating toward the kidney.

FIG. 20 is a flow chart showing at least some steps of a technique 860 for use with system 840, in accordance with some applications of the invention.

Step 862 comprises detecting a preliminary value of a parameter of a subject, such as a parameter indicative of blood pressure. e.g., as described hereinabove. As noted throughout this application, although blood pressure is used as an example of such a parameter, one or more other parameters may be alternatively or additionally be detected and used, such as a parameter indicative of heart rate, heart rate variability, and/or blood flow of the subject. It is hypothesized that or some applications of technique 860 a parameter indicative of heart rate and/or heart rate variability may be more suitable that a parameter indicative of blood pressure, due to the relative kinetics of these parameters in response to renal nerve activity. However, for simplicity, FIGS. 20-21B and the descriptions thereof generally relate to the parameter as being indicative of blood pressure, e.g., mean arterial blood pressure (MAP).

Step 864 comprises (1) initiating action potentials of renal nerve 770 by control unit 32 driving electrode unit 842 to apply the excitatory current to a first site of the renal artery, and (2) after the start of the application of the excitatory current, detecting (i) a first value of the parameter (i.e., an "excited" value), and subsequently (ii) detecting a second value (i.e., also an "excited" value) of the parameter. The first value is typically detected within 60 seconds of the start of the application of the excitatory current (e.g., within 45 seconds of the start, e.g., within 30 seconds of the start, such as 5-30 seconds or within 15 seconds from the start). That is, a duration 926 (graphs 1 of FIGS. 21A-B) is typically no more than 60 seconds. The second value is detected after the first value is detected. The second value is typically detected at least 60 seconds after the start of the application of the excitatory current (e.g., 1-4 minutes after the start). That is, a duration 928 (graphs 1 of FIGS. 21A-B) is typically greater than 60 seconds. Alternatively or additionally, in some applications, the second value is detected after at least 15 seconds from the start, e.g., after 30 seconds from the start, e.g., after 45 seconds from the start. It is hypothesized that (1) the first value is at least in part indicative of the blood pressure response to action potentials that propagate toward the CNS (e.g., a CNS response to afferent action potentials), and (2) the second value is at least in part indicative of the blood pressure response to action potentials that propagate toward the kidney (e.g., a hormonal response to efferent action potentials).

Figure 21A:
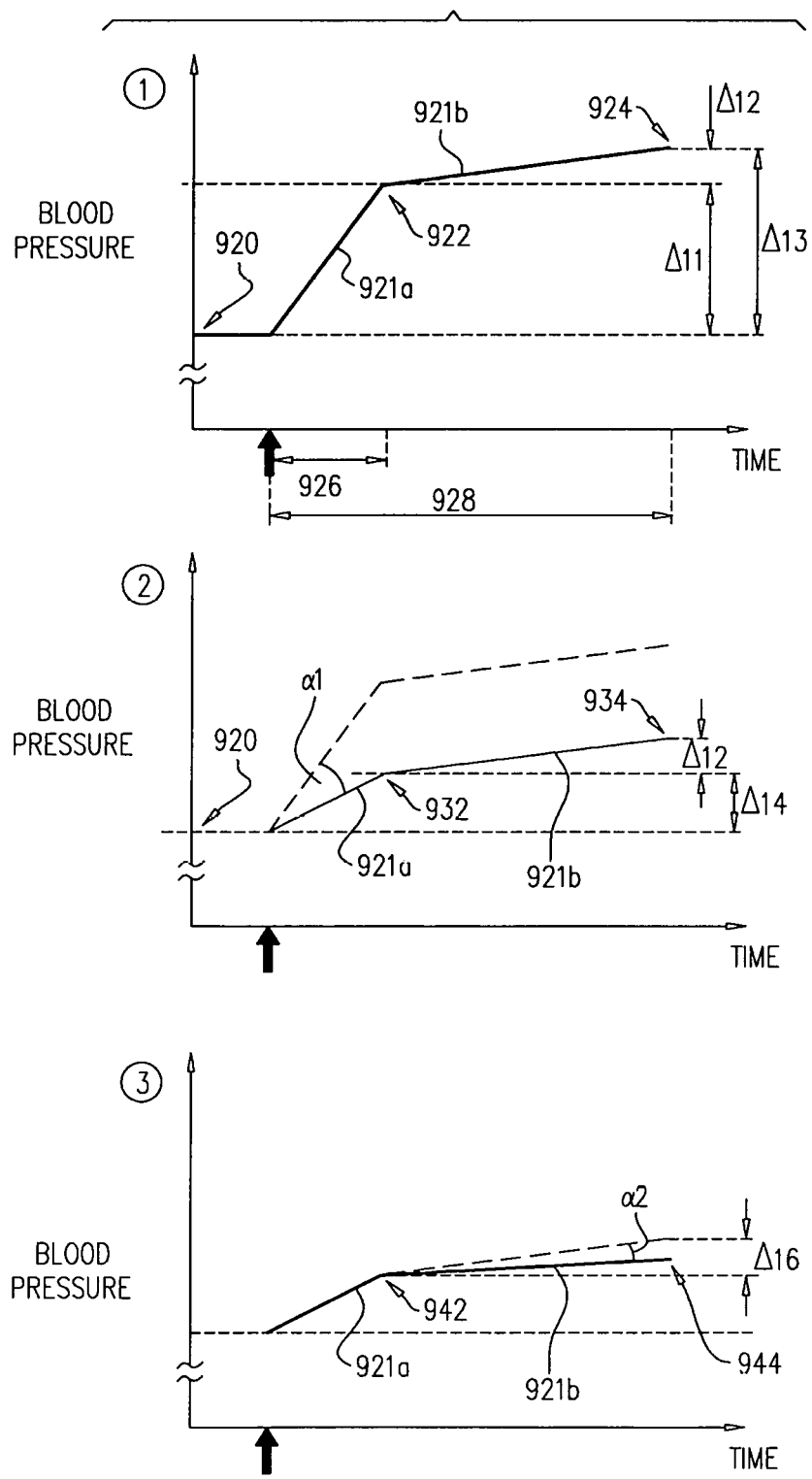
Figure 21B:
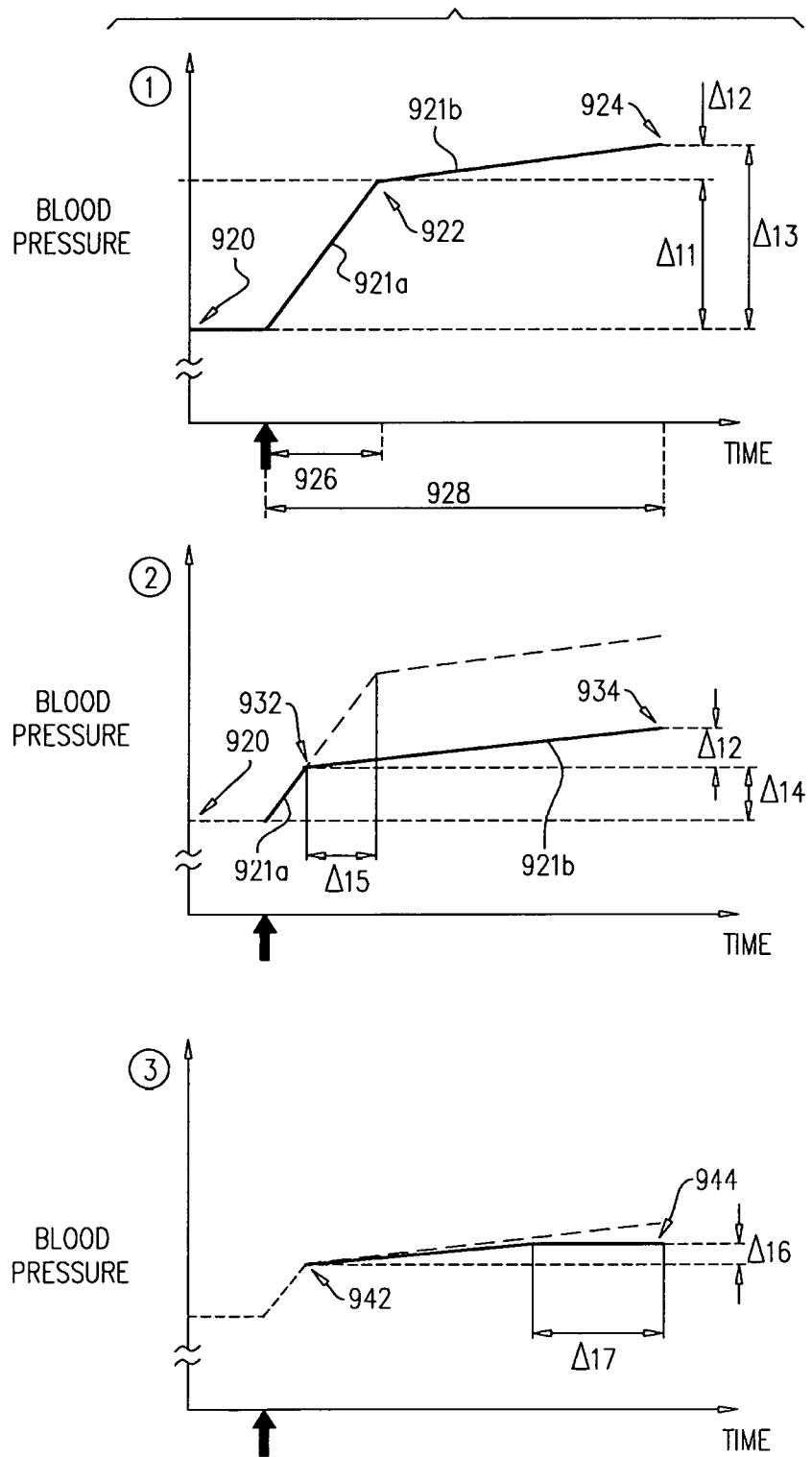

Graphs 1 of FIGS. 21A and 21B show example plots of the preliminary value (920), the first "excited" value (922), and the second "excited" value (924), as detected in step 864. The time of the start of application of the excitatory current is shown by a bold arrow on the X axis. A difference delta_11 between preliminary value 920 and the first ("excited") value 922, and a difference delta_12 between value 922 and the second ("excited") value 924, are shown. A difference delta_13 is the sum of delta_11 and delta_12, and thereby represents the total increase in blood pressure following application of the excitatory current. The graphs of FIGS. 21A and 21B may be considered to show "legs" of the response. A first leg 921a represents the increase in blood pressure at least in part duc to the faster CNS-directed aspect of the response to excitation of the renal nerve. A second leg 921b represents the increase in blood pressure at least in part due to the slower kidney-directed aspect of the response to excitation of the renal nerve. It is to be understood that the graphs of FIGS. 21A-B are used to schematically illustrate, and distinguish between, these two aspects, and do not necessarily reflect the actual kinetics of the response.

Subsequently, control unit 32 drives ablation unit 24a to apply ablation energy to a second site of the renal artery (step 866), which is closer to the aorta and CNS than is the first site. Thus, ablation at the second site is hypothesized to inhibit propagation of action potentials from the first site toward the CNS, but not to inhibit propagation of action potentials from the first site toward kidney 10.

Step 868 comprises (1) initiating action potentials of renal nerve 770 by control unit 32 driving electrode unit 842 to again apply the excitatory current to the first site of the renal artery, and (2) after the start of the application of the excitatory current, detecting (i) a third value 932 of the parameter (i.e., an "ablated" value), and subsequently (ii) detecting a fourth value 934 of the parameter (i.e., an "ablated" value). As described for the first and second values, the third value is typically detected within 60 seconds of the start of the application of the excitatory current, and the fourth value is typically detected at least 60 seconds after the start of the application of the excitatory current.

Graphs 2 of FIGS. 21A and 21B show example plots of third ("ablated") value 932, and fourth ("ablated") value 934, as detected in step 868. The plot from the respective graph 1 is shown as a broken line. The time of the start of application of the excitatory current is shown by a bold arrow on the X axis. A difference delta_14 between value 920 and value 932 is shown as being smaller than difference delta_11. That is, the increase in blood pressure to which leg 921a corresponds is shown as being smaller subsequent to ablation step 866. However, the increase in blood pressure to which leg 921b corresponds is shown as remaining the same; delta_12 also indicates the difference between values 932 and 934.

The inventors hypothesize that the ablation-mediated reduction in excitation-mediated blood pressure increase may manifest in more than one way. FIGS. 21A and 21B are both provided (i.e., as opposed to only one of these figures) so as to illustrate two such manifestations: FIG. 21A shows the reduction manifesting as a reduction in the rate of blood pressure increase, whereas FIG. 21B shows the reduction manifesting as a reduction in the duration of blood pressure increase. For example, with reference to graphs 2 of FIGS. 21A and 21B, graph 2 of FIG. 21A shows a slower rate of blood pressure increase during leg 921a compared to leg 921a of the respective graph 1 (as indicated by angle alpha_1), whereas graph 2 of FIG. 21B shows a shorter duration of leg 921a compared to leg 921a of the respective graph 1 (as indicated by difference delta_115). It is to be noted that these different manifestations may result in the same final reduction in blood pressure increase (e.g., as represented by delta_14 in both FIG. 21A and FIG. 21B).

The third and fourth values (i.e., the "ablated" values) are compared to the first and second values (i.e., the "excited" values) and/or the preliminary value (step 870), and at least in part responsively to a relationship (e.g., a difference, such as an arithmetic subtraction, a ratio, or any other expression of a difference) between the compared values, a decision 872 is made (for example, by control unit 32) whether to continue ablating at the second site (i.e., to apply another application of ablation energy to the second site). In some applications, decision 872 is made in response to a relationship (e.g., a difference) between the first and second blood pressure values, and/or a relationship (e.g., a difference) between the third and fourth blood pressure values.

If and when it is determined that sufficient ablation has been achieved at the second site (e.g., once value delta_14 is determined to be sufficiently small and/or smaller than value delta_11), ablation at a third site of the renal artery begins. (Alternatively, treatment may end at this point, with no ablation having been performed at the third site.) Control unit drives ablation unit 24a to apply ablation energy to the third site (step 874), which is closer to kidney 10 than is the first site. Thus, ablation at the second site is hypothesized to inhibit propagation of action potentials from the first site toward kidney 10, but not to inhibit propagation of action potentials from the first site toward the CNS.

Step 876 comprises (1) initiating action potentials of renal nerve 770 by control unit 32 driving electrode unit 842 to again apply the excitatory current to the first site of the renal artery, and (2) after the start of the application of the excitatory current, detecting (i) a fifth value 942 of the parameter (i.e., an "ablated" value), and subsequently (ii) detecting a sixth value 944 of the parameter (i.e., an "ablated" value). As described for the first and second values, the fifth value is typically detected within 60 seconds of the start of the application of the excitatory current, and the sixth value is typically detected at least 60 seconds after the start of the application of the excitatory current.

Graphs 3 of FIGS. 21A and 21B show example plots of fifth ("ablated") value 942, and sixth ("ablated") value 944, as detected in step 876. For each graph 3, the plot from the respective graph 2 is shown as a broken line. The time of the start of application of the excitatory current is shown by a bold arrow on the X axis. A difference delta_16 between value 942 and value 944 is shown as being smaller than difference delta_12. That is, the increase in blood pressure to which leg 921b corresponds is shown as being smaller subsequent to ablation step 874. However, the increase in blood pressure to which leg 921a corresponds is shown as remaining the same.

As described hereinabove, FIGS. 21A and 21B illustrate different possible manifestations of the ablation-mediated reduction in excitation-mediated blood pressure. Graph 3 of FIG. 21A shows a slower rate of blood pressure increase during leg 921b compared to leg 921b of the respective graph 2 (as indicated by angle alpha_2), whereas graph 3 of FIG. 21B shows a shorter duration of leg 921b compared to leg 921b of the respective graph 2 (as indicated by difference delta_17). It is to be noted that these different manifestations may result in the same final reduction in blood pressure increase (e.g., as represented by delta_16 in both FIG. 21A and FIG. 21B).

In the example shown in FIGS. 19-21B, ablation energy is applied to the second site (closer to the aorta and CNS than is the first site) by ablation unit 24a, which is proximal to electrode unit 842 prior to application of ablation energy by ablation unit 24b to the third site (closer to the kidney than is the first site). However, it is to be understood that the first application of ablation energy may instead be applied by ablation unit 24b to the third site.

Although electrode unit 842 is shown as comprising two electrodes 850a and 850b, and control unit 32 is described as applying the excitatory current by driving the excitatory current between these two electrodes, for some applications, electrode unit 842 is monopolar, and is used in combination with an extracorporeal return electrode. Similarly, for applications in which ablation units 24a and 24h are RF ablation units, the ablation units may be bipolar (i.e., each comprising more than one electrode) or monopolar.

The fifth and sixth values (i.e., the "ablated" values following ablation at the third site) are compared to one or more of: the third and fourth values (i.e., the "ablated" values following ablation at the second site), the first and second values (i.e., the "excited" values), and/or the preliminary value (step 878), and at least in part responsively to a relationship (e.g., a difference) between the compared values, a decision 880 is made (e.g., by control unit 32) whether to continue ablating at the third site and/or at the second site (i.e., to apply another application of ablation energy to the second and/or third site). For some applications, between steps 872 and 874, another "preliminary" value is detected (e.g., while the subject is at rest, and without application of excitatory current). This other preliminary value may be additionally or alternatively used in comparison step 878, and/or may be used to decide whether to proceed with ablation step 874 or to end the treatment.

It is hypothesized that, for some applications, the apparatus and techniques described with reference to FIGS. 19-21B advantageously provide information regarding the state of ablation of both (1) nerve fibers that carry action potentials that influence the kidney-influenced aspect of renal nerve-influenced blood pressure control (e.g., efferent nerve fibers), and (2) nerve fibers that carry action potentials that influence the CNS-influenced aspect of renal nerve-influenced blood pressure control (e.g., afferent nerve fibers). Using this information, system 840 (e.g., control unit 32 thereof, and/or a user thereof) may achieve a desired degree of inhibition of each of these aspects while avoiding ablation in excess of that required to achieve that desired degree of inhibition.

Figure 29:
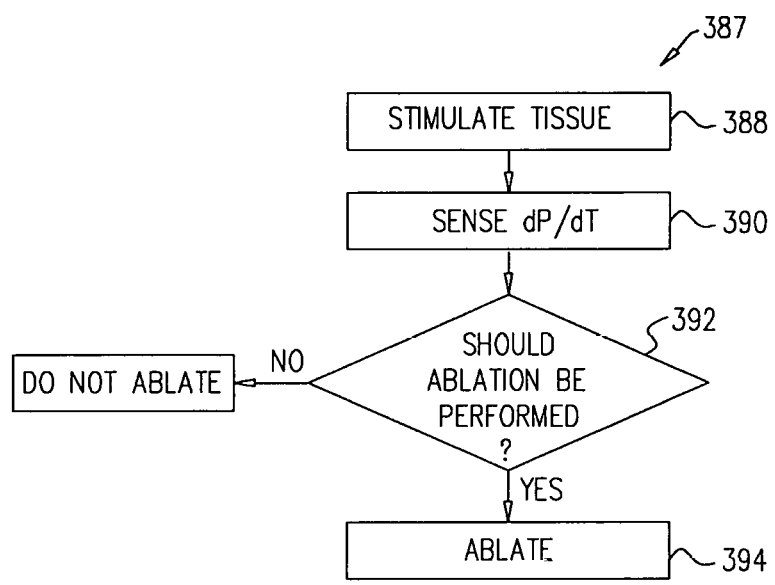
FIG. 29 shows a flow chart for a method for deciding whether to perform an ablation, in accordance with some applications of the present invention.

Reference is now additionally made to FIG. 29, which shows a flow chart for a method 387 for deciding whether to perform an ablation, in accordance with some applications of the present invention. As noted above. FIG. 21A illustrates the inventors' hypothesis that the ablation-mediated reduction in excitation-mediated blood pressure increase may be manifested as a reduction in the rate of blood pressure increase. It follows from this hypothesis that a rate of blood pressure increase, in response to a stimulation, may be indicative of whether an ablation should be performed. This idea is applied in some applications of the present invention, as shown in FIG. 29.

At a stimulating step 388, one or more stimulating electrodes disposed within the renal artery are used to stimulate tissue of the renal nerve, by passing a stimulating current through the wall of the renal artery. Following the start of the stimulation, at a rate-of-change-sensing step 390, a sensor is used to sense a rate of change of the subject's blood pressure (dP/dt). At a deciding step 392, in response to the rate of change, the physician decides whether to ablate the tissue. In response to deciding to ablate the tissue, the physician ablates the tissue, at an ablating step 394.

In some applications, the decision as to whether to ablate the tissue is in response to a rate of change of MAP. It has been observed by the inventors that in some cases, MAP does not begin to increase immediately upon the start of the stimulation. Hence, in some applications, the rate of change of MAP is sensed over a period of time that begins some time after the start of stimulation, e.g., within 30 seconds or ten seconds of the start of the stimulation, e.g., at two seconds after the start of stimulation. (As noted above, the start of stimulation is marked by a bold arrow on the time axis of the graphs in FIGS. 21A-B.) In some applications, the period of time over which the rate of change is sensed ends within two minutes of the start of the stimulation. Alternatively or additionally, the rate of change may be sensed up to an end of the stimulation. (Typically, the duration of the stimulation is at least one and/or less than two minutes.) In general, the period of time over which the rate of change is sensed may end before or after the end of duration 926. (In general, the expression "dP/dt," as used within the present description, may apply to MAP—i.e., "dP/dt" may include within its scope "d(MAP)/dT.")

Typically, following the sensing of the rate of change of MAP, at least one rate of change value is compared to a threshold. In some applications, a moving window (e.g., having a duration of at least three and/or less than 10 seconds) may be used, the rate of change of MAP being computed continually over the moving window. (For example, the rate of change of MAP may be computed for the time period between two and five seconds, then for the time period between 2.5 and 5.5 seconds, then for the time period between three and six seconds, etc.) If the rate of change during a particular window exceeds the threshold, the physician may decide to ablate the tissue; otherwise, the physician may decide not to ablate the tissue. (In the latter case, steps 388, 390, and 392 may then be repeated for a different location within the blood vessel.)

In some applications, a stimulating current is passed through the wall of the renal artery at each of a plurality of sites, and the rate of change of blood pressure is sensed for each of the stimulations. The plurality of sites may include a plurality of longitudinal sites (i.e., sites that are spaced longitudinally from each other), and/or a plurality of circumferential sites (i.e., sites that are spaced circumferentially from each other), along the wall of the renal artery. In response to the sensed rates of change of blood pressure, the physician decides (a) to ablate the tissue at at least one of the sites, and (b) not to ablate the tissue at at least another one of the sites. In some applications, ablation is performed only after mapping the area of the blood vessel, i.e., identifying the hot spots. In other words, in some applications, steps 388 and 390 are first performed at a plurality of sites, and only afterwards is ablating step 394 performed.

Reference is now additionally made to FIG. 30, which is a schematic illustration showing data used to decide whether to perform an ablation, in accordance with some applications of the present invention. In some applications, alternatively or additionally to sensing a rate of change of MAP, respective rates of change of blood pressure during one or more heartbeats are sensed. In response to the respective rates of change of blood pressure, at deciding step 392, the physician decides whether to ablate the tissue. In some applications, the decision as to whether to ablate the tissue is in response to respective maximum rates of change of blood pressure. For example, FIG. 30 shows a plurality of heartbeats, indexed from i to i+4, for which both an electrocardiogram (ECG) signal and an arterial blood pressure signal are shown. For each heartbeat, a portion of the arterial blood pressure signal that generally shows the maximum rate of change, relative to other portions of the arterial blood pressure signal, is marked. It is hypothesized by the inventors that a faster upswing in arterial pressure is indicative of a greater degree of responsiveness to the stimulation, relative to a slower upswing. It is further hypothesized by the inventors that in some cases, the rate of the downswing in arterial pressure (following each peak in arterial blood pressure) may alternatively or additionally be indicative of the degree of responsiveness to the stimulation. Hence, in some applications, deciding step 392 is performed in response to the rate of the downswing, alternatively or additionally to being performed in response to the rate of the upswing.

In some applications, the rate of change for each heartbeat is compared to a threshold, and if the threshold is crossed for a particular heartbeat, it is decided to perform an ablation. Alternatively, in some applications, the respective maximum rates of change over a certain number of heartbeats (e.g., 10 heartbeats) are averaged. The average maximum rate is then compared to a threshold, and the decision as to whether to ablate is performed in response to the comparison. Alternatively or additionally, a maximum of the maximum rates of change may be identified, and the decision as to whether to ablate is performed in response thereto.

In general, the sensing of the respective rates of change of blood pressure during one or more heartbeats, as described hereinabove, may be performed over a relatively short period of time, e.g., under one minute (e.g., under 10 seconds, or 10-30 seconds). In contrast, sensing the rate of change of MAP, as described hereinabove with reference to FIGS. 21A-B, typically takes longer. Furthermore, the effect of stimulation on the per-heartbeat rates of change may be observable after a relatively short period of stimulation, whereas the effect on MAP may be observable only after a longer period of stimulation. Thus, it may be advantageous to use the per-heartbeat rates of change, rather than the rate of change of MAP, in that the overall procedure time (whether for ablation or for mapping) may be substantially reduced.

In some applications, method 387 is practiced following a first ablation, in order to decide whether to perform a second ablation. That is, following a first performance of steps 388, 390, 392, and 394, steps 388 and 390 are again performed, i.e., a second stimulation, and sensing of dP/dt, are performed. Subsequently, the physician decides whether to perform a second ablation of the tissue, in response to a difference between (i) the rate of change of blood pressure of the subject following the start of the first stimulation, and (ii) the rate of change of blood pressure of the subject following the start of the second stimulation. For example, if the rate of change has sufficiently decreased following the first ablation, the physician may decide not to perform a second ablation.

In general, sensor 26 and control unit 32 (e.g., as shown in FIG. 1) may be used to practice the techniques described hereinabove with reference to FIGS. 21A-B and FIGS. 29-30. That is, sensor 26 may sense the blood pressure of the subject, following a start of the stimulation of the tissue, and control unit 32 may compute the rate of change of the sensed blood pressure, as described hereinabove. For example, the control unit may compute dP/dt (e.g., the maximum of dP/dt) for each of one or more heartbeats, and/or compute a rate of change of MAP. The control unit then compares the rate of change to a threshold, and generates an output in response to the comparison. For example, the control unit may drive interface 33 (FIG. 1) to output a visual and/or audio message that indicates to the physician that the threshold has been exceeded, and in response to the output, the physician may decide to ablate the tissue. In some applications, the control unit computes the threshold. For example, the control unit may compute a first rate of change of blood pressure, following a start of a first stimulation of the tissue by the stimulating electrodes. (This first rate of change is designated as the threshold.) Subsequently, the tissue may be ablated. Following the ablation, the tissue may be stimulated again, and the control unit may again compute a rate of change of blood pressure. The control unit may then compare the second rate of change to the first rate of change, and generate an output in response thereto. This output may help the physician decide whether a second ablation should be performed.

Figure 22A:
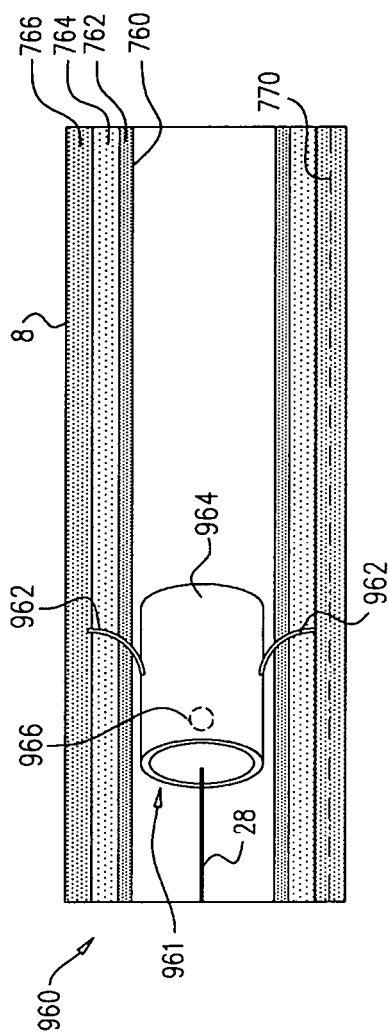
FIGS. 22A-B are, respectively, a schematic illustration of a system, and a now chart of at least some steps of a technique for use with the system, in accordance with some applications of the invention.
Figure 22B:
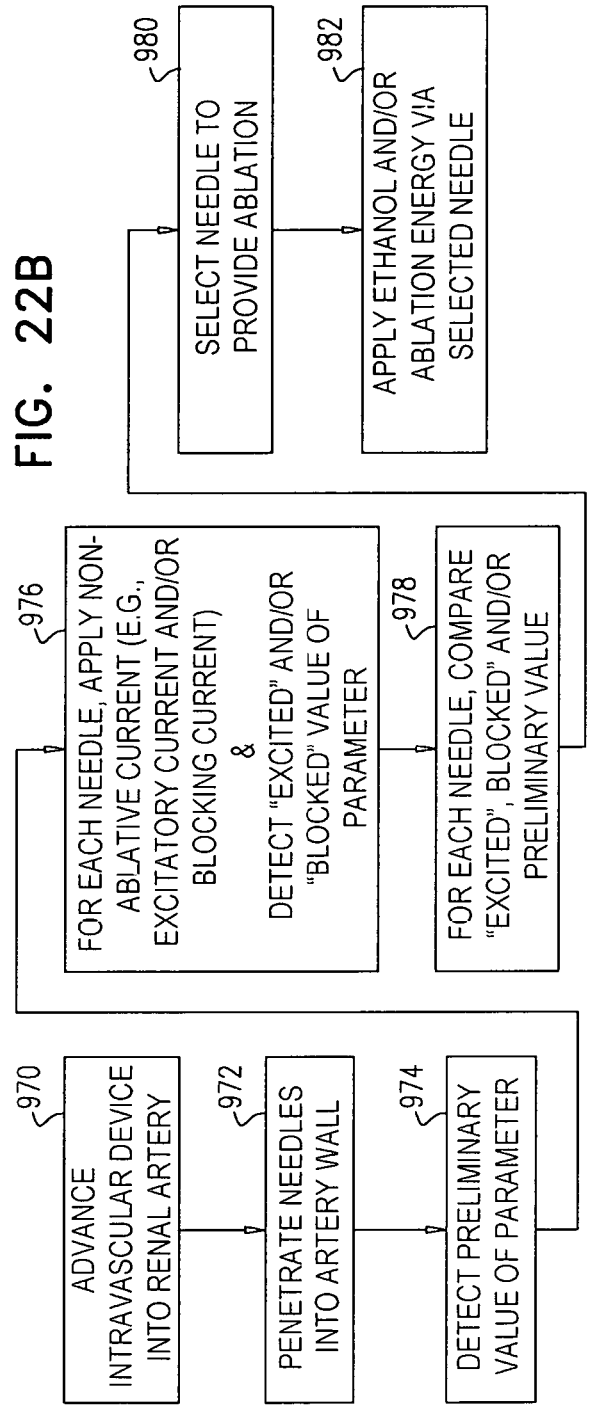

Reference is made to FIGS. 22A-B, which are, respectively, a schematic illustration of a system 960, and a flow chart of at least some steps of a technique for use with the system, in accordance with some applications of the invention. System 960 comprises an intravascular device 961 at a distal portion of the system, typically coupled to catheter 28. Device 961 comprises a plurality of needles 962 having a retracted state, being radially-extendable into an extended state, and being configured to penetrate the wall of artery 8 when moved toward the extended state. Typically, device 961 comprises a body 964 from which needles 962 are extendable, and which further typically houses the needles when they are in the retracted state. FIG. 22A shows system 960 with needles 962 in the extended state, having penetrated the wall of artery 8. System 960 typically further comprises sensor 26 and control unit 32, as described hereinabove (with control unit 32 configured to execute the steps described with reference to system 960).

System 960 (e.g., control unit 32 thereof) is configured to apply non-ablative current to the wall of artery 8 (e.g., to renal nerve 770) via needles 962, and to subsequently ablate one or more portions of the renal nerve, also via the needles. The non-ablative current may be a non-ablative blocking current, and/or may be an excitatory current, e.g., as described hereinabove, mutatis mutandis. The ablation may be achieved by driving ablation energy (e.g., an RF current) via the needles. Alternatively or additionally, needles 962 may be hollow, and ablation may be achieved by pumping a liquid comprising ethanol through the needles, e.g., as described in the following reference, which is incorporated herein by reference: Fischell, Tim A., et al. "Ethanol-mediated perivascular renal sympathetic denervation: preclinical validation of safety and efficacy in a porcine model." EuroIntervention: journal of EuroPCR in collaboration with the Working Group on Interventional Cardiology of the European Society of Cardiology 9.1 (2013): 140-147. For such applications, system 960 (e.g., device 961 thereof) comprises a reservoir 966 configured to store the liquid, and in fluid communication with needles 962.

Described hereinabove are several techniques in which a non-ablative current is applied to the renal artery, and one or more values of a factor of the subject are detected (e.g., in advance of ablation), including (a) techniques for screening subjects for renal nerve ablation, (b) techniques for assessing a degree of ablation achieved, (c) techniques for identifying a target site of the renal artery for ablation, and (d) techniques for determining the depth of a renal nerve within the artery wall. System 960 may be used in combination with each of these techniques, mutatis mutandis, e.g., by modifying each technique such that the non-ablative energy is applied via needles 962, and such that ablation is performed by applying the ablative energy and/or pumping the liquid via the needles. At least some steps of a non-limiting example of such a modification is shown in FIG. 22B.

For some applications, the technique shown in FIG. 22B may be considered to be a modification of the general technique described with reference to FIGS. 15A-F, whereby excitation and ablation are performed via needles 962, rather than via electrodes 752 (or whereby electrodes 752 are configured to reversibly extend radially outward and penetrate the wall of the renal artery).

Device 961 is advanced into the lumen of renal artery 8 (step 970), and needles 962 are extended radially outward such that they penetrate the wall of the artery (step 972). Step 974 comprises detecting a preliminary value of a parameter indicative of blood pressure, e.g., as described hereinabove. Typically, step 974 is performed after step 972 (e.g., such that the presence of needles 962 is taken into account in the preliminary value), but may alternatively be performed before step 972. For some applications, two preliminary values are detected; one before and one after step 972.

Step 976 generally corresponds to the steps shown in FIGS. 15B-F, whereby the non-ablative current (e.g., the excitatory or blocking current) is applied to various circumferential portions of the artery wall (but via needles 962 rather than electrodes 752), and a value of the factor is detected after the start of each application of the current. Subsequently, the values are compared (step 978), and one or more of needles 962 is selected (e.g., automatically by control unit 32, or by the operating physician) to be used for the ablation. As described hereinabove, the ablation may be performed by application of ablative energy (e.g., RF current) or by the ethanol-comprising liquid via the selected needle(s) (step 982).

For some applications, needles 962 have more than one extended state, and are advanceable to more than one depth into the wall of artery 8. For such applications, system 960 may be used to determine a preferred depth of needles 962 (e.g., the distance between endothelium 760 and nerve 770) before their use in ablation.

As mentioned with respect to more than one of the intravascular devices described hereinabove, although the electrode unit(s) and ablation unit(s) are shown as distinct elements, for some applications the intravascular device is an integrated unit that comprises and/or defines both the electrode unit(s) and the ablation unit(s) (e.g., disposed on a single body 23). Intravascular device 961 as shown in FIG. 22A serves as both an electrode unit (e.g., for application of non-ablative current, such as excitatory current) and as an ablation unit. Therefore, device 961 is an example of such an "integrated" intravascular device.

Figure 23A:
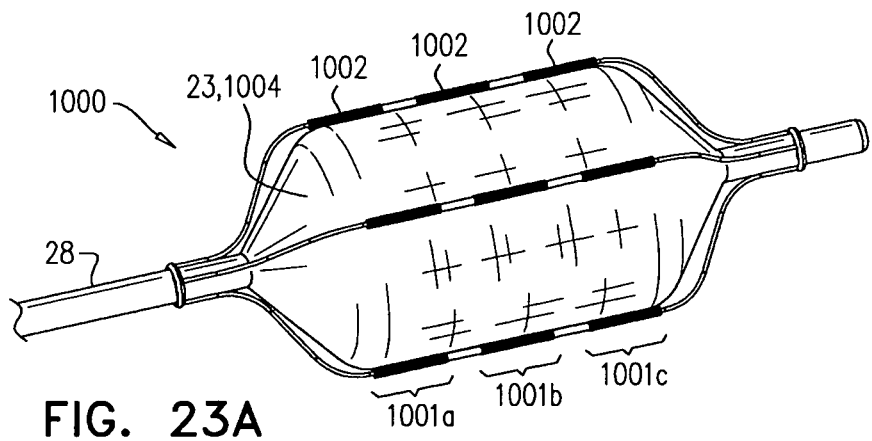
FIGS. 23A-B, 24, 25A-B, and 26 are schematic illustrations of intravascular devices each comprising a body and a plurality of electrodes, in accordance with some applications of the invention.
Figure 23B:
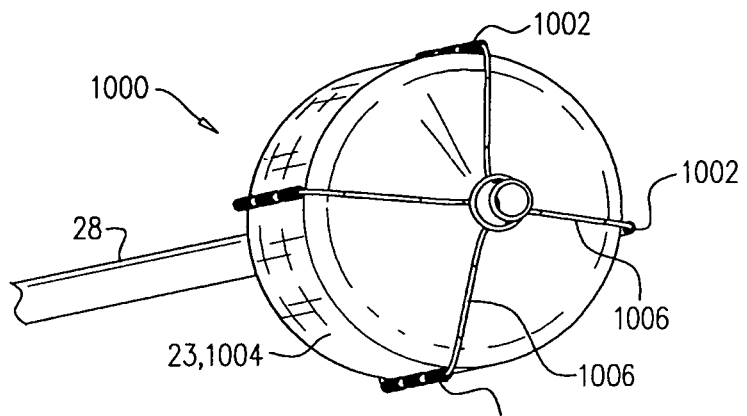
Figure 24:
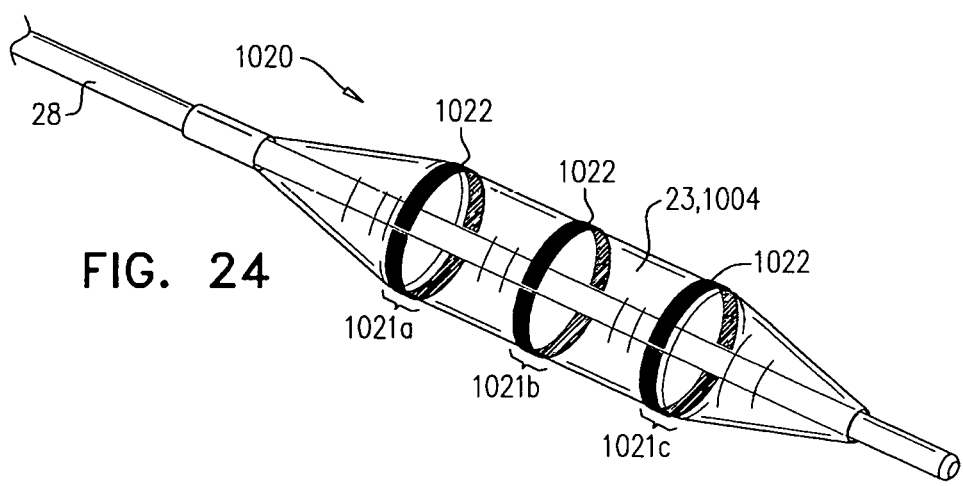
Figure 25:
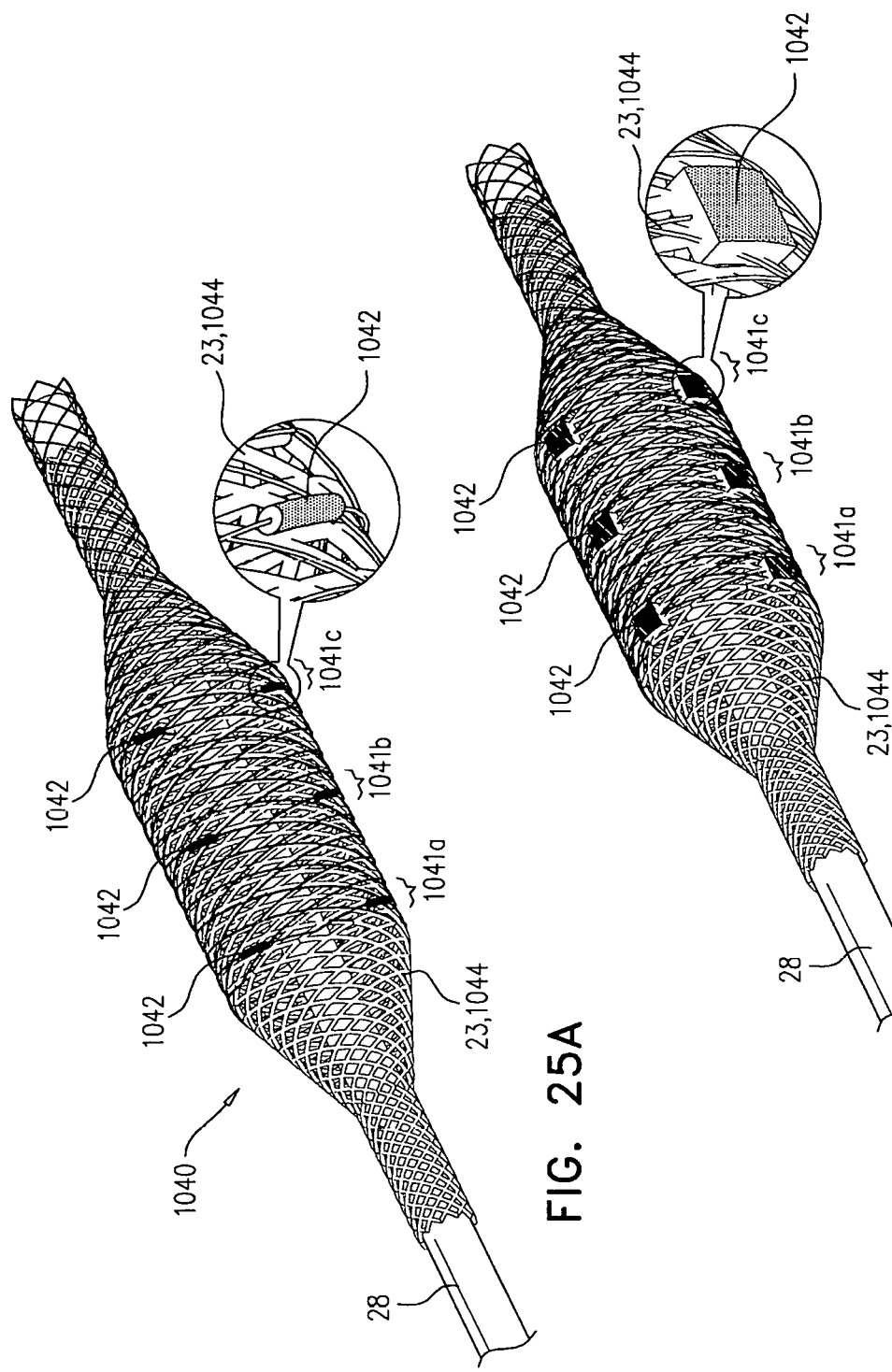
Figure 26:
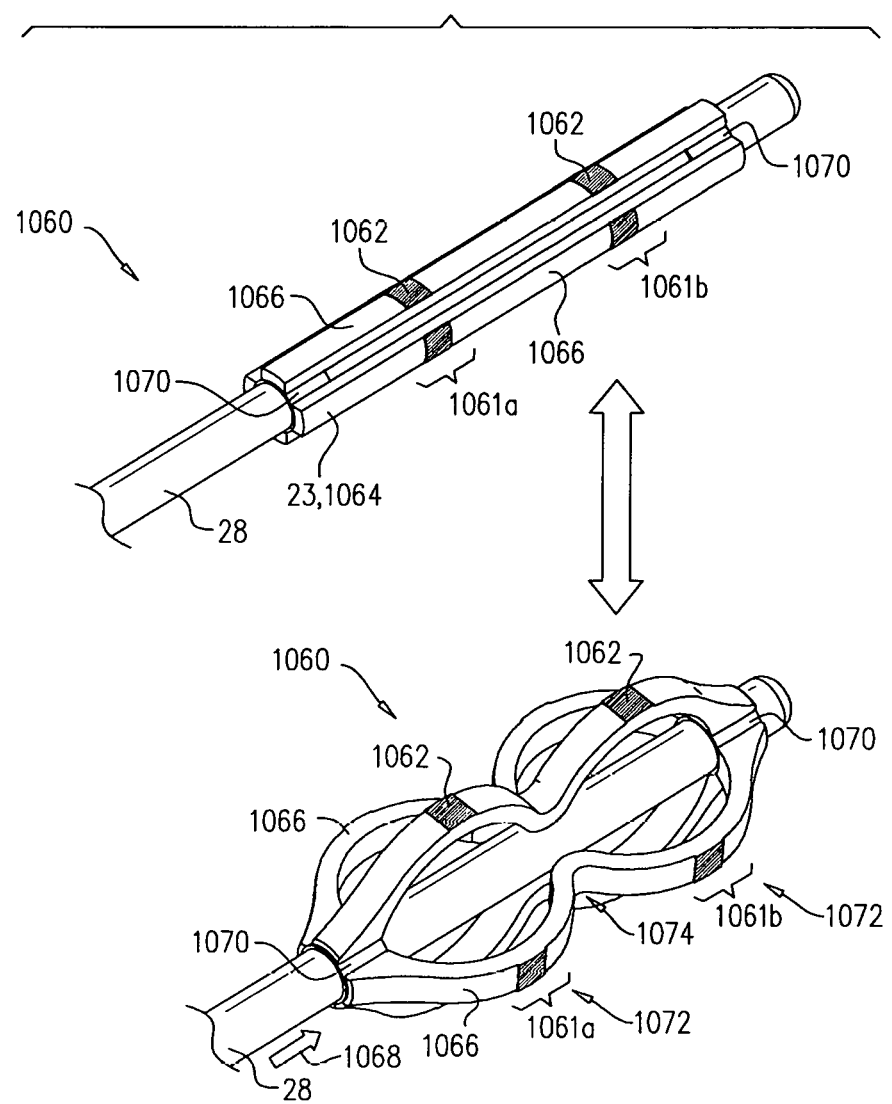

Reference is now made to FIGS. 23A-26, which are schematic illustrations of intravascular devices each comprising a body and a plurality of electrodes, in accordance with some applications of the invention. Each electrode described hereinabove, whether a component of an electrode unit (e.g., for application of excitatory and/or blocking current) or a component of an ablation unit (e.g., an RF ablation unit), is typically disposed on a body 23. As described hereinabove, (1) for some applications the body is generally non-occlusive (e.g., in an expanded state of the body in which the electrodes arranged on the body are disposed against the wall of the artery, the body retains at least some (e.g., most) fluid communication between the aorta and the kidney), and (2) for some applications the body is generally occlusive, e.g., in the expanded state of the body the body, the body inhibits most or all fluid communication between the aorta and the kidney. FIGS. 23A-24 are examples of intravascular devices comprising a body 23 that is typically occluding, and FIGS. 25-26 are examples of intravascular devices comprising a body 23 that is typically non-occluding.

FIGS. 23A-B show side and end views, respectively, of an intravascular device 1000, comprising a plurality of electrodes 1002 disposed on a balloon 1004, which serves as body 23 of device 1000. Intravascular device 1000 is typically disposed at a distal portion of catheter 28, and balloon 1004 is typically inflated via the catheter. Inflation of balloon 1004 expands the balloon radially outward from a central longitudinal axis of device 1000 (i.e., moves the balloon into an expanded state), thereby placing electrodes 1002 in contact with the wall of the artery in which the device is disposed. Balloon 1004 is typically occlusive. For some applications, balloon 1004 is at least partially compliant, e.g., so as to conform to the wall of the artery while reducing excess force on localized sites of the wall. For example, a portion of balloon 1004 that is disposed in a narrower portion of the artery may stop expanding once it reaches the wall of the artery, while another portion of the balloon that is disposed in a wider portion of the artery continues to expand until it reaches the wall of the artery.

For some applications, device 1000 does not comprise balloon 1004, and instead conductors 1006, which electrically couple electrodes 1002 to control unit 32 (not shown) define, comprise, and/or are coupled to (e.g., embedded within) struts which are compressible radially-inward for delivery via a catheter, and automatically expand upon being exposed from the catheter within the artery. For example, the struts may be elastically-bendable wires, e.g., comprising a polymer such as nylon and/or a metal such as nitinol, biased to assume an expanded state. For such applications, the struts collectively serve as body 23 of device 1000. For applications in which device 1000 does not comprise balloon 1004, device 1000 is typically generally non-occlusive.

FIG. 24 shows an intravascular device 1020 comprising a plurality of electrodes 1022 disposed on balloon 1004, which serves as body 23 of device 1020. Device 1000 is typically disposed at a distal portion of catheter 28. Balloon 1004 and inflation thereof is described with reference to FIGS. 23A-B. Balloon 1004 thereby serves as a body 23 of device 1020, and is typically occlusive.

Expansion within the renal artery of a body that is occlusive (e.g., inflation of balloon 1004), may itself increase blood pressure. Therefore, for some applications in which the body of the intravascular device is occluding, and in which a preliminary value of the detected factor (e.g., blood pressure) is detected (e.g., while the subject is at rest, and/or before application of excitatory, blocking, and/or ablating current), the preliminary value is detected subsequently to expansion of the body (e.g., inflation of balloon 1004), e.g., so as to control for blood pressure increase resulting from the occlusion.

FIGS. 25A-B show an intravascular device 1040 comprising a plurality of electrodes 1042 disposed on an expandable wire structure 1044, which serves as body 23 of device 1040. Intravascular device 1040 is typically disposed at a distal portion of catheter 28. Typically, reversible expansion of structure 1044 is controllable from outside of the subject, and independently of a state of deployment of the device from any sheath via which the device may be delivered. Structure 1044 may be stent-like, may comprise a frame cut from a metallic tube, or may comprise a wire that is braided into a generally tubular shape. The frame of structure 1044 is typically non-occlusive. FIGS. 25A-B differ only in the shape of electrodes 1042.

FIG. 26 shows an intravascular device 1060 comprising a plurality of electrodes 1062 disposed on an expandable structure 1064, which serves as body 23 of device 1060. Intravascular device 1060 is typically disposed at a distal portion of catheter 28. Typically, reversible expansion of structure 1064 is controllable from outside of the subject, and independently of a state of deployment of the device from any sheath via which the device may be delivered. The upper image of FIG. 26 shows device 1060 in a contracted state thereof (e.g., for transluminal delivery), and the lower image shows the device in an expanded state thereof (e.g., an operational state). Movement of device 1060 from its contracted state toward its expanded state moves electrodes 1042 radially outward from a central longitudinal axis of the device, e.g., so as to place the electrodes in contact with the wall of the renal artery.

Device 1060 comprises a plurality of longitudinal struts 1066 that, in the contracted state, are typically disposed generally parallel to the central longitudinal axis of the device, and are arranged circumferentially around this axis. For some applications the central longitudinal axis of device 1060 is defined by a distal portion of catheter 28. Movement of one end of each strut 1066 closer to the other end of the strut (e.g., as indicated by arrow 1068) causes movement of a middle portion of the strut away from the central longitudinal axis of device 1060. Typically, each end of each strut 1066 is coupled to a respective ring 1070, which thereby couples the struts to each other. At least one ring 1070 is slidable with respect to catheter 28, and sliding of that ring toward another ring thereby causes movement of the middle portion of each strut radially outward. Expansion of device 1060 shapes (e.g., curves) each strut 1066, and this curvature defines a lobe 1072 of device 1060. Each electrode 1062 is disposed at a middle portion of a strut, such that the radially-outward movement moves the electrodes radially outward, for placement against the wall of the artery.

For some applications, and as shown, more than one strut 1066 is arranged longitudinally end to end, such that a respective more than one lobe 1072 is defined when device 1060 expands. Typically, the longitudinally-arranged struts are coupled to each other at a join 1074, which typically does not move radially substantially outward during expansion. For some applications, join 1074 comprises a ring that is slidable over catheter 28 (not shown). For some applications, both lobes 1072 expand (e.g., simultaneously) in response to force applied to a single ring 1070. For some applications, device 1060 is configured to facilitate application of force to more than one ring independently, such that each lobe 1072 is expandable independently of the other.

Typically, each lobe is expandable to a different distance from the central longitudinal axis compared to the other lobes. For some applications, such as those in which both lobes expand in response to force applied to a single ring, struts 1066 are sufficiently flexible to stop moving radially outward when they experience resistance provided by the wall of the artery. Thus, when a first strut contacts the wall of the artery, further expansion of device 1060 is possible until subsequent struts also contact the wall. For some applications, such as those in which each lobe is independently expandable, this independent control facilitates the expansion of each lobe to a different distance compared to the other lobes.

In some applications, at least one (e.g., each one) of the struts comprises exactly one lobe, i.e., the strut is not coupled to the catheter at a join 1074 between the ends of the strut.

Reference is again made to FIGS. 23A-26. Typically, each of the intravascular devices has a transverse diameter of greater than 1 mm and/or less than 3 umm, such as 1-3 mm (e.g., 1.5-2.5 mm) when in its contracted state, and a transverse diameter of greater than 3 mm and/or less than 10 mm, such as 3-10 mm (e.g., 4-8 mm) when in its expanded state. Typically the longitudinal distance between electrodes (e.g., the distance between each longitudinal site at which electrodes are disposed) is greater than 2 mm and/or less than 15 mm, such as 2-15 mm (e.g., 2-10 mm).

Typically, each intravascular device has electrodes disposed at more than one longitudinal site. Device 1000 has electrodes disposed at three longitudinal sites 1001a, 1001h, and 1001c; device 1020 has electrodes disposed at three longitudinal sites 1021a, 1021b, and 1021c; device 1040 has electrodes disposed at three longitudinal sites 1041a, 1041h, and 1041c; and device 1060 has electrodes disposed at two longitudinal sites 1061a and 1061b. For some applications, conductors (e.g., wires, and/or components of a flexible printed circuit board; PCB) extend longitudinally along the intravascular device, conducting current to an electrode at each longitudinal site, e.g., as shown for devices 1000 and 1060. For example, each PCB may comprise electrodes of different longitudinal sites. Conductors 1006 are shown in FIGS. 23A-B, but are not visible in FIG. 26. It is to be understood that a conductor extends along (e.g., within) each strut 1066 of device 1060. For some applications, a separate PCB provides the electrodes for each longitudinal site, e.g., as may be the case for device 1020.

Figure 27A:
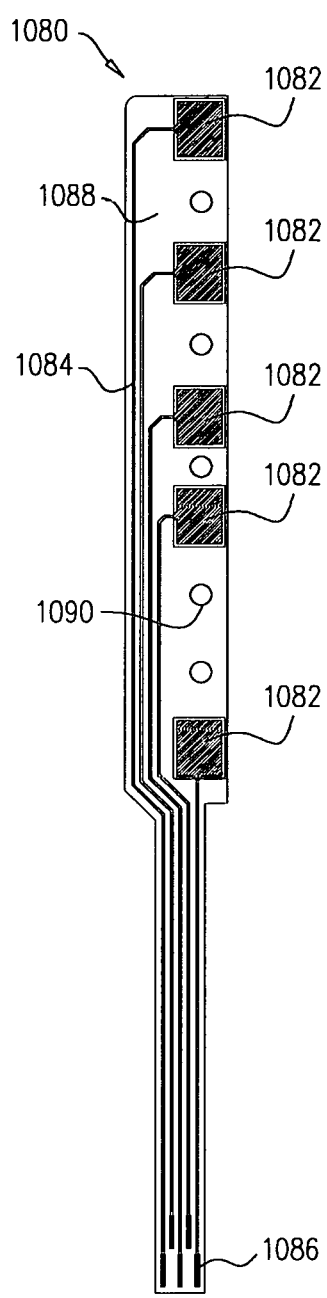
FIGS. 27A-C are schematic illustrations of respective printed circuit boards (PCBs) each comprising a plurality of electrodes and conductors disposed on a substrate, in accordance with some applications of the invention.
Figure 27B:
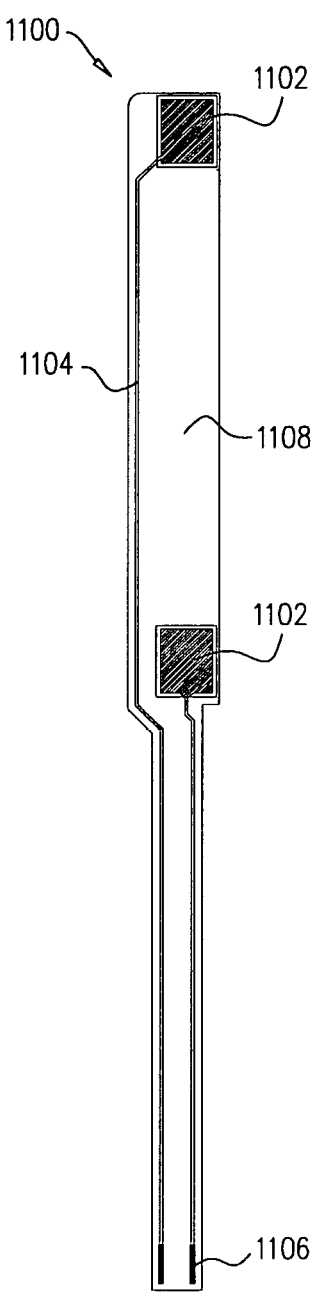
Figure 27C:
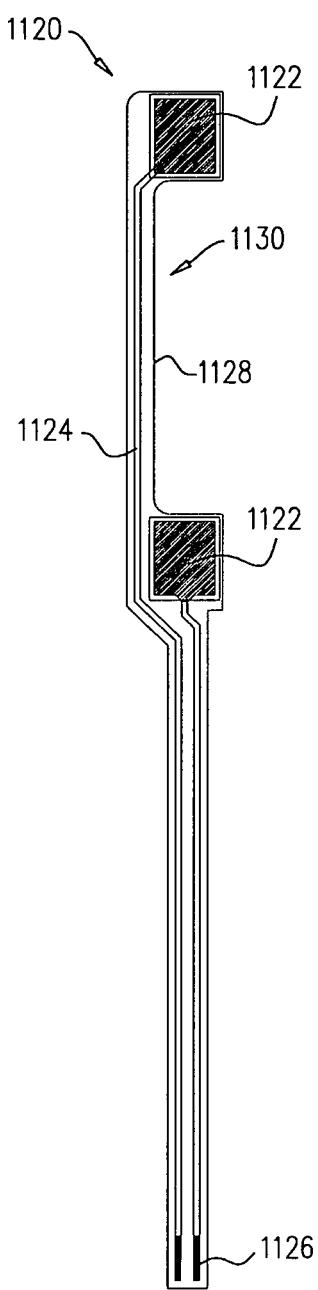

Reference is made to FIGS. 27A-C, which are schematic illustrations of respective PCBs, each comprising a plurality of electrodes and conductors disposed on a substrate, in accordance with some applications of the invention. The PCBs shown in FIGS. 27A-C may be used to provide the electrodes of one or more of the intravascular devices described hereinabove, mutatis mutandis.

FIG. 27A shows a PCB 1080 comprising five electrodes 1082 each coupled to a respective conductor 1084 that extends to an interface 1086, via which the PCB is electrically coupled (e.g., soldered) to the rest of the system (e.g., to a control unit). Electrodes 1082, conductor 1084, and typically interface 1086 are disposed on a substrate 1088, which is typically flexible.

FIG. 27B shows a PCB 1100 comprising two electrodes 1102 each coupled to a respective conductor 1104 that extends to an interface 1106, via which the PCB is electrically coupled (e.g., soldered) to the rest of the system (e.g., to a control unit). Electrodes 1102, conductor 1104, and typically interface 1106 are disposed on a substrate 1108, which is typically flexible.

FIG. 27C shows a PCB 1120 comprising two electrodes 1122 each coupled to a respective conductor 1124 that extends to an interface 1126, via which the PCB is electrically coupled (e.g., soldered) to the rest of the system (e.g., to a control unit). Electrodes 1122, conductor 1124, and typically interface 1126 are disposed on a substrate 1128, which is typically flexible.

Flexibility of the PCBs may be increased by removal of substrate material on which no conducting element is disposed. For example, holes 1090 (FIG. 27A) and/or cutouts 1130 (FIG. 27C) may be made in the PCB.

In general, it is to be noted that although the distal portion(s) of the apparatus (including the electrode and ablation units) are shown as being disposed within renal artery 8 generally midway between kidney 10 and the ostium of the renal artery from aorta 12, this positioning is purely for simplicity; the distal portion may be disposed closer to the renal artery (e.g., generally at the ostium), or closer to the kidney. For some applications, the intravascular device being used is placed consecutively at more than one site along a longitudinal axis of renal artery 8 (i.e., between its ostium from aorta 12 and the kidney), so as to identify a longitudinal site at which the effect of the excitatory current is greatest, e.g., thereby identifying a longitudinal site at which the ablation energy is to be subsequently applied. For some applications, such testing of longitudinal sites is used to screen subjects likely to be responsive to ablation treatment, and thereby for some subjects ablation energy is not subsequently applied.

For some applications of the invention, at least ablation unit 24 of one or more of the intravascular devices described hereinabove may be configured to be implanted in renal artery 8. For such applications, ablation unit 24 comprises or is coupled to an antenna, configured to wirelessly receive energy (e.g., from an extracorporeal transmitter), and to responsively apply an application of the ablation energy. For some such applications, one or more characteristics (e.g., intensity) of the ablation energy is controllable via the extracorporeal transmitter. For some such applications, the entire intravascular device is implantable in renal artery 8.

For example, ablation unit 24 and/or the entire intravascular device may comprise a stent, transluminally advanceable via a catheter independently of other components of the described system (such as catheter 28 and/or sensor 26). Alternatively, ablation unit 24 and/or the entire intravascular device may be (i) coupled to catheter 28 as shown in FIGS. 1, 5A-B. 6, 7, and 8, and (ii) implantable in renal artery 8 by being decoupled from the longitudinal member while disposed within the renal artery.

Some of the applications described hereinabove may include driving a current between different subsets (e.g., pairs) of electrodes at generally the same time. Purely as an illustrative example, the step shown in FIG. 15B shows excitatory current being driven between electrode pair 750a and 752a at generally the same time as current is driven between all the other electrode pairs (e.g., electrodes 750b and 752h, 750c and 752c, and 750d and 752d). For such applications, one or more characteristics of the current may be configured (e.g., modified) so as to reduce unexpected and/or undesired crossing of current paths, e.g., such that current returns via the intended return electrode, rather than another (e.g., adjacent) return electrode. Using the example of FIG. 15B, it may be desirable that current from electrode 750b return via electrode 752b, rather than via another electrode (e.g., electrode 752a or 752c), e.g., such that overall the current is distributed evenly around the circumference of the artery.

For some applications, the characteristic of the current driven between one of the electrode pairs is different from that of the current driven between another of the electrode pairs. For example, the current driven between each electrode pair may have a different frequency and/or pulse width to that driven between the other electrode pairs, and/or may be phased so as to not coincide with that driven between the other electrode pairs. Thus, for some applications, although current is driven between more than one electrode pair at generally the same time (e.g., on a timescale of seconds or longer), at any specific time (e.g., on a timescale of milliseconds) the current is actually only driven between one electrode pair. For example, to refrain from cross-talk between stimulation circuits (i.e., pairs of electrodes between which current is driven), there may be a time interval of 100 microseconds between stimulating currents that are driven between respective pairs of electrodes, i.e., the interphase delay may be 100 microseconds.

In some applications, electrical stimulation is applied in the form of biphasic symmetric square pulses, e.g., having a pulse width of at least 0.5 and/or less than 4 msec, e.g., 2 msec. Typically, stimulation is applied at 20 Hz, e.g., with a current amplitude of at least 10 and/or less than 30 mAmp, e.g., 16 mAmp.

For some applications, one or more parameters of the excitatory current (such as, but not limited to, amperage, frequency, and pulse width) are modified during the duration of the application of the excitatory current (e.g., according to a pre-determined program, and/or in response to detected changes in the detected parameter). (Purely as an illustrative example, the frequency of the current may begin at 20 Hz, and change in 2 Hz increments every 15 seconds.) That is, throughout the present patent application (including the specification and the claims) an "application of excitatory current" may mean (a) an application of excitatory current that remains uniform throughout its duration, or (b) an application of excitatory current that changes with respect to at least one parameter at least once during its duration.

Throughout the present application are descriptions of applications in which current is applied by and/or between various electrodes. In some descriptions, the electrodes are described explicitly or implicitly as bipolar electrodes, and in some descriptions the electrodes are described explicitly or implicitly as monopolar electrodes. It is to be understood that the choice of using monopolar or bipolar electrodes may be dependent on a particular application and/or a particular subject, and that the scope of the present invention includes the use of monopolar or bipolar electrodes for each described application, mutatis mutandis.

Furthermore, for some systems described herein, the intravascular device may comprise both monopolar and bipolar electrodes (or the electrodes of the intravascular device are configurable to serve as monopolar or bipolar electrodes), such that the operating physician (or the control unit of the system) may select a type of electrode that is preferable for a given subject. Purely as an example, each electrode 1002 of device 1000 (FIGS. 23A-B) as shown may in fact represent more than one electrode, such as (A) a pair of bipolar electrodes and a single monopolar electrode, or (B) two electrodes that are switchable between two configurations: (i) a pair of bipolar electrodes, and (ii) a monopolar electrode (and one deactivated electrode).

For some applications, this mono/bipolar selection and/or configuration of electrodes is performed as part of the one or more applications of non-ablating current applied prior to the application of ablation energy. That is, the applications of non-ablating current may include monopolar applications and bipolar applications, and the selection/configuration may be performed based on values (e.g., blood pressure values) detected after each of these applications of non-ablating current. For some such applications, ablation energy (e.g., RF current) is subsequently applied using the same selection/configuration of electrodes as that which provided the greatest response to the non-ablating current. For some applications, the use of both monopolar and bipolar electrodes may increase the accuracy of the locating of the renal nerve.

For some applications of the invention, the temperature of the wall of the renal artery is modified prior to, during, and/or after application of one or more of the currents and/or ablation energy described hereinabove. For example, the electrodes described herein may be disposed on a balloon that is inflatable with a fluid (e.g., a liquid) that is cooler or warmer than the surrounding tissue. Alternatively or additionally, warming may be achieved using ultrasound. This temperature modification is typically not ablative in itself; the tissue is not cooled to less than 10 degrees C., and is not warmed to more than 45 degrees C. (and is further typically not warmed to more than 42 degrees C.). Thus, the temperature of the tissue is modified to fall within a range of 10-36 degrees C. (e.g., 10-30 degrees C. such as 10-20 degrees C.), or a range of 38-42 degrees C. (e.g., 40-42 degrees C.) or 40-45 degrees C. (e.g., 42-45 degrees C.). Rather, the temperature modification is hypothesized to modify the responsiveness of the renal nerve to the excitatory current. For example, it may be advantageous to warm the renal nerve so as to increase its responsiveness to the excitatory current, and thereby increase the sensitivity of the "testing" steps of the techniques described hereinabove (i.e., the steps in which one or more applications of non-ablating current are applied prior to the application of ablation energy). It is to be noted, therefore, that for some applications localized warming of the renal nerve is performed prior to ablation. Conversely, it may be advantageous to cool the renal nerve so as to reduce responsiveness, and thereby reduce background "noise" during testing.

For some applications, the systems described hereinabove (e.g., the intracorporal devices thereof) comprise at least one temperature sensor, configured to detect the temperature of an electrode and/or surrounding tissue. For example, the temperature sensor may facilitate accurate modification of the temperature of the wall of the artery as described in the previous paragraph. Alternatively or additionally, the temperature sensor may be configured to monitor the increase in temperature of tissue and/or electrodes during the ablation itself.

As described hereinabove, sensor 26 is configured to detect a factor of the subject, such as a factor indicative of blood pressure, heart rate (e.g., heart rate variability), and/or blood flow. It is therefore to be noted that throughout this application, where blood pressure is used, one or more other factors may be used instead. For example, after the start of an application of excitatory current, increased renal nerve activity may be indirectly detected by detecting reduced heart rate variability, in place of detecting increased blood pressure.

For some applications, rather than sensor 26 being intracorporal, the sensor is extracorporeal, and control unit 32 is configured to receive values of the detected factor from the sensor e.g., by interfacing with the sensor, or simply by providing a user interface for an operator to input the detected values. For some such applications, the sensor is not provided as a component of the apparatus, and the apparatus is configured to receive the values from a commercially-available sensor.

Throughout this application, steps of techniques are described. Some such steps are described as being performed by an operator (e.g., an operating physician). Some such steps are described as being performed by a control unit (e.g., control unit 32), i.e., automatically. FIG. 11 shows an example of a technique in which some steps are performed by an operator and some steps are performed by a control unit. It is to be understood that for some applications, steps described in this application may be performed by an operator (e.g., manually) or by a control unit (e.g., automatically). For example, for some applications an operator may advance an intravascular device of a system into an artery and activate the control unit of the system, and the control unit automatically performs one or more of the following steps (according to a respective technique described hereinabove): (1) driving electrodes to apply one or more applications of non-ablating current (e.g., excitatory and/or blocking current), (2) receiving one or more detected values from a sensor (e.g., by operating and/or powering the sensor), (3) driving the ablation unit to apply ablation energy, and/or (4) at least in part responsively to the detected values, selecting a next step.

For some applications, ultrasound may be used to facilitate application of current to the blood vessel (e.g., to the renal artery). For example, ultrasound may be used to identify the distance of the adventitia and/or renal nerve from the lumen of the blood vessel. Alternatively or additionally, ultrasound may be used to induce action potentials in the nerve (e.g., to facilitate induction of action potentials by the excitatory current, or in place of the excitatory current). For some applications, this is performed using apparatus and/or techniques described in one or more of the following references, which are incorporated herein by reference:

US Patent Application Publication 2012-0283502 to Mishelevich et al.;

Norton, Stephen J. "Can ultrasound be used to stimulate nerve tissue?." Biomedical engineering online 2.1 (2003): 6; and Gavrilov, L. R., E. M. Tsirulnikov, and I. ab I. Davies. "Application of focused ultrasound for the stimulation of neural structures." Ultrasound in medicine & biology 22.2 (1996): 179-192.

For some applications, ultrasound is used to non-ablatively increase the temperature of the artery wall prior to, during, and/or after application of one or more of the currents and/or ablation energy described hereinabove.

Throughout the present application (including the specification and the claims) a "difference" and/or a "relationship" between values may include an arithmetic subtraction, a ratio, or any other expression of a difference or relationship between the values.

It will be understood that, although the terms "first," "second," etc. may be used herein to describe various elements, these elements should not be limited by these terms. These terms are generally only used to distinguish one element from another. Thus, a "first" element (e.g., a first electrode unit) discussed herein could also be termed a "second" element (e.g., a second electrode unit) without departing from the teachings of the present disclosure.

In general, methods described herein as applying to stimulation and/or ablation of a renal nerve may also be applied to other nerves, e.g., those which are associated with: the superior mesenteric vein, posterior, anterior, inferior pancrcaticoduodenal veins, middle colic vein, right colic vein, ileocolic vein, anterior, posterior cecal veins, hepatic portal vein, posterior superior pancreaticoduodenal vein, prepyloric vein, anterior superior pancreaticoduodenal vein, hepatic portal vein, posterior superior pancrcaticoduodenal vein, superior mesenteric vein, anterior superior pancreaticoduodenal vein, anterior inferior pancreaticoduodenal vein, posterior inferior pancreaticoduodenal vein, or a vein that vascularizes the duodenum.

In general, control unit 32 may be embodied as a single control unit 32, or a cooperatively networked or clustered set of control units. Control unit 32 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. Such program code and/or data, when provided to the control unit, produce a machine or special-purpose computer, configured to perform the tasks described herein. Typically, control unit 32 is connected to one or more sensors (e.g., sensor 26) via one or more wired or wireless connections. Control unit 32 is typically configured to receive signals from the one or more sensors, and to process these signals as described herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with tissue of a renal nerve passing longitudinally within a wall of a renal artery of a subject, the apparatus comprising:
   a catheter, configured to be placed within the renal artery;
   one or more stimulating electrodes coupled to the catheter and configured to stimulate the tissue of the renal nerve by passing a stimulating current through the wall of the renal artery;
   a sensor configured to sense blood pressure information of the subject; and
   a control unit, configured to:
      drive the one or more stimulating electrodes to stimulate the tissue of the renal nerve,
      receive the blood pressure information from the sensor,
      based on the received blood pressure information, compute a maximum intra-heartbeat blood pressure increase rate for at least one heartbeat that follows a start of the driving of the one or more stimulating electrodes to stimulate the tissue of the renal nerve,
      compare the maximum intra-heartbeat blood pressure increase rate to a threshold, and
      generate, in response to the comparison, an output indicating whether an ablation of the tissue of the renal nerve should be performed.

2. The apparatus according to claim 1, wherein:
the control unit is further configured to:
   prior to the driving of the one or more stimulating electrodes, perform a prior driving of the one or more stimulating electrodes to stimulate the tissue of the renal nerve, and
   compute the threshold by computing the maximum intra-heartbeat blood pressure increase rate for at least one heartbeat that follows a start of the prior driving of the one or more stimulating electrodes.

3. The apparatus according to claim 1, wherein:
the at least one heartbeat that follows the start of the driving of the one or more electrodes to stimulate the tissue of the renal nerve is exactly one heartbeat that follows the start of the driving of the one or more electrodes to stimulate the tissue of the renal nerve,
the maximum intra-heartbeat blood pressure increase rate for the at least one heartbeat is a maximum intra-heartbeat blood pressure increase rate for the exactly one heartbeat, and
the control unit is configured to:
   based on the received blood pressure information, compute the maximum intra-heartbeat blood pressure increase rate for the exactly one heartbeat,
   compare, to the threshold, the maximum intra-heartbeat blood pressure increase rate for the exactly one heartbeat, and
   generate the output in response to the comparison, to the threshold, of the maximum intra-heartbeat blood pressure increase rate for the exactly one heartbeat.

4. The apparatus according to claim 1, wherein:
the at least one heartbeat that follows the start of the driving of the one or more electrodes to stimulate the tissue of the renal nerve is a plurality of heartbeats that follow the start of the driving of the one or more electrodes to stimulate the tissue of the renal nerve,
the maximum intra-heartbeat blood pressure increase rate for the at least one heartbeat is a maximum intra-heartbeat blood pressure increase rate for the plurality of heartbeats, and
the control unit is configured to:
   based on the received blood pressure information, compute the maximum intra-heartbeat blood pressure increase rate for the plurality of heartbeats,
   compare, to the threshold, the maximum intra-heartbeat blood pressure increase rate for the plurality of heartbeats, and
   generate the output in response to the comparison, to the threshold, of the maximum intra-heartbeat blood pressure increase rate for the plurality of heartbeats.

5. The apparatus according to claim 1, wherein:
the at least one heartbeat that follows a start of the driving of the one or more electrodes to stimulate the tissue of the renal nerve is a plurality of heartbeats that follow the start of the driving of the one or more electrodes to stimulate the tissue of the renal nerve,
the maximum intra-heartbeat blood pressure increase rate for the at least one heartbeat is a maximum intra-heartbeat blood pressure increase rate for each of the plurality of heartbeats, and
the control unit is configured to:
   based on the received blood pressure information, compute the maximum intra-heartbeat blood pressure increase rate for each of the plurality of heartbeats,
   from the maximum intra-heartbeat blood pressure increase rate for each of the plurality of heartbeats, compute a mean maximum intra-heartbeat blood pressure increase rate for the plurality of heartbeats,
   compare, to the threshold, the mean maximum intra-heartbeat blood pressure increase rate, and
   generate the output in response to the comparison, to the threshold, of the mean maximum intra-heartbeat blood pressure increase rate.

6. A method for use with tissue of a renal nerve passing longitudinally within a wall of a renal artery of a subject, the method comprising:

using one or more stimulating electrodes disposed within the renal artery, stimulating the tissue of the renal nerve by passing a stimulating current through the wall of the renal artery;

using a sensor, determining a maximum intra-heartbeat blood pressure increase rate for at least one heartbeat that follows a start of the stimulating of the tissue of the renal nerve;

in response to the maximum intra-heartbeat blood pressure increase rate, deciding whether to ablate or to not ablate the tissue of the renal nerve; and in response to deciding to ablate the tissue of the renal nerve, ablating the tissue of the renal nerve.

7. The method according to claim 6, wherein determining the maximum intra-heartbeat blood pressure increase rate comprises sensing respective maximum intra-heartbeat blood pressure increase rates for a plurality of heartbeats, and wherein deciding whether to ablate the tissue of the renal nerve comprises deciding whether to ablate the tissue of the renal nerve in response to an average of the respective maximum intra-heartbeat blood pressure increase rates.

8. The method according to claim 6, wherein:
determining the maximum intra-heartbeat blood pressure increase rate comprises determining respective maximum intra-heartbeat blood pressure increase rates for a plurality of heartbeats,
the method further comprises identifying a largest maximum intra-heartbeat blood pressure increase rate of the plurality of heartbeats, and
wherein deciding whether to ablate the tissue of the renal nerve comprises deciding whether to ablate the tissue of the renal nerve in response to the largest maximum intra-heartbeat blood pressure increase rate.

9. The method determining the maximum intra-heartbeat blood pressure increase rate according to claim 6,
wherein stimulating the tissue of the renal nerve comprises stimulating the tissue of the renal nerve during a second stimulation,
wherein the method further comprises, prior to the second stimulation:
using the one or more stimulating electrodes to stimulate the tissue of the renal nerve by passing the stimulating current through the wall of the renal artery, during a first stimulation;
using the sensor, determining a maximum intra-heartbeat blood pressure increase rate for at least one heartbeat that follows a start of the first stimulation; and
performing a first ablation of the tissue of the renal nerve, and
wherein deciding whether to ablate the tissue of the renal nerve comprises deciding whether to perform a second ablation of the tissue of the renal nerve, in response to a difference between (i) the maximum intra-heartbeat blood pressure increase rate for the at least one heartbeat that follows the start of the first stimulation, and (ii) the maximum intra-heartbeat blood pressure increase rate for the at least one heartbeat that follows the start of the second stimulation.

10. The method according to claim 6,
wherein stimulating the tissue of the renal nerve comprises stimulating the tissue of the renal nerve by passing the stimulating current through the wall of the renal artery at each of a plurality of sites,
wherein determining the maximum intra-heartbeat blood pressure increase rate comprises determining a maximum intra-heartbeat blood pressure increase rate for each of the stimulations of the plurality of sites, and
wherein deciding whether to ablate the tissue of the renal nerve comprises (a) deciding to ablate the tissue of the renal nerve at at least one of the plurality of sites, and (b) deciding not to ablate the tissue of the renal nerve at at least another one of the plurality of sites, in response to the determined maximum intra-heartbeat blood pressure increase rates.

11. The method according to claim 10, wherein the plurality of sites includes a plurality of longitudinal sites along the wall of the renal artery, and wherein passing the respective stimulating currents through the wall of the renal artery at the plurality of sites comprises passing the respective stimulating currents through the wall of the renal artery at the plurality of longitudinal sites.

12. The method according to claim 10, wherein the plurality of sites includes a plurality of circumferential sites along the wall of the renal artery, and wherein passing the respective stimulating currents through the wall of the renal artery at the plurality of sites comprises passing the respective stimulating currents through the wall of the renal artery at the plurality of circumferential sites.

13. The method according to claim 6, wherein determining the maximum intra-heartbeat blood pressure increase rate for the at least one heartbeat that follows the start of the stimulating of the tissue of the renal nerve comprises determining the maximum intra-heartbeat blood pressure increase rate for exactly one heartbeat that follows the start of the stimulating of the tissue of the renal nerve.

* * * * *